United States Patent
Eveleth et al.

(10) Patent No.: US 11,479,591 B2
(45) Date of Patent: Oct. 25, 2022

(54) RECOMBINANT MODIFIED FIBROBLAST GROWTH FACTORS AND THERAPEUTIC USES THEREOF

(71) Applicant: TREFOIL THERAPEUTICS, INC., San Diego, CA (US)

(72) Inventors: David Eveleth, San Diego, CA (US); Jennifer Jenkins-Eveleth, San Diego, CA (US); Amuthakannan Subramaniam, San Diego, CA (US); Ralph Bradshaw, Encinitas, CA (US)

(73) Assignee: TREFOIL THERAPEUTICS, INC., San Diego, CA (US)

(*) Notice: Subject to any disclaimer, the term of this patent is extended or adjusted under 35 U.S.C. 154(b) by 0 days.

(21) Appl. No.: 16/611,182

(22) PCT Filed: May 4, 2018

(86) PCT No.: PCT/US2018/031189
§ 371 (c)(1),
(2) Date: Nov. 5, 2019

(87) PCT Pub. No.: WO2018/204847
PCT Pub. Date: Nov. 8, 2018

(65) Prior Publication Data
US 2020/0190158 A1  Jun. 18, 2020

Related U.S. Application Data

(60) Provisional application No. 62/584,624, filed on Nov. 10, 2017, provisional application No. 62/502,540, filed on May 5, 2017, provisional application No. 62/502,529, filed on May 5, 2017.

(51) Int. Cl.
| | | |
|---|---|---|
| *C07K 14/50* | (2006.01) | |
| *A61P 27/02* | (2006.01) | |
| *A61K 38/00* | (2006.01) | |
| *A61K 38/18* | (2006.01) | |
| *A61K 9/00* | (2006.01) | |
| *C12N 15/86* | (2006.01) | |

(52) U.S. Cl.
CPC .......... *C07K 14/501* (2013.01); *A61K 9/0048* (2013.01); *A61P 27/02* (2018.01); *C12N 15/86* (2013.01); *A61K 38/00* (2013.01); *A61K 38/1825* (2013.01)

(58) Field of Classification Search
None
See application file for complete search history.

(56) References Cited

U.S. PATENT DOCUMENTS

| | | |
|---|---|---|
| 5,033,252 A | 7/1991 | Carter |
| 5,052,558 A | 10/1991 | Carter |
| 5,323,907 A | 6/1994 | Kalvelage |
| 5,552,528 A | 9/1996 | Burgess et al. |
| 6,642,026 B2 * | 11/2003 | Stegmann ............ C07K 14/501 435/69.1 |
| 7,595,296 B1 | 9/2009 | Blaber et al. |
| 7,659,379 B1 | 2/2010 | Blaber et al. |
| 7,696,171 B1 | 4/2010 | Blaber et al. |
| 7,776,825 B1 | 8/2010 | Blaber et al. |
| 7,790,682 B1 | 9/2010 | Blaber et al. |
| 8,119,776 B1 | 2/2012 | Blaber et al. |
| 8,153,770 B1 | 4/2012 | Blaber et al. |
| 8,153,771 B1 | 4/2012 | Blaber et al. |
| 8,461,111 B2 | 6/2013 | Blaber et al. |
| 2005/0227929 A1 | 10/2005 | Masferrer |
| 2011/0224404 A1 | 9/2011 | Blaber et al. |
| 2013/0130983 A1 | 5/2013 | Blaber et al. |

FOREIGN PATENT DOCUMENTS

| | | |
|---|---|---|
| EP | 0791576 A2 | 8/1997 |
| GB | 2223496 A | 4/1990 |
| JP | 2007535306 A | 12/2007 |
| JP | 2014534172 A | 12/2014 |
| WO | WO-9917800 A1 | 4/1999 |
| WO | WO-0138357 A2 | 5/2001 |
| WO | WO-2015048188 A2 | 4/2015 |
| WO | WO-2015061361 A1 | 4/2015 |
| WO | WO-2015198175 A1 | 12/2015 |
| WO | WO-2016172153 A2 | 10/2016 |
| WO | WO-2016172156 A2 | 10/2016 |
| WO | WO-2017026156 A1 | 2/2017 |
| WO | WO-2018204847 A2 | 11/2018 |

OTHER PUBLICATIONS

Azher et al., Clinical Ophthalmology Jan. 2017:11 185-191.*
Heiligenhaus et al., Investigative Ophthalmology & Visual Science, Aug. 2001, vol. 42, No. 9.*
Fredj-Reygrobellet et al., Curr Eye Res 6(10):1205-1209 (1987).*
Baird et al. The fibroblast growth factor family. Cancer Cells 3:239-243 (1991).
Burgess et al. The heparin-binding (fibroblast) growth factor family of proteins. Annu Rev. Biochem. 58:575-606 (1989).
Cheng et al. Spinal Cord Repair with Acidic Fibroblast Growth Factor as a Treatment for a Patient with Chronic Paraplegia. Spine 29(14):E284-E288 (2004).
Ganesan et al. Chemical Warfare Agents. Journal of Pharmacy and Bioallied Sciences 2.3:166-178 (2010).
Jiang et al. Coated microneedles for drug delivery to the eye. Invest Ophthalmol Vis Sci 48(9):4038-4043 (2007).
Joyce et al. Relationship among oxidative stress, DNA damage, and proliferative capacity in human corneal endothelium. Invest Ophthalmol Vis Sci 50:2116-2122 (2009).

(Continued)

*Primary Examiner* — Marianne P Allen
(74) *Attorney, Agent, or Firm* — Wilson Sonsini Goodrich & Rosati

(57) ABSTRACT

Described herein are modified fibroblast growth factor (FGF) polypeptides, pharmaceutical compositions and medicaments that include such modified FGF polypeptides, and methods of using such modified FGF polypeptides to treat or prevent conditions that benefit from administration of FGFs.

14 Claims, 12 Drawing Sheets

Specification includes a Sequence Listing.

(56) References Cited

OTHER PUBLICATIONS

Kanavi et al. Chronic and delayed mustard gas keratopathy: a histopathologic and immunohistochemical study. Eur. J Ophthalmol. 20(5):839-43 (2010).
Kay et al. Corneal endothelial modulation: a factor released by leukocytes induces basic fibroblast growth factor that modulates cell shape and collagen. Invest Ophthalmol Vis Sci 34(3):663-72 (1993).
Koevary. Pharmacokinetics of topical ocular drug delivery: potential uses for the treatment of diseases of the posterior segement and beyond. Curr. Drug Metab. 4(3):213-222 (2003).
Lee et al. Common and distinct pathways for cellular activities in FGF-2 signaling induced by IL-1 beta in corneal endothelial cells. Invest Ophthalmol Vis Sci 50(5):2067-2076(2009).
Lee et al. Review on the systemic delivery of insulin via the ocular route. Int. J. Pharm. 233(1-2):1-18 (2002).
Lin. Functional recovery of chronic complete idiopathic transverse myelitis after administration of neurotrophic factors. Spinal Cord 44:254-257 (2006).
McKeehan et al. The heparan sulfate-fibroblast growth factor family: diversity of structure and function. Prog. Nucleic Acid Res. Mol. Biol. 59:135-176 (1998).
Ornitz el al. Receptor specificity of the fibroblast growth factor family. J Biol Chem 271(25):15292-15297 (1996).
Reuss et al. Fibroblast growth factors and their receptors in the central nervous system. Cell Tissue Res. 313:139-157 (2003).
Rosano et al. Recombinant protein expression in *Escherichia coli*: advances and challenges. Frontiers in Microbiology 5:172 (2014).
Tewari-Singh et al. Cutaneous exposure to vesicant phosgene oxime: Acute effects on the skin and systemic toxicity. Toxicol Appl Pharmacol. 317:25-32 (2017).
Tewari-Singh et al. Mustard vesicating agent-induced toxicity in the skin tissue and silibinin as a potential countermeasure. Ann N Y Acad Sci. 1374(1):184-92 (2016).
Tsuji et al. Preparation of 3-acetoacetylaminobenzo[b]furan derivatives with cysteinyl leukotriene receptor 2 antagonistic activity. Org. Biomol. Chem. 1:3139-3141 (2003).
Xia et al. Pharmacokinetic properties of 2nd-generation fibroblast growth factor-1 mutants for therapeutic application. PLoS one 7(11):e48210 (12 pgs) (2012).
Zhang et al. Receptor specificity of the fibroblast growth factor family. The complete mammalian FGF family. J Biol Chem 281(23):15694-15700 (2006).
Dhanushkodi et al., Healing of Ocular Herpetic Disease Following Treatment with an Engineered FGF-1 as Associated with Increased Corneal Anti-Inflammatory M2 Macrophages. Frontiers in Immunology 12(673763) 1-12 (2021).
Benmohamed et al. Decreased reactivation of a herpes simplex virus type 1 (HSV-1) latency-associated transcript (LAT) mutant using the in vivo mouse UV-B model of induced reactivation. J Neurovirol 21(5):508-17 (2015).
Mori et al., Direct binding of integrin avP3 to FGFI plays a role in FGFI signaling. J Biol Chem 283(26):18066-18075 (2008).
Yamaji et al., A novel fibroblast growth factor-I (FGFI) mutant that acts as an FGF antagonist. PloS one 5(4):e10273 (2010).

\* cited by examiner

FIG. 6

Histopathological grading

Paraformaldehyde fixed, paraffin embedded, H&E stain

| Epidermal Layer | Stromal Layer |
|---|---|
| Total Epidermal Differentiation | Stroma |
| 1 Normal 3 layer, good differentiation<br>2 Disruption in differentiation<br>3 Single layer only<br>4 Single layer, partial coverage<br>5 No epidermis present | 1 No disruption/vacuoles present<br>2 Vacuoles around some keratocytes<br>3 Vacuoles around most keratocytes<br>4 Generalized disruption to stroma |
| Basal Layer | Keratocytes |
| 1 Columnar formation proper orientation<br>2 Columnar and rounded with some orientation<br>3 Rounded, erratic orientation<br>4 Rounded, erratic orientation, partial coverage<br>5 No BL present | 1 Increased number of keratocytes<br>2 Present, in normal alignment to EPI<br>3 Abnormal number, shape (mild)<br>4 Abnormal number, shape (moderate)<br>5 Loss of keratocytes |
| Epithelial Intracellular Adhesion (EIA) | |
| 1 No breaks in EIA<br>2 Mild breaks in EIA<br>3 Moderate breaks in EIA<br>4 No EIA – cells separated<br>5 No epithelium present | |

RECOMBINANT MODIFIED FIBROBLAST GROWTH FACTORS AND THERAPEUTIC USES THEREOF

CROSS-REFERENCE

This application is a U.S. National Stage Entry of PCT/US2018/031189, filed May 4, 2018, which claims the benefit to U.S. Provisional Application No. 62/502,529, filed on May 5, 2017, U.S. Provisional Patent Application No. 62/502,540 filed May 5, 2017, and U.S. Provisional Patent Application No. 62/584,624 filed on Nov. 10, 2017, each incorporated herein by reference in its entirety.

The instant application contains a Sequence Listing which has been submitted electronically in ASCII format and is hereby incorporated by reference in its entirety. Said ASCII copy, created on Nov. 5, 2019, is named 45341-705_831_SL.txt and is 276,505 bytes in size.

FIELD OF THE INVENTION

Described herein are modified fibroblast growth factor (FGF) polypeptides, pharmaceutical compositions and medicaments that include such modified FGF polypeptides, and methods of using such modified FGF polypeptides to treat or prevent conditions that benefit from administration of FGFs.

BACKGROUND OF THE INVENTION

FGFs are large polypeptides widely expressed in developing and adult tissues (Baird et al., Cancer Cells, 3:239-243, 1991) and play roles in multiple physiological functions (McKeehan et al., Prog. Nucleic Acid Res. Mol. Biol. 59:135-176, 1998; Burgess, W. H. et al., Annu Rev. Biochem. 58:575-606 (1989). The FGF family includes at least twenty-two members (Reuss et al., Cell Tissue Res. 313:139-157 (2003)).

SUMMARY OF THE INVENTION

Provided herein in one embodiment is a recombinant modified FGF-1 polypeptide comprising the sequence set forth as SEQ ID NO: 1 with one or more mutations, wherein the polypeptide comprises an N-terminal methionine residue positioned upstream to the first residue of SEQ ID NO: 1. In some embodiments, the polypeptide further comprises an extension peptide positioned between the N-terminal methionine residue and the first residue of SEQ ID NO: 1. In some embodiments, the extension peptide comprises one or more amino acid residues of SEQ ID NO: 3. In some embodiments, the extension peptide comprises any one of the sequences set forth in SEQ ID NOS. 4-8. In some embodiments, the modified FGF-1 polypeptide is the mature form of the polypeptide. In some embodiments, the modified FGF-1 polypeptide comprises a sequence selected from SEQ ID NOS: 14-18.

One embodiment provides a recombinant modified FGF-1 polypeptide comprising the sequence set forth as SEQ ID NO: 1 with one or more mutations, wherein the polypeptide further comprises an extension peptide positioned upstream to the first residue of SEQ ID NO: 1. In some embodiments, the extension peptide comprises one or more amino acids of SEQ ID NO: 3. In some embodiments, the extension peptide comprises any one of the sequences as set forth in SEQ ID NOS. 4-8. In some embodiments, the modified FGF-1 polypeptide is the mature form of the polypeptide. In some embodiments, the modified FGF-1 polypeptide comprises a sequence selected from SEQ ID NOS: 24-28.

One embodiment provides a recombinant modified FGF-1 polypeptide comprising the sequence set forth as SEQ ID NO: 1 with one or more mutations, wherein the polypeptide further comprises a truncation of one or more of the first five residues of SEQ ID NO: 1, and wherein the polypeptide comprises an extension peptide at the N-terminus of the polypeptide. In some embodiments, the modified FGF-1 polypeptide comprises a sequence selected from SEQ ID NOS: 93-117. In some embodiments, the polypeptide further comprises a methionine residue N-terminal to the extension peptide. In some embodiments, the modified FGF-1 polypeptide is the mature form of the polypeptide. In some embodiments, the modified FGF-1 polypeptide comprises a sequence selected from SEQ ID NOS: 118-141 and 207. In some embodiments, the modified FGF-1 polypeptide is expressed in a form that comprises 136 amino acids. In some embodiments, the modified FGF-1 polypeptide comprises at least 141 amino acids in its mature form.

One embodiment provides a recombinant modified FGF-1 polypeptide comprising a mutation at position 67 of SEQ ID NO: 1. In some embodiments, the polypeptide further comprises a truncation of one or more of the first five residues of SEQ ID NO: 1. In some embodiments, the modified FGF-1 polypeptide comprises a sequence selected from SEQ ID NOS: 146-149. In some embodiments, the polypeptide further comprises an extension peptide. In some embodiments, the extension peptide comprises one or more amino acid residues of SEQ ID NO: 3. In some embodiments, the extension peptide fragment comprises any one of the sequences set forth in SEQ ID NOS. 4-8. In some embodiments, the modified FGF-1 polypeptide is the mature form of the polypeptide. In some embodiments, the modified FGF-1 polypeptide comprises a sequence selected from SEQ ID NOS: 174-204.

One embodiment provides a recombinant modified FGF-1 polypeptide comprising a sequence as set forth in SEQ ID NO. 2. In some embodiments, the modified FGF-1 polypeptide is the mature form of the polypeptide. In some embodiments, the modified FGF-1 polypeptide comprises one or more mutations selected from the group consisting of: Cys16Ser, Ala66Cys, and Cys117Val.

One embodiment provides a recombinant modified FGF-1 polypeptide, wherein the modified FGF-1 comprises one or more mutations of SEQ ID NO: 1, said mutation is selected from the group consisting of: Lys12Val, Cys16Ser, Ala66Cys, Cys117Val, and Pro134Val, and wherein the modified FGF-1 polypeptide further comprises at least one residue of the peptide ALTEK.

One embodiment provides a recombinant modified FGF-1 polypeptide, comprising the following mutations of SEQ ID NO: 1: Cys16Ser, Ala66Cys, and Cys117Val, wherein the modified FGF-1 polypeptide comprises a methionine residue positioned upstream to the first residue of SEQ ID NO: 1, and at least one residue of the peptide ALTEK located between the N-terminal methionine and position 1 of SEQ ID NO: 1. In some embodiments, the modified FGF-1 polypeptide is not expressed with an extension peptide and is produced by a method that does not involve a step of removing an extension peptide.

In one embodiment is provided a pharmaceutical composition comprising the recombinant polypeptide of any one of the embodiments described above. In some embodiments, the pharmaceutical composition further comprises a pharmaceutically acceptable carrier, excipient, or diluent. In some embodiments, the pharmaceutical composition is a liquid ophthalmic formulation. In some embodiments, the pharmaceutical formulation is administered topically, microneedle into the cornea, or intracamerally.

Provided herein in one embodiment is a method for producing a recombinant modified FGF-1 polypeptide, the method comprising: expressing the modified FGF-1 polypeptide in a host cell and maturing the expressed polypeptide in the cytoplasm of the host cell, wherein the modified FGF-1 polypeptide comprises one or more mutations of SEQ ID NO: 1, and is expressed with an N-terminal methionine residue positioned upstream to the first residue of SEQ ID NO: 1.

Provided herein in one embodiment is a method for producing a recombinant modified FGF-1 polypeptide, the method comprising: expressing the modified FGF-1 polypeptide in a host cell and maturing the expressed polypeptide in the cytoplasm of the host cell, wherein the modified FGF-1 polypeptide comprises one or more mutations of SEQ ID NO: 1, an extension peptide between the N-terminal residue and position 1 of SEQ ID NO: 1, and is expressed with an N-terminal methionine residue.

Provided herein in one embodiment is a method for producing a recombinant modified FGF-1 polypeptide, the method comprising: expressing the modified FGF-1 polypeptide in a host cell and maturing the expressed polypeptide in the cytoplasm of the host cell, wherein the modified FGF-1 polypeptide comprises one or more mutations of SEQ ID NO: 1, an extension peptide fragment, a truncation of one or more of the first five residues of SEQ ID NO:1, and wherein the polypeptide is expressed with an N-terminal methionine residue positioned upstream to the first residue of SEQ ID NO: 1. In some embodiments, the N-terminal methionine residue is retained during maturation of the polypeptide. In some embodiments, the N-terminal methionine residue is cleaved off of the polypeptide, by a cleavage enzyme, during maturation of the polypeptide. In some embodiments, the cleavage enzyme is methionine aminopeptidase (metAP). In some embodiments, the metAP is bacterial metAP, yeast metAP, or human metAP. In some embodiments, the cleavage enzyme is bacterial metAP. In some embodiments, the method comprises expressing a modified FGF-1 polypeptide comprising a sequence as set forth in SEQ ID NO: 14 or SEQ ID NO: 16. In some embodiments, the method comprises expressing a modified FGF-1 polypeptide comprising a sequence as set forth in SEQ ID NO: 2. In some embodiments, SEQ ID NO: 2 is the sequence of the polypeptide after maturation in the cytoplasm of the host cell.

One embodiment provides a method for producing a recombinant modified FGF-1 polypeptide, the method comprising: expressing the modified FGF-1 polypeptide in a host cell and maturing the expressed polypeptide in the cytoplasm of the host cell, wherein the modified FGF-1 polypeptide comprises a mutation at position 67 of SEQ ID NO: 1. In some embodiments, the modified FGF-1 polypeptide further comprises an extension peptide fragment, and a truncation of one or more of the first five residues of SEQ ID NO:1, and wherein the polypeptide is expressed with an N-terminal methionine residue positioned upstream to the first residue of SEQ ID NO: 1. In some embodiments, the method comprises cleavage of the N-terminal methionine residue using cyanogen bromide.

One embodiment provides a method for producing a recombinant modified FGF-1 polypeptide according to any one of the above described embodiments, the method comprising: expressing the modified FGF-1 polypeptide in a host cell, binding the expressed polypeptide to an affinity material via an affinity tag; cleaving the affinity tag to release the polypeptide, and eluting the polypeptide from the affinity material using an agent. In some embodiments, the affinity tag comprises poly-histidine, poly-lysine, poly-aspartic acid, or poly-glutamic acid. In some embodiments, the agent comprises methanol, 2-propanol, or another alcohol, dimethyl sulfoxide (DMSO), dimethylformamide (DMF), acetone, or another organic solvent. In some embodiments, the affinity material is a resin framework. In some embodiments, the affinity material is an ion exchange resin. In some embodiments, the polypeptide is expressed in the cytoplasm of the host cell and is not secreted into the periplasmic space. In some embodiments, the host cell is microbial. In some embodiments, the microbial expression system is selected from the group consisting of an *E. coli* expression system, a *Caulobacter* crescent expression system, and a *Proteus mirabilis* expression system. In some embodiments, the microbial expression system is an *E. coli* expression system.

One embodiment provides a method of treating or preventing an ocular disease, disorder or condition in a mammal comprising administering to the mammal a modified FGF-1 according to this disclosure or a pharmaceutical composition according to this disclosure. In some embodiments, the ocular disease, disorder or condition is a disease, disorder, or condition of the cornea or ocular surface. In some embodiments, the ocular disease, disorder or condition is a disease, disorder, or condition of the corneal endothelium. In some embodiments, the disease, disorder, or condition of the corneal endothelium is Fuch's dystrophy, bullous keratopathy, congenital hereditary endothelial dystrophy 1, congenital hereditary endothelial dystrophy 2, posterior polymorphous corneal dystrophy, or a dry eye syndrome. In some embodiments, the ocular disease, disorder or condition is Fuch's dystrophy. In some embodiments, the ocular disease, disorder or condition is a disease, disorder, or condition of the corneal epithelium. In some embodiments, the disease, disorder, or condition of the corneal epithelium is a dry eye syndrome or corneal epithelial damage from corneal surgery or transplantation. In some embodiments, the corneal surgery is photorefractive keratotomy (PRK) or laser-assisted in situ keratomileusis (LASIK). In some embodiments, the ocular disease, disorder or condition is a disease, disorder, or condition of the corneal stroma. In some embodiments, the disease, disorder, or condition of the corneal stroma is keratoconus, lattice corneal dystrophy, granular corneal dystrophy, macular corneal dystrophy, Schnyder crystalline corneal dystrophy, congenital stromal corneal dystrophy, or fleck corneal dystrophy.

One embodiment provides a method of transplanting corneal cells to a mammal or enhancing the success of cell transplantation comprising treating the corneal cells to be transplanted with a modified FGF-1 according to any one of the above described embodiments, prior to, during or after transplanting the corneal cells to the mammal. One embodiment provides a method of preventing scarring during tissue regeneration comprising administering a modified FGF-1 according to any one of the above described embodiments. In some embodiments, the modified FGF-1 is administered to a mammal after undergoing a trabeculectomy.

One embodiment provides a method of treating or preventing a chemical or vesicant induced injury in a patient, the method comprising administering to the patient a modified FGF-1 polypeptide according to any one of the above described embodiments. In some embodiments, the chemical or vesicant induced injury is an ocular injury or a skin injury. In some embodiments, the ocular injury is a corneal injury.

One embodiment provides a method of treatment of corneal injury in a patient, the method comprising administering a modified FGF-1 polypeptide according to this disclosure or a pharmaceutical composition according to this disclosure, wherein the corneal injury is induced by a chemical or a vesicant, and wherein the administering the modified FGF-1 promotes regeneration of cornea, prevents degeneration of the cornea, and prevents long term sequelae to the chemical injury. In some embodiments, the modified FGF-1 is administered over a period of about 7 days to about 40 years to prevent degeneration of corneal tissue. In some embodiments, the corneal tissue comprises corneal epithelium, stroma, corneal endothelium, or corneal innervation. In some embodiments, the corneal injury is a stromal injury. In some embodiments, the stromal injury comprises stromal scarring and corneal opacity.

One embodiment provides a method of preventing long-term corneal injury in a patient, the method comprising administering a modified FGF-1 polypeptide according to this disclosure or a pharmaceutical composition according to this disclosure, wherein the corneal injury is caused by a chemical or a vesicant agent. In some embodiments, the corneal injury is corneal endothelial injury. In some embodiments, administering the modified FGF-1 polypeptide enhances the function of corneal endothelial cells and prevents or reduces long term degeneration of the cornea. In some embodiments, administering the modified FGF-1 polypeptide prevents corneal edema and secondary anterior keratopathies. In some embodiments, administering the modified FGF-1 polypeptide prevents loss of corneal endothelial cells. In some embodiments, the corneal injury is a stromal injury. In some embodiments, the stromal injury comprises stromal scarring and corneal opacity. In some embodiments, the corneal injury is mustard gas keratopathy (MGK). In some embodiments, administering the modified FGF-1 polypeptide results in amelioration of histopathological conditions associated with MGK. In some embodiments, the histopathological conditions include hyperplasia of corneal epithelial layer and epithelial-stromal cell separation. In some embodiments, administering the modified FGF-1 polypeptide results in reduction in edema and elimination of corneal erosions. In some embodiments, the corneal erosion is characterized by de-epithelialization of the cornea. In some embodiments, administering the modified FGF-1 polypeptide reduces the severity of corneal de-epithelialization. In some embodiments, administering the modified FGF-1 polypeptide results in faster re-epithelialization of the cornea.

One embodiment provides a method of regenerating ocular surface epithelium in a patient exposed to a chemical or a vesicant, the method comprising ocular administration of a modified FGF-1 polypeptide according to any one of the above described embodiments. In some embodiments, the ocular surface epithelium is corneal epithelium.

One embodiment provides a method of preventing ocular epithelial injury in a patient exposed to a chemical or a vesicant, the method comprising ocular administration of a modified FGF-1 polypeptide according to any one of the above described embodiments. In some embodiments, the ocular injury is corneal injury caused by exposure to a vesicant. In some embodiments, the corneal injury is corneal epithelial detachment. In some embodiments, administering the modified FGF-1 polypeptide results in reduction in the severity of corneal epithelial detachment following exposure to the vesicant. In some embodiments, administering the modified FGF-1 polypeptide results in reduction in edema and elimination of corneal erosions. In some embodiments, the corneal erosion is characterized by de-epithelialization of the cornea. In some embodiments, administering the modified FGF-1 polypeptide reduces the severity of corneal de-epithelialization. In some embodiments, administering the modified FGF-1 polypeptide results in faster re-epithelialization of the cornea. In some embodiments, the modified FGF-1 polypeptide is administered over a period of up to two weeks or until complete regeneration of the corneal epithelium. In some embodiments, a first dose of the modified FGF-1 polypeptide is administered within 48 hours after exposure to the vesicant. In some embodiments, administering the chemical comprises chlorine gas, phosgene, an alkali, or an acid. In some embodiments, the vesicant comprises sulfur mustard (SM), nitrogen mustard (NM), lewisite, or half mustard (2-chloroethyl ethyl sulfide (CEES)). In some embodiments, the vesicant is NM. In some embodiments, administering the modified FGF-1 polypeptide suppresses NM induced up-regulation of ADAM17. In some embodiments, the chemical or vesicant induced injury is chemical burn. In some embodiments, administering the chemical burn is caused by chlorine gas, phosgene, an alkali, or an acid. In some embodiments, administering the modified FGF-1 polypeptide comprises mutations of positions 16, 66, and 117 of SEQ ID NO: 1. In some embodiments, the mutations are Cys16Ser, Ala66Cys, and Cys117Val. In some embodiments, the modified FGF-1 polypeptide is less susceptible to oxidation upon exposure to a vesicant. In some embodiments, the vesicant is NM.

One embodiment provides a method of treating herpetic keratopathy comprising administering to a mammal modified a FGF-1 polypeptide according to any embodiments of this disclosure or a pharmaceutical composition according to this disclosure. In some embodiments, the herpetic keratopathy is caused by a primary infection by herpes simplex virus. In some embodiments, the herpetic keratopathy is a chronic herpetic keratopathy. In some embodiments, the herpetic keratopathy is secondary to an infection by herpes simplex virus. In some embodiments, the herpetic keratopathy that is secondary to an infection by herpes simplex virus comprises neurotrophic keratopathy. In some embodiments, the modified FGF-1 polypeptide according to this disclosure or the pharmaceutical composition according to this disclosure is administered twice daily. In some embodiments, the modified FGF-1 polypeptide according to this disclosure or the pharmaceutical composition according to this disclosure is administered for a duration of 30 days. In some embodiments, administration of the modified FGF-1 polypeptide according to any this disclosure or the pharmaceutical composition according to this disclosure results in healing of corneal ulcer, reduction of duration of pain and inflammation, reduction in pain and inflammation, reduction in corneal opacity, haze, scarring, or any combinations thereof. In some embodiments, the corneal ulcer comprises a herpetic corneal ulcer. In some embodiments, the mammal is a human.

One embodiment provides a method of treating or preventing chemical or vesicant induced injury in a patient, the method comprising administering to the patient a modified FGF-1 comprising one or more mutations of at positions 12, 16, 66, 117, and 134 of SEQ ID NO: 1. In some embodiments, the chemical or vesicant induced injury is an ocular injury or a skin injury. In some embodiments, the ocular injury is a corneal injury.

One embodiment provides a method of treatment of corneal injury in a patient, the method comprising administering to the patient a modified FGF-1 polypeptide comprising one or more mutations at positions 12, 16, 66, 117, and 134 of SEQ ID NO: 1, wherein the corneal injury is induced by a chemical or a vesicant, and wherein the administering the modified FGF-1 promotes regeneration of cornea, prevents degeneration of the cornea, and prevents long term sequelae to the chemical injury. In some embodiments, the modified FGF-1 is administered over a period of about 7 days to about 40 years to prevent degeneration of corneal tissue. In some embodiments, the corneal tissue comprises corneal epithelium, stroma, corneal endothelium, or corneal innervation. In some embodiments, the corneal injury is a stromal injury. In some embodiments, the stromal injury comprises stromal scarring and corneal opacity.

One embodiment provides a method of preventing long-term corneal injury in a patient, the method comprising administering to the patient a modified FGF-1 polypeptide comprising one or more mutations at positions 12, 16, 66, 117, and 134 of SEQ ID NO: 1, wherein the corneal injury is caused by a chemical or a vesicant agent. In some embodiments, the corneal injury is a corneal endothelial injury. In some embodiments, administering the modified FGF-1 polypeptide enhances the function of the corneal endothelial cells and prevents or reduces long term degeneration of the cornea. In some embodiments, administering the modified FGF-1 polypeptide prevents corneal edema and secondary anterior keratopathies. In some embodiments, administering the modified FGF-1 polypeptide prevents loss of corneal endothelial cells. In some embodiments, the corneal injury is a stromal injury. In some embodiments, the stromal injury comprises stromal scarring and corneal opacity. In some embodiments, the corneal injury is mustard gas keratopathy (MGK). In some embodiments, administration of the modified FGF-1 polypeptide results in amelioration of histopathological conditions associated with MGK. In some embodiments, histopathological conditions include hyperplasia of corneal epithelial layer and epithelial-stromal cell separation. In some embodiments, administration of the modified FGF-1 polypeptide results in reduction in edema and elimination of corneal erosions. In some embodiments, the corneal erosion is characterized by de-epithelialization of the cornea. In some embodiments, administration of the modified FGF-1 polypeptide reduces the severity of corneal de-epithelialization. In some embodiments, administration of the modified FGF-1 polypeptide results in faster re-epithelialization of the cornea.

One embodiment provides a method of regenerating ocular surface epithelium in a patient exposed to a chemical or a vesicant, the method comprising ocular administration of a modified FGF-1 polypeptide comprising one or more mutations at positions 12, 16, 66, 117, and 134 of SEQ ID NO: 1. In some embodiments, the ocular surface epithelium is corneal epithelium.

One embodiment provides a method of preventing ocular epithelial injury in a patient exposed to a chemical or a vesicant, the method comprising ocular administration of a modified FGF-1 polypeptide comprising one or more mutations at positions 12, 16, 66, 117, and 134 of SEQ ID NO: 1. In some embodiments, the ocular injury is corneal injury caused by exposure to a vesicant. In some embodiments, the corneal injury is corneal epithelial detachment. In some embodiments, administration of the modified FGF-1 polypeptide results in reduction in the severity of corneal epithelial detachment following exposure to the vesicant. In some embodiments, administration of the modified FGF-1 polypeptide results in reduction in edema and elimination of corneal erosions. In some embodiments, the corneal erosion is characterized by de-epithelialization of the cornea. In some embodiments, administration of the modified FGF-1 polypeptide reduces the severity of corneal de-epithelialization. In some embodiments, administration of the modified FGF-1 polypeptide results in faster re-epithelialization of the cornea. In some embodiments, the modified FGF-1 polypeptide is administered over a period of up to two weeks or until complete regeneration of the corneal epithelium. In some embodiments, a first dose of the modified FGF-1 polypeptide is administered within 48 hours after exposure to the vesicant. In some embodiments, the chemical comprises chlorine gas, phosgene, an alkali, or an acid. In some embodiments, the vesicant comprises sulfur mustard (SM), nitrogen mustard (NM), lewisite, or half mustard (2-chloroethyl ethyl sulfide (CEES)). In some embodiments, wherein the vesicant is NM. In some embodiments, administration of the modified FGF-1 polypeptide suppresses NM induced up-regulation of ADAM17. In some embodiments, the chemical or vesicant induced injury is chemical burn. In some embodiments, the chemical burn is caused by chlorine gas, phosgene, an alkali, or an acid. In some embodiments, the modified FGF-1 polypeptide comprises mutations of positions 16, 66, and 117 of SEQ ID NO: 1. In some embodiments, the mutations are Cys16Ser, Ala66Cys, and Cys117Val. In some embodiments, the modified FGF-1 polypeptide is less susceptible to oxidation upon exposure to a vesicant. In some embodiments, the vesicant is NM. In some embodiments, the modified FGF-1 polypeptide comprises a sequence as set forth in any one of SEQ ID NOs: 2, and 9-207. In some embodiments, the modified FGF-1 polypeptide comprises a sequence as set forth in any one of SEQ ID NOs: 2, 9-204, and 207. In some embodiments, the modified FGF-1 polypeptide comprises a sequence as set forth in any one of SEQ ID NOs: 205 and 206. In some embodiments, the modified FGF-1 polypeptide comprises a sequence as set forth in SEQ ID NO: 2. In some embodiments, the modified FGF-1 polypeptide comprises a sequence as set forth in SEQ ID NO: 205. In some embodiments, the modified FGF-1 polypeptide comprises a sequence as set forth in SEQ ID NO: 206.

One embodiment provides a method of treating herpetic keratopathy comprising administering to a mammal a modified FGF-1 polypeptide comprising a sequence as set forth in any one of SEQ ID NOs: 205 and 206, or a pharmaceutical composition comprising the same. In some embodiments, the herpetic keratopathy is caused by a primary infection by herpes simplex virus. In some embodiments, the herpetic keratopathy is a chronic herpetic keratopathy. In some embodiments, the herpetic keratopathy is secondary to an infection by herpes simplex virus. In some embodiments, the herpetic keratopathy that is secondary to an infection by herpes simplex virus comprises neurotrophic keratopathy. In some embodiments, the modified FGF-1 polypeptide comprising a sequence as set forth in any one of SEQ ID Nos: 205 and 206, or a pharmaceutical composition comprising the same, is administered twice daily. In some embodiments, the modified FGF-1 polypeptide comprising a sequence as set forth in any one of SEQ ID Nos: 205 and 206, or a pharmaceutical composition comprising the same, is administered for a duration of 30 days. In some embodiments, administration of the modified FGF-1 polypeptide comprising a sequence as set forth in any one of SEQ ID Nos: 205 and 206, or a pharmaceutical composition comprising the same, results in healing of corneal ulcer, reduction of duration of pain and inflammation, reduction in pain and inflammation, reduction in corneal opacity, haze, scarring, or any combinations thereof. In some embodiments, the corneal ulcer comprises a herpetic corneal ulcer.

One embodiment provides a method of treating herpetic keratopathy comprising administering to a mammal a modified FGF-1 polypeptide comprising a sequence as set forth in any one of SEQ ID NOs: 2, 9-204, and 207, or a pharmaceutical composition comprising the same. In some embodiments, the herpetic keratopathy is caused by a primary infection by herpes simplex virus. In some embodiments, the herpetic keratopathy is a chronic herpetic keratopathy. In some embodiments, the herpetic keratopathy is secondary to an infection by herpes simplex virus. In some embodiments, the herpetic keratopathy that is secondary to an infection by herpes simplex virus comprises neurotrophic keratopathy. In some embodiments, the modified FGF-1 polypeptide comprising a sequence as set forth in any one of SEQ ID Nos: 2, 9-204 and 207, or a pharmaceutical composition comprising the same, is administered twice daily. In some embodiments, the modified FGF-1 polypeptide comprising a sequence as set forth in any one of SEQ ID Nos: 2, 9-204, and 207, or a pharmaceutical composition comprising the same, is administered for a duration of 30 days. In some embodiments, administration of the modified FGF-1 polypeptide comprising a sequence as set forth in any one of SEQ ID Nos: 2, 9-204 and 207, or a pharmaceutical composition comprising the same, results in healing of corneal ulcer, reduction of duration of pain and inflammation, reduction in pain and inflammation, reduction in corneal opacity, haze, scarring, or any combinations thereof. In some embodiments, the corneal ulcer comprises a herpetic corneal ulcer. In some embodiments, the mammal is a human.

INCORPORATION BY REFERENCE

All publications and patent applications mentioned in this specification are herein incorporated by reference in their entireties to the same extent as if each individual publication or patent application was specifically and individually indicated to be incorporated by reference.

BRIEF DESCRIPTION OF DRAWINGS

FIG. 6 shows an exemplary histopathological grading scheme for assessing the effects of vesicant induced corneal injury.

FIG. 10 illustrates the suppression of ADAM17 activation in corneal cells treated with an exemplary modified FGF-1 polypeptide (TTHX1114) after exposure to a vesicant.

DETAILED DESCRIPTION

Figure 1:
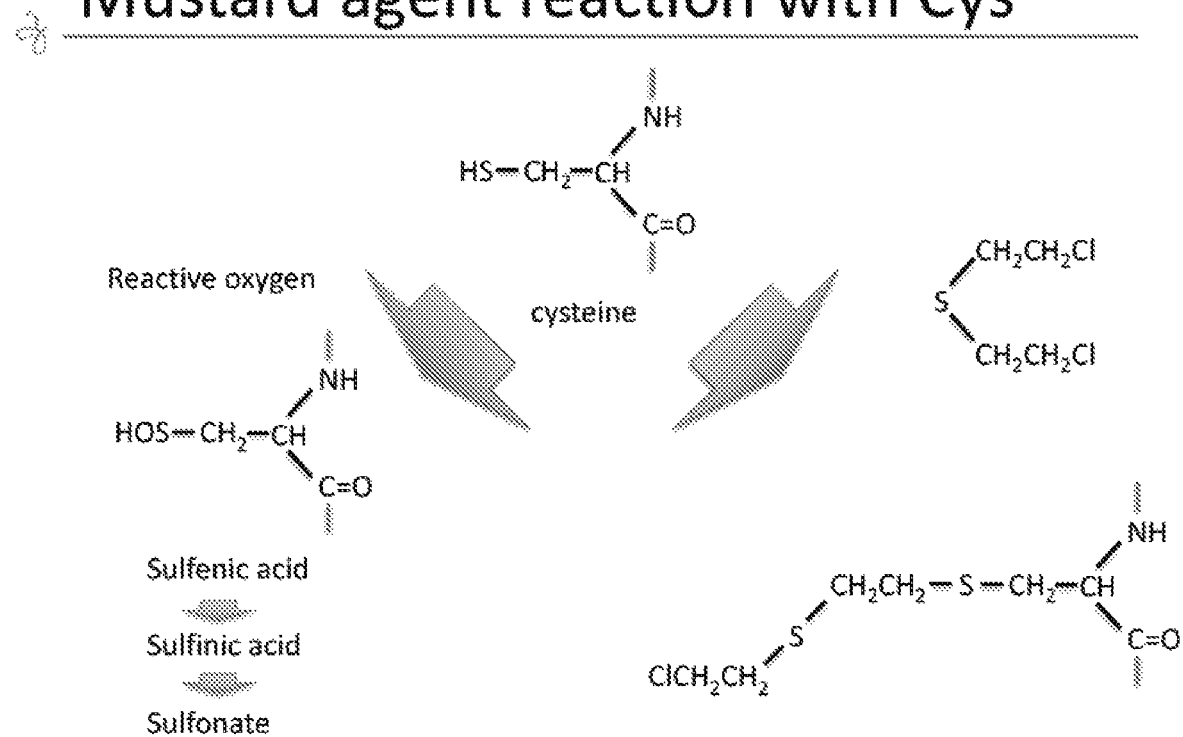
FIG. 1 illustrates the reaction of mustard gas with cysteine.

Diseases of and injuries to the eyes can be severely debilitating, and occur in a wide variety of forms. One class of ocular disease is mustard gas keratopathy. Mustard gas is a vesicant poisonous gas that was first released by the German Army on a battlefield at Ypres in April 1915 during World War I. Exposure to mustard gas can lead to long-term complications, which develop over the years. The cornea becomes scarred and irregular, and cholesterol and calcium are deposited in its tissues, resulting in progressive impairment of vision. Slit-lamp examination reveals that the episcleral tissues display a characteristic underglaze. White porcelain appearance and unusual vascular anomalies are common. These appear as enlarged, distorted vessels, sometimes with an ampulliform outline accompanied by varicosities and sausage-like vessels. With the passage of time, dense opacification of the cornea results, being most evident in the central and lower sections, as the upper portion has been protected by the overhanging eyelid. Predominant histopathological features of MGK include, for example, irregular epithelial thickness, degenerative changes, thickened epithelial basement membrane, keratocytes loss, and destroyed Bowman layer. (Kanavi et al., *Chronic and delayed mustard gas keratopathy: a histopathologic and immunohistochemical study*, Eur. J Ophthalmol. 2010 September-October; 20(5):839-43). Typically, within one day of corneal vesicant exposure, the corneal epithelium (CE) sloughs from the basement membrane (BM), corneal edema develops in the denuded stroma and full-thickness keratocytosis is apparent within the wound margins. By five days, an epithelial cap is regenerated and corneal edema begins to subside. One week after exposure, the CE is partially stratified, with rudimentary hemidesmosomal attachments. Despite this apparent improvement, corneas develop clinical signatures of chronic injury as soon as three weeks after exposure, including persistently elevated corneal edema, recurring corneal erosions and neovascularization. By eight weeks, the basement membrane zone undergoes severe degeneration. Further, MGK affected corneas appear to exhibit delayed wound healing process.

Provided herein are modified FGF-1 polypeptides, pharmaceutical compositions and medicaments that include such modified peptides, and methods of using such modified FGF-1 polypeptides to treat various conditions, such as ocular disease, disorders and conditions (e.g., Fuch's dystrophy), vesicant agent induced corneal epithelial and endothelial injuries (e.g., Mustard Gas Keratopathy (MGK)), wound healing, cardiovascular diseases (e.g., ischemia), and neurological conditions (e.g., amylotrophic lateral sclerosis (ALS)).

Also provided herein is a method of treating a chemical or vesicant induced injury by administering a modified fibroblast growth factors (FGF-1) polypeptides, or pharmaceutical composition or medicaments that include such modified peptides. In some embodiments, the method comprises treating mustard gas keratopathy (MGK), induced by a chemical injury, e.g., a chemical burn, by administering modified FGF-1 polypeptides described herein. In some embodiments, the method comprises treating mustard gas keratopathy (MGK), induced by a vesicant, e.g., nitrogen mustard (NM), by administering modified FGF-1 polypeptides described herein. In some embodiments, the method comprises treating a chemical or thermal injury caused by a chemical warfare agent, e.g., phosgene.

In some embodiments described herein, where the modified FGF-1 polypeptide is expressed with an N-terminal methionine (N-Met) residue, the polypeptide is subsequently purified without a step requiring proteolytic cleavage for removal of an N-terminal peptide. Accordingly, in some embodiments, the present disclosure provides a modified FGF-1 polypeptide that is prepared by a rapid purification method, without involving a proteolytic cleavage step for removal of an N-terminal peptide. This is particularly advantageous for production of the modified FGF-1 polypeptides per good manufacturing practice (GMP) guidelines. The advantages include the lack of a cleavage step, including eliminating the need for subsequent purification of the cleaved product and removal of the reagents used for cleavage. The further advantage of this is an increase in yield due to decreased handling and the alleviation of the need to test for residual cleavage reagents and contaminants introduced for the cleavage and subsequent separation of cleaved from uncleaved material.

The modified FGF-1 polypeptides described herein, can have increased stability (e.g. thermostability), reduced number of buried free thiols, and/or increased effective heparan sulfate proteoglycan (HSPG) affinity.

Several other advantages are associated with the use of the modified FGF-1 polypeptides in the methods described herein. For example, the modified FGF-1 polypeptides described herein can be administered without heparin in its pharmaceutical composition or formulation (e.g., an ophthalmic formulation), avoiding potential safety issues related to its biologic origin. In addition, avoidance of heparin allows the use of higher doses of the modified FGF-1 polypeptides without complications resulting from local heparin-induced adverse events or preexisting anti-heparin antibodies. Furthermore, in the absence of heparin, immediate binding of the modified FGF to tissue is maximized and systemic distribution is significantly reduced. The modified FGF-1 polypeptides described herein are also advantage of having enhanced local sequestration and reduced redistribution kinetics, thus increasing the elimination half-life and mean residence time (MRT) at the site of delivery, and allowing for a reduced dosing frequency. This can be the result of modified FGF-1 polypeptides described herein that have increased stability (e.g. thermostability), reduced number of buried free thiols, and/or increased effective heparan sulfate proteoglycan (HSPG) affinity.

The FGF-1 polypeptides of the present disclosure comprise, in various embodiments, modifications at the N-terminus of the polypeptide, such as an addition, a truncation, or a combination of additions and truncations. In some embodiments, the modification is the addition of a single N-terminal methionine residue. In some embodiments, the modification is the addition of an extension peptide. In some embodiments, the modification is a truncation of one or more of the first five residues of a FGF-1 polypeptide. In some embodiments, the FGF-1 polypeptides comprise a sequence as set forth in SEQ ID NO: 1, with one or more mutations, in addition to the N-terminal modification.

Several examples of the modified FGF-1 polypeptides disclosed herein comprise an N-terminal methionine (N-Met) residue in a mature form of the polypeptide. The retention of biological activity when amino acids are added to the N-terminus of a protein is unpredictable. Some proteins are tolerant of this and some are not, and the retention of biological activity and the potential for changes in stability are only determined empirically. The present disclosure identifies that the addition of N-terminal Met residues are tolerated with retention of biological activity and stability.

Certain Terminology

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

The section headings used herein are for organizational purposes only and are not to be construed as limiting the subject matter described. Unless defined otherwise, all technical and scientific terms used herein have the same meaning as is commonly understood to which the claimed subject matter belongs. In the event that there is a plurality of definitions for terms herein, those in this section prevail. All patents, patent applications, publications and published nucleotide and amino acid sequences (e.g., sequences available in GenBank or other databases) referred to herein are incorporated by reference. Where reference is made to a URL or other such identifier or address, it is understood that such identifiers can change and particular information on the internet can come and go, but equivalent information can be found by searching the internet. Reference thereto evidences the availability and public dissemination of such information.

As used herein, the term "Percent (%) amino acid sequence identity" with respect to a sequence is defined as the percentage of amino acid residues in a candidate sequence that are identical with the amino acid residues in the specific sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer softwares such as EMBOSS MATCHER, EMBOSS WATER, EMBOSS STRETCHER, EMBOSS NEEDLE, EMBOSS LALIGN, BLAST, BLAST-2, ALIGN or Megalign (DNASTAR) software. Those skilled in the art can determine appropriate parameters for measuring alignment, including any algorithms needed to achieve maximal alignment over the full length of the sequences being compared.

Definition of standard chemistry terms may be found in reference works, including but not limited to, Carey and Sundberg "ADVANCED ORGANIC CHEMISTRY $4^{TH}$ ED." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology.

Unless specific definitions are provided, the nomenclature employed in connection with, and the laboratory procedures and techniques of, analytical chemistry, synthetic organic chemistry, and medicinal and pharmaceutical chemistry described herein are those recognized in the field. Standard techniques can be used for chemical syntheses, chemical analyses, pharmaceutical preparation, formulation, and delivery, and treatment of patients. Standard techniques can be used for recombinant DNA, oligonucleotide synthesis, and tissue culture and transformation (e.g., electroporation, lipofection). Reactions and purification techniques can be performed e.g., using kits of manufacturer's specifications or as commonly accomplished in the art or as described herein. The foregoing techniques and procedures can be generally performed of conventional methods and as described in various general and more specific references that are cited and discussed throughout the present specification.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods, compounds, compositions described herein.

The terms "treat," "treating" or "treatment" include alleviating, abating or ameliorating a disease, disorder or condition symptoms, preventing additional symptoms, ameliorating or preventing the underlying metabolic causes of symptoms, inhibiting the disease, disorder, or condition, e.g., arresting the development of the disease, disorder or condition, relieving the disease, disorder or condition, causing regression of the disease, disorder or condition, relieving a condition caused by the disease, disorder or condition, or stopping the symptoms of the disease, disorder or condition. The terms "treat," "treating" or "treatment", include, but are not limited to, prophylactic and/or therapeutic treatments.

The term "acceptable" or "pharmaceutically acceptable", with respect to a formulation, composition or ingredient, refers to having no persistent detrimental effect on the general health of the subject being treated or does not abrogate the biological activity or properties of the modified FGF described herein, and is relatively nontoxic.

The term "amelioration" of the symptoms of a particular disease, disorder or condition by administration of a particular modified FGF or pharmaceutical composition refers to any lessening of severity, delay in onset, slowing of progression, or shortening of duration, whether permanent or temporary, lasting or transient that can be attributed to or associated with administration of the modified FGF or pharmaceutical composition.

The term "combination" or "pharmaceutical combination" as used herein, means a product that results from the mixing or combining of more than one active ingredient and includes both fixed and non-fixed combinations of the active ingredients. The term "fixed combination" means that one active ingredient (e.g., a modified FGF) and a co-agent are both administered to a patient simultaneously in the form of a single entity or dosage. The term "non-fixed combination" means that one active ingredient (e.g., a modified FGF) and a co-agent are administered to a patient as separate entities either simultaneously, concurrently or sequentially with no specific intervening time limits, wherein such administration provides effective levels of the two agents in the body of the patient. The latter also applies to cocktail therapy, e.g., the administration of three or more active ingredients.

The term "pharmaceutical composition" as used herein refers to one or more modified FGF-1 polypeptides with one or more other chemical components, such as carriers, stabilizers, diluents, dispersing agents, suspending agents, thickening agents, and/or excipients. The pharmaceutical composition facilitates administration of the modified FGF-1 polypeptides to an organism. Multiple techniques of administering a modified FGF-1 polypeptide exist in the art including, but not limited to: topical, ophthalmic, intraocular, periocular, intravenous, oral, aerosol, parenteral, and administration.

The term "carrier," as used herein, refers to relatively nontoxic chemical compounds or agents that facilitate the incorporation of an agent of interest (e.g., a modified FGF) into cells or tissues.

The term "diluent" refers to chemical compounds that are used to dilute the agent of interest (e.g., a modified FGF) prior to delivery. Diluents can also be used to stabilize agents because they can provide a more stable environment. Salts dissolved in buffered solutions (which also can provide pH control or maintenance) are utilized as diluents in the art, including, but not limited to a phosphate buffered saline solution.

The terms "co-administration" or the like, are meant to encompass administration of the selected agents (e.g., a modified FGF or composition thereof and a co-agent) to a single patient, and are intended to include treatment regimens in which the agents are administered by the same or different route of administration or at the same or different time.

The terms "effective amount" or "therapeutically effective amount," refer to a sufficient amount of a modified FGF-1 polypeptide, agent, combination or pharmaceutical composition described herein administered which will relieve to some extent one or more of the symptoms of the disease, disorder or condition being treated. The result can be reduction and/or alleviation of the signs, symptoms, or causes of a disease, or any other desired alteration of a biological system. For example, an "effective amount" for therapeutic uses is the amount of the modified FGF, agent, combination or pharmaceutical composition required to provide a desired pharmacologic effect, therapeutic improvement, or clinically significant decrease in disease symptoms without undue adverse side effects. An appropriate "effective amount" in any individual case may be determined using techniques, such as a dose escalation study. The term "therapeutically effective amount" includes, for example, a prophylactically effective amount. It is understood that "an effect amount" can vary from subject to subject due to variation in metabolism of the modified FGF, combination, or pharmaceutical composition, age, weight, general condition of the subject, the condition being treated, the severity of the condition being treated, and the judgment of the prescribing physician. By way of example only, therapeutically effective amounts may be determined by routine experimentation, including but not limited to a dose escalation clinical trial.

The term "prophylactically effective amount," refers that amount of a modified FGF, compound, agent, combination or pharmaceutical composition described herein applied to a patient which will relieve to some extent one or more of the symptoms of a disease, condition or disorder being treated. In such prophylactic applications, such amounts may depend on the patient's state of health, weight, and the like. It is considered well within the skill of the art for one to determine such prophylactically effective amounts by routine experimentation, including, but not limited to, a dose escalation clinical trial.

The term "subject" or "patient" as used herein, refers to an animal, which is the object of treatment, observation or experiment. By way of example only, a subject may be, but is not limited to, a mammal including, but not limited to, a human.

The terms "enhance" or "enhancing" means to increase or prolong either in potency or duration a desired effect. By way of example, "enhancing" the effect of therapeutic agents singly or in combination refers to the ability to increase or prolong, either in potency, duration and/or magnitude, the effect of the agents on the treatment of a disease, disorder or condition. When used in a patient, amounts effective for this use will depend on the severity and course of the disease, disorder or condition, previous therapy, the patient's health status and response to the drugs, and the judgment of the treating physician.

The term "modulate," means to interact with a target (e.g., a FGF receptor) either directly or indirectly so as to alter the activity of the target, including, by way of example only, to enhance the activity of the target, to inhibit or antagonize the activity of the target, to limit the activity of the target, or to extend the activity of the target. In some embodiments, modified FGF-1 polypeptides and pharmaceutical compositions described herein can modulate the activity of one or more respective targets (e.g., one or more FGF receptors). In some embodiments, the modified FGF-1 polypeptides described herein modulate (e.g., increase) the activity of one or more FGF receptors on a cell (e.g., a corneal endothelial cell), resulting, e.g., in cell migration and/or cell proliferation.

As used herein, the term "target" or refers to a biological molecule (e.g., a target protein or protein complex), such as an FGF receptor, or a portion of a biological molecule capable of being bound by a selective binding agent (e.g., a modified FGF) or pharmaceutical composition described herein. As used herein, the term "non-target" refers to a biological molecule or a portion of a biological molecule that is not selectively bound by a selective binding agent or pharmaceutical composition described herein.

The term "target activity" or "cell response" refers to a biological activity capable of being modulated by a modified FGF or any cellular response that results from the binding of a modified FGF to a FGF receptor. Certain exemplary target activities and cell responses include, but are not limited to, binding affinity, signal transduction, gene expression, cell migration, cell proliferation, cell differentiation, and amelioration of one or more symptoms associated with an ocular disease, disorder or condition.

The terms "herpetic keratitis", "herpes simplex keratitis", "HSK", "herpetic keratopathy", "herpes corneae", and "herpetic keratoconjunctivitis" refer to an ocular disease, disorder, or condition that is typically caused by herpes simplex virus (HSV).

Expressed and Mature Forms of the Modified FGF-1 Polypeptides

FGFs stimulate a family seven FGF receptor isoforms, and each FGF stimulates a different pattern of receptors to achieve its specific effect. See, e.g., Ornitz et al. (1996) The Journal of biological chemistry, 1996, 271(25):15292-7; Zhang et al. (2006) The Journal of biological chemistry, 2006, 281(23):15694-700). In some embodiments, modified FGF-1 polypeptide is preferable because it binds to and stimulates all seven FGF receptor isoforms. See Ornitz et al. (1996) The Journal of biological chemistry, 1996, 271(25): 15292-7.

Embodiments disclosed herein relate to a modified FGF-1 polypeptide or a pharmaceutical composition (e.g., an ophthalmic formulation) comprising a modified FGF-1 polypeptide. Embodiments disclosed herein also relate to a method of treating a chemical or a vesicant injury by administering a modified FGF-1 polypeptide or a pharmaceutical composition (e.g., an ophthalmic formulation) comprising a modified FGF-1 polypeptide. A modified FGF-polypeptide, as used herein, refers to a recombinant FGF that includes a substitution or mutation of one or more different amino acid residues and/or one or more deletions of one or more amino acid residues and/or one or more additions of one or more amino acid residues of SEQ ID NO: 1.

Provided herein, in a first embodiment, is a modified FGF-1 polypeptide comprising the sequence set forth as SEQ ID NO: 1, with one or more mutations, wherein the modified polypeptide further comprises a methionine residue upstream to the first residue of SEQ ID NO: 1. In some embodiments, the modified FGF-1 polypeptide comprising the N-terminal methionine (N-Met) residue is a mature form of the polypeptide. In some instances, the modified FGF-1 polypeptide, according to the first embodiment, comprises one or more mutations at positions 12, 16, 66, 117, and 134 of SEQ ID NO: 1. In some embodiments, the modified FGF-1 polypeptide is expressed in a host cell with a methionine residue upstream to the first residue of SEQ ID NO: 1. In some embodiments, the modified FGF-1 polypeptide is not subject to N-terminal processing for removal of the N-Met residue during maturation. Thus, in some embodiments, the mature form of a modified FGF-1 comprises an N-Met residue and one or more mutations at positions 12, 16, 66, 117, and 134 of SEQ ID NO: 1. An exemplary modified FGF-1 sequence, comprising an N-Met residue, is disclosed as SEQ ID NO: 2.

The present disclosure identifies that a modified FGF-1 as described herein, comprising an N-Met residue in its mature form, has similar biological activity as a version without the N-Met residue. N-terminal methionine removal, or excision, is a co-translational process that occurs as soon as a polypeptide emerges from the ribosome. The removal of the N-terminal methionine involves the substrate specificities of a cleavage enzyme, methionine aminopeptidase (metAP), which recognizes a methionine residue which is followed by an amino acid residue with a small side chain, such as alanine, glycine, proline, serine, threonine, or valine. Due to this substrate sequence specificity, the modified FGF-1 of the first embodiment, which comprises an N-Met residue followed by phenylalanine, see position 1 of SEQ ID NO: 1, is not processed by metAP. Thus, by expressing the modified FGF-1 with a methionine residue directly upstream of SEQ ID NO: 1, a mature modified FGF-1, comprising methionine as its N-terminal residue, can be obtained. In some embodiments, the modified FGF-1 according to the first embodiment is not expressed with an N-terminal peptide and therefore is not subject to proteolytic cleavage for removal of the same, during subsequent purification.

Provided herein, in a second embodiment, is a modified FGF-1 polypeptide comprising the sequence set forth as SEQ ID NO: 1, with one or more mutations, wherein the modified polypeptide further comprises a methionine residue upstream to the first residue of SEQ ID NO: 1, and one or more amino acids of the peptide set forth as SEQ ID NO: 3. A peptide comprising one or more residues of SEQ ID NO: 3 is herein referred to as an "extension peptide." Thus, the modified FGF-1 according to the second embodiment comprises the sequence set forth as SEQ ID NO: 1, with one or more mutations, a methionine residue upstream to the first residue of SEQ ID NO: 1, and an extension peptide positioned between the methionine residue and the first residue of SEQ ID NO:1. In some embodiments, the modified FGF-1 polypeptide comprising the N-terminal methionine and an extension peptide, positioned between the methionine residue and the first residue of SEQ ID NO: 1, is a mature form of the polypeptide. In some embodiments, the modified FGF-1 polypeptide comprises one or more mutations at positions 12, 16, 66, 117, and 134 of SEQ ID NO: 1, which polypeptide is expressed in a host cell with a methionine residue upstream to the first residue of SEQ ID NO: 1, and further an extension peptide positioned between the methionine residue and the first residue of SEQ ID NO: 1. In some embodiments, the modified FGF-1 polypeptide according to the second embodiment is expressed with an extension peptide comprising five residues of SEQ ID NO: 3, positioned between the methionine residue and the first residue of SEQ ID NO: 1. In some embodiments, the modified FGF-1 polypeptide according to the second embodiment is expressed with four residues of SEQ ID NO: 3, positioned between the methionine residue and the first residue of SEQ ID NO: 1. In some embodiments, the modified FGF-1 polypeptide according to the second embodiment is expressed with three residues of SEQ ID NO: 3, positioned between the methionine residue and the first residue of SEQ ID NO: 1. In some embodiments, the modified FGF-1 polypeptide according to the second embodiment is expressed with two residues of SEQ ID NO: 3, positioned between the methionine residue and the first residue of SEQ ID NO: 1. In some embodiments, the modified FGF-1 polypeptide according to the second embodiment is expressed with one residue of SEQ ID NO: 3, positioned between the methionine residue and the first residue of SEQ ID NO: 1. Exemplary sequences of the extension peptide include SEQ ID NOS: 4-8.

In some instances, the modified FGF-1 polypeptide of the second embodiment, comprising an extension peptide and an N-terminal methionine residue, is not subject to N-terminal processing for removal of the methionine residue, whereas in some instances the methionine is excised by a cleavage enzyme. Typically, the cleavage enzyme is methionine aminopeptidase (metAP). Thus, in some examples, the mature form of the modified FGF-1 polypeptide according to the second embodiment comprises an N-Met residue followed by an extension peptide as described herein. Exemplary sequences of mature forms of modified FGF-1 polypeptides according to the second embodiment, comprising an N-terminal methionine, and one or more residues of the extension peptide, positioned between the methionine residue and the first residue of SEQ ID NO:1, are set forth as SEQ ID NOS: 9-13, wherein the sequences further comprise one or more mutations at amino acids corresponding to positions 12, 16, 66, 117, and 134 of SEQ ID NO: 1. Additional exemplar sequences of mature modified FGF-1 polypeptides comprising an N-terminal methionine, and an extension peptide are set forth as SEQ ID NOS: 14-18. In some other examples, the mature form of the modified FGF-1 polypeptide according to the second embodiment does not comprise an N-Met residue but includes only an extension peptide. Exemplary sequences of mature forms of modified FGF-1 polypeptides according to the second embodiment, comprising an extension peptide, positioned upstream to the first residue of SEQ ID NO:1 are set forth as SEQ ID NOS: 19-23, wherein the sequences further comprise one or more mutations at amino acids corresponding to positions 12, 16, 66, 117, and 134 of SEQ ID NO: 1. Additional exemplar sequences of mature modified FGF-1 polypeptides comprising one or more residues of the extension peptide are set forth as SEQ ID NOS: 24-28. In some embodiments, the methionine residue is cleaved by metAP when the extension peptide starts with an alanine (as in SEQ ID NO: 4) or with a threonine (as in SEQ ID NO: 5). In those instance, the mature FGF-1 polypeptide does not comprise an N-terminal methionine residue, e.g., SEQ ID NOS: 19, 21, 24, and 26.

Provided herein, in a third embodiment, is a modified FGF-1 polypeptide comprising the sequence set forth as SEQ ID NO: 1, with one or more mutations, wherein the modified polypeptide further comprises an extension peptide positioned upstream to the first residue of SEQ ID NO: 1. In some embodiments, the modified FGF-1 polypeptide comprising an extension peptide is a mature form of the polypeptide. In some embodiments, the modified FGF-1 polypeptide comprising one or more mutations at positions 12, 16, 66, 117, and 134 of SEQ ID NO: 1, which polypeptide is expressed in a host cell with one or more amino acid residues of the extension peptide positioned upstream to the first residue of SEQ ID NO: 1. Exemplary sequences of the modified FGF-1 polypeptides comprising an extension peptide, expressed without an N-terminal methionine residue, are set forth as SEQ ID NOS: 19-23, wherein the sequences further comprise one or more mutations at amino acids corresponding to positions 12, 16, 66, 117, and 134 of SEQ ID NO: 1. Additional exemplar sequences of mature modified FGF-1 polypeptides comprising one or more residues of the extension peptide, and expressed without an N-terminal methionine residue, are set forth as SEQ ID NOS: 24-28.

Provided herein, in a fourth embodiment, is a modified FGF-1 polypeptide comprising the sequence set forth as SEQ ID NO: 1, with one or more mutations, wherein the modified polypeptide further comprises a truncation of one or more of the first five residues of SEQ ID NO: 1. In some embodiments, the modified FGF-1 polypeptide comprising the truncation of one or more of the first five residues of SEQ ID NO: 1 is the mature form of the polypeptide. In some embodiments, the modified FGF-1 polypeptide comprises one or more mutations at positions 12, 16, 66, 117, and 134 of SEQ ID NO: 1, wherein one or more of the first five residues of SEQ ID NO: 1 is deleted. In some cases, the modified FGF-1 polypeptide comprising truncations is expressed with an N-terminal methionine residue. For instance, the modified FGF-1 polypeptide, according to the fourth embodiment, can have a sequence wherein the N-Met residue is followed by the second residue, asparagine, of SEQ ID NO: 1. In some cases, the modified FGF-1 polypeptide comprises an N-Met residue followed by the third residue, leucine, of SEQ ID NO: 1. In some cases, the modified FGF-1 polypeptide comprises an N-Met residue followed by the fourth residue, proline, of SEQ ID NO: 1. In some cases, the modified FGF-1 polypeptide comprises an N-Met residue followed by the fifth residue, proline, of SEQ ID NO:1. An extension peptide can be positioned in between the N-Met residue and the first, second, third, fourth, or fifth residue of SEQ ID NO: 1. Examples of a mature form of the modified FGF-1 polypeptide according to the fourth embodiment wherein an N-Met residue is followed by the second, third, fourth, or fifth residue of SEQ ID NO: 1 are shown in SEQ ID NOS: 37-40, wherein the sequences further comprise one or more mutations at amino acids corresponding to positions 12, 16, 66, 117, and 134 of SEQ ID NO: 1. Additional examples of modified FGF-1 polypeptides comprising truncations and an N-Met residue, are provided in SEQ ID NOS: 41-44.

The present disclosure also relates to modified FGF-1 polypeptides comprising one or more mutations of SEQ ID NO: 1, wherein the polypeptides are expressed with an N-Met residue followed by an extension peptide, and the extension peptide is followed by truncation of one or more of the first five residues of SEQ ID NO: 1. In some embodiments, the modified FGF-1 polypeptide comprises one or more mutations at positions 12, 16, 66, 117, and 134 of SEQ ID NO: 1, wherein the polypeptide is expressed with an N-Met residue followed by an extension peptide, and the extension peptide is followed by truncation of one or more of the first five residues of SEQ ID NO: 1. Examples of such sequences expressed with an N-Met residue followed by an extension peptide, which extension peptide is followed by truncation of one or more of the first five residues of SEQ ID NO: 1 are disclosed as SEQ ID NOS: 45-68, wherein the sequences further comprise one or more mutations at amino acids corresponding to positions 12, 16, 66, 117, and 134 of SEQ ID NO: 1. In some examples, the N-terminal methionine is cleaved off by N-terminal processing and accordingly the mature form of the modified FGF-1 polypeptide comprises only one or more residues of the leader fragment followed by truncation of one or more of the first five residues of SEQ ID NO: 1, as exemplified in SEQ ID NOS: 69-92, wherein the exemplary sequences further comprise one or more mutations at amino acids corresponding to positions 12, 16, 66, 117, and 134 of SEQ ID NO: 1. Additional examples of sequences without N-Met residue but including an extension peptide and truncations of N-terminal residues, are provided in SEQ ID NO: 93-117.

In some examples, the N-Met residue is retained in the mature modified FGF-1 polypeptide sequence, and accordingly the mature forms comprise sequences as exemplified in SEQ ID NO: 45-68, further comprising one or more mutations at amino acids corresponding to positions 12, 16, 66, 117, and 134 of SEQ ID NO: 1. Additional examples of sequences comprising an N-Met residue, an extension peptide and truncations of N-terminal residues, are provided in SEQ ID NO: 118-141 and 207.

The truncated versions of the modified FGF-1 polypeptides comprising one or more mutations at positions 12, 16, 66, 117, and 134 of SEQ ID NO: 1, are, in a fifth embodiment, expressed without an N-terminal methionine residue, and further without an extension peptide. In some examples, mature modified FGF-1 polypeptides according to the fifth embodiment comprise a sequence as set forth in SEQ ID NOS: 29-32, wherein the sequences further comprise one or more mutations at amino acids corresponding to positions 12, 16, 66, 117, and 134 of SEQ ID NO: 1. In some examples, the modified FGF-1 polypeptides according to the fifth embodiment comprise a sequence selected from the group consisting of SEQ ID NOS: 33-36.

In instances where the modified FGF-1 polypeptide, or its truncated version, comprising one or more mutations at positions 12, 16, 66, 117, and 134 of SEQ ID NO: 1, is expressed with an N-terminal methionine followed by an extension peptide, the methionine residue is either retained or cleaved off of the N-terminus during maturation of the polypeptide after expression. In some examples, where the modified FGF-1 polypeptide is expressed with an alanine next to the N-Met residue, e.g., SEQ ID NO: 14, the methionine is cleaved, to yield a mature FGF-1 polypeptide that does not comprise an N-Met residue, e.g., SEQ ID NO: 19. In some examples, where the modified FGF-1 polypeptide is expressed with a threonine next to the N-Met residue, e.g., SEQ ID NO: 16, the methionine is cleaved, to yield a mature FGF-1 polypeptide that does not comprise an N-Met residue, e.g., SEQ ID NO: 20. In some examples, where the modified FGF-1 polypeptide is expressed with a glutamic acid next to the N-Met residue, e.g., SEQ ID NO: 17, the methionine is not cleaved, to yield a mature FGF-1 that comprise an N-terminal methionine and has the same sequence as the expressed form.

Provided herein, in a sixth embodiment, is a modified FGF-1 polypeptide comprising the sequence set forth as SEQ ID NO: 1, comprising a mutation at position 67. In some embodiments, the modified FGF-1 polypeptide comprises a mutation at position 67 of SEQ ID NO: 1, one or more further mutations at positions 12, 16, 66, 117, and 134, and is expressed with an N-Met residue. The internal methionine at position 67 can be replaced, for example, with an alanine residue. In absence of the internal methionine at position 67, the N-terminal methionine of the modified FGF-1 polypeptide can be cleaved, post-expression; using cyanogen bromide (CNBr), an agent that specifically cleaves the amide bond after methionine residues. In some cases, the modified FGF-1 polypeptides according to the sixth embodiment are expressed with an extension peptide. In some other cases, modified FGF-1 polypeptides according to the sixth embodiment are expressed in a form comprising truncations of one or more of the first five residues of SEQ ID NO: 1, as exemplified in SEQ ID NOS: 142-149, wherein the sequences further comprise one or more mutations at amino acids corresponding to positions 12, 16, 66, 117, and 134 of SEQ ID NO: 1. In yet other examples, the modified FGF-1 polypeptides according to the sixth embodiment are expressed in a form comprising an extension peptide and truncations of one or more of the first five residues of SEQ ID NO: 1, as exemplified in SEQ ID NOS: 151-175. Additional examples of the modified FGF-1 polypeptides according to the sixth embodiment, in their mature forms, are set forth in SEQ ID NOS: 174-204. Among the modified FGF-1 polypeptides expressed in a form that comprises an internal methionine mutation, in cases where the polypeptide is expressed with an N-terminal methionine followed by an alanine or a threonine residue from the extension peptide, e.g., SEQ ID NO: 175 and SEQ ID NO: 177, respectively, the N-terminal methionine can be cleaved off during maturation of the polypeptide either by metAP or using CNBr.

Provided herein, in a seventh embodiment, is a modified FGF-1 polypeptide comprising the sequence set forth as SEQ ID NO: 205, for use in a method as described herein. Provided herein, in an eighth embodiment, is a modified FGF-1 polypeptide comprising the sequence set forth as SEQ ID NO: 206, for use in a method as described herein The present disclosure further relates to modified FGF-1 polypeptides comprising any combination of deletion, insertion, and substitution of SEQ ID NO: 1, provided that said modified polypeptide comprises one or more mutations of SEQ ID NO: 1. Amino acid substitutions may be introduced into a modified FGF-1 polypeptide and the products screened for a desired activity, e.g., retained/improved effectivity in treating ocular disorders, increased potency in amelioration of Fuch's dystrophy, improved treatment of mustard gas keratopathy. Amino acid substitutions may also be introduced into a modified FGF-1 polypeptide and the products screened for a desired physicochemical property, e.g., less prone to aggregation, improved solubility, prolonged half-life, ease of formulating as an ophthalmic pharmaceutical, enhanced stability, improved shelf-life. Both conservative and non-conservative amino acid substitutions are contemplated.

The modified FGF-1 polypeptide, as in any of the above embodiments, is expressed in a form that comprises at least 136 amino acids. In some embodiments, the modified FGF-1 polypeptide is expressed in a form that comprises 137 amino acids. In some embodiments, the modified FGF-1 polypeptide is expressed in a form that comprises 138 amino acids. In some embodiments, the modified FGF-1 polypeptide is expressed in a form that comprises 139 amino acids. In some embodiments, the modified FGF-1 polypeptide is expressed in a form that comprises 140 amino acids. In some embodiments, the modified FGF-1 polypeptide is expressed in a form that comprises 141 amino acids. In some embodiments, the modified FGF-1 polypeptide is expressed in a form that comprises 142 amino acids. In some embodiments, the modified FGF-1 polypeptide is expressed in a form that comprises 143 amino acids. In some embodiments, the modified FGF-1 polypeptide is expressed in a form that comprises 144 amino acids. In some embodiments, the modified FGF-1 polypeptide is expressed in a form that comprises 145 amino acids. In some embodiments, the modified FGF-1 polypeptide is expressed in a form that comprises 146 amino acids.

The modified FGF-1 polypeptide, as in any of the above embodiments, comprises at least 136 amino acids in the mature form. In some examples, the modified FGF-1 polypeptide comprises 137 amino acids in the mature form. In some examples, the modified FGF-1 polypeptide comprises 138 amino acids in the mature form. In some examples, the modified FGF-1 polypeptide comprises 139 amino acids in the mature form. In some examples, the modified FGF-1 polypeptide comprises 140 amino acids in the mature form. In some examples, the modified FGF-1 polypeptide comprises 141 amino acids in the mature form. In some examples, the modified FGF-1 polypeptide comprises 142 amino acids in the mature form. In some examples, the modified FGF-1 polypeptide comprises 143 amino acids in the mature form. In some examples, the modified FGF-1 polypeptide comprises 144 amino acids in the mature form. In some examples, the modified FGF-1 polypeptide comprises 145 amino acids in the mature form. In some examples, the modified FGF-1 polypeptide comprises 146 amino acids in the mature form.

In some embodiments, the sequence of the modified FGF-1 polypeptide comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to SEQ ID NO: 1, provided that said polypeptide comprises an N-Met residue in the mature form of the polypeptide. In some embodiments, the sequence of the modified FGF-1 polypeptide comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to any of the sequences selected from SEQ ID NO: 9-13, provided that said polypeptide comprises the N-Met residue in its mature form, and the polypeptide comprises one or more mutations at amino acid positions corresponding to positions 12, 16, 66, 117, and 134 of SEQ ID NO: 1. In some embodiments, the sequence of the modified FGF-1 polypeptide comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to any of the sequences selected from SEQ ID NO: 14-18, provided that said polypeptide comprises the N-Met residue in its mature form. In some embodiments, the sequence of the modified FGF-1 polypeptide comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to any of the sequences selected from SEQ ID NO: 19-23, provided that said polypeptide does not comprise the N-Met residue in its mature form, and the polypeptide comprises one or more mutations at amino acid positions corresponding to positions 12, 16, 66, 117, and 134 of SEQ ID NO: 1. In some embodiments, the sequence of the modified FGF-1 polypeptide comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to any of the sequences selected from SEQ ID NO: 24-28, provided that said polypeptide does not comprise an N-Met residue in its mature form. In some embodiments, the sequence of the modified FGF-1 polypeptide comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to any of the sequences selected from SEQ ID NO: 19-23, provided that said polypeptide does not comprise an N-Met residue in its mature form, and the polypeptide comprises one or more mutations at amino acid positions corresponding to positions 12, 16, 66, 117, and 134 of SEQ ID NO: 1. In some embodiments, the sequence of the modified FGF-1 polypeptide comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to any of the sequences selected from SEQ ID NO: 37-40, provided that said polypeptide comprises an N-Met residue in its mature form, and the polypeptide comprises one or more mutations at amino acid positions corresponding to positions 12, 16, 66, 117, and 134 of SEQ ID NO: 1. In some embodiments, the sequence of the modified FGF-1 polypeptide comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to any of the sequences selected from SEQ ID NO: 41-44, provided that said polypeptide comprises an N-Met residue in its mature form. In some embodiments, the sequence of the modified FGF-1 polypeptide comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to any of the sequences selected from SEQ ID NO: 45-68, provided that said polypeptide comprises one or more mutations at amino acid positions corresponding to positions 12, 16, 66, 117, and 134 of SEQ ID NO: 1, and said polypeptide does not comprise an N-Met residue in its mature form. In some embodiments, the sequence of the modified FGF-1 polypeptide comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to any of the sequences selected from SEQ ID NO: 69-92, comprises one or more mutations at amino acid positions corresponding to positions 12, 16, 66, 117, and 134 of SEQ ID NO: 1, and said polypeptide comprises an N-Met residue in its mature form. In some embodiments, the sequence of the modified FGF-1 polypeptide comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to any of the sequences selected from SEQ ID NO: 93-117, provided that said polypeptide does not comprise an N-Met residue in its mature form. In some embodiments, the sequence of the modified FGF-1 polypeptide comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to any of the sequences selected from SEQ ID NO: 118-141 and 207, provided that said polypeptide comprises an N-Met residue in its mature form. In some embodiments, the sequence of the modified FGF-1 polypeptide comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to any of the sequences selected from SEQ ID NOS: 29-32, provided that said polypeptide comprises one or more mutations at amino acid positions corresponding to positions 12, 16, 66, 117, and 134 of SEQ ID NO: 1. In some embodiments, the sequence of the modified FGF-1 polypeptide comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to any of the sequences selected from SEQ ID NOS: 33-36.

In some embodiments, the sequence of the modified FGF-1 polypeptide comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to any of the sequences selected from SEQ ID NOS: 142-204.

In some embodiments, the modified FGF-1 polypeptide comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to SEQ ID NO: 1 mutated at position 12 with, for example, the mutation Lys12Val, and wherein said modified FGF-1 polypeptide comprises an N-terminal methionine in its mature form. In some embodiments, the modified FGF-1 polypeptide comprises a sequence with a mutation at position 12 of SEQ ID NO: 1, for example the mutation Lys12Val, and with truncation of one or more of the first five residue of SEQ ID NO: 1, wherein said modified FGF-1 polypeptide comprises an N-Met residue in its mature form. In some embodiments, the modified FGF-1 polypeptide comprises a sequence with a mutation at position 12 of SEQ ID NO: 1, for example the mutation Lys12Val, with an extension peptide, and with truncation of one or more of the first five residue of SEQ ID NO: 1, wherein said modified FGF-1 polypeptide comprises an N-met residue in its mature form. In some embodiments, the modified FGF-1 polypeptide comprises a sequence with mutations at position 12 of SEQ ID NO: 1, for example the mutation Lys12Val, wherein the polypeptide further comprises a mutation of the methionine at position 67 of SEQ ID NO: 1, and is expressed with a methionine at the N-terminus, which methionine is cleaved off of the polypeptide in its mature form.

In some embodiments, the modified FGF-1 polypeptide comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to SEQ ID NO: 1 mutated at position 16 with, for example, the mutation Cys16Ser, and wherein said modified FGF-1 polypeptide comprises an N-met residue in its mature form. In some embodiments, the modified FGF-1 polypeptide comprises a sequence with a mutation at position 16 of SEQ ID NO: 1, for example the mutation Cys16Ser, and with truncation of one or more of the first five residue of SEQ ID NO: 1, wherein said modified FGF-1 polypeptide comprises an N-met residue in its mature form. In some embodiments, the modified FGF-1 polypeptide comprises a sequence with a mutation at position 16 of SEQ ID NO: 16, for example the mutation Cys16Ser, with an extension peptide, and with truncation of one or more of the first five residue of SEQ ID NO: 1, wherein said modified FGF-1 polypeptide comprises an N-met residue. In some embodiments, the modified FGF-1 polypeptide comprises a sequence with mutations at position 16 of SEQ ID NO: 1, for example the mutation Cys16Ser, wherein the polypeptide further comprises a mutation of the methionine at position 67 of SEQ ID NO: 1, and is expressed with a methionine at the N-terminus, which methionine is cleaved off of the polypeptide in its mature form.

In some embodiments, the modified FGF-1 polypeptide comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to SEQ ID NO: 1 mutated at position 66 with, for example, the mutation Ala66Cys, and wherein said modified FGF-1 polypeptide comprises an N-terminal methionine in its mature form. In some embodiments, the modified FGF-1 polypeptide comprises a sequence with a mutation at position 66 of SEQ ID NO: 1, for example the mutation Ala66Cys, and with truncation of one or more of the first five residue of SEQ ID NO: 1, wherein said modified FGF-1 polypeptide comprises an N-met residue in its mature form. In some embodiments, the modified FGF-1 polypeptide comprises a sequence with a mutation at position 66 of SEQ ID NO: 1, for example the mutation Ala66Cys, with an extension peptide, and with truncation of one or more of the first five residue of SEQ ID NO: 1, wherein said modified FGF-1 polypeptide is expressed with an N-Met residue. In some embodiments, the modified FGF-1 polypeptide comprises a sequence with mutations at position 66 of SEQ ID NO: 1, for example the mutation Ala66Cys, wherein the polypeptide further comprises a mutation of the methionine at position 67 of SEQ ID NO: 1, and is expressed with a methionine at the N-terminus, which methionine is cleaved off of the polypeptide in its mature form.

In some embodiments, the modified FGF-1 polypeptide comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to SEQ ID NO: 1 mutated at position 117 with, for example, the mutation Cys117Val, and wherein said modified FGF-1 polypeptide comprises an N-met residue in its mature form. In some embodiments, the modified FGF-1 polypeptide comprises a sequence with a mutation at position 117 of SEQ ID NO: 1, for example the mutation Cys117Val, and with truncation of one or more of the first five residue of SEQ ID NO: 1, wherein said modified FGF-1 polypeptide comprises an N-met residue in its mature form. In some embodiments, the modified FGF-1 polypeptide comprises a sequence with a mutation at position 117 of SEQ ID NO: 1, for example the mutation Cys117Val, with an extension peptide, and with truncation of one or more of the first five residue of SEQ ID NO: 1, wherein said modified FGF-1 polypeptide comprises an N-met residue in its mature form. In some embodiments, the modified FGF-1 polypeptide comprises a sequence with mutations at position 117 of SEQ ID NO: 1, for example the mutation Cys117Val, wherein the polypeptide further comprises a mutation of the methionine at position 67 of SEQ ID NO: 1, and is expressed with a methionine at the N-terminus, which methionine is cleaved off of the polypeptide in its mature form.

In some embodiments, the modified FGF-1 polypeptide comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to SEQ ID NO: 1 mutated at position 134 with, for example, the mutation Pro134Val, and wherein said modified FGF-1 polypeptide comprises an N-terminal methionine in its mature form. In some embodiments, the modified FGF-1 polypeptide comprises a sequence with a mutation at position 134 of SEQ ID NO: 1, for example the mutation Pro134Val, and with truncation of one or more of the first five residue of SEQ ID NO: 1, wherein said modified FGF-1 polypeptide comprises an N-met residue in its mature form. In some embodiments, the modified FGF-1 polypeptide comprises a sequence with a mutation at position 134 of SEQ ID NO: 1, for example the mutation Pro134Val, with an extension peptide, and with truncation of one or more of the first five residue of SEQ ID NO: 1, wherein said modified FGF-1 polypeptide comprises an N-met residue in its mature form. In some embodiments, the modified FGF-1 polypeptide comprises a sequence with mutations at position 134 of SEQ ID NO: 1, for example the mutation Pro134Val, wherein the polypeptide further comprises a mutation of the methionine at position 67 of SEQ ID NO: 1, and is expressed with a methionine at the N-terminus, which methionine is cleaved off of the polypeptide in its mature form.

In some embodiments, the modified FGF-1 polypeptide comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to SEQ ID NO: 1 mutated at positions 16, 66, and 117 of SEQ ID NO: 1, with, for example, the mutation Cys16Ser, Ala66Cys, and Cys117Val, and wherein said modified FGF-1 polypeptide comprises an N-met residue in its mature form. In some embodiments, the modified FGF-1 polypeptide comprises a sequence with mutations at positions 16, 66, and 117 of SEQ ID NO: 1, with, for example, the mutation Cys16Ser, Ala66Cys, and Cys117Val, and with truncation of one or more of the first five residue of SEQ ID NO: 1, wherein said modified FGF-1 polypeptide comprises an N-met residue in its mature form. In some embodiments, the modified FGF-1 polypeptide comprises a sequence with mutations at positions 16, 66, and 117 of SEQ ID NO: 1, with, for example, the mutation Cys16Ser, Ala66Cys, and Cys117Val, with an extension peptide, and with truncation of one or more of the first five residue of SEQ ID NO: 1, wherein said modified FGF-1 polypeptide comprises an N-met residue. In some embodiments, the modified FGF-1 polypeptide comprises a sequence with mutations at positions 16, 66, and 117 of SEQ ID NO: 1, with, for example, the mutation Cys16Ser, Ala66Cys, and Cys117Val, wherein the polypeptide further comprises a mutation of the methionine at position 67 of SEQ ID NO: 1, and is expressed with a methionine at the N-terminus, which methionine is cleaved off of the polypeptide in its mature form.

In some embodiments, the sequence of the modified FGF-1 polypeptide comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to a sequence selected from SEQ ID NOs: 2, and 9-204 and 207. In some embodiments, the sequence of the modified FGF-1 polypeptide comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to SEQ ID NO: 205 or 206.

In some embodiments, the modified FGF-1 polypeptide is thermostable. As used herein, a thermostable FGF (e.g., a thermostable FGF-1) refers to an FGF having a modified amino acid sequence relative to SEQ ID NO: 1 that is also more stable than the polypeptide of SEQ ID NO: 1 under the same conditions. Examples of mutations capable of conferring thermostability to FGF (e.g., FGF-1) and methods for assessing thermostability are described, for example, in U.S. Pat. Nos. 7,790,682; 7,595,296; 7,696,171; 7,776,825; 7,659,379; 8,119,776; 8,153,770; 8,153,771; and 8,461,111; U.S. Patent Application Publication Nos. 2011/0224404 and 2013/0130983; and in Xia et al. *PloS one*. (2012) 7(11): e48210. In some embodiments, positions 12 and/or 134 are mutated in FGF-1 to generate a modified FGF-1 that is thermostable.

In some embodiments, the modified FGF-1 polypeptide includes one or more modifications that reduce the number of reactive thiols (e.g., free cysteines). Examples such modifications in FGF-1 are described, for example, in U.S. Pat. Nos. 7,790,682; 7,595,296; 7,696,171; 7,776,825; 7,659,379; 8,119,776; 8,153,770; 8,153,771; and 8,461,111; U.S. Patent Application Publication Nos. 2011/0224404 and 2013/0130983; and in Xia et al. *PloS one*. (2012) 7(11): e48210. In some embodiments, positions 83 and/or 117 are mutated in SEQ ID NO: 1 to generate a modified FGF-1 that reduces the number of reactive thiols.

In some embodiments, the modified FGF includes one or more modifications that enable formation of an internal disulfide linkage. In some embodiments, position 66 is mutated in SEQ ID NO: 1 to generate a modified FGF-1 that comprises an internal disulfide linkage.

In some embodiments, the modified FGF-1 polypeptides described herein can be administered without exogenous heparin in the formulation for stability, they can be formulated and applied without heparin and thus are more able to bind to the tissue heparans. Such modified FGF-1 polypeptides have a high affinity for tissue heparans that are exposed in a surgical, traumatic or dystrophic conditions and disease-states and so bind to diseased tissue on application. In addition, the modified FGF-1 polypeptides being more thermally stable are suitable for formulation and storage at room temperature. The stability of the modified FGF-1 polypeptides also makes them suitable for administration in both solution (e.g., immediate release) and sustained-release formulations.

In some embodiments, the modified FGF-1 polypeptide is SEQ ID NO: 1 that has been modified at one or more of positions 12, 16, 66, 117, and 134. In some embodiments, the modified FGF is SEQ ID NO: 1 that has been modified at positions 16, 66, and 117. The amino acid positions can be substituted with, e.g., Ser, Cys, Val, or other amino acids to create disulfide linkages between modified amino acids and wild-type amino acids. In some embodiments, the modified FGF comprises the amino acid sequence of SEQ ID NO: 2, also referred to as N-Met THX1114. In some embodiments, the modified FGF-1 polypeptide comprises one or more mutations selected from the group consisting of: Lys12Val, Pro134Val, Ala66Cys, Cys117Val, and Pro134Val. In some embodiments, the modified FGF-1 polypeptide comprises the sequence of SEQ ID NO: 2.

In some embodiments, the modified FGF-1 polypeptides or compositions described herein may be prepared as prodrugs. A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug.

The modified FGF-1 polypeptides described herein may be labeled isotopically (e.g., with a radioisotope) or by other means, including, but not limited to, the use of chromophores or fluorescent moieties, bioluminescent labels, photoactivatable or chemiluminescent labels.

The present discloser further relates to modified FGF polypeptides comprising N-terminal modification(s), wherein the modified FGF polypeptide can be any member of the FGF family, including FGF-1 (SEQ ID NO: 1), FGF-2, FGF-3, FGF-4, FGF-5, FGF-6, FGF-7, FGF-8, FGF-9, FGF-10, FGF-11, FGF-12, FGF-13, FGF-14, FGF-15, FGF-16, FGF-17, FGF-18, FGF-19, FGF-20, FGF-21, FGF-22, and FGF-23, and FGF-24.

In some embodiments, the synthesis of modified FGF-1 polypeptides as described herein is accomplished using means described in the art, using the methods described herein, or by a combination thereof.

In some embodiments, the sequence of the modified FGF comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to SEQ ID NO: 1 mutated at one or more positions 16, 66, and 117 with, for example, the mutations Cys16Ser, Ala66Cys, and Cys117Val. In some embodiments, the modified FGF comprises the wild-type human FGF-1 sequence with a mutation at positions 16, 66 and 117, for example the mutations Cys16Ser, Ala66Cys, and Cys117Val.

Recombinant Techniques for Preparation of Modified FGF-1 Polypeptides

A variety of host-expression vector systems may be utilized to produce the modified FGF-1 polypeptides provided herein. Such host-expression systems represent vehicles by which the modified FGF-1 polypeptides may be produced and subsequently purified, but also represent cells that may, when transformed or transfected with the appropriate nucleotide coding sequences, exhibit the modified gene product in situ. Examples of host-expression systems include but are not limited to, bacteria, insect, plant, mammalian, including human host systems, such as, but not limited to, insect cell systems infected with recombinant virus expression vectors (e.g., baculovirus) containing nucleotide sequences coding for the modified FGF-1 polypeptides; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing coding sequences for the modified FGF-1 polypeptides; or mammalian cell systems, including human cell systems, e.g., HT1080, COS, CHO, BHK, 293, 3T3, harboring recombinant expression constructs containing promoters derived from the genome of mammalian cells, e.g., metallothionein promoter, or from mammalian viruses, e.g., the adenovirus late promoter; the vaccinia virus 7.5K promoter, or from yeast-derived plasmids e.g., pSH19 and pSH15, or from bacteriophages such as lambda phase and derivatives thereof. Examples of bacterial expression systems include but are not limited to *Escherichia coli*-derived plasmids (e.g., pBR322, pBR325, pUC12, pUC13, and pET-3); *Bacillus subtilis*-derived plasmids (e.g., PUB110, pTP5, and pC194).

In some embodiments, a host cell strain is chosen such that it modulates the expression of the inserted sequences, or modifies and processes the gene product in the specific fashion desired. Such modifications and processing of protein products may be important for the function of the protein. Different host cells have specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product may be used. Such mammalian host cells, including human host cells, include but are not limited to HT1080, CHO, VERO, BHK, HeLa, COS, MDCK, 293, 3T3, and WI38.

For long-term, high-yield production of recombinant peptides, stable expression is desired. For example, cell lines that stably express the recombinant modified FGF-1 polypeptides may be engineered. In some embodiments, rather than using expression vectors that contain viral origins of replication, host cells can be transformed with DNA controlled by appropriate expression control elements, e.g., promoter, enhancer, sequences, transcription terminators, polyadenylation sites, and the like, and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci that in turn can be cloned and expanded into cell lines. In some examples, this method may advantageously be used to engineer cell lines that express the modified FGF-1 polypeptide product. Such engineered cell lines may be particularly useful in screening and evaluation of compounds that affect the biological of the gene product.

Disulfide Bond Formation in Modified FGF-1 Polypeptides

In some embodiments, the modified FGF-1 polypeptide of the present disclosure comprises the following mutations in SEQ ID NO: 1-Cys16Ser, Ala66Cys, and Cys117Val, wherein the polypeptide includes an internal disulfide bond between the cysteine residues at positions 66 and 83. For many recombinant proteins, the formation of correct disulfide bonds is vital for attaining their biologically active three-dimensional conformation. The formation of erroneous disulfide bonds can lead to protein misfolding and aggregation into inclusion bodies. In *E. coli*, cysteine oxidation typically takes places in the periplasm, where disulfide bonds are formed in disulfide exchange reactions catalyzed by a myriad of enzymes, mainly from the Dsb family (Rosano, G. L., & Ceccarelli, E. A. (2014). *Recombinant protein expression in Escherichia coli: advances and challenges*. Frontiers in Microbiology, 5, 172). By contrast, disulfide bond formation in the cytoplasm is rare. This situation affects the production of recombinant proteins with disulfide bonds that are produced in the cytoplasm, such as a modified FGF-1 polypeptide comprising an internal disulfide linkage between Cys66 and Cys83. Accordingly, in some examples, an engineered *E. coli* strain that possess an oxidative cytoplasmic environment that favors disulfide bond formation is selected as a host cell for expression of the modified FGF-1 polypeptides (Rosano, G. L., & Ceccarelli, E. A. (2014). *Recombinant protein expression in Escherichia coli: advances and challenges*. Frontiers in Microbiology, 5, 172). Examples of such strains include but are not limited to Origami (Novagen), which has a trxB-gor-genotype in the K-12 background, and SHuffle® T7 Express strain (NEB), which has a trxB-gor-genotype in a BL21 (DE3) background and constitutively expresses a chromosomal copy of the disulfide bond isomerase DsbC. It has been shown that DsbC promotes the correction of mis-oxidized proteins into their correct form and is also a chaperone that can assist in the folding of proteins that do not require disulfide bonds. Without being bound by a particular theory, it is contemplated that due to the action of DsbC, less target protein, such as the modified FGF-1 polypeptide comprising an internal disulfide linkage between Cys66 and Cys83, aggregates into inclusion bodies. Thus, in certain embodiments, the present disclosure identifies an improved method for cytoplasmic production of a modified FGF-1 polypeptide comprising internal disulfide linkage between Cys16 and Cys83.

In some embodiments where the modified FGF-1 polypeptide is expressed with an N-Met residue, the polypeptide is subsequently purified without a step requiring proteolytic cleavage for removal of an N-terminal peptide. Accordingly, in some embodiments, the present disclosure provides a method of rapid purification of the modified FGF-1 polypeptides described herein, without involving a proteolytic cleavage step for removal of an N-terminal peptide. This is particularly advantageous for production of the modified FGF-1 polypeptides per good manufacturing practice (GMP) guidelines. The advantages include the lack of a cleavage step, including eliminating the need for subsequent purification of the cleaved product and removal of the reagents used for cleavage. The further advantage of this is an increase in yield due to decreased handling and the alleviation of the need to test for residual cleavage reagents and contaminants introduced for the cleavage and subsequent separation of cleaved from uncleaved material.

Methods of Use

Provided herein, in one embodiment, is a method of treating an ocular disease, disorder or condition in a mammal comprising administering to the mammal a modified FGF-1 polypeptide as described in the above embodiments. In some instances, the modified FGF-1 polypeptide for use in the methods described herein comprises a sequence selected from SEQ ID NOs: 2, and 9-204, and 207. Provided herein, in one embodiment, is a method of treating an ocular disease, disorder or condition in a mammal comprising administering to the mammal a modified FGF-1 polypeptide comprising a sequence as set forth in SEQ ID NO: 205 or 206.

In some embodiments, the ocular disease, disorder or condition to be treated is a disease, disorder, or condition of the corneal endothelial layer. Diseases, disorders, or conditions of the corneal endothelial layer include, but are not limited to, Fuch's dystrophy, bullous keratopathy, congenital hereditary endothelial dystrophy 1, congenital hereditary endothelial dystrophy 2, posterior polymorphous corneal dystrophy, and dry eye syndromes.

Without being bound by theory, it is believed a solution of a modified FGF-1 polypeptide injected intracamerally into the aqueous humor of the eye binds to the endothelial surface and especially any areas of the cornea that are not covered by a healthy endothelial layer. The modified FGF stimulates the growth and migration of the endothelial cells. This reduces the corneal edema associated with the endothelial dystrophy and reduces the likelihood for a need for a corneal or endothelial transplant. The action of the modified FGF can occur at a site other than the site of greatest dystrophy (typically at the corneal center) and also results in stimulation of endothelial cells in the corneal periphery and endothelial progenitor pools in the trabecular meshwork (TM).

In some embodiments, the ocular disease, disorder or condition to be treated is a disease, disorder, or condition of the corneal epithelium. Diseases, disorders or conditions of the corneal epithelium include, but are not limited to, dry eye syndromes, inflammatory conditions such as Stevens-Johnson syndrome, and corneal epithelial defects.

In some embodiments, the ocular disease, disorder or condition to be treated is herpetic keratopathy. Herpetic keratopathy typically is an infection of the cornea caused by Herpes Simplex virus (HSV). Primary infection can be the result of direct exposure of the host's mucous membranes to infectious HSV. Following primary infection and the establishment of latency in the sensory ganglia, the virus can be stimulated to enter an infectious cycle, from which it returns to the cornea. Once there, this recurrent infection can cause various complications, in particular an inflammatory response, which if strong enough can compromise the integrity of the cornea, leading to corneal ulcer, opacity, haze, scarring and in severe cases blindness. Secondary to herpes infection, there can be development of chronic herpetic keratopathy, neurotrophic keratopathy, or both. For example, stromal infections, which are immune-mediated and are the leading cause of corneal blindness in developed countries occur as a result of chronic viral reactivation, and lead to neurotrophic keratopathy, a degenerative condition. A normal cornea is densely innervated, but lacks blood vessels. Subsequent episodes following primary viral infection can not only damage nerves, leading to decreased corneal sensation (corneal hypoesthesia), but also lead to angiogenesis, and neovascularization.

In further embodiments, the modified FGF-1 polypeptides described herein can be used to treat epithelial basement membrane dystrophy, Meesmann juvenile epithelial corneal dystrophy, gelatinous drop-like corneal dystrophy, Lisch epithelial corneal dystrophy, subepithelial mucinous corneal dystrophy, Reis-Bucklers corneal dystrophy, or Thiel-Behnke dystrophy, and recurrent corneal erosions.

In some embodiments, the ocular condition includes damage to the cornea (e.g., the corneal surface or endothelial layer at the interface of the cornea and aqueous humor) or surgical disruption caused by corneal surgeries, including PRK, LASIK, and any penetrating corneal surgery or keratoplasty.

Also provided herein is a method of treating a chemical or vesicant agent induced injury by administering a modified fibroblast growth factors (FGF-1) polypeptides, or pharmaceutical composition or medicaments that include such modified peptides.

Also provided herein in one embodiment is a method of treating a chemical or vesicant injury by administering a modified FGF-1 polypeptide as described herein. In some embodiments, the method comprises treating a skin injury or an ocular injury caused by a chemical or a vesicant agent. In some embodiments, the method comprises treating mustard gas keratopathy, induced by a vesicant, e.g., nitrogen mustard (NM), by administering modified FGF-1 as polypeptides described herein. Treating MGK with a modified FGF-1 polypeptide, as described herein, in some embodiments, results in amelioration of histopathological conditions associated with MGK, such as hyperplasia of corneal epithelial layer, epithelial-stromal cell separation edema, corneal erosions. The administration of modified FGF-1 of the present disclosure, in certain embodiments, results in reduction in edema and elimination of corneal erosions. Corneal erosion is typically characterized by de-epithelialization of the cornea and in some examples; administration of the modified FGF-1 results in faster re-epithelialization of the cornea or reduces the severity of corneal de-epithelialization. In one embodiment is described a method of regenerating ocular surface epithelium in a patient exposed to a chemical or a vesicant, by administering a modified FGF-1 as described herein. In some embodiments, the method promotes regeneration of cornea, prevents degeneration of the cornea, and prevents long term sequelae to the chemical injury. In some examples, the method comprises treating a corneal endothelial injury, a corneal epithelial injury, or a corneal stromal injury. In instances where the method treats corneal endothelial injuries, administering a modified FGF-1, as described herein, enhances the function of corneal endothelial cells and prevents long term degeneration of the cornea. In some instances, where the method treats corneal endothelial injuries, administering a modified FGF-1, as described herein, prevents corneal edema and secondary anterior keratopathies. In some instances, where the method treats corneal endothelial injuries, administering a modified FGF-1, as described herein, prevents loss of corneal endothelial cells. In some embodiments, the method results in reduction of the severity of corneal epithelial detachment. In some embodiments, the method comprises treating a stromal injury such as stromal scarring and corneal opacity.

In some embodiments, the ocular condition includes accidental trauma or chemical or thermal injury to the cornea. In some examples, the chemical or thermal injury is a chemical burn. In some examples, the chemical or thermal injury is caused by a vesicant agent. In some examples, the chemical or thermal injury is caused by a chemical warfare agent.

A multitude of household and occupational compounds have the potential to induce chemical burns to the eye and skin. Without prompt intervention, irreversible visual loss and disfigurement may prevail. Agents that rapidly neutralize both acid and alkali agents without heat release and limit diffusion, are contemplated to be effective in treating chemical injuries. Exemplary chemical injuries include, but are not limited to, alkali injuries, acid injuries. Common sources of chemical burns include sulfuric acid ($H_2SO_4$), hydrochloric acid (HCl), sodium hydroxide (NaOH), lime (CaO), silver nitrate ($AgNO_3$), hydrogen peroxide ($H_2O_2$), chlorine gas and any strong oxidant.

Exemplary chemical warfare agent that can cause the chemical or thermal injury described herein, is phosgene, an urticant, or a nettle agent. Phosgene is a highly toxic, colorless gas at room temperature and standard pressure that condenses at 0° C. to a fuming liquid. Its molecular formula is $COCl_2$. Phosgene is extremely toxic by acute (short-term) inhalation exposure. Severe respiratory effects, including pulmonary edema, pulmonary emphysema, and death have been reported in humans. Severe ocular irritation and dermal burns may result following eye or skin exposure. Chronic (long-term) inhalation exposure to phosgene may also cause irreversible pulmonary changes, such as emphysema and fibrosis. Its exposure can result in widespread and devastating effects including high mortality due to its fast penetration and ability to cause immediate severe cutaneous injury. Results from a recent study show that topical cutaneous exposure to phosgene vapor causes blanching of exposed skin with an erythematous ring, necrosis, edema, mild urticaria and erythema within minutes after exposure out to 8 h post-exposure, in a mouse model. These clinical skin manifestations are accompanied with increases in skin thickness, apoptotic cell death, mast cell degranulation, myeloperoxidase activity indicating neutrophil infiltration, p53 phosphorylation and accumulation, and an increase in COX-2 and TNFα levels. Topical phosgene-exposure also resulted in the dilatation of the peripheral vessels with a robust increase in RBCs in vessels of the liver, spleen, kidney, lungs and heart tissues. It is contemplated that these events could cause a drop in blood pressure leading to shock, hypoxia and death. See, Tewari-Singh N, Goswami D G, Kant R, Crouch C R, Casillas R P, Orlicky D J, Agarwal R, *Cutaneous exposure to vesicant phosgene oxime: Acute effects on the skin and systemic toxicity*, Toxicol Appl Pharmacol. 2017 Feb. 15; 317:25-32.

In some embodiments, the modified FGF-1 polypeptide may be used in a method of treating, preventing, or ameliorating the various skin injuries caused by vesicant exposure.

Figure 12:
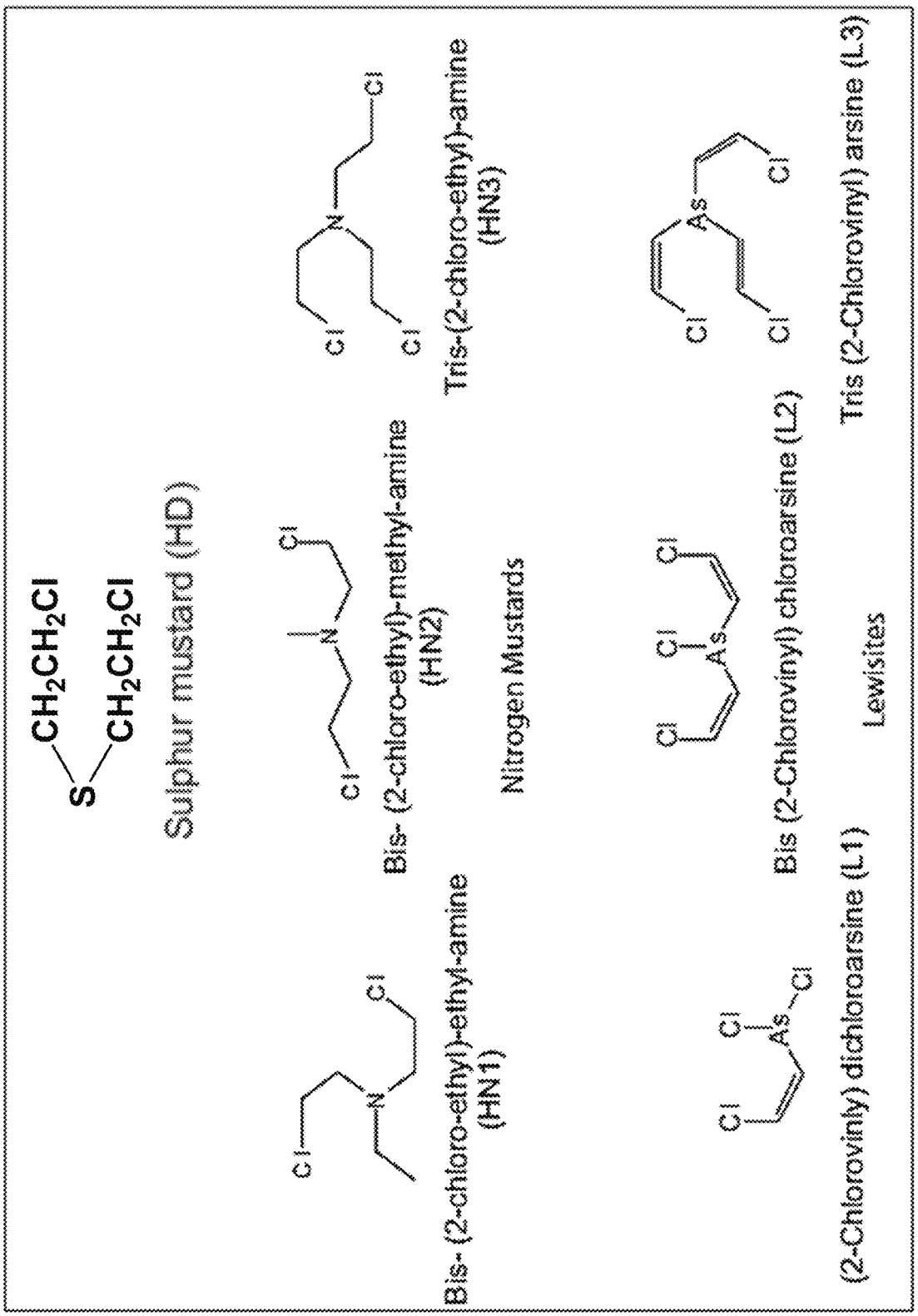
FIG. 12 shows structures of exemplary vesicants.

Vesicants, or vesicant agents, or blistering agents are toxic compounds that produce skin injuries resembling those caused by burns. These agents on inhalation affect the upper respiratory tract as well as the lungs, producing pulmonary edema. See, e.g., Ganesan, K., S. K. Raza, and R. Vijayaraghavan (2010) *Chemical Warfare Agents*, Journal of Pharmacy and Bioallied Sciences 2.3: 166-178. These agents can also cause severe eye injuries. There are two forms of vesicants: mustards and arsenicals. The most important substance in this class of chemical warfare agents is sulfur mustard. Other members include nitrogen mustards (HN1, HN2 and HN3), and arsenic vesicants such as lewisites (L1, L2 and L3), ethyldichloroarsine, methyldichloroarsine, phenyldichloriarsine. FIG. 12 shows some example structures of vesicant agents. Specific examples of vesicant agents include but are not limited to sulfur mustard (SM), bis-(2-chloroethyl) sulfide, chloroethylethyl sulfide (CEES), lewisite, and 2-chloro-N-(2-chloroethyl)-N-methylethanamine hydrochloride, a member of the family of nitrogen mustard (NM). As used throughout this disclosure, the terms vesicant, vesication-causing agent or chemical, vesicating agent, and the like, are taken to mean vesicants as specifically enumerated herein, and other compounds, such as toxins and/or chemical warfare agents. Sulfur mustard is the vesicant with the highest military significance since its use in WWI. The nitrogen mustards were synthesized in the 1930s but were not produced in large amounts for warfare. Mechlorethamine (HN2, Mustargen) has found more peaceful applications as a cancer chemotherapeutic agent and has remained the standard compound for this purpose for many years. Lewisite (L) was synthesized in 1918 for military purpose due to its non-flammable property and toxicity similar to mustard, but has probably not been used on a battlefield. The mustards are radiomimetic and are extremely toxic to dividing cells. Mustards are lipophilic and readily penetrate the skin, most textiles and rubber. After passing through the cellular membrane, sulfur mustard is converted to highly reactive sulphonium ion. It irreversibly alkylates DNA, RNA and protein, causing cell death; the most important target is DNA. Mustard alkylates the purine bases of DNA and damages them. Lewisite is absorbed by the skin much faster, and it causes immediate pain and irritation in the affected organ and produces more systematic symptoms. It directly binds to the sulfhydryl groups and inactivates them.

The use of sulfur mustard (SM), and other vesicating agents in chemical warfare has been long known. More recently, in August 2015, SM was used by ISIS in an attack on Kurdish forces in Iraq, as well as an attack in Syria. Mustard agents injure the eyes, the skin, and the lungs, with the eyes being the most sensitive. Because symptoms do not manifest until 2 to 4 hours after exposure, exposed persons do not immediately know they are exposed to mustard. This delay has contributed to confusion and panic when symptoms of exposure finally develop. For the eyes, these consist of blepharospasm, lacrimation, irritation, pain, and photophobia. Corneal injuries resulting from ocular exposure to sulfur mustard (SM) vapor are the most prevalent chemical warfare injury. Ocular exposures exhibit three distinct, dose-dependent clinical trajectories: complete injury resolution, immediate transition to a chronic injury, or apparent recovery followed by the subsequent development of persistent ocular manifestations. These latter two trajectories include a constellation of corneal symptoms that are collectively known as mustard gas keratopathy (MGK). Tissue-specific damage during the acute injury can decrement the regenerative capacities of corneal endothelium and limbal stem cells, thereby predisposing the cornea to the chronic or delayed forms of MGK.

For some patients MGK occurs a few weeks after exposure; in others it took years to manifest. This keratopathy is characterized by corneal conjunctivalization and limbal stem cell deficiency. It has been shown that in the human corneal endothelium, gaps due to CEC loss are typically filled by spreading of proximal CECs. These morphological changes compensate for endothelial loss until the barrier between the cornea and aqueous humor can no longer be maintained, resulting in persistent corneal edema and secondary anterior keratopathies. Because adult human CECs do not proliferate in vivo, any loss of CECs therefore potentially represents a permanent reduction in endothelial capacity. Thus, while endothelial function can be restored after a mild injury by CEC spreading, more severe injuries may exceed the repair capacity of the human endothelium. Rabbits are distinct from humans in that they can undergo limited CEC proliferation, giving them an improved capacity to recover from CEC loss. However, as in humans, sufficiently severe injury to the rabbit endothelium also results in irreversible corneal decompensation and secondary keratopathies.

Based on the above studies, it has been hypothesized that vesicant-induced endothelial failure may be the causal mechanism underlying MGK pathogenesis. This hypothesis is consistent with the dose dependence between SM and the development of MGK that has been observed in humans and rabbits, as well as the different clinical trajectories (resolved chronic MGK and delayed-onset MGK) that have been reported in human casualties. According to this hypothesis, cornea exposure to low doses of vesicant may result in an acute epithelial lesion, with minimal endothelial toxicity, and corneas recover without long-term complications. Alternatively, exposure to doses of a vesicant that cause irreparable injury to the corneal endothelium could result in endothelial barrier failure, producing a persistent edema with secondary anterior keratopathies. Following a severe injury, there may be no apparent delay between the acute injury and MGK onset.

Hence, a composition and method for minimizing or preventing injury due to sulfur mustard and similarly acting chemical toxicants, particularly chemical warfare agents, is an important pursuit for scientists working for the U.S. Department of Defense. Recent studies have shown that as vesicating agents, mustard compounds lead to a loss of epithelial-stromal attachment. In the cornea, microbullae are formed, and once enough have accrued, the corneal epithelium is unable to hold fast to the basement membrane, causing the epithelial tissue to slough. Thus, an effective post-exposure therapy for SM is desired to enhance the ability of the corneal epithelium to remain attached to the stroma. Without being bound by a theory, it is contemplated that the ability of the corneal epithelium to remain attached to the stroma might allow some basal epithelia the opportunity to recover in situ, maintaining their connections with their basement membrane and stroma. It has also been hypothesized that one of the key players in the epithelial-stromal integrity is collagen XVII (i.e., BP180), a trans-membranous component of the hemidesmosome. Cleavage of collagen XVII by ADAM ("A Disintegrin And Metalloproteinase") family of proteins, including ADAMS, ADAM10, and/or ADAM17 after injury releases epithelial cells from their basement membrane, and this cleavage allows them to migrate.

ADAM17, also known as TNF-a converting enzyme or TACE, is a general response to injury as well as a "sheddase" for releasing collagen XVII. It was postulated that corneal microblistering, induced by vesicant agent exposure, is in part due to activation of ADAM17, which is capable of cleaving collagen XVII. Experimental data confirmed the induction of ADAM17 expression at the basement membrane zone of corneas exposed to vesicant agent NM. Thus, agents that are able to inhibit the post-exposure upregulation of ADAM17 expression are contemplated to be useful for attenuation of corneal injuries caused by vesicant agents.

The present disclosure provides modified FGF-1 polypeptides that treat, reduce the adverse effects or, and otherwise aid in the healing of exposure to vesicant agents, such as SM and NM. The modified FGF-1 polypeptides disclosed herein are capable of preventing the overexpression of ADAM17 following exposure to a vesicant agent, such as SM and/or NM.

The present disclosure also provides a method of treating, preventing, reducing the adverse effects of, and otherwise aiding the healing of exposure to chemical or vesicant induced injury, by administering a modified FGF-1 polypeptide. In some embodiments, the methods disclosed herein further prevent the overexpression of ADAM17 following exposure to a vesicant agent, such as SM and/or NM.

Wild type FGF-1 proteins, e.g., SEQ ID NO: 1, which have unpaired cysteine residues that are susceptible to oxidation and alkylation. See FIG. 1. In some embodiments of the present disclosure where the modified FGF-1 polypeptides do not comprise unpaired cysteine residues, such modified FGF-1 polypeptides are less susceptible to oxidation and/or alkylation by vesicant agents. Experimental data has also indicated reduction in levels of FGF-1 and its mRNA are known to result from exposure to mustard agents and it is hypothesized that this loss may play a role in the slow healing of mustard-induced lesions in the cornea. In some embodiments of the present disclosure, the modified FGF-1 polypeptides, which do not comprise free cysteine residues and accordingly are less or not susceptible to cysteine modification, are effective in accelerating the healing of corneal mustard lesions.

In some embodiments of the present disclosure, the method comprises administering a modified FGF-1 polypeptide that do not comprise unpaired cysteine residues, which modified FGF-1 polypeptides are less susceptible to oxidation and/or alkylation by vesicant agents. In some embodiments of the present disclosure, the method comprises administering a modified FGF-1 polypeptides, which do not comprise free cysteine residues and accordingly are less or not susceptible to cysteine modification. In some embodiments, the method disclosed herein is effective in accelerating the healing of corneal lesions associated with MGK.

Exposure to vesicant agents, such as sulfur mustard (SM) and nitrogen mustard (NM) can cause severe skin injury with delayed blistering. Depending upon the dose and time of their exposure, edema and erythema can potentially develop into blisters, ulceration, necrosis, desquamation, and pigmentation changes, which persist weeks and even years after exposure. See, e.g., Tewari-Singh N, Agarwal R, *Mustard vesicating agent-induced toxicity in the skin tissue and silibinin as a potential countermeasure*, Ann N Y Acad Sci. 2016 June; 1374(1):184-92. Another exemplary vesicant agent Phosgene Oxime (CX), an urticant or nettle agent, is also a potential chemical warfare and terrorist weapon.

In some embodiments, the ocular disease, disorder or condition to be treated is a disease, disorder, or condition of the corneal stroma. Diseases, disorders or conditions of the corneal stroma include, but are not limited to, keratoconus, lattice corneal dystrophy, granular corneal dystrophy, macular corneal dystrophy, Schnyder crystalline corneal dystrophy, congenital stromal corneal dystrophy, fleck corneal dystrophy, trauma or chemical or thermal injury, or injury secondary to infections such as trachoma.

In further embodiments, the modified FGF-1 polypeptides described herein can be applied before, during, or after corneal transplantations procedures (e.g., corneal transplantation or procedures involving Descemet's membrane) that involve disruption of the cornea (e.g., corneal endothelial structure) where acceleration of healing of corneal or ocular surface cells and/or improving the cellular response (e.g., by increasing the viability and/or longevity of the transplanted cells) to insult would result in a therapeutic benefit.

In additional embodiments, the modified FGF-1 polypeptides described herein can be used to increase the viability and health of corneal cells or corneal progenitors being prepared for transplantation. Modified FGF-1 polypeptides added to the organ culture medium for donated corneas or other donated corneal tissue stimulates the corneal cells and increases the length of time the corneas can be stored before transplantation, as well as increasing the probability that a cornea will have sufficient healthy cells to be useful for transplantation. Also, the modified FGF-1 polypeptides can be used in culture media when culturing corneal progenitor cells to stimulate growth of those cells.

Further embodiments relate to methods of modulating the activity of one or more fibroblast growth factor receptors (FGFRs) in a corneal endothelial cell comprising contacting said corneal endothelial cell with a modified FGF (e.g., a modified FGF-1, such as one comprising the sequence of SEQ ID NO: 2). Such methods can be used to increase or stimulate the activity of one or more FGFRs, which can result in increased cell migration and/or cell proliferation.

In additional embodiments are described methods of treating a metabolic disease by administering a modified FGF-1 polypeptide according to the present disclosure. Exemplary metabolic diseases that can be treated with the disclosed modified FGF-1 polypeptides include but are not limited to: (1) glucose utilization disorders and the sequelae associated therewith, including diabetes mellitus (Type I and Type-2), gestational diabetes, hyperglycemia, insulin resistance, abnormal glucose metabolism, "pre-diabetes" (Impaired Fasting Glucose (IFG) or Impaired Glucose Tolerance (IGT)), and other physiological disorders associated with, or that result from, the hyperglycemic condition, including, for example, histopathological changes such as pancreatic β-cell destruction; (2) dyslipidemias and their sequelae such as, for example, atherosclerosis, coronary artery disease, cerebrovascular disorders and the like; (3) other conditions which may be associated with the metabolic syndrome, such as obesity and elevated body mass (including the co-morbid conditions thereof such as, but not limited to, nonalcoholic fatty liver disease (NAFLD), nonalcoholic steatohepatitis (NASH), and polycystic ovarian syndrome (PCOS)), and also include thromboses, hypercoagulable and prothrombotic states (arterial and venous), hypertension, cardiovascular disease, stroke and heart failure; (4) disorders or conditions in which inflammatory reactions are involved, including atherosclerosis, chronic inflammatory bowel diseases (e.g., Crohn's disease and ulcerative colitis), asthma, lupus erythematosus, arthritis, or other inflammatory rheumatic disorders; (5) disorders of cell cycle or cell differentiation processes such as adipose cell tumors, lipomatous carcinomas including, for example, liposarcomas, solid tumors, and neoplasms; (6) neurodegenerative diseases and/or demyelinating disorders of the central and peripheral nervous systems and/or neurological diseases involving neuroinflammatory processes and/or other peripheral neuropathies, including Alzheimer's disease, multiple sclerosis, Parkinson's disease, progressive multifocal leukoencephalopathy and Guillian-Barre syndrome; (7) skin and dermatological disorders and/or disorders of wound healing processes, including erythemato-squamous dermatoses; and (8) other disorders such as syndrome X, osteoarthritis, and acute respiratory distress syndrome. Also described are methods of reducing fed and fasting blood glucose, improving insulin sensitivity and glucose tolerance, reducing systemic chronic inflammation, ameliorating hepatic steatosis in a mammal, reducing food intake, or combinations thereof, by administering a therapeutically effective amount of a disclosed modified FGF-1 polypeptide (or nucleic acid molecules encoding such).

In some embodiments, the modified FGF-1 polypeptides are administered for wound healing. Examples of wounds include, but are not limited to, abrasions, avulsions, blowing wounds (e.g., open pneumothorax), burn wounds, contusions, gunshot wounds, incised wounds, open wounds, penetrating wounds, perforating wounds, puncture wounds, séton wounds, stab wounds, surgical wounds, subcutaneous wounds, diabetic lesions, or tangential wounds. Additional examples of wounds that can be treated by the compounds and compositions described herein include acute conditions or wounds, such as thermal burns, chemical burns, radiation burns, burns caused by excess exposure to ultraviolet radiation (e.g., sunburn); damage to bodily tissues, such as the perineum as a result of labor and childbirth; injuries sustained during medical procedures, such as episiotomies; trauma-induced injuries including cuts, incisions, excoriations; injuries sustained from accidents; post-surgical injuries, as well as chronic conditions, such as pressure sores, bedsores, conditions related to diabetes and poor circulation, and all types of acne. In addition, the wound can include dermatitis, such as impetigo, intertrigo, folliculitis and eczema, wounds following dental surgery; periodontal disease; wounds following trauma; and tumor-associated wounds. Yet other examples of wounds include animal bites, arterial disease, insect stings and bites, bone infections, compromised skin/muscle grafts, gangrene, skin tears or lacerations, skin aging, surgical incisions, including slow or non-healing surgical wounds, intracerebral hemorrhage, aneurysm, dermal asthenia, and post-operation infections.

A therapeutic peptide of the present invention may also be used to treat external wounds caused by, but not limited to scrapes, cuts, lacerated wounds, bite wounds, bullet wounds, stab wounds, burn wounds, sun burns, chemical burns, surgical wounds, bed sores, radiation injuries, all kinds of acute and chronic wounds, wounds or lesions created by cosmetic skin procedures. The peptide may also be used to ameliorate the effects of skin aging. The peptide may accelerate wound healing in an external wound and/or improve the cosmetic appearance of wounded areas, or skin subject to aging and disease. The peptide may be used to treat internal injury caused by, but not limited to, disease, surgery, gunshots, stabbing, accidents, infarcts, ischemic injuries, to organs and tissues including but not limited to heart, bone, brain, spinal cord, retina, peripheral nerves and other tissues and organs commonly subject to acute and chronic injury, disease, congenital and developmental malformation and aging processes.

In some embodiments, the modified FGF-1 polypeptides are administered for treating burn injury. Exemplary burn wounds include, but are not limited to, "burn ulcers" including, for example, ulceration that occur as a result of a burn injury, including a first degree burn (i.e., superficial, reddened area of skin); a second degree burn (a blistered injury site which may heal spontaneously after the blister fluid has been removed); a third degree burn (burn through the entire skin and usually require surgical intervention for wound healing); scalding (may occur from scalding hot water, grease or radiator fluid); a thermal burn (may occur from flames, usually deep burns); a chemical burn (may come from acid and alkali, usually deep burns); an electrical burn (either low voltage around a house or high voltage at work); an explosion flash (usually superficial injuries); and contact burns (usually deep and may occur from muffler tail pipes, hot irons, and stoves). As used herein, a delayed or difficult to heal wound may include, for example, a wound that is characterized at least in part by 1) a prolonged inflammatory phase, 2) a slow forming extracellular matrix (ECM), and 3) a decreased rate of epithelialization. It has been shown that growth factors, e.g. FGF-1, play an important role in nerve regeneration and nerve healing. FGF-1 has been suggested for use in regenerating nervous system tissue following spinal cord injury or trauma, such as brachial plexus injury, neuroimmunologic disorders, such as acute or idiopathic transverse myelitis (TM), or any other disease or condition where regeneration and/or protection of neurons or neural tissue is desired, since FGF-1 is believed to stimulate neural proliferation and growth and may be neuroprotective. See, e.g., Cheng, H. et al., "Spinal Cord Repair with Acidic Fibroblast Growth Factor as a Treatment for a Patient with Chronic Paraplegia," SPINE 29(14):E284-E288 (2004); and Lin, P-H., "Functional recovery of chronic complete idiopathic transverse myelitis after administration of neurotrophic factors," Spinal Cord 44:254-257 (2006). FGF-1 is known to have a neurotrophic activity, promote axonal growth, and exert beneficial effects in models of spinal cord injury and axon regeneration. Accordingly, in some embodiments the modified FGF-1 polypeptide of the present disclosure promotes neural regeneration and can be used in methods of treating conditions that benefit from neural regeneration. In some example methods, the neurological condition is amyotrophic lateral sclerosis (ALS). In some example methods, the neurological condition is acute or idiopathic transverse myelitis (TM). In certain instances, the modified FGF-1 polypeptide can be administered in combination with other growth factors, as well as other pharmaceutically active components, for treating conditions that benefit from neural; regeneration.

Pharmaceutical Compositions, Methods of Administration, and Dosing

Pharmaceutical compositions comprising a modified FGF-polypeptide as described herein may be formulated in a conventional manner using one or more physiologically acceptable carriers including excipients and auxiliaries which facilitate processing of the active compounds into preparations which can be used pharmaceutically. Proper formulation is dependent upon the route of administration chosen. Additional details about suitable excipients for pharmaceutical compositions described herein may be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

A pharmaceutical composition, as used herein, refers to a mixture of a modified FGF with other chemical components, such as carriers, stabilizers, diluents, dispersing agents, suspending agents, thickening agents, and/or excipients, and, optionally, other therapeutic and/or prophylactic ingredients. The pharmaceutical composition facilitates administration of the modified FGF to an organism. In practicing the methods of treatment or use provided herein, therapeutically effective amounts of modified FGF-1 polypeptides described herein are administered in a pharmaceutical composition to a mammal having an ocular disease, disorder, or condition to be treated. In some embodiments, the mammal is a human. A therapeutically effective amount can vary widely depending on the severity of the disease, the age and relative health of the subject, the potency of the compound used and other factors. A pharmaceutically acceptable or suitable composition includes an ophthalmologically suitable or acceptable composition.

A pharmaceutical composition (e.g., for delivery by injection or for application as an eye drop) may be in the form of a liquid or solid. A liquid pharmaceutical composition may include, for example, one or more of the following: sterile diluents such as water for injection, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose. A parenteral preparation can be enclosed in ampoules, disposable syringes or multiple dose vials made of glass or plastic. Physiological saline is commonly used as an excipient, and an injectable pharmaceutical composition or a composition that is delivered ocularly (for example, as an eye drop) is preferably sterile.

A modified FGF-polypeptide or pharmaceutical composition described herein can be delivered to a subject by any suitable means, including, for example, topically, intraocularly, intracamerally, orally, parenterally, intravenously, intraperitoneally, intranasally (or other delivery methods to the mucous membranes, for example, of the nose, throat, and bronchial tubes), or by local administration to the eye, or by an intraocular or periocular device. Modes of local administration can include, for example, topical application, eye drops, intraocular injection or periocular injection. Periocular injection typically involves injection of the compound under the conjunctiva or into the Tennon's space (beneath the fibrous tissue overlying the eye). Intraocular injection typically involves injection of the modified FGF or pharmaceutical composition into the vitreous. In certain embodiments, the administration is non-invasive, such as by topical application or eye drops. In some embodiments, the administration is via a combination of topical and intracameral method.

A modified FGF or pharmaceutical composition described herein can be formulated for administration using pharmaceutically acceptable (suitable) carriers or vehicles as well as techniques routinely used in the art. A pharmaceutically acceptable or suitable carrier includes an ophthalmologically suitable or acceptable carrier. A carrier is selected according to the solubility of the particular modified FGF. Suitable ophthalmological compositions and formulations include those that are administrable locally to the eye, such as by eye drops, injection or the like. In the case of eye drops, the formulation can also optionally include, for example, ophthalmologically compatible agents such as isotonizing agents such as sodium chloride, concentrated glycerin, and the like; buffering agents such as sodium phosphate, sodium acetate, and the like; surfactants such as polyoxyethylene sorbitan mono-oleate (also referred to as Polysorbate 80), polyoxyl stearate 40, polyoxyethylene hydrogenated castor oil, and the like; stabilization agents such as sodium citrate, sodium edentate, and the like; preservatives such as benzalkonium chloride, parabens, and the like; and other ingredients. Preservatives can be employed, for example, at a level of from about 0.001 to about 1.0% weight/volume. The pH of the formulation is usually within the range acceptable to ophthalmologic formulations, such as within the range of about pH 4 to 8.

For injection, the modified FGF or pharmaceutical composition can be provided in an injection grade saline solution, in the form of an injectable liposome solution, slow-release polymer system or the like. Intraocular and periocular injections are known to those skilled in the art and are described in numerous publications including, for example, Spaeth, Ed., *Ophthalmic Surgery: Principles of Practice*, W. B. Sanders Co., Philadelphia, Pa., 85-87, 1990.

In some embodiments, the modified FGF or pharmaceutical composition (e.g., an ophthalmic formulation) is administered via microneedles into the cornea (Jiang et al. (2007). *Invest Ophthalmol Vis Sci* 48(9): 4038-4043). A microneedle array is coated with the modified FGF or pharmaceutical composition and pressed against the cornea such that the microneedles penetrate into the corneal stroma but do not penetrate the entire cornea. It is then removed, and the modified FGF or pharmaceutical composition is left behind in the corneal stroma. This modified FGF or pharmaceutical composition can stimulates the corneal cells to proliferate and migrate, and suppresses the scarring response that the stromal cells normally have.

For delivery of a composition comprising at least one of the modified FGF-1 polypeptides described herein via a mucosal route, which includes delivery to the nasal passages, throat, and airways, the composition may be delivered in the form of an aerosol. The compound may be in a liquid or powder form for intramucosal delivery. For example, the composition may be delivered via a pressurized aerosol container with a suitable propellant, such as a hydrocarbon propellant (e.g., propane, butane, isobutene). The composition may be delivered via a non-pressurized delivery system such as a nebulizer or atomizer.

Suitable oral dosage forms include, for example, tablets, pills, sachets, or capsules of hard or soft gelatin, methylcellulose or of another suitable material easily dissolved in the digestive tract. Suitable nontoxic solid carriers can be used which include, for example, pharmaceutical grades of mannitol, lactose, starch, magnesium stearate, sodium saccharin, talcum, cellulose, glucose, sucrose, magnesium carbonate, and the like. (See, e.g., *Remington: The Science and Practice of Pharmacy* (Gennaro, $21^{st}$ Ed. Mack Pub. Co., Easton, Pa. (2005)).

The modified FGF-1 polypeptides or pharmaceutical compositions described herein may be formulated for sustained or slow-release. Such compositions may generally be prepared using well known technology and administered by, for example, periocular, intraocular, rectal, oral or subcutaneous implantation, or by implantation at the desired target site, or by topical application. Sustained-release formulations may contain an agent dispersed in a carrier matrix and/or contained within a reservoir surrounded by a rate controlling membrane. Excipients for use within such formulations are biocompatible, and may also be biodegradable; preferably the formulation provides a relatively constant level of active component release. The amount of active compound contained within a sustained-release formulation depends upon the site of implantation, the rate and expected duration of release, and the nature of the condition to be treated or prevented.

Systemic drug absorption of a drug or composition administered via an ocular route is known to those skilled in the art (see, e.g., Lee et al., *Int. J. Pharm.* 233:1-18 (2002)). In one embodiment, a compound described herein is delivered by a topical ocular delivery method (see, e.g., *Curr. Drug Metab.* 4:213-22 (2003)). The composition may be in the form of an eye drop, salve, or ointment or the like, such as, aqueous eye drops, aqueous ophthalmic suspensions, non-aqueous eye drops, and non-aqueous ophthalmic suspensions, gels, ophthalmic ointments, etc. For preparing a gel, for example, carboxyvinyl polymer, methyl cellulose, sodium alginate, hydroxypropyl cellulose, ethylene maleic anhydride polymer and the like can be used.

In another embodiment, the modified FGF solution or pharmaceutical composition (e.g., an ophthalmic formulation) contains hyaluronic acid, carboxymethyl cellulose, or other polysaccharides that provide increased ocular tolerability, viscosity and osmolality to produce a comfortable ocular solution.

The dose of the modified FGF or pharmaceutical composition comprising at least one of the modified FGF-1 polypeptides described herein may differ, depending upon the patient's (e.g., human) condition, that is, stage of the ocular disease, disorder, or condition, general health status, age, and other factors that a person skilled in the medical art will use to determine dose. When the composition is used as eye drops, for example, one to several drops per unit dose, preferably 1 or 2 drops (about 50 µl per 1 drop), may be applied about 1 to about 6 times daily.

Pharmaceutical compositions may be administered in a manner appropriate to the disease, disorder, or condition to be treated (or prevented) as determined by persons skilled in the medical arts. An appropriate dose and a suitable duration and frequency of administration will be determined by such factors as the condition of the patient, the type and severity of the patient's disease, disorder, or condition, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free, or a lessening of symptom severity). For prophylactic use, a dose should be sufficient to prevent, delay the onset of, or diminish the severity of an ocular disease, disorder, or condition. Optimal doses may generally be determined using experimental models and/or clinical trials. The optimal dose may depend upon the body mass, weight, or blood volume of the patient.

In various embodiments, a modified FGF-1 polypeptide of the present disclosure may be administered as a daily dose over a period of time to a subject. In some embodiments, a modified FGF-1 polypeptide of the present disclosure may be administered chronically or long-term. In some embodiments, a modified FGF-1 polypeptide of the present disclosure may be administered for a period of days, weeks, months, years or continued therapy over the lifetime of a subject. In some embodiments, a modified FGF-1 polypeptide of the present disclosure may be administered for a period of about 7 days, 15 days, about 21 days, about 30 days, about 3 months, about 6 months, about 12 months, about 18 months, about 2 years, about 5 years, about 7 years, about 10 years, about 15 years, about 20 years, about 25 years, about 30 years, about 35 years, or about 40 years. In some embodiments, a treatment regime may be determined for an individual subject dependent on various factors. In some examples, the treatment regimen is dependent on the level of exposure to a compound causing a chemical or thermal injury, such as a vesicant compound. In some embodiments, the treatment regimen is about 2 weeks for an acute exposure and several months to a year for a long term exposure. In some embodiments, the treatment regimen is chronic. In some examples, a factor may include, but not be limited to, a determination of the change in the extent of degeneration of corneal tissue in response to administration of a modified FGF-1 polypeptide of the present disclosure. In some examples, a factor may include, but not be limited to, amelioration of MGK sequelae in response to administration of a modified FGF-1 polypeptide of the present disclosure. In some examples, a factor may include, but not be limited to, healing of corneal endothelial lesions in response to administration of a modified FGF-1 polypeptide of the present disclosure. In some examples, a factor may include, but not be limited to, corneal epithelial cell proliferation in response to administration of a modified FGF-1 polypeptide of the present disclosure. In some examples, a factor may include, but not be limited to, reduction of symptoms associated with Fuch's dystrophy in response to administration of a modified FGF-1 polypeptide of the present disclosure. In embodiments, a subject exhibiting an immediate response to the composition, for example, an immediate reduction in symptoms associated with Fuch's dystrophy, may require less frequent doses than a subject exhibiting a response to the composition at a later time or after several doses.

The doses of the modified FGF-1 polypeptides or pharmaceutical compositions can be suitably selected depending on the clinical status, condition and age of the subject, dosage form and the like. In the case of eye drops, a modified FGF described herein can be administered, for example, from about 10 ug/ml to about 100 mg/ml of the modified FGF one to seven times per week.

Also provided are methods of manufacturing the modified FGF-1 polypeptides and pharmaceutical compositions described herein. A composition comprising a pharmaceutically acceptable excipient or carrier and at least one of the modified FGF-1 polypeptides described herein may be prepared by synthesizing the modified FGF according to any one of the methods described herein or practiced in the art and then formulating the compound with a pharmaceutically acceptable carrier. Formulation of the composition will be appropriate and dependent on several factors, including but not limited to, the delivery route, dose, and stability of the compound.

At least one modified FGF described herein can be administered to human or other nonhuman vertebrates. In certain embodiments, the modified FGF is substantially pure, in that it contains less than about 5% or less than about 1%, or less than about 0.1%, of other organic molecules, such as contaminating intermediates or by-products that are created, for example, in one or more of the steps of a synthesis method. In other embodiments, a combination of one or more modified FGF-1 polypeptides described herein can be administered.

The compositions described herein can be administered for prophylactic and/or therapeutic treatments. In therapeutic applications, the compositions are administered to a patient already suffering from a disease or condition, in an amount sufficient to cure or at least partially arrest the symptoms of the disease or condition. Amounts effective for this use will depend on the severity and course of the disease or condition, previous therapy, the patient's health status, weight, and response to the drugs, and the judgment of the treating physician.

In prophylactic applications, compositions described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like.

In the case wherein the patient's condition does not improve, upon the doctor's discretion the administration of the compositions may be administered chronically, that is, for an extended period of time, including throughout the duration of the patient's life in order to ameliorate or otherwise control or limit the symptoms of the patient's disease or condition.

In the case wherein the patient's status does improve, upon the doctor's discretion the administration of the compositions may be given continuously; alternatively, the dose of drug being administered may be temporarily reduced or temporarily suspended for a certain length of time (i.e., a "drug holiday").

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained. Patients can, however, require intermittent treatment on a long-term basis upon any recurrence of symptoms.

The desired dose may conveniently be presented in a single dose or as divided doses administered simultaneously (or over a short period of time) or at appropriate intervals, for example as two, three, four or more sub-doses per day.

The pharmaceutical composition described herein may be in unit dosage forms suitable for single administration of precise dosages. In unit dosage form, the formulation is divided into unit doses containing appropriate quantities of one or more modified FGF-1 polypeptides. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative.

Toxicity and therapeutic efficacy of such therapeutic regimens can be determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are preferred. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized.

Combination Treatments

The modified FGF-1 polypeptides and pharmaceutical compositions may also be used in combination with other therapeutic agents that are selected for their therapeutic value for the condition to be treated. The modified FGF-1 polypeptides and pharmaceutical compositions may also be used in combination with other therapeutic agents that are selected for their therapeutic value for treating the vesicant injury. Such agents do not have to be administered in the same pharmaceutical composition, and may, because of different physical and chemical characteristics, have to be administered by different routes. The determination of the mode of administration and the advisability of administration, where possible, in the same pharmaceutical composition, is well within the knowledge of the clinician. The initial administration can be made according to established protocols recognized in the field, and then, based upon the observed effects, the dosage, modes of administration and times of administration can be modified by the clinician.

The particular choice of these optional additional agents used will depend upon the diagnosis of the attending physicians and their judgment of the condition of the patient and the appropriate treatment protocol. The agents may be administered concurrently (e.g., simultaneously, essentially simultaneously or within the same treatment protocol) or sequentially, depending upon the nature of the disease, disorder, or condition, the condition of the patient, and the actual choice of agents used. The determination of the order of administration, and the number of repetitions of administration of each therapeutic agent during a treatment protocol, is well within the knowledge of the physician after evaluation of the disease being treated and the condition of the patient.

The pharmaceutical agents which make up the combination therapy disclosed herein may be a combined dosage form or in separate dosage forms intended for substantially simultaneous administration. The pharmaceutical agents that make up the combination therapy may also be administered sequentially, with either therapeutic compound being administered by a regimen calling for two-step administration. The two-step administration regimen may call for sequential administration of the active agents or spaced-apart administration of the separate active agents. The time period between the multiple administration steps may range from, a few minutes to several hours, depending upon the properties of each pharmaceutical agent, such as potency, solubility, bioavailability, plasma half-life and kinetic profile of the pharmaceutical agent. Circadian variation of the target molecule concentration may also determine the optimal dose interval.

Therapeutically-effective dosages can vary when the drugs are used in treatment combinations. Methods for experimentally determining therapeutically-effective dosages of drugs and other agents for use in combination treatment regimens are described in the literature. For example, the use of metronomic dosing, i.e., providing more frequent, lower doses in order to minimize toxic side effects, has been described extensively in the literature. Combination treatment further includes periodic treatments that start and stop at various times to assist with the clinical management of the patient.

For example, the modified may be incorporated into formulations that contain other active ingredients such as steroids, antibiotics, anti-inflammatories, cytokines such as IL-1 or analogs of IL-1, or antagonists of cytokines such as inhibitors of IL-17.

Other exemplary cytokines include, but are not limited to, interleukins (e.g., IL-2, IL-3, IL-4, IL-5, IL-6, IL-7, IL-8, IL-9, IL-10, IL-11, IL-12, IL-13, IL-15, IL-16, IL-17, IL-18, IL-1α, IL-1β, and IL-1 RA), granulocyte colony stimulating factor (G-CSF), granulocyte-macrophage colony stimulating factor (GM-CSF), oncostatin M, erythropoietin, leukemia inhibitory factor (LIF), interferons, B7.1 (also known as CD80), B7.2 (also known as B70, CD86), TNF family members (TNF-α, TNF-β, LT-β, CD40 ligand, Fas ligand, CD27 ligand, CD30 ligand, 4-1BBL, Trail), and migration inhibitory factor MIF.

In some embodiments, combinations or pharmaceutical compositions described herein are administered in immunosuppressive therapy to reduce, inhibit, or prevent activity of the immune system. Immunosuppressive therapy is clinically used to: prevent the rejection of transplanted organs and tissues; treatment of autoimmune diseases or diseases that are most likely of autoimmune origin; and treatment of some other non-autoimmune inflammatory diseases.

In some embodiments, the modified FGF-1 polypeptides and pharmaceutical compositions described herein are administered with one or more anti-inflammatory agent including, but not limited to, non-steroidal anti-inflammatory drugs (NSAIDs) and corticosteroids (glucocorticoids).

NSAIDs include, but are not limited to: aspirin, salicylic acid, gentisic acid, choline magnesium salicylate, choline salicylate, choline magnesium salicylate, choline salicylate, magnesium salicylate, sodium salicylate, diflunisal, carprofen, fenoprofen, fenoprofen calcium, fluorobiprofen, ibuprofen, ketoprofen, nabutone, ketolorac, ketorolac tromethamine, naproxen, oxaprozin, diclofenac, etodolac, indomethacin, sulindac, tolmetin, meclofenamate, meclofenamate sodium, mefenamic acid, piroxicam, meloxicam, and COX-2 specific inhibitors (such as, but not limited to, celecoxib, rofecoxib, valdecoxib, parecoxib, etoricoxib, lumiracoxib, CS-502, JTE-522, L-745,337 and NS398).

Corticosteroids, include, but are not limited to: betamethasone, prednisone, alclometasone, aldosterone, amcinonide, beclometasone, betamethasone, budesonide, ciclesonide, clobetasol, clobetasone, clocortolone, clopredol, cortisone, cortivazol, deflazacort, deoxycorticosterone, desonide, desoximetasone, desoxycortone, dexamethasone, diflorasone, diflucortolone, difluprednate, fluclorolone, fludrocortisone, fludroxycortide, flumetasone, flunisolide, fluocinolone acetonide, fluocinonide, fluocortin, fluocortolone, fluorometholone, fluperolone, fluprednidene, fluticasone, formocortal, halcinonide, halometasone, hydrocortisone/cortisol, hydrocortisone aceponate, hydrocortisone buteprate, hydrocortisone butyrate, loteprednol, medrysone, meprednisone, methylprednisolone, methylprednisolone aceponate, mometasone furoate, paramethasone, prednicarbate, prednisone/prednisolone, rimexolone, tixocortol, triamcinolone, and ulobetasol.

Other agents used as anti-inflammatories include those disclosed in U.S. patent publication 2005/0227929, herein incorporated by reference.

Some commercially available anti-inflammatories include, but are not limited to: Arthrotec® (diclofenac and misoprostol), Asacol® (5-aminosalicyclic acid), Salofalk® (5-aminosalicyclic acid), Auralgan® (antipyrine and benzocaine), Azulfidine® (sulfasalazine), Daypro® (oxaprozin), Lodine® (etodolac), Ponstan® (mefenamic acid), Solumedrol® (methylprednisolone), Bayer® (aspirin), Bufferin®

(aspirin), Indocin® (indomethacin), Vioxx® (rofecoxib), Celebrex® (celecoxib), Bextra® (valdecoxib), Arcoxia® (etoricoxib), Prexige® (lumiracoxib), Advil®, Motrin® (ibuprofen), Voltaree® (diclofenac), Orudis® (ketoprofen), Mobic® (meloxicam), Relafen® (nabumetone), Aleve®, Naprosyn® (naproxen), Feldene® (piroxicam).

In one embodiment, compositions described herein are administered with leukotriene receptor antagonists including, but are not limited to, BAY u9773 (see EP 00791576; published 27 Aug. 1997), DUO-LT (Tsuji et al, *Org. Biomol. Chem.*, 1, 3139-3141, 2003), zafirlukast (Accolate®), montelukast (Singulair®), prankulast (Onon®), and derivatives or analogs thereof.

In some embodiments, the modified FGF-1 polypeptides and pharmaceutical compositions described herein are administered with one or more Rho kinase inhibitors. In some embodiments, the modified FGF-1 polypeptides and pharmaceutical compositions described herein are administered with one or more additional growth factors, including, but not limited to epidermal growth factor (EGF) and nerve growth factor (NGF). See, e.g., see Joyce et al. (2009) *Invest Ophthalmol. Vis Sci.* 50:2116-2122, vascular endothelial growth factor (VEGF), transforming growth factor alpha and beta (TGF-alpha and TFG-beta), platelet-derived endothelial growth factor (PD-ECGF), platelet-derived growth factor (PDGF), tumor necrosis factor alpha (TNF-alpha), hepatocyte growth factor (HGF), insulin like growth factor (IGF), erythropoietin, colony stimulating factor (CSF), macrophage-CSF (M-CSF), granulocyte/macrophage CSF (GM-CSF) and nitric oxidcsynthase (NOS).

Kits/Articles of Manufacture

For use in the therapeutic applications described herein, kits and articles of manufacture are also provided herein. Such kits can include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. The containers can be formed from a variety of materials such as glass or plastic.

The articles of manufacture provided herein contain packaging materials. Packaging materials for use in packaging pharmaceutical products include, e.g., U.S. Pat. Nos. 5,323, 907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of ophthalmic formulations of the modified FGF-1 polypeptides and pharmaceutical compositions provided herein are contemplated as are a variety of treatments for any ocular disease, disorder, or condition that would benefit by administration of a modified FGF ore pharmaceutical composition described herein.

For example, the container(s) can include a modified FGF such as a modified FGF-1 having a sequence of SEQ ID NO: 2. The container(s) optionally have a sterile access port. Such kits optionally comprising compounds with an identifying descriptions or labels or instructions relating to their use in the methods described herein.

A kit will typically may include one or more additional containers, each with one or more of various materials (such as reagents, optionally in concentrated form, and/or devices) desirable from a commercial and user standpoint for use of a modified FGF described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

In certain embodiments, a modified FGF pharmaceutical composition can be presented in a pack or dispenser device which can contain one or more unit dosage forms containing a compound provided herein. The pack can for example contain metal or plastic foil, such as a blister pack. The pack or dispenser device can be accompanied by instructions for administration. The pack or dispenser can also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration for prescription drugs, or the approved product insert. Compositions containing a modified FGF provided herein formulated in a compatible pharmaceutical carrier can also be prepared, placed in an appropriate container, and labeled for treatment of an indicated condition.

EXAMPLES

These examples are provided for illustrative purposes only and not to limit the scope of the claims provided herein. The starting materials and reagents used in the examples described herein may be synthesized or can be obtained from commercial sources.

Example 1: Exemplary Modified FGF-1 Polypeptide with an N-Terminal Methionine (N-Met) has Similar Activity as a Version without the N-Met The study is directed towards modified FGF-1 polypeptides comprising the sequence of SEQ ID NO: 2 (N-Met-TTHX1114) or SEQ ID NO: 205 (TTHX1001). The modified FGF-1 polypeptides are generated using methods as described above in the Recombinant Techniques section.

Experimental Methods and Results

The biological activity of the test polypeptides are assessed in a NIH-3T3 cell proliferation assay. Results indicate no difference between the modified FGF-1 polypeptides of SEQ ID NO: 2 and SEQ ID NO: 205, in terms of effectivity in inducing proliferation of the fibroblast cells.

Example 2: Effects of Modified FGF-1 Polypeptides on Human Corneal Endothelial Cell (HCEC) Proliferation The study is directed towards modified FGF-1 polypeptides comprising the sequence of SEQ ID NO: 2 (N-Met-TTHX1114) or SEQ ID NO: 205 (TTHX1001). The modified FGF-1 polypeptides are generated using methods as described above in the Recombinant Techniques section.

Experimental Methods and Results

Primary cultures (passage 1) of human corneal endothelial cells from a healthy donor are seeded onto 24 well plates in the presence of fetal bovine serum (FBS, 8%) and 24 hours later treated with the varying concentrations of N-Met-TTHX1114 (SEQ ID NO: 2), TTHX1001 (SEQ ID NO: 205), or wt-FGF-1 (SEQ ID NO: 1) in media with low (0.8%) FBS. The 8% FBS group serves as positive control. Results indicate that N-Met-TTHX1114 is more potent than TTHX1001 or wt-FGF-1 in stimulating human corneal epithelial cell proliferation and is dose responsive therein. The $EC_{50}$ of N-Met-TTHX1114 is about 100-fold lower than the wt-FGF-1 or the other tested modified FGF-1 polypeptide (TTHX1001; SEQ ID NO: 205).

Example 3: Nitrogen Mustard Induced Injury of Cornea

The study is directed towards the effect of modified FGF-1 polypeptides comprising the sequence of SEQ ID NO: 2 (N-Met-TTHX1114) on treatment of nitrogen mustard (NM) induced corneal injury. The modified FGF-1 polypeptides are generated using methods as described above in the Recombinant Techniques section.

Experimental Methods

Figure 3:
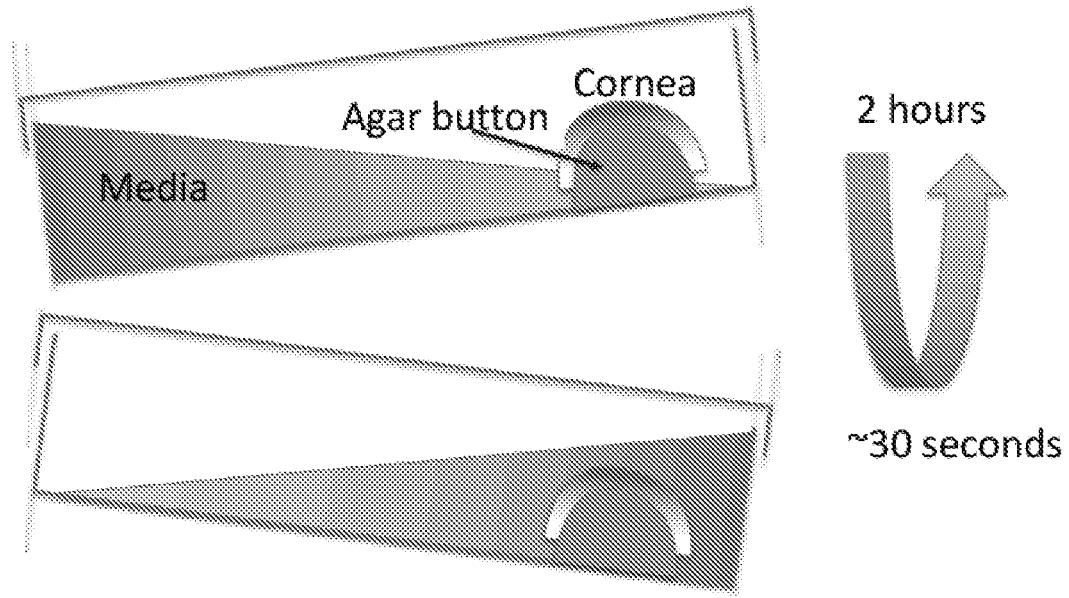
FIG. 3 illustrates an exemplary rabbit corneal organ culture model system.

A rabbit corneal organ culture model system was used to evaluate healing after exposure to NM. Rabbit eyes (8-12 weeks old) are obtained and corneas with 2-mm scleral rims are dissected from the eyes, placed epithelial-side down into a spot plate, and the concavities were filled with 558 C molten agar (0.75%) in Dulbecco's modified Eagle's medium (DMEM). A non-limiting example of the set-up is shown in FIG. 3. Once the solution is gelled, the corneas are inverted so that the epithelial layer is accessible. Cultures are placed in 60-mm diameter pyrex tissue culture dishes. High glucose DMEM is prepared containing 13MEM-NEAA (minimal essential medium non-essential amino acids), 13 RMPI 1640 Vitamin Solution, 13 antibiotic/antimycotic, ascorbic acid (0.45 mM), and ciprofloxacin (10 lg/ml). High glucose DMEM is added up to the scleral rims, leaving the corneas exposed to air. The dishes are placed in a 37° C. humidified incubator with 5% $CO_2$. The epithelium of each culture is moistened with 5004 medium, added dropwise onto the central cornea every 7 to 9 hours. The vesicating agent, NM, is added dropwise onto the central cornea. Cornea samples (peeled off their agar support) are either put epithelial side down in cryomolds containing Optimal Cutting Temperature (OCT, Tissue-Tek; Sakura, Torrance, Calif., USA) compound and flash frozen for histology and immunofluorescence, or directly snap frozen for further protein analyses including Western blot and ADAM17 activity assays (InnoZyme TACE activity assay kit; Calbiochem, Billerica, Mass., USA).

NM is used to induce corneal injury. NM, in powdered solid form (catalog No. 122564; Sigma-Aldrich) is first dissolved in PBS to 100 mM, and then diluted with medium to 10 mM. Ten microliters are applied to deliver 100 nmol vesicant to the cornea. After applying NM onto the central corneas, the cultures are returned to the 37° C. incubator for 2 hours without removing the vesicant. After this incubation, contaminated medium is removed, and fresh medium is added to the central cornea until the level in the dish reached the top of the scleral rim. Control unexposed and exposed corneas are then returned to 37° C. for a 22-hour incubation, being removed for only three short periods to add 20 μL medium to the exposed samples not receiving N-Met-TTHX1114 therapy, or to add 20 μL of N-Met-TTHX1114 as therapy to the central corneas. The first-met-TTHX1114 application is left on for 8 hours, the second for 9 hours, and the third for 5 hours. Thus, the length of the 2-hour exposure and the subsequent treatment is 24 hours in total.

For experiments analyzing how fast NM exposure induced ADAM17, cultures are set up as described. For the shortest exposure time, the NM solution is applied to a cornea, then immediately washed off and the sample is put in protein isolation extraction buffer. This is repeated with two other corneas to collect three 0-minute exposures. For the 5- and 10-minute exposures, NM is added to the sets of three corneas accordingly, insuring none are accidentally under- or overexposed to NM. All corneas are extracted and processed for ADAM17 activity assays.

The InnoZyme ADAM17/TACE Activity Kit (Calbiochem) is used to quantify the enzyme's activity from corneal extracts according to the vendor's provided protocol. Briefly, 400 μL wash buffer (from the InnoZyme kit) is applied to 96-well plates precoated with anti-human ADAM17 antibody, followed by two washes. Triplicate samples of corneal extracts and InnoZyme kit standards (100 μL) are each added to three sets of wells. Plates are sealed and incubated 1 hour with gentle shaking at room temperature. Then, plates are washed with 400 μL wash buffer five times. ADAM17 substrate supplied in the kit (100 μL) is added to each well and incubated for 5 hours at 37° C. Fluorescence is measured at an excitation wavelength of 324 nm and an emission wavelength of 405 nm, and is reported as relative fluorescence units on graphs. For immunodetection of ADAM17, OCT-embedded sections on slides are first fixed in 20° C. methanol for 10 minutes. Nonspecific binding is blocked for 1 hour with 5% normal goat serum (NGS) in PBS with 0.05% Tween-20 (PBST). A mouse monoclonal antibody against the ectodomain (amino acids 18-671) of human ADAM 17 (5 μg/mL in 1.5% NGS, MAB9304; R&D Systems, Minneapolis, Minn., USA), which is found to detect only the active enzyme by immunofluorescence, is applied to the slides for a 1-hour incubation at room temperature, then the slides are washed three times for 10 minutes in PBST. For negative control slides, the same volume of PBST is applied to sections as that of primary antibody used on test sections, followed by the same wash volume. Goat anti-mouse IgG conjugated to AlexaFluor488 (1:1000; Invitrogen, Carlsbad, Calif., USA) in 1.5% NGS is applied for 1 hour at room-temperature incubation. After washing with PBST three times for 5 minutes, 0.4 mg/mL DAPI is applied to sections for 5 minutes to counterstain the nuclei. Prolong Gold is used in cover slipping the slides.

Results

Histopathology of NM Induced Injury in Corneal Organ Cultures

Injury inflicted by NM includes the following: (a) hyperplasia of the epithelial layer, which is apparent by the increase in the number and depth of epithelial cells pushing down into the stroma. This is referred to as downward hyperplasia. Unexposed (naïve) cornea shows some downward hyperplasia but it isn't as extensive as cornea exposed to NM; (b) basal cell nuclei rising up toward the top of the basal epithelial cells; and (c) epithelial-stromal separation. The histopathological effects are visible as early as four days post-exposure. An exemplary histopathological grading scheme for assessing the effects of NM induced corneal injury is shown in FIG. 6. Histopathological grading is improved by treatment with N-Met-TTHX1114. The N-Met-TTHX1114 treated corneal sections exhibit lower score (indicative of lesser injury) compared to sections from untreated corneas.

Treatment of NM Exposed Corneal Cells with N-Met-TTHX1114 Protects Against Injury Treatment of NM-exposed cornea with TTHX1114 protects the cornea from histopathological injury induced by NM. Following NM-exposure, the N-Met-TTHX1114 treated cornea does not exhibit downward hyperplasia. Further, epithelial-stromal separation is not visible in corneas treated with N-Met-TTHX1114.

NM Exposures Reduces FGF-1 Levels in Rabbit Cornea

Figure 9:
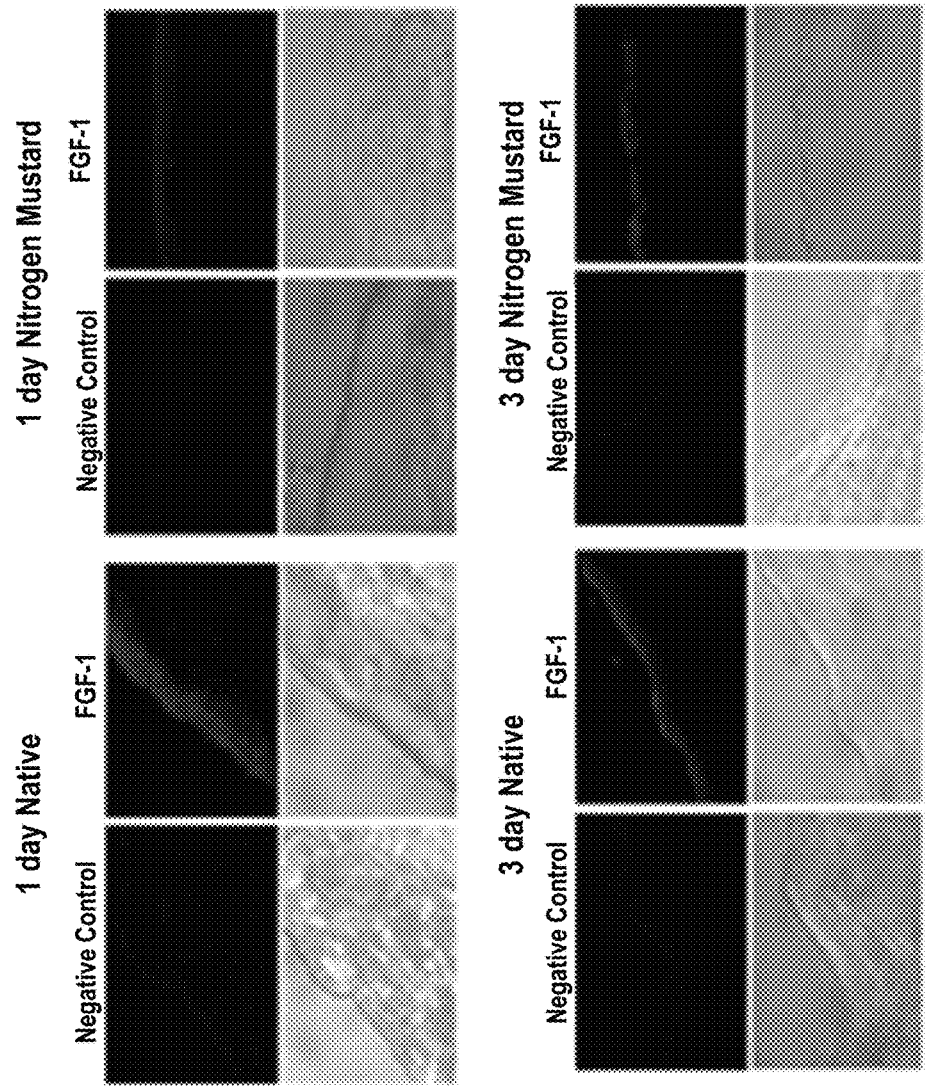
FIG. 9 demonstrates corneal levels of FGF-1 following exposure to a vesicant.

Rabbit corneal sections, exposed to NM, are incubated with anti-FGF-1 antibodies. In exposed corneas, a reduction of FGF-1 level is observed, as shown in FIG. 9. Corneal sections exposed to NM, 1 day (upper panel of FIG. 9), and 3 days (lower panel of FIG. 9) post-exposure, demonstrate enhanced suppression of FGF-1 compared to naïve corneal sections.

NM Exposures Induces ADAM17 Activation in Rabbit Cornea

In NM exposed corneas, intense fluorescent signal is observed at the basement membrane zone where the ADAM17 enzyme would need to be positioned in order to degrade collagen XVII ADAM17 is not appreciably detected in unexposed corneas.

N-Met-TTHX1114 Treatment Reduces NM Exposure Induced ADAM17 Activation in Rabbit Cornea Upon treatment of corneas with TTH1114, ADAM17 fluorescent signal is attenuated in peripheral and central cornea. The attenuation or lack of ADAM17 fluorescent signal corresponds with better histologic appearance of the corneal epithelial-stromal junction.

N-Met-TTHX1114 Treatment Ameliorates NM Exposure Induced Suppression of Corneal Epithelial Proliferation Peripheral corneal epithelial layer stimulation is assessed by via EdU incorporation of corneal epithelial cells (CECs). Primary cultures of rabbit CECs are established using standard procedures, e.g., the procedure described by Kay et al. (Kay et al. Investigative ophthalmology & visual science. 1993; 34(3):663-72; Lee et al., Investigative ophthalmology & visual science. 2009; 50(5):2067-76). The cells are exposed to NM for two hours. Proliferation assays are performed in 12-well plates using, e.g., a Click-IT assay kit (Life Technologies). Incorporation of EdU into corneal epithelial cells is an indicator of epithelial proliferation. The percentage corneal epithelial cells incorporating EdU are lower when treated with N-Met-TTHX1114, following NM-exposure, compared to untreated controls.

Example 4: Sulfur Mustard Induced Injury of Corneal Endothelial Cells

The study is directed towards the effect of modified FGF-1 polypeptides comprising the sequence of SEQ ID NO: 2 (N-Met-TTHX1114) on treatment of sulfur mustard (SM) induced corneal injury. The modified FGF-1 polypeptides are generated using methods as described above in the Recombinant Techniques section.

Experimental Methods

Rabbits are exposed to sulfur mustard in cohorts of 8 to 16 animals during a 4-month period. One day before exposure, a 4-in$^2$ region on each rabbit's back is clipped, and a fentanyl patch (25 µg/h) is placed anterior to the scapula. On the day of exposure, rabbits are anesthetized with an intramuscular administration of 15 mg/kg of ketamine and 7 mg/kg of xylazine, and physiological parameters are recorded. The corneas of anesthetized rabbits are exposed to SM vapor for 2.5 min. Two minutes after exposure, exposed eyes are gently rinsed with 10 mL sterile saline to flush residual agent.

A first group of rabbits are euthanized 24 hours after exposure. Five minutes after euthanasia, 20 µL of a 0.1 mg/mL solution of AlexaFluor 488 (Life Technologies, Carlsbad, Calif.) dissolved in PBS (pH 7.4) is injected into the anterior chamber through a 30-gauge needle using a 100-µL Hamilton glass syringe (Hamilton Company, Reno, Nev.). After 10 minutes, corneas are excised and washed three times for 1 minute in 10 mL PBS. Corneas are transferred to 14-mL round-bottom tubes (Becton Dickinson, Franklin Lakes, N.J.) with 100 µL PBS and incubated on ice in the dark with gentle agitation. After 30 minutes, supernatant is diluted 1:5 in PBS and analyzed for fluorescence on a Synergy MX fluorophotometer (Biotek, Winooski, Vt.) using an excitation wavelength of 488±10 nm, emission wavelength of 524±10 nm, and a gain of 50. Representative corneas are imaged with a blue diode and FITC filter set in a Versadoc MP 4000 (Bio-Rad Laboratories, Hercules, Calif.).

The remaining rabbits are further divided into a test group, treated with N-Met-TTHX1114 at varying doses, and a sham control group, treated with control vehicle. The treatments are carried out for about two weeks. Rabbits are returned to cages and provided food and water ad libitum. Fentanyl patches are replaced after every 72 hours to manage discomfort through 6 days after the exposure and applied liberally thereafter as needed. Animals are monitored daily for signs of pain and distress. Corneal injury is clinically evaluated on a regular basis using pachymetry, fluorescein exclusion assays, and slit-lamp evaluations.

Results

Sulfur Mustard (SM) Exposure Causes Corneal Endothelial Injury

Corneas visualized at 370 nm by scanning electron microscopy (SEM) 24 hours after SM exposure exhibit a centripetal injury, with extensive loss of corneal endothelial cells (CECs) in the central cornea and increased retention toward the exposure margins. To obtain a more comprehensive overview of SM-induced changes in the corneal endothelium, the fine structure of the posterior cornea is evaluated by electron microscopy. Enface scanning electron micrographs of unexposed corneas reveals a continuous layer of polygonal cells of regular shape and size, with interdigitated borders, apical microvilli, and infrequent cilia. Within 24 hours of exposure, all corneal endothelia exhibit evidence of an acute lesion, with extensive central CEC loss and more diffuse vesication in the exposure penumbra. The CECs within the exposed region displays two general morphologies, namely, enlarged (highly attenuated) polymorphic cells and rounded or spindle-shaped cells. Most CECs exhibit atypical apical membrane morphologies and lack cell-to-cell interdigitations. In regions of CEC vesication, denuded Descemet's membrane (DM) is covered by a complex arbor of CEC lamellipodia and filopodia. The TEM imaging of corneal cross-sections confirmed the centripetal injury pattern, with CEC morphology progressively normalizing toward the injury margin. Denuded DM near the central lesion is infiltrated by extensively arborized cellular processes. At more distal regions, overlapping cellular processes with loss of junctional complexes is common, suggestive of a motile population. The rounded CEC population observed by SEM is found exclusively overlying polymorphic endothelium and display signs of necrosis or apoptosis.

Treatment with N-Met-TTHX1114 Resolves Corneal Endothelial Injuries

Eight weeks after exposure, endothelial cell morphology and structure are compared between test group (also referred to as resolved eyes) and sham control group (which later develops MGK). Resolved eyes are distinguished by the absence of characteristic MGK sequelae during clinical evaluations such as corneal erosions, neovascularization, or corneal haze and had corneal thicknesses that are statistically indistinguishable from sham-exposed controls by 6 weeks. Enface scanning micrographs of resolved eyes are found to be strikingly similar to sham-exposed controls, with a well-organized monolayer of polygonal cells. The average CEC size is increased in resolved eyes compared with control corneas; otherwise, resolved corneas do not exhibit significant variability across the posterior surface. In contrast, the sham-control treated rabbits with MGK endothelia reveal extensive variability in cell shape and cell size among animals, indicative of a dynamic injury process. Focal variability in endothelial morphology is routinely observed in individual corneas, with some regions exhibiting enlarged but mosaic CECs and other regions displaying significant disorganization, with variable degrees of apical blebbing, areas showing denuded DM, and clearly delineated cell boundaries lacking. These phenomena are not observed in the N-Met-TTHX1114 treated resolved endothelium. Transmission Electron Microscope images of N-Met-TTHX1114 treated resolved corneas are very similar to naïve endothelium. In contrast, sham-control treated endothelium with MGK pathology exhibit diffusive thickening of the posterior DM, consistent with either edema and/or the deposition of a retrocorneal fibrous membrane. The MGK corneas also exhibit extensive markers of CEC stress or injury, including cytoplasmic rarefication, excessive vacuolization, and swollen endoplasmic reticuli. There is a high frequency of overlapping cell processes, similar to 24-hour images and suggestive of an ongoing attempt to repopulate recently denuded DM.

Example 5: Modified FGF-1 (N-Met-TTHX1114) is Effective in Wound Healing

This study is directed towards the effect of a modified FGF-1 polypeptide comprising the sequence of SEQ ID NO: 2 (N-Met-TTHX1114) on rate of wound healing.

Experimental Methods

Female C57BL/Ks-db/db diabetic mice, 11 weeks old, are obtained from Jackson Laboratories, and housed in sterile microisolator boxes with sterile water and bedding and are kept in a semi-barrier quarantine facility.

Skin Organ Culture

Skin biopsy specimens from healing impaired mice are cultured in suitable culture medium. Briefly, tissue samples are incubated at 37° C. in DMEM (Gibco) medium supplemented with 0.25% heat-inactivated bovine serum (Gibco). The skin specimens are treated daily for 2 days or 3 days with 0, 1, 10, and 100 μg/mL N-Met-TTHX1114. The tissue samples are then labeled for 24 hours with 4 μCi of [methyl-$^3$H]thymidine (from a stock solution containing 20 Ci/mmol; New England Biolabs). After thymidine labeling, the skin specimens are washed, solubilized, and assayed for radioactivity count.

Wound-Closure Model

Mice are anesthetized with intraperitoneal injections of 110 mg ketamine and 9 mg xylazine per kg of body weight. The mid-back and thoracic skin is shaved and disinfected with a 2% chlorhexidine surgical scrub followed by a 70% ethanol.

A template 1.6 cm in diameter is used to mark a 2.0-cm$^2$ circle on the mid-dorsal area, and a single full-thickness wound is created by blunt excision with sterile curved iris scissors. Wound areas typically increase to approximately 2.3 cm$^2$ soon after injury, presumably because of contraction of the dermis along the wound perimeter. All surgical and subsequent healing analysis procedures are performed in a laminar flow hood using a full aseptic techniques. Filter-sterilized growth factors, at varying doses, and corresponding vehicle control solutions are applied topically, on days 0, 3, and 7 after injury. The wounds are covered with a semi-transparent Bioclusive dressing for protection, maintenance of a moist environment, and prevention of crust formation. Wound fluid samples are taken at day 10 after injury and cultured for aerobic and anaerobic microorganisms. Animals from cultures that exhibit more than 50 colonies per wound are excluded from the study analysis. Prevention of even mild or subclinical infection results in a consistent maximal healing impairment, thus providing a large wound-healing window for evaluation of treatment effects.

Healing Analysis

Wound appearances are recorded photographically, and their perimeters are traced onto sterile glass slides applied directly to the exposed wound surfaces after prewetting with a drop of sterile physiologic saline.

Measurements are made immediately after wounding and twice weekly thereafter until the wounds are completely closed. Wound areas and perimeters are determined from the glass-slide tracings using suitable computerized image analysis (e.g., using Presage C V-6; Advanced Imaging Concepts, Princeton, N.J.). Statistical significances of differences between groups are evaluated using an unpaired two-tailed Student t test. Healing expressed as a decrease in percent initial area is converted to linear ingrowth from the wound edges by dividing the difference in wound areas by the average wound perimeters at sequential time intervals. Total ingrowth at a specific time is the sum of the incremental ingrowth distances up until that time. This transformation linearizes closure as a function of time, thereby allowing expression of healing as kinetic rates that are constant over time. Wounds are considered fully healed when moist granulation tissue is no longer apparent, indicating a functional epidermal water-permeability barrier.

Results

Skin biopsy specimens, from the healing impaired mice, incorporates [methyl-$^3$H] thymidine in response to daily doses of N-Met-TTHX1114. The cells within the skin respond mitogenically to N-Met-TTHX1114 in a dose-dependent manner. Thus, N-Met-TTHX111 induces DNA synthesis in skin organ cultures.

Further, full-thickness dermal excisional wounds, about 1.6 cm in diameter, close substantially faster in responses of doses of N-Met-TTHX1114, applied during the first week following wound initiation, compared to treatment with control vehicle. Thus, N-Met-TTHX1114 accelerates wound closure.

Moreover, gross appearance and mean size of vehicle and N-Met-TTHX1114 treated wounds differ significantly. The N-Met-TTHX1114 treated wounds show signs of neovascularization, such as visible reddening and leakage of serous fluids, as early as 3 days following treatment. In contrast, the wounds receiving control vehicle contain little or no visible serous fluids and substantially less apparent signs of neoangiogenesis.

Example 6: Treatment of Herpetic Keratopathy Using a Modified FGF-1 Polypeptides (N-Met-TTHX1114 or TTHX-1114)

This study is directed towards using a modified FGF-1 polypeptide comprising the sequence of SEQ ID NO: 2 (N-Met-TTHX1114) or SEQ ID NO: 205 (TTHX1001) for the treatment of herpetic keratopathy.

Methods

A group of patients with herpetic keratopathy is selected for this study. The patients are divided into three subgroups. Patients in the first sub-group are administered, ocularly, an ophthalmic formulation, such as an eye drop, containing about 500 pg/ml (i.e., 5 µg/ml) of N-met TTHX1114 (SEQ ID NO: 2) formulated in phosphate buffered saline (at pH 7.2), 0.3% propylene glycol, 0.4% polyethylene glycol 400, and 0.05% hydroxypropyl guar. Patients in the second sub-group are administered, ocularly, an ophthalmic formulation, such as an eye drop, containing about 500 pg/ml (i.e., 5 µg/ml) of TTHX1001 (SEQ ID NO: 205) formulated in phosphate buffered saline (at pH 7.2), 0.3% propylene glycol, 0.4% polyethylene glycol 400, and 0.05% hydroxypropyl guar. Patients in the third sub-group are administered, ocularly, a sham ophthalmic formulation that does not contain the N-Met-TTHX1114 (SEQ ID NO: 2) or the TTHX1001 (SEQ ID NO: 205) but is otherwise identical to what is administered to the first and the second sub-group. For all three subgroups, the eye drop is either self-administered by the patient or administered by a nurse or a caregiver. The N-Met-TTHX1114 (SEQ ID NO: 2) containing ophthalmic formulation, the TTHX1001 (SEQ ID NO: 205) containing ophthalmic formulation, and the sham ophthalmic formulation are administered, respectively to patients in the first, second, and the third sub-group, twice daily for up to 30 days.

Results

It is observed that the ophthalmic formulation containing the N-Met-TTHX1114 (SEQ ID NO: 2) and the ophthalmic formulation containing the TTHX1001 (SEQ ID NO: 205) results in healing of the herpetic corneal ulcer within about 14 days in majority of the patients belonging to the first and the second sub-groups, along with reduction in the duration of pain and inflammation. Furthermore, eyes of patients in the first and the second sub-groups, treated respectively with the N-Met-TTHX1114 (SEQ ID NO: 2) containing ophthalmic formulation and the TTHX1001 (SEQ ID NO: 205) containing ophthalmic formulation have less corneal haze and scarring than patients in the third sub-group, who were treated with the sham.

Example 7: Treatment of Chronic Herpetic Keratopathy Using a Modified FGF-1 Polypeptides (N-Met-TTHX1114 or TTHX-1001)

This study is directed towards using a modified FGF-1 polypeptide comprising the sequence of SEQ ID NO: 2 (N-Met-TTHX1114) or SEQ ID NO: 205 (TTHX1001) for the treatment of chronic herpetic keratopathy.

Methods

A group of patients with chronic herpetic keratopathy is selected for this study. The patients are divided into three subgroups. Patients in the first sub-group are administered, ocularly, an ophthalmic formulation, such as an eye drop, containing about 500 pg/ml (i.e., 5 µg/ml) of N-Met-TTHX1114 (SEQ ID NO: 2) formulated in phosphate buffered saline (at pH 7.2), 0.3% propylene glycol, 0.4% polyethylene glycol 400, and 0.05% hydroxypropyl guar. Patients in the second sub-group are administered, ocularly, an ophthalmic formulation, such as an eye drop, containing about 500 pg/ml (i.e., 5 µg/ml) of TTHX1001 (SEQ ID NO: 205) formulated in phosphate buffered saline (at pH 7.2), 0.3% propylene glycol, 0.4% polyethylene glycol 400, and 0.05% hydroxypropyl guar. Patients in the third sub-group are administered, ocularly, a sham ophthalmic formulation that does not contain the N-Met-TTHX1114 (SEQ ID NO: 2) or the TTHX1001 (SEQ ID NO: 205) but is otherwise identical to what is administered to the first and the second sub-group. For all three subgroups, the eye drop is either self-administered by the patient or administered by a nurse or a caregiver. The N-Met-TTHX1114 (SEQ ID NO: 2) containing ophthalmic formulation, the TTHX1001 (SEQ ID NO: 205) containing ophthalmic formulation, and the sham ophthalmic formulation are administered, respectively to patients in the first, second, and the third sub-group, twice daily for up to 30 days.

Results

It is observed that the ophthalmic formulation containing the N-Met-TTHX1114 (SEQ ID NO: 2) and the ophthalmic formulation containing the TTHX1001 (SEQ ID NO: 205) result in healing of corneal ulcer in majority of the patients belonging to the first and the second sub-groups, along with reduction in of pain and inflammation. Furthermore, eyes of patients in the first and the second sub-groups, treated respectively with the N-Met-TTHX1114 (SEQ ID NO: 2) containing ophthalmic formulation and the TTHX1001 (SEQ ID NO: 205) containing ophthalmic formulation, have less corneal opacity haze and scarring than patients in the third sub-group, who are treated with the sham.

Example 8: Treatment of Neurotrophic Keratopathy Using Modified FGF-1 Polypeptides (N-Met-TTHX1114 or TTHX-1001)

This study is directed towards using a modified FGF-1 polypeptide comprising the sequence of SEQ ID NO: 2 (N-Met-TTHX1114) or SEQ ID NO: 205 (TTHX1001) for the treatment of neurotrophic keratopathy secondary to herpes infection.

Methods

A group of patients with neurotrophic keratopathy is selected for this study. The patients are divided into three subgroups. Patients in the first sub-group are administered, ocularly, an ophthalmic formulation, such as an eye drop, containing about 500 pg/ml (i.e., 5 µg/ml) of N-Met-TTHX1114 (SEQ ID NO: 2) formulated in phosphate buffered saline (at pH 7.2), 0.3% propylene glycol, 0.4% polyethylene glycol 400, and 0.05% hydroxypropyl guar. Patients in the second sub-group are administered, ocularly, an ophthalmic formulation, such as an eye drop, containing about 500 pg/ml (i.e., 5 µg/ml) of TTHX1001 (SEQ ID NO: 205) formulated in phosphate buffered saline (at pH 7.2), 0.3% propylene glycol, 0.4% polyethylene glycol 400, and 0.05% hydroxypropyl guar. Patients in the third sub-group are administered, ocularly, a sham ophthalmic formulation that does not contain the N-Met-TTHX1114 (SEQ ID NO: 2) or the TTHX1001 (SEQ ID NO: 205) but is otherwise identical to what is administered to the first and the second sub-group. For all three subgroups, the eye drop is either self-administered by the patient or administered by a nurse or a caregiver. The N-Met-TTHX1114 (SEQ ID NO: 2)

containing ophthalmic formulation, the TTHX1001 (SEQ ID NO: 205) containing ophthalmic formulation, and the sham ophthalmic formulation are administered, respectively to patients in the first, second, and the third sub-group, twice daily for up to 30 days.

Results

It is observed that the ophthalmic formulation containing the N-Met-TTHX1114 (SEQ ID NO: 2) and the ophthalmic formulation containing the TTHX1001 (SEQ ID NO: 205) result in healing of corneal ulcer in majority of the patients belonging to the first and the second sub-groups, along with reduction in of pain and inflammation. Furthermore, eyes of patients in the first and the second sub-groups, treated respectively with the N-Met-TTHX1114 (SEQ ID NO: 2) containing ophthalmic formulation and the TTHX1001 (SEQ ID NO: 205) containing ophthalmic formulation, have less corneal opacity haze and scarring than patients in the third sub-group, who are treated with the sham.

Example 9: Treatment of Recurrent Herpetic Keratopathy and the Suppression of Reactivation of Latent Virus Using Modified FGF-1 Polypeptides (N-Met-TTHX1114 or TTHX1001)

This study is directed towards using a modified FGF-1 polypeptides comprising the sequence of SEQ ID NO: 2 (N-Met-TTHX1114) or SEQ ID NO: 205 (TTHX1001) for the treatment of neurotrophic keratopathy secondary to herpes infection.

Methods

A group of patients with recurrent keratopathy is selected for this study. The patients have experienced at least one episode of herpetic keratopathy. For treatment of recurrent herpetic keratopathy and the suppression of reactivation of latent virus, the patients are divided into three subgroups. Patients in the first sub-group are administered, ocularly, an ophthalmic formulation, such as an eye drop, containing about 50 pg/ml to about 500 pg/ml (i.e., 5 µg/ml) of N-Met-TTHX1114 (SEQ ID NO: 2) formulated in phosphate buffered saline (at pH 7.2), 0.3% propylene glycol, 0.4% polyethylene glycol 400, and 0.05% hydroxypropyl guar. Patients in the second sub-group are administered, ocularly, an ophthalmic formulation, such as an eye drop, containing about 50 pg/ml to 500 pg/ml (i.e., 5 µg/ml) of TTHX1001 (SEQ ID NO: 205) formulated in phosphate buffered saline (at pH 7.2), 0.3% propylene glycol, 0.4% polyethylene glycol 400, and 0.05% hydroxypropyl guar. Patients in the third sub-group are administered, ocularly, a sham ophthalmic formulation that does not contain the N-Met-TTHX1114 (SEQ ID NO: 2) or the TTHX1001 (SEQ ID NO: 205) but is otherwise identical to what is administered to the first and the second sub-group. For all three subgroups, the eye drop is either self-administered by the patient or administered by a nurse or a caregiver. The N-Met-TTHX1114 (SEQ ID NO: 2) containing ophthalmic formulation, the TTHX1001 (SEQ ID NO: 205) containing ophthalmic formulation, and the sham ophthalmic formulation are administered, respectively to patients in the first, second, and the third sub-group, twice daily for up to 30 days.

Results

It is observed that the ophthalmic formulations containing the N-Met-TTHX1114 (SEQ ID NO: 2) and the ophthalmic formulation containing the TTHX1001 (SEQ ID NO: 205) increase the disease free interval and reduces the severity of the reactivated virus lesions, with patients receiving the modified FGF-1 having a longer period of time without recurrent disease than patients in the third sub-group, who are treated with the sham.

Example 10: Effects of Modified FGF-1 Polypeptides on Human Corneal Endothelial Cell (HCEC) Proliferation The study is directed towards modified FGF-1 polypeptides comprising the sequence of SEQ ID NO: 206 (TTHX1114) or SEQ ID NO: 205 (TTHX1001). The modified FGF-1 polypeptides are generated using methods as described above in the Recombinant Techniques section.

Experimental Methods and Results

Figure 2:
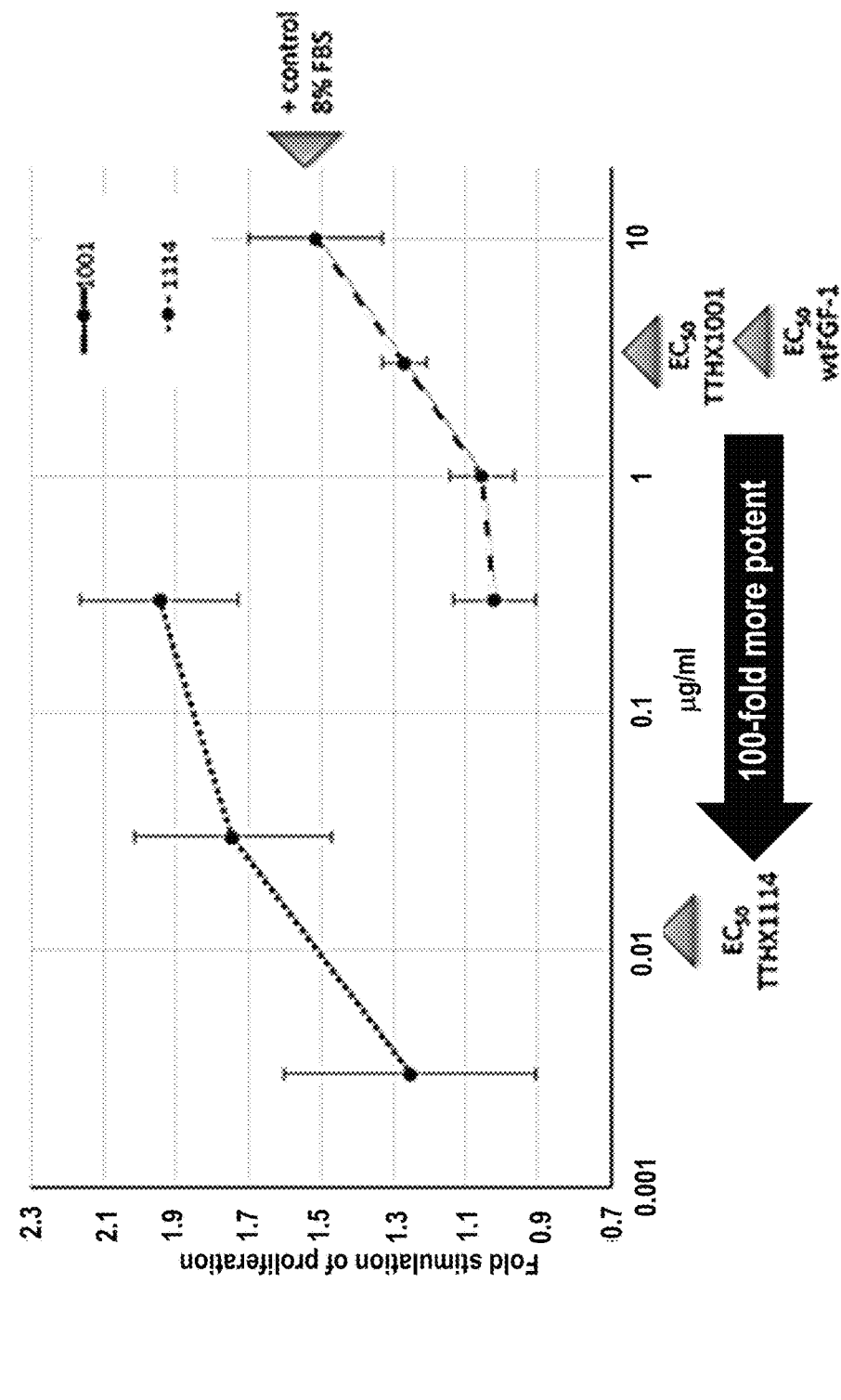
FIG. 2 illustrates the effect of exemplary modified FGF-1 polypeptides (TTHX1114 and TTHX1001) according to the present disclosure on the in vitro proliferation of human corneal endothelial cells. The dotted line corresponds to TTHX1114 and the dashed line corresponds to TTHX1001.

Primary cultures (passage 1) of human corneal endothelial cells from a healthy donor are seeded onto 24 well plates in the presence of fetal bovine serum (FBS, 8%) and 24 hours later treated with the varying concentrations of TTHX1114 (SEQ ID NO: 206), TTHX1001 (SEQ ID NO: 205), or wt-FGF-1 (SEQ ID NO: 1) in media with low (0.8%) FBS. The 8% FBS group serves as positive control. Results indicated that TTHX1114 was more potent than TTHX1001 or wt-FGF-1 in stimulating human corneal epithelial cell proliferation and was dose responsive therein. The $EC_{50}$ of TTHX1114 was about 100-fold lower than the wt-FGF-1 or the other tested modified FGF-1 polypeptide (TTHX1001; SEQ ID NO: 205), as illustrated in FIG. 2.

Example 11: Nitrogen Mustard Induced Injury of Cornea

The study is directed towards the effect of modified FGF-1 polypeptides comprising the sequence of SEQ ID NO: 206 (TTHX1114) on treatment of nitrogen mustard (NM) induced corneal injury. The modified FGF-1 polypeptides were generated using methods as described above in the Recombinant Techniques section.

Experimental Methods

A rabbit corneal organ culture model system was used to evaluate healing after exposure to NM. Rabbit eyes (8-12 weeks old) were obtained and corneas with 2-mm scleral rims were dissected from the eyes, placed epithelial-side down into a spot plate, and the concavities were filled with 558 C molten agar (0.75%) in Dulbecco's modified Eagle's medium (DMEM). A non-limiting example of the sett-up is shown in FIG. 3. Once the solution gelled, the corneas were inverted so that the epithelial layer was accessible. Cultures were placed in 60-mm diameter pyrex tissue culture dishes. High glucose DMEM was prepared containing 13MEM-NEAA (minimal essential medium non-essential amino acids), 13 RMPI 1640 Vitamin Solution, 13 antibiotic/antimycotic, ascorbic acid (0.45 mM), and ciprofloxacin (10 µg/ml). High glucose DMEM was added up to the scleral rims, leaving the corneas exposed to air. The dishes were placed in a 37° C. humidified incubator with 5% $CO_2$. The epithelium of each culture was moistened with 500 µL medium, added dropwise onto the central cornea every 7 to 9 hours. The vesicating agent, NM, was added dropwise onto the central cornea. Cornea samples (peeled off their agar support) were either put epithelial side down in cryomolds containing Optimal Cutting Temperature (OCT, Tissue-Tek; Sakura, Torrance, Calif., USA) compound and flash frozen for histology and immunofluorescence, or directly snap frozen for further protein analyses including Western blot and ADAM17 activity assays (InnoZyme TACE activity assay kit; Calbiochem, Billerica, Mass., USA).

NM was used to induce corneal injury. NM, in powdered solid form (catalog No. 122564; Sigma-Aldrich) was first dissolved in PBS to 100 mM, and then diluted with medium to 10 mM. Ten microliters were applied to deliver 100 nmol vesicant to the cornea. After applying NM onto the central corneas, the cultures were returned to the 37° C. incubator for 2 hours without removing the vesicant. After this incubation, contaminated medium was removed, and fresh medium was added to the central cornea until the level in the dish reached the top of the scleral rim. Control unexposed and exposed corneas were then returned to 37° C. for a 22-hour incubation, being removed for only three short periods to add 20 µL medium to the exposed samples not receiving TTHX1114 therapy, or to add 20 µL of TTHX1114 as therapy to the central corneas. The first TTHX1114 application was left on for 8 hours, the second for 9 hours, and the third for 5 hours. Thus, the length of the 2-hour exposure and the subsequent treatment was 24 hours in total.

For experiments analyzing how fast NM exposure induced ADAM17, cultures were set up as described. For the shortest exposure time, the NM solution was applied to a cornea, then immediately washed off and the sample was put in protein isolation extraction buffer. This was repeated with two other corneas to collect three 0-minute exposures. For the 5- and 10-minute exposures, NM was added to the sets of three corneas accordingly, insuring none were accidentally under- or overexposed to NM. All corneas were extracted and processed for ADAM17 activity assays.

The InnoZyme ADAM17/TACE Activity Kit (Calbiochem) was used to quantify the enzyme's activity from corneal extracts according to the vendor's provided protocol. Briefly, 400 µL wash buffer (from the InnoZyme kit) was applied to 96-well plates precoated with anti-human ADAM17 antibody, followed by two washes. Triplicate samples of corneal extracts and InnoZyme kit standards (100 µL) were each added to three sets of wells. Plates were sealed and incubated 1 hour with gentle shaking at room temperature. Then, plates were washed with 400 µL wash buffer five times. ADAM17 substrate supplied in the kit (100 µL) was added to each well and incubated for 5 hours at 37° C. Fluorescence was measured at an excitation wavelength of 324 nm and an emission wavelength of 405 nm, and was reported as relative fluorescence units on graphs. For immunodetection of ADAM17, OCT-embedded sections on slides were first fixed in 208 C methanol for 10 minutes. Nonspecific binding was blocked for 1 hour with 5% normal goat serum (NGS) in PBS with 0.05% Tween-20 (PBST). A mouse monoclonal antibody against the ectodomain (amino acids 18-671) of human ADAM 17 (5 µg/mL in 1.5% NGS, MAB9304; R&D Systems, Minneapolis, Minn., USA), which was found to detect only the active enzyme by immunofluorescence, was applied to the slides for a 1-hour incubation at room temperature, then the slides were washed three times for 10 minutes in PBST. For negative control slides, the same volume of PBST was applied to sections as that of primary antibody used on test sections, followed by the same wash volume. Goat anti-mouse IgG conjugated to AlexaFluor488 (1:1000; Invitrogen, Carlsbad, Calif., USA) in 1.5% NGS was applied for 1 hour at room-temperature incubation. After washing with PBST three times for 5 minutes, 0.4 mg/mL DAPI was applied to sections for 5 minutes to counterstain the nuclei. Prolong Gold was used in cover slipping the slides.

Results

Histopathology of NM Induced Injury in Corneal Organ Cultures

Figure 4:
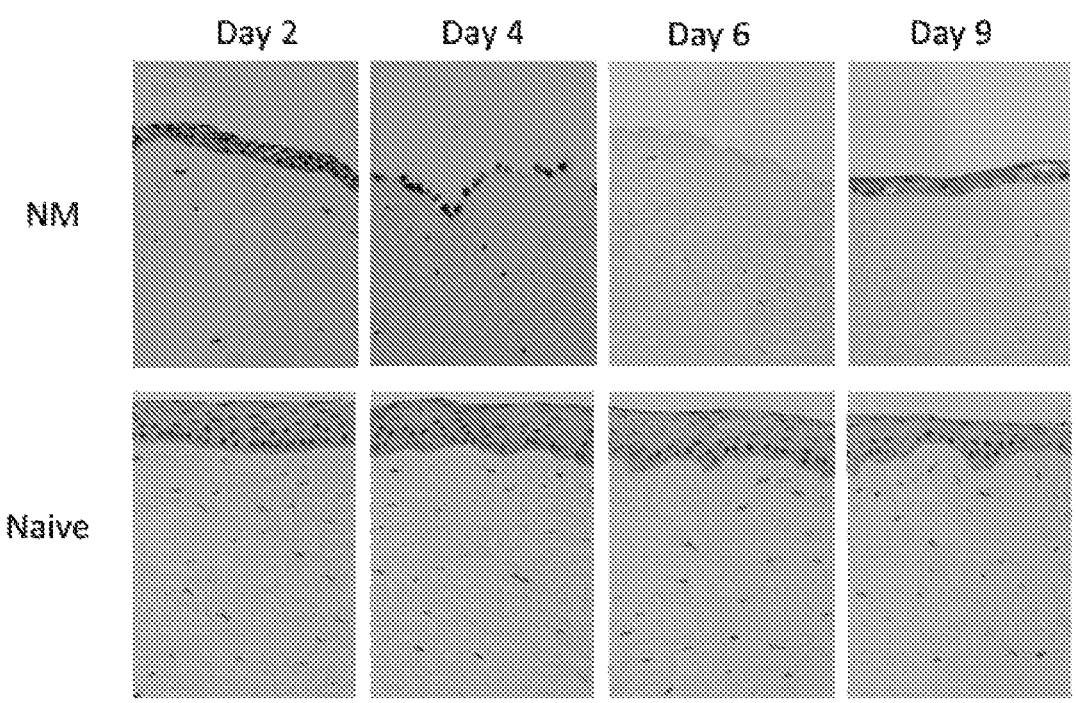
FIG. 4 shows a time course for vesicant injury to the cornea.

Injury inflicted by NM included the following: (a) hyperplasia of the epithelial layer, which was apparent by the increase in the number and depth of epithelial cells pushing down into the stroma. This is referred to as downward hyperplasia. Unexposed (naïve) cornea (FIG. 4, lower panel) also showed some downward hyperplasia but it wasn't as extensive as cornea exposed to NM (FIG. 4, upper panel); (b) basal cell nuclei rising up toward the top of the basal epithelial cells; and (c) epithelial-stromal separation. The histopathological effects were visible as early as four days post-exposure.

Figure 7:
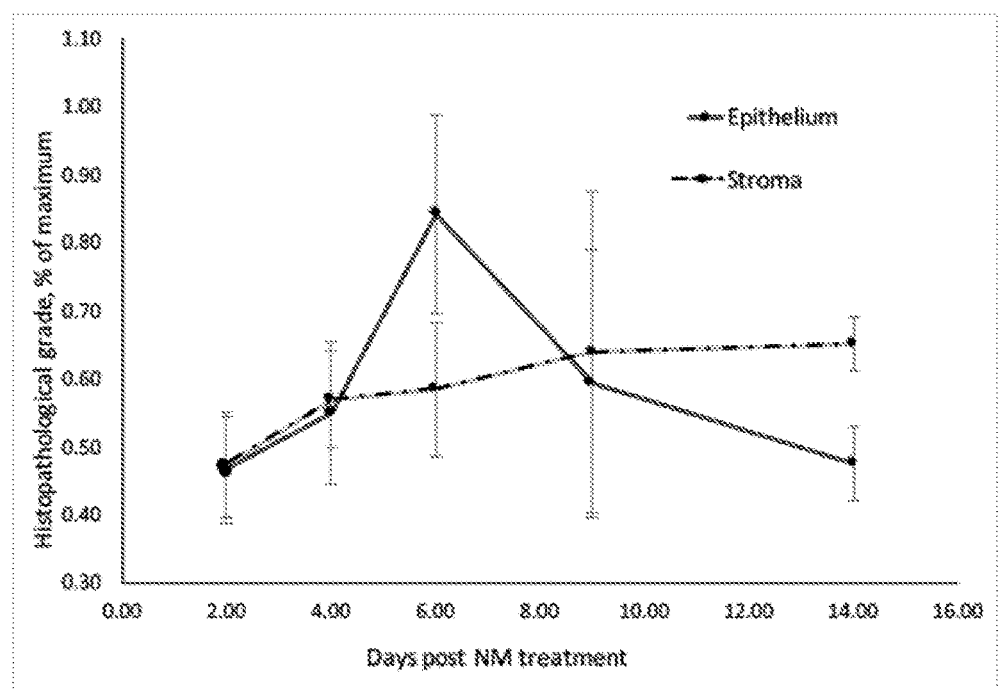
FIG. 7 shows histopathological grading of corneal and stromal injury upon vesicant exposure. The continuous like corresponds to "Epithelium," and the dashed line corresponds to 'Stroma."

An exemplary histopathological grading scheme for assessing the effects of NM induced corneal injury is shown in FIG. 6, and NM induced histopathological grading of corneal and stromal injuries is also illustrated in the plot of FIG. 7.

Treatment of NM Exposed Corneal Cells with TTHX1114 Protects Against Injury

Figure 5:
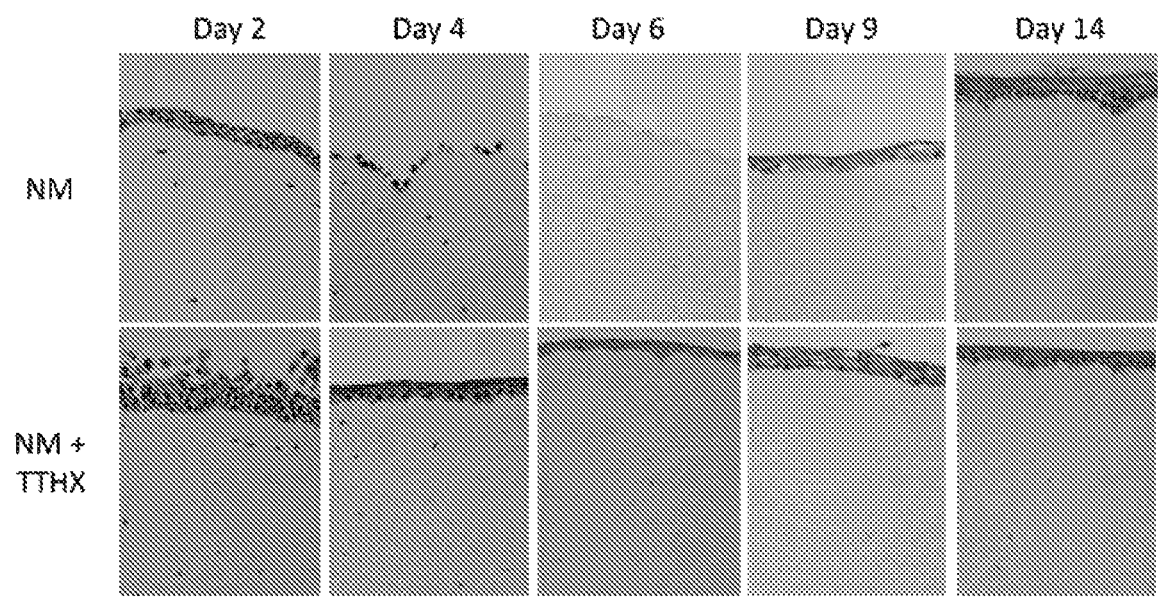
FIG. 5 illustrates the effect of treatment with an exemplary modified FGF-1 polypeptide (TTHX114), upon vesicant induced injury, assessed by histopathological staining.

Treatment of NM-exposed cornea with TTHX1114 protected the cornea from histopathological injury induced by NM. As seen in FIG. 5, on day 4 following NM-exposure, the TTHX1114 treated cornea did not exhibit downward hyperplasia (compare upper and lower panels of FIG. 5). Further, epithelial-stromal separation, as seen in upper panel of FIG. 4, was not visible in corneas treated with TTHX1114 (day 6, lower panel, FIG. 5).

Figure 8:
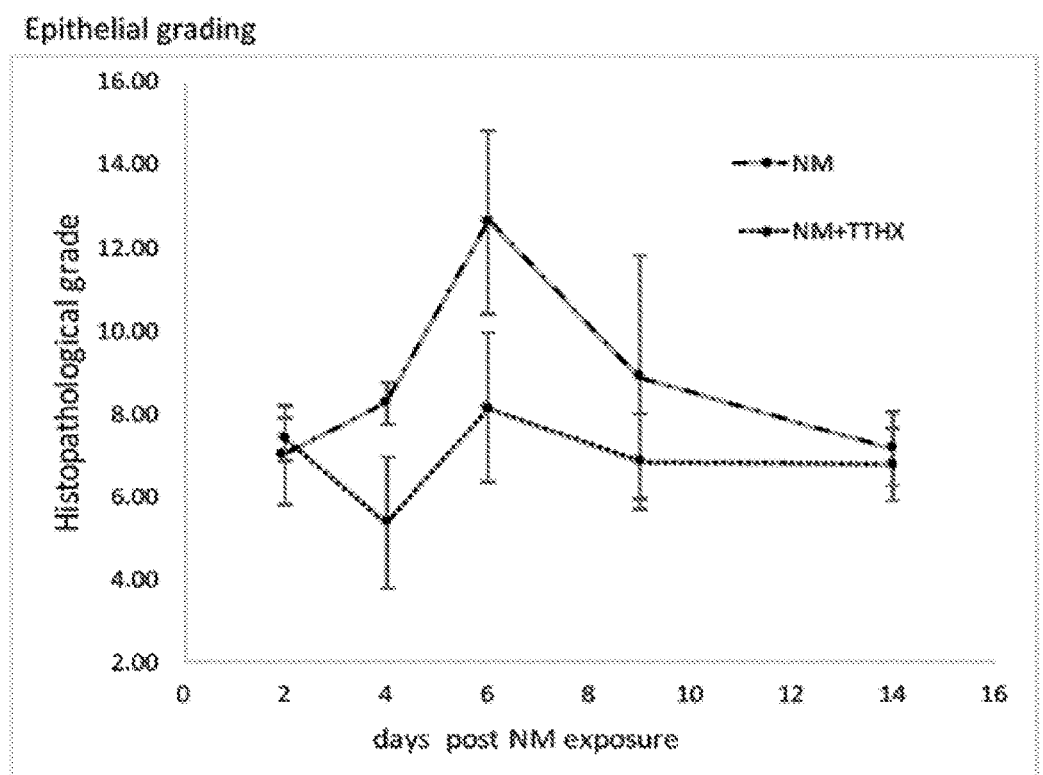
FIG. 8 shows reduced histopathological grading of vesicant injury in corneal cells treated with an exemplary modified FGF-1 polypeptide (TTHX1114). The dashed line corresponds to "NM" and the dotted line corresponds to "NM+TTHX."

Histopathological grading of NM induced injury was also found to be reduced in corneas treated with TTHX1114. The results are shown in FIG. 8.

TTHX1114 Protects NM Exposures Reduces FGF-1 Levels in Rabbit Cornea

Rabbit corneal sections, exposed to NM, were incubated with anti-FGF-1 antibodies. In exposed corneas, a reduction of FGF-1 level was observed, as shown in FIG. 9. Corneal sections exposed to NM, 1 day (upper panel of FIG. 9), and 3 days (lower panel of FIG. 9) post-exposure, demonstrated enhanced suppression of FGF-1 compared to naïve corneal sections.

NM Exposures Induces ADAM17 Activation in Rabbit Cornea

Figure 10A:
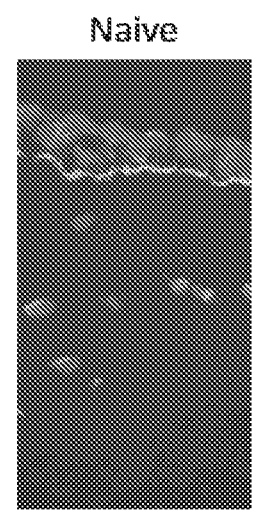
FIG. 10A shows a corneal section which was not exposed to NM.
Figure 10B:
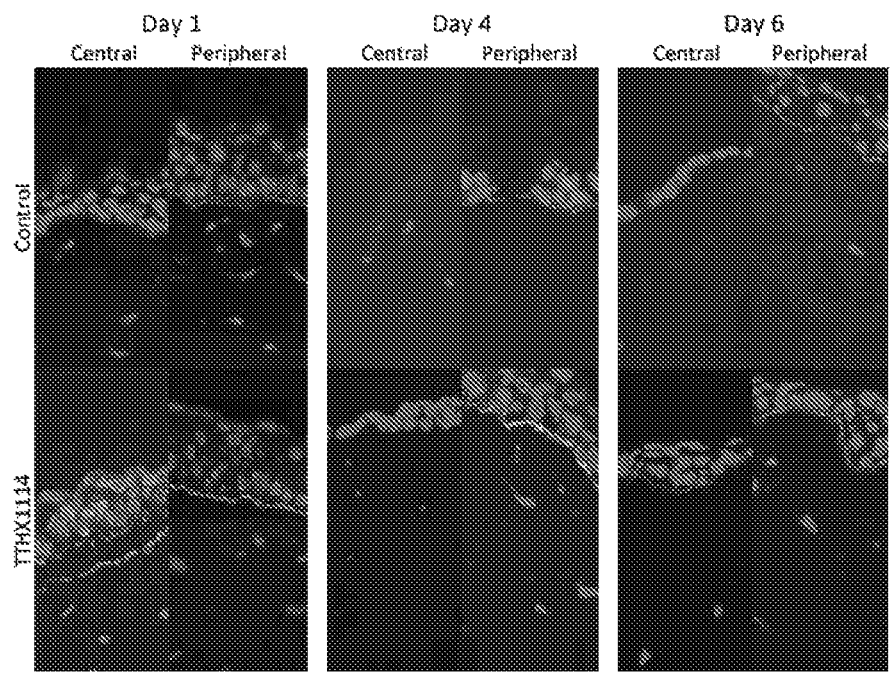
FIG. 10B shows a comparison of exposed cornea with (lower panel) or without (upper panel) treatment with an exemplary polypeptide (TTHX1114).

In NM exposed corneas, intense fluorescent signal was observed at the basement membrane zone where the ADAM17 enzyme would need to be positioned in order to degrade collagen XVII (upper panel of FIG. 10B showing ADAM17 immunofluorescence results on days 1, 4, and 6 post-exposure). ADAM17 was not appreciably detected in unexposed corneas (FIG. 10A).

TTHX1114 Treatment Reduces NM Exposure Induced ADAM17 Activation in Rabbit Cornea Upon treatment of corneas with TTH1114, ADAM17 fluorescent signal was attenuated in peripheral and central cornea (lower panel FIG. 10B). The attenuation or lack of ADAM17 fluorescent signal corresponded with better histologic appearance of the corneal epithelial-stromal junction.

Figure 11:
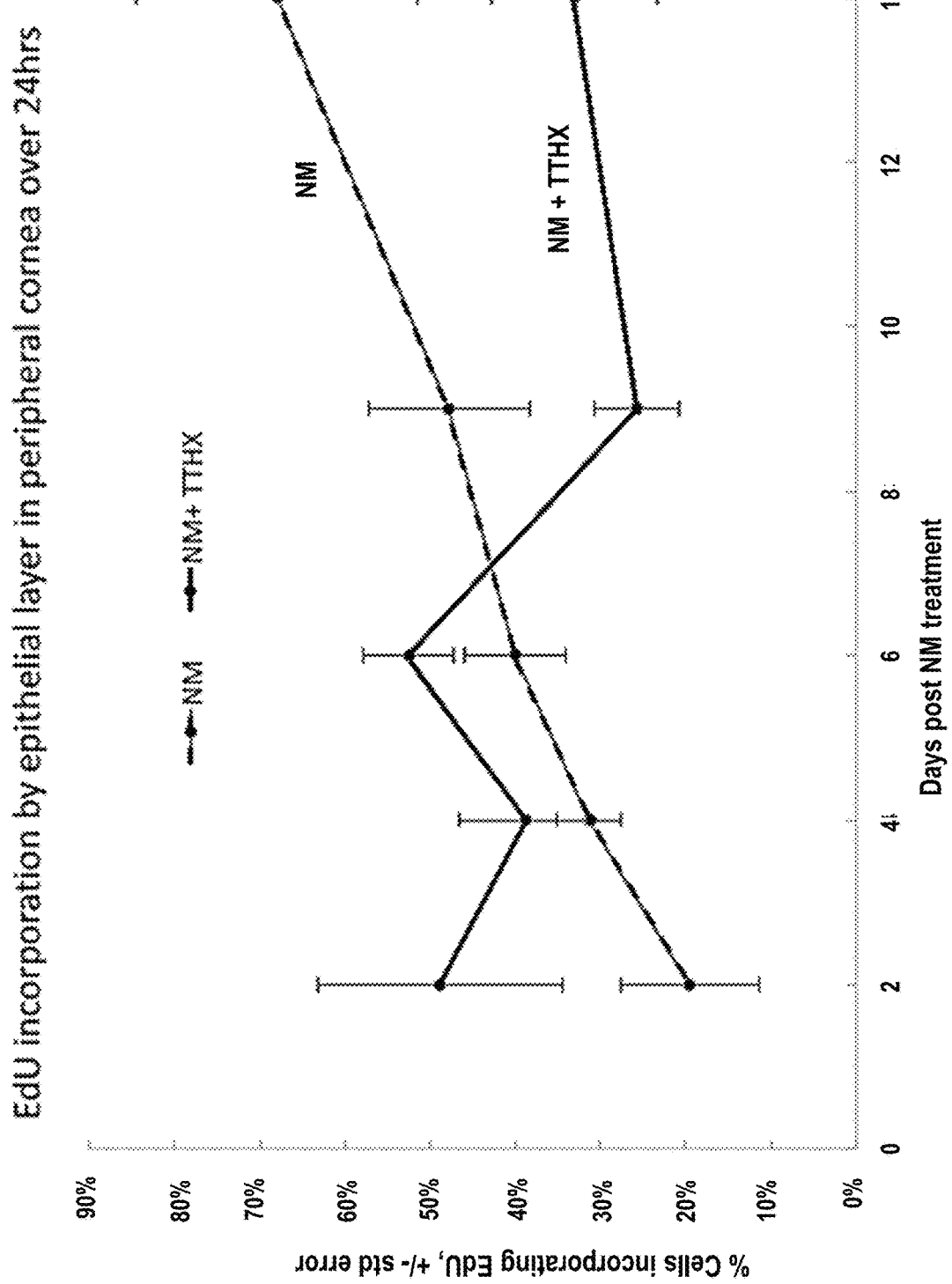
FIG. 11 illustrates the proliferation of corneal epithelial cells exposed to a vesicant and treated with an exemplary modified FGF-1 polypeptide (TTHX1114), measured by EdU incorporation. The dashed line corresponds to "NM" and the solid line corresponds to "NM+TTHX."

TTHX1114 Treatment Ameliorates NM Exposure Induced Suppression of Corneal Epithelial Proliferation Peripheral corneal epithelial layer was stimulation was assessed by via EdU incorporation of corneal epithelial cells (CECs). Primary cultures of rabbit CECs were established using standard procedures, e.g., the procedure described by Kay et al. (Kay et al. Investigative ophthalmology & visual science. 1993; 34(3):663-72; Lee et al., Investigative ophthalmology & visual science. 2009; 50(5):2067-76). The cells are exposed to NM for two hours. Proliferation assays were performed in 12-well plates using, e.g., a Click-IT assay kit (Life Technologies). Incorporation of EdU into corneal epithelial cells were assessed as an indicator of epithelial proliferation. The percentage corneal epithelial cells incorporating EdU were lower when treated with TTHX1114, following NM-exposure, as seen in FIG. 11.

Example 12: Sulfur Mustard Induced Injury of Corneal Endothelial Cells

The study is directed towards the effect of modified FGF-1 polypeptides comprising the sequence of SEQ ID NO: 206 (TTHX1114) on treatment of sulfur mustard (SM) induced corneal injury. The modified FGF-1 polypeptides are generated using methods as described above in the Recombinant Techniques section.

Experimental Methods

Rabbits are exposed in cohorts of 8 to 16 animals during a 4-month period. One day before exposure, a 4-in$^2$ region on each rabbit's back is clipped, and a fentanyl patch (25 μg/h) is placed anterior to the scapula. On the day of exposure, rabbits are anesthetized with an intramuscular administration of 15 mg/kg of ketamine and 7 mg/kg of xylazine, and physiological parameters are recorded. The corneas of anesthetized rabbits are exposed to SM vapor for 2.5 min using a vapor cup delivery system as previously described. Two minutes after exposure, exposed eyes are gently rinsed with 10 mL sterile saline to flush residual agent.

A first group of rabbits are euthanized 24 hours after exposure. Five minutes after euthanasia, 20 μL of a 0.1 mg/mL solution of AlexaFluor 488 (Life Technologies, Carlsbad, Calif.) dissolved in PBS (pH 7.4) is injected into the anterior chamber through a 30-gauge needle using a 100-μL Hamilton glass syringe (Hamilton Company, Reno, Nev.). After 10 minutes, corneas are excised and washed three times for 1 minute in 10 mL PBS. Corneas are transferred to 14-mL round-bottom tubes (Becton Dickinson, Franklin Lakes, N.J.) with 100 μL PBS and incubated on ice in the dark with gentle agitation. After 30 minutes, supernatant is diluted 1:5 in PBS and analyzed for fluorescence on a Synergy MX fluorophotometer (Biotek, Winooski, Vt.) using an excitation wavelength of 488±10 nm, emission wavelength of 524±10 nm, and a gain of 50. Representative corneas are imaged with a blue diode and FITC filter set in a Versadoc MP 4000 (Bio-Rad Laboratories, Hercules, Calif.).

The remaining rabbits are further divided into a test group, treated with TTHX1114 at varying doses, and a sham control group, treated with control vehicle. The treatments are carried out for about two weeks. Rabbits are returned to cages and provided food and water ad libitum. Fentanyl patches are replaced after every 72 hours to manage discomfort through 6 days after the exposure and applied liberally thereafter as needed. Animals are monitored daily for signs of pain and distress. Corneal injury is clinically evaluated on a regular basis using pachymetry, fluorescein exclusion assays, and slit-lamp evaluations.

Results

Sulfur Mustard (SM) Exposure Causes Corneal Endothelial Injury

Corneas visualized at 370 nm by SEM 24 hours after SM exposure exhibit a centripetal injury, with extensive loss of corneal endothelial cells (CECs) in the central cornea and increased retention toward the exposure margins. To obtain a more comprehensive overview of SM-induced changes in the corneal endothelium, the fine structure of the posterior cornea is evaluated by electron microscopy. Enface scanning electron micrographs of sham-exposed corneas reveals a continuous layer of polygonal cells of regular shape and size, with interdigitated borders, apical microvilli, and infrequent cilia. Within 24 hours of exposure, all corneal endothelia exhibit evidence of an acute lesion, with extensive central CEC loss and more diffuse vesication in the exposure penumbra. The CECs within the exposed region displayed two general morphologies, namely, enlarged (highly attenuated) polymorphic cells and rounded or spindle-shaped cells. Most CECs exhibit atypical apical membrane morphologies and lack cell-to-cell interdigitations. In regions of CEC vesication, denuded Descemet's membrane (DM) is covered by a complex arbor of CEC lamellipodia and filopodia. The TEM imaging of corneal cross-sections confirmed the centripetal injury pattern, with CEC morphology progressively normalizing toward the injury margin. Denuded DM near the central lesion is infiltrated by extensively arborized cellular processes. At more distal regions, overlapping cellular processes with loss of junctional complexes is common, suggestive of a motile population. The rounded CEC population observed by SEM is found exclusively overlying polymorphic endothelium and display signs of necrosis or apoptosis.

Treatment with TTHX1114 Resolves Corneal Endothelial Injuries

Eight weeks after exposure, endothelial cell morphology and structure are compared between test group (also referred to as resolved) and sham control group (which later develops MGK). Resolved eyes are distinguished by the absence of characteristic MGK sequelae during clinical evaluations such as corneal erosions, neovascularization, or corneal haze and had corneal thicknesses that are statistically indistinguishable from sham-exposed controls by 6 weeks. Enface scanning micrographs of resolved eyes are found to be strikingly similar to sham-exposed controls, with a well-organized monolayer of polygonal cells. The average CEC size is increased in resolved eyes compared with control corneas; otherwise, resolved corneas do not exhibit significant variability across the posterior surface. In contrast, the sham-control treated rabbits with MGK endothelia reveal extensive variability in cell shape and cell size among animals, indicative of a dynamic injury process. Focal variability in endothelial morphology is routinely observed in individual corneas, with some regions exhibiting enlarged but mosaic CECs and other regions displaying significant disorganization, with variable degrees of apical blebbing, areas showing denuded DM, and clearly delineated cell boundaries lacking. These phenomena are not observed in the TTHX1114 treated resolved enodthelium. Transmission Electron Microscope images of TTHX1114 treated resolved corneas is very similar to naïve endothelium. In contrast, sham-control treated endothelium with MGK pathology exhibit diffusive thickening of the posterior DM, consistent with either edema and/or the deposition of a retrocorneal fibrous membrane. The MGK corneas also exhibit extensive markers of CEC stress or injury, including cytoplasmic rarefication, excessive vacuolization, and swollen endoplasmic reticuli. There is a high frequency of overlapping cell processes, similar to 24-hour images and suggestive of an ongoing attempt to repopulate recently denuded DM.

Example 13: Treatment of Herpetic Keratopathy Using a Modified FGF-1 Polypeptide (TTHX1114)

This study is directed towards using a modified FGF-1 polypeptide comprising the sequence of SEQ ID NO: 206 (TTHX1114) for the treatment of herpetic keratopathy.

Methods

A group of patients with herpetic keratopathy is selected for this study. The patients are divided into two subgroups. Patients in the first sub-group are administered, ocularly, an ophthalmic formulation, such as an eye drop, containing about 500 pg/ml (i.e., 5 µg/ml) of TTHX1114 (SEQ ID NO: 206) formulated in phosphate buffered saline (at pH 7.2), 0.3% propylene glycol, 0.4% polyethylene glycol 400, and 0.05% hydroxypropyl guar. Patients in the second sub-group are administered, ocularly, a sham ophthalmic formulation that does not contain the TTHX1114 (SEQ ID NO: 206) but is otherwise identical to what is administered to the first and the second sub-group. For both subgroups, the eye drop is either self-administered by the patient or administered by a nurse or a caregiver. The TTHX1114 (SEQ ID NO: 206) containing ophthalmic formulation and the sham ophthalmic formulation are administered, respectively to patients in the first and second sub-groups, twice daily for up to 30 days.

Results

It is observed that the ophthalmic formulation containing the TTHX1114 (SEQ ID NO: 206) results in healing of the herpetic corneal ulcer within about 14 days in majority of the patients belonging to the first sub-group, along with reduction in the duration of pain and inflammation. Furthermore, eyes of patients in the first sub-group, treated with the TTHX1114 (SEQ ID NO: 206) containing ophthalmic formulation have less corneal haze and scarring than patients in the third sub-group, who were treated with the sham.

Example 14: Treatment of Chronic Herpetic Keratopathy Using a Modified FGF-1 Polypeptide (TTHX1114)

This study is directed towards using a modified FGF-1 polypeptide comprising the sequence of SEQ ID NO: 206 (TTHX1114)

Methods

A group of patients with chronic herpetic keratopathy is selected for this study. The patients are divided into two subgroups. Patients in the first sub-group are administered, ocularly, an ophthalmic formulation, such as an eye drop, containing about 500 pg/ml (i.e., 5 µg/ml) of N-Met-TTHX1114 (SEQ ID NO: 2) formulated in phosphate buffered saline (at pH 7.2), 0.3% propylene glycol, 0.4% polyethylene glycol 400, and 0.05% hydroxypropyl guar. Patients in the second sub-group are administered, ocularly, a sham ophthalmic formulation that does not contain the TTHX1114 (SEQ ID NO: 206) but is otherwise identical to what is administered to the first and the second sub-group. For both subgroups, the eye drop is either self-administered by the patient or administered by a nurse or a caregiver. The TTHX1114 (SEQ ID NO: 206) containing ophthalmic formulation and the sham ophthalmic formulation are administered, respectively to patients in the first and second sub-group, twice daily for up to 30 days.

Results

It is observed that the ophthalmic formulation containing the TTHX1114 (SEQ ID NO: 206) result in healing of corneal ulcer in majority of the patients belonging to the first sub-group, along with reduction in of pain and inflammation. Furthermore, eyes of patients in the first sub-groups, treated with the TTHX1114 (SEQ ID NO: 206) containing ophthalmic formulation have less corneal opacity haze and scarring than patients in the third sub-group, who are treated with the sham.

Example 15: Treatment of Neurotrophic Keratopathy Using a Modified FGF-1 Polypeptide (TTHX1114)

This study is directed towards using a modified FGF-1 polypeptide comprising the sequence of SEQ ID NO: 206 (TTHX1114) for the treatment of neurotrophic keratopathy secondary to herpes infection.

Methods

A group of patients with neurotrophic keratopathy is selected for this study. The patients are divided into two subgroups. Patients in the first sub-group are administered, ocularly, an ophthalmic formulation, such as an eye drop, containing about 500 pg/ml (i.e., 5 µg/ml) of TTHX1114 (SEQ ID NO: 206) formulated in phosphate buffered saline (at pH 7.2), 0.3% propylene glycol, 0.4% polyethylene glycol 400, and 0.05% hydroxypropyl guar. Patients in the second sub-group are administered, ocularly, a sham ophthalmic formulation that does not contain the TTHX1114 (SEQ ID NO: 206) but is otherwise identical to what is administered to the first sub-group. For both subgroups, the eye drop is either self-administered by the patient or administered by a nurse or a caregiver. The TTHX1114 (SEQ ID NO: 206) containing ophthalmic formulation and the sham ophthalmic formulation are administered, respectively to patients in the first and the second sub-group, twice daily for up to 30 days.

Results

It is observed that the ophthalmic formulation containing the TTHX1114 (SEQ ID NO: 206) results in healing of corneal ulcer in majority of the patients belonging to the first sub-group, along with reduction in of pain and inflammation. Furthermore, eyes of patients in the first sub-group, treated respectively with the TTHX1114 (SEQ ID NO: 206) containing ophthalmic formulation, have less corneal opacity haze and scarring than patients in the third sub-group, who are treated with the sham.

Example 16: Treatment of Recurrent Herpetic Keratopathy and the Suppression of Reactivation of Latent Virus Using a Modified FGF-1 Polypeptide (TTHX1114)

This study is directed towards using a modified FGF-1 polypeptides comprising the sequence of SEQ ID NO: 206 (TTHX1114) for the treatment of neurotrophic keratopathy secondary to herpes infection.

Methods

A group of patients with recurrent keratopathy is selected for this study. The patients have experienced at least one episode of herpetic keratopathy. For treatment of recurrent herpetic keratopathy and the suppression of reactivation of latent virus, the patients are divided into two subgroups. Patients in the first sub-group are administered, ocularly, an ophthalmic formulation, such as an eye drop, containing about 50 pg/ml to about 500 pg/ml (i.e., 5 µg/ml) of TTHX1114 (SEQ ID NO: 206) formulated in phosphate buffered saline (at pH 7.2), 0.3% propylene glycol, 0.4% polyethylene glycol 400, and 0.05% hydroxypropyl guar. Patients in the third sub-group are administered, ocularly, a sham ophthalmic formulation that does not contain the TTHX1114 (SEQ ID NO: 206) but is otherwise identical to what is administered to the first and the second sub-group. For both subgroups, the eye drop is either self-administered by the patient or administered by a nurse or a caregiver. The TTHX1114 (SEQ ID NO: 206) containing ophthalmic formulation and the sham ophthalmic formulation are administered, respectively to patients in the first and the second sub-group, twice daily for up to 30 days.

Results

It is observed that the ophthalmic formulation containing the TTHX1114 (SEQ ID NO: 206) increases the disease free interval and reduces the severity of the reactivated virus lesions, with patients receiving the modified FGF-1 having a longer period of time without recurrent disease than patients in the second sub-group, who are treated with the sham.

| SEQUENCES | |
|---|---|
| SEQUENCE | No. |
| FNLPPGNYKKPKLLYCSNGGHFLRILPDGTVDGTRDRSDQHIQLQLSAESVGEVYIKSTETGQYLAMDTDGLLYGSQTPNEECLFLERLEENHYNTYISKKHAEKNWFVGLKKNGSCKRGPRTHYGQKAILFLPLPVSSD | 1 |
| MFNLPPGNYKKPKLLYSSNGGHFLRILPDGTVDGTRDRSDQHIQLQLSAESVGEVYIKSTETGQYLCMDTDGLLYGSQTPNEECLFLERLEENHYNTYISKKHAEKNWFVGLKKNGSVKRGPRTHYGQKAILFLPLPVSSD | 2 |
| MAEGEITTFTALTEK | 3 |
| ALTEK | 4 |
| LTEK | 5 |
| TEK | 6 |
| EK | 7 |
| K | 8 |
| MALTEKFNLPPGNYKKPKLLYCSNGGHFLRILPDGTVDGTRDRSDQHIQLQLSAESVGEVYIKSTETGQYLAMDTDGLLYGSQTPNEECLFLERLEENHYNTYISKKHAEKNWFVGLKKNGSCKRGPRTHYGQKAILFLPLPVSSD | 9 |
| MLTEKFNLPPGNYKKPKLLYCSNGGHFLRILPDGTVDGTRDRSDQHIQLQLSAESVGEVYIKSTETGQYLAMDTDGLLYGSQTPNEECLFLERLEENHYNTYISKKHAEKNWFVGLKKNGSCKRGPRTHYGQKAILFLPLPVSSD | 10 |
| MTEKFNLPPGNYKKPKLLYCSNGGHFLRILPDGTVDGTRDRSDQHIQLQLSAESVGEVYIKSTETGQYLAMDTDGLLYGSQTPNEECLFLERLEENHYNTYISKKHAEKNWFVGLKKNGSCKRGPRTHYGQKAILFLPLPVSSD | 11 |
| MEKFNLPPGNYKKPKLLYCSNGGHFLRILPDGTVDGTRDRSDQHIQLQLSAESVGEVYIKSTETGQYLAMDTDGLLYGSQTPNEECLFLERLEENHYNTYISKKHAEKNWFVGLKKNGSCKRGPRTHYGQKAILFLPLPVSSD | 12 |
| MKFNLPPGNYKKPKLLYCSNGGHFLRILPDGTVDGTRDRSDQHIQLQLSAESVGEVYIKSTETGQYLAMDTDGLLYGSQTPNEECLFLERLEENHYNTYISKKHAEKNWFVGLKKNGSCKRGPRTHYGQKAILFLPLPVSSD | 13 |
| MALTEKFNLPPGNYKKPKLLYSSNGGHFLRILPDGTVDGTRDRSDQHIQLQLSAESVGEVYIKSTETGQYLCMDTDGLLYGSQTPNEECLFLERLEENHYNTYISKKHAEKNWFVGLKKNGSVKRGPRTHYGQKAILFLPLPVSSD | 14 |
| MLTEKFNLPPGNYKKPKLLYSSNGGHFLRILPDGTVDGTRDRSDQHIQLQLSAESVGEVYIKSTETGQYLCMDTDGLLYGSQTPNEECLFLERLEENHYNTYISKKHAEKNWFVGLKKNGSVKRGPRTHYGQKAILFLPLPVSSD | 15 |
| MTEKFNLPPGNYKKPKLLYSSNGGHFLRILPDGTVDGTRDRSDQHIQLQLSAESVGEVYIKSTETGQYLCMDTDGLLYGSQTPNEECLFLERLEENHYNTYISKKHAEKNWFVGLKKNGSVKRGPRTHYGQKAILFLPLPVSSD | 16 |
| MEKFNLPPGNYKKPKLLYSSNGGHFLRILPDGTVDGTRDRSDQHIQLQLSAESVGEVYIKSTETGQYLCMDTDGLLYGSQTPNEECLFLERLEENHYNTYISKKHAEKNWFVGLKKNGSVKRGPRTHYGQKAILFLPLPVSSD | 17 |
| MKFNLPPGNYKKPKLLYSSNGGHFLRILPDGTVDGTRDRSDQHIQLQLSAESVGEVYIKSTETGQYLCMDTDGLLYGSQTPNEECLFLERLEENHYNTYISKKHAEKNWFVGLKKNGSVKRGPRTHYGQKAILFLPLPVSSD | 18 |
| ALTEKFNLPPGNYKKPKLLYCSNGGHFLRILPDGTVDGTRDRSDQHIQLQLSAESVGEVYIKSTETGQYLAMDTDGLLYGSQTPNEECLFLERLEENHYNTYISKKHAEKNWFVGLKKNGSCKRGPRTHYGQKAILFLPLPVSSD | 19 |
| LTEKFNLPPGNYKKPKLLYCSNGGHFLRILPDGTVDGTRDRSDQHIQLQLSAESVGEVYIKSTETGQYLAMDTDGLLYGSQTPNEECLFLERLEENHYNTYISKKHAEKNWFVGLKKNGSCKRGPRTHYGQKAILFLPLPVSSD | 20 |
| TEKFNLPPGNYKKPKLLYCSNGGHFLRILPDGTVDGTRDRSDQHIQLQLSAESVGEVYIKSTETGQYLAMDTDGLLYGSQTPNEECLFLERLEENHYNTYISKKHAEKNWFVGLKKNGSCKRGPRTHYGQKAILFLPLPVSSD | 21 |
| EKFNLPPGNYKKPKLLYCSNGGHFLRILPDGTVDGTRDRSDQHIQLQLSAESVGEVYIKSTETGQYLAMDTDGLLYGSQTPNEECLFLERLEENHYNTYISKKHAEKNWFVGLKKNGSCKRGPRTHYGQKAILFLPLPVSSD | 22 |

| SEQUENCES | |
|---|---|
| SEQUENCE | No. |
| KENLPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 23 |
| ALTEKENLPPGNYKKPKLLYSSNGGHFLRILPDGTVDGTRDRSDQHIQLQLSAESVGEVYIKSTETGQY<br>LCMDTDGLLYGSQTPNEECLFLERLEENHYNTYISKKHAEKNWFVGLKKNGSVKRGPRTHYGQKAILFL<br>PLPVSSD | 24 |
| LTEKENLPPGNYKKPKLLYSSNGGHFLRILPDGTVDGTRDRSDQHIQLQLSAESVGEVYIKSTETGQYL<br>CMDTDGLLYGSQTPNEECLFLERLEENHYNTYISKKHAEKNWFVGLKKNGSVKRGPRTHYGQKAILFLP<br>LPVSSD | 25 |
| TEKENLPPGNYKKPKLLYSSNGGHFLRILPDGTVDGTRDRSDQHIQLQLSAESVGEVYIKSTETGQYLC<br>MDTDGLLYGSQTPNEECLFLERLEENHYNTYISKKHAEKNWFVGLKKNGSVKRGPRTHYGQKAILFLPL<br>PVSSD | 26 |
| EKENLPPGNYKKPKLLYSSNGGHFLRILPDGTVDGTRDRSDQHIQLQLSAESVGEVYIKSTETGQYLCM<br>DTDGLLYGSQTPNEECLFLERLEENHYNTYISKKHAEKNWFVGLKKNGSVKRGPRTHYGQKAILFLPLP<br>VSSD | 27 |
| KENLPPGNYKKPKLLYSSNGGHFLRILPDGTVDGTRDRSDQHIQLQLSAESVGEVYIKSTETGQYLCMD<br>TDGLLYGSQTPNEECLFLERLEENHYNTYISKKHAEKNWFVGLKKNGSVKRGPRTHYGQKAILFLPLPV<br>SSD | 28 |
| NLPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 29 |
| LPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 30 |
| PPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 31 |
| PGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 32 |
| NLPPGNYKKPKLLYSSNGGHFLRILPDGTVDGTRDRSDQHIQLQLSAESVGEVYIKSTETGQYLCMDTD<br>GLLYGSQTPNEECLFLERLEENHYNTYISKKHAEKNWFVGLKKNGSVKRGPRTHYGQKAILFLPLPVSS<br>D | 33 |
| LPPGNYKKPKLLYSSNGGHFLRILPDGTVDGTRDRSDQHIQLQLSAESVGEVYIKSTETGQYLCMDTDG<br>LLYGSQTPNEECLFLERLEENHYNTYISKKHAEKNWFVGLKKNGSVKRGPRTHYGQKAILFLPLPVSSD | 34 |
| PPGNYKKPKLLYSSNGGHFLRILPDGTVDGTRDRSDQHIQLQLSAESVGEVYIKSTETGQYLCMDTDGL<br>LYGSQTPNEECLFLERLEENHYNTYISKKHAEKNWFVGLKKNGSVKRGPRTHYGQKAILFLPLPVSSD | 35 |
| PGNYKKPKLLYSSNGGHFLRILPDGTVDGTRDRSDQHIQLQLSAESVGEVYIKSTETGQYLCMDTDGLL<br>YGSQTPNEECLFLERLEENHYNTYISKKHAEKNWFVGLKKNGSVKRGPRTHYGQKAILFLPLPVSSD | 36 |
| MNLPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 37 |
| MLPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 38 |
| MPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 39 |
| MPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 40 |
| MNLPPGNYKKPKLLYSSNGGHFLRILPDGTVDGTRDRSDQHIQLQLSAESVGEVYIKSTETGQYLCMDT<br>DGLLYGSQTPNEECLFLERLEENHYNTYISKKHAEKNWFVGLKKNGSVKRGPRTHYGQKAILFLPLPVS<br>SD | 41 |

| SEQUENCES | |
|---|---|
| SEQUENCE | No. |
| MLPPGNYKKPKLLYSSNGGHFLRILPDGTVDGTRDRSDQHIQLQLSAESVGEVYIKSTETGQYLCMDTD<br>GLLYGSQTPNEECLFLERLEENHYNTYISKKHAEKNWFVGLKKNGSVKRGPRTHYGQKAILFLPLPVSS<br>D | 42 |
| MPPGNYKKPKLLYSSNGGHFLRILPDGTVDGTRDRSDQHIQLQLSAESVGEVYIKSTETGQYLCMDTDG<br>LLYGSQTPNEECLFLERLEENHYNTYISKKHAEKNWFVGLKKNGSVKRGPRTHYGQKAILFLPLPVSSD | 43 |
| MPGNYKKPKLLYSSNGGHFLRILPDGTVDGTRDRSDQHIQLQLSAESVGEVYIKSTETGQYLCMDTDGL<br>LYGSQTPNEECLFLERLEENHYNTYISKKHAEKNWFVGLKKNGSVKRGPRTHYGQKAILFLPLPVSSD | 44 |
| MALTEKNLPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 45 |
| MALTEKLPPGNYKKPKLLYSSNGGHFLRILPDGTVDGTRDRSDQHIQLQLSAESVGEVYIKSTETGQYL<br>CMDTDGLLYGSQTPNEECLFLERLEENHYNTYISKKHAEKNWFVGLKKNGSVKRGPRTHYGQKAILFLP<br>LPVSSD | 46 |
| MALTEKPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 47 |
| MALTEKPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 48 |
| MLTEKFNLPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 49 |
| MLTEKNLPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 50 |
| MLTEKLPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 51 |
| MLTEKPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 52 |
| MLTEKPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 53 |
| MTEKFNLPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 54 |
| MTEKNLPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 55 |
| MTEKLPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 56 |
| MTEKPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 57 |
| MTEKPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 58 |
| MEKFNLPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 59 |
| MEKNLPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 60 |

| SEQUENCES | |
|---|---|
| SEQUENCE | No. |
| MEKLPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 61 |
| MEKPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 62 |
| MEKPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 63 |
| MKFNLPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 64 |
| MKNLPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 65 |
| MKLPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 66 |
| MKPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 67 |
| MKPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 68 |
| ALTEKNLPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 69 |
| ALTEKLPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 70 |
| ALTEKPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 71 |
| ALTEKPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 72 |
| LTEKENLPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 73 |
| LTEKNLPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 74 |
| LTEKLPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 75 |
| LTEKPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 76 |
| LTEKPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 77 |
| TEKENLPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 78 |
| TEKNLPPGNYKKPKLLYCSNGGHFLRILPDGTVDGTRDRSDQHIQLQLSAESVGEVY<br>IKSTETGQYLAMDTDGLLYGSQTPNEECLFLERLEENHYNTYISKKHAEK<br>NWFVGLKKNGSCKRGPRTHYGQKAILFLPLPVSSD | 79 |

SEQUENCES

| SEQUENCE | No. |
|---|---|
| TEKLPPGNYKKPKLLYCSNGGHFLRILPDGTVDGTRDRSDQHIQLQLSAESVGEVY IKSTETGQYLAMDTDGLLYGSQTPNEECLFLERLEENHYNTYISKKHAEK NWFVGLKKNGSCKRGPRTHYGQKAILFLPLPVSSD | 80 |
| TEKPPGNYKKPKLLYCSNGGHFLRILPDGTVDGTRDRSDQHIQLQLSAESVGEVY IKSTETGQYLAMDTDGLLYGSQTPNEECLFLERLEENHYNTYISKKHAEK NWFVGLKKNGSCKRGPRTHYGQKAILFLPLPVSSD | 81 |
| TEKPGNYKKPKLLYCSNGGHFLRILPDGTVDGTRDRSDQHIQLQLSAESVGEVY IKSTETGQYLAMDTDGLLYGSQTPNEECLFLERLEENHYNTYISKKHAEK NWFVGLKKNGSCKRGPRTHYGQKAILFLPLPVSSD | 82 |
| EKFNLPPGNYKKPKLLYCSNGGHFLRILPDGTVDGTRDRSDQHIQLQLSAESVGEVY IKSTETGQYLAMDTDGLLYGSQTPNEECLFLERLEENHYNTYISKKHAEK NWFVGLKKNGSCKRGPRTHYGQKAILFLPLPVSSD | 83 |
| EKNLPPGNYKKPKLLYCSNGGHFLRILPDGTVDGTRDRSDQHIQLQLSAESVGEVY IKSTETGQYLAMDTDGLLYGSQTPNEECLFLERLEENHYNTYISKKHAEK NWFVGLKKNGSCKRGPRTHYGQKAILFLPLPVSSD | 84 |
| EKLPPGNYKKPKLLYCSNGGHFLRILPDGTVDGTRDRSDQHIQLQLSAESVGEVY IKSTETGQYLAMDTDGLLYGSQTPNEECLFLERLEENHYNTYISKKHAEK NWFVGLKKNGSCKRGPRTHYGQKAILFLPLPVSSD | 85 |
| EKPPGNYKKPKLLYCSNGGHFLRILPDGTVDGTRDRSDQHIQLQLSAESVGEVY IKSTETGQYLAMDTDGLLYGSQTPNEECLFLERLEENHYNTYISKKHAEK NWFVGLKKNGSCKRGPRTHYGQKAILFLPLPVSSD | 86 |
| EKPGNYKKPKLLYCSNGGHFLRILPDGTVDGTRDRSDQHIQLQLSAESVGEVY IKSTETGQYLAMDTDGLLYGSQTPNEECLFLERLEENHYNTYISKKHAEK NWFVGLKKNGSCKRGPRTHYGQKAILFLPLPVSSD | 87 |
| KFNLPPGNYKKPKLLYCSNGGHFLRILPDGTVDGTRDRSDQHIQLQLSAESVGEVY IKSTETGQYLAMDTDGLLYGSQTPNEECLFLERLEENHYNTYISKKHAEK NWFVGLKKNGSCKRGPRTHYGQKAILFLPLPVSSD | 88 |
| KNLPPGNYKKPKLLYCSNGGHFLRILPDGTVDGTRDRSDQHIQLQLSAESVGEVY IKSTETGQYLAMDTDGLLYGSQTPNEECLFLERLEENHYNTYISKKHAEK NWFVGLKKNGSCKRGPRTHYGQKAILFLPLPVSSD | 89 |
| KLPPGNYKKPKLLYCSNGGHFLRILPDGTVDGTRDRSDQHIQLQLSAESVGEVY IKSTETGQYLAMDTDGLLYGSQTPNEECLFLERLEENHYNTYISKKHAEK NWFVGLKKNGSCKRGPRTHYGQKAILFLPLPVSSD | 90 |
| KPPGNYKKPKLLYCSNGGHFLRILPDGTVDGTRDRSDQHIQLQLSAESVGEVY IKSTETGQYLAMDTDGLLYGSQTPNEECLFLERLEENHYNTYISKKHAEK NWFVGLKKNGSCKRGPRTHYGQKAILFLPLPVSSD | 91 |
| KPGNYKKPKLLYCSNGGHFLRILPDGTVDGTRDRSDQHIQLQLSAESVGEVY IKSTETGQYLAMDTDGLLYGSQTPNEECLFLERLEENHYNTYISKKHAEK NWFVGLKKNGSCKRGPRTHYGQKAILFLPLPVSSD | 92 |
| ALTEKNLPPGNYKKPKLLYSSNGGHFLRILPDGTVDGTRDRSDQHIQLQLSAESVGEVYIKSTETGQYL CMDTDGLLYGSQTPNEECLFLERLEENHYNTYISKKHAEKNWFVGLKKNGSVKRGPRTHYGQKAILFLP LPVSSD | 93 |
| ALTEKLPPGNYKKPKLLYSSNGGHFLRILPDGTVDGTRDRSDQHIQLQLSAESVGEVYIKSTETGQYLC MDTDGLLYGSQTPNEECLFLERLEENHYNTYISKKHAEKNWFVGLKKNGSVKRGPRTHYGQKAILFLPL PVSSD | 94 |
| ALTEKPPGNYKKPKLLYSSNGGHFLRILPDGTVDGTRDRSDQHIQLQLSAESVGEVYIKSTETGQYLCM DTDGLLYGSQTPNEECLFLERLEENHYNTYISKKHAEKNWFVGLKKNGSVKRGPRTHYGQKAILFLPLP VSSD | 96 |
| ALTEKPGNYKKPKLLYSSNGGHFLRILPDGTVDGTRDRSDQHIQLQLSAESVGEVYIKSTETGQYLCMD TDGLLYGSQTPNEECLFLERLEENHYNTYISKKHAEKNWFVGLKKNGSVKRGPRTHYGQKAILFLPLPV SSD | 97 |
| LTEKFNLPPGNYKKPKLLYSSNGGHFLRILPDGTVDGTRDRSDQHIQLQLSAESVGEVYIKSTETGQYL CMDTDGLLYGSQTPNEECLFLERLEENHYNTYISKKHAEKNWFVGLKKNGSVKRGPRTHYGQKAILFLP LPVSSD | 98 |

| SEQUENCES | |
|---|---|
| SEQUENCE | No. |
| LTEKNLPPGNYKKPKLLYSSNGGHFLRILPDGTVDGTRDRSDQHIQLQLSAESVGEVYIKSTETGQYLC MDTDGLLYGSQTPNEECLFLERLEENHYNTYISKKHAEKNWFVGLKKNGSVKRGPRTHYGQKAILFLPL PVSSD | 99 |
| LTEKLPPGNYKKPKLLYSSNGGHFLRILPDGTVDGTRDRSDQHIQLQLSAESVGEVYIKSTETGQYLCM DTDGLLYGSQTPNEECLFLERLEENHYNTYISKKHAEKNWFVGLKKNGSVKRGPRTHYGQKAILFLPLP VSSD | 100 |
| LTEKPPGNYKKPKLLYSSNGGHFLRILPDGTVDGTRDRSDQHIQLQLSAESVGEVYIKSTETGQYLCMD TDGLLYGSQTPNEECLFLERLEENHYNTYISKKHAEKNWFVGLKKNGSVKRGPRTHYGQKAILFLPLPV SSD | 101 |
| LTEKGNYKKPKLLYSSNGGHFLRILPDGTVDGTRDRSDQHIQLQLSAESVGEVYIKSTETGQYLCMDT DGLLYGSQTPNEECLFLERLEENHYNTYISKKHAEKNWFVGLKKNGSVKRGPRTHYGQKAILFLPLPVS SD | 102 |
| TEKFNLPPGNYKKPKLLYSSNGGHFLRILPDGTVDGTRDRSDQHIQLQLSAESVGEVYIKSTETGQYLC MDTDGLLYGSQTPNEECLFLERLEENHYNTYISKKHAEKNWFVGLKKNGSVKRGPRTHYGQKAILFLPL PVSSD | 103 |
| TEKNLPPGNYKKPKLLYSSNGGHFLRILPDGTVDGTRDRSDQHIQLQLSAESVGEVYIKSTETGQYLCM DTDGLLYGSQTPNEECLFLERLEENHYNTYISKKHAEKNWFVGLKKNGSVKRGPRTHYGQKAILFLPLP VSSD | 104 |
| TEKLPPGNYKKPKLLYSSNGGHFLRILPDGTVDGTRDRSDQHIQLQLSAESVGEVYIKSTETGQYLCMD TDGLLYGSQTPNEECLFLERLEENHYNTYISKKHAEKNWFVGLKKNGSVKRGPRTHYGQKAILFLPLPV SSD | 105 |
| TEKPPGNYKKPKLLYSSNGGHFLRILPDGTVDGTRDRSDQHIQLQLSAESVGEVYIKSTETGQYLCMDT DGLLYGSQTPNEECLFLERLEENHYNTYISKKHAEKNWFVGLKKNGSVKRGPRTHYGQKAILFLPLPVS SD | 106 |
| TEKGNYKKPKLLYSSNGGHFLRILPDGTVDGTRDRSDQHIQLQLSAESVGEVYIKSTETGQYLCMDTD GLLYGSQTPNEECLFLERLEENHYNTYISKKHAEKNWFVGLKKNGSVKRGPRTHYGQKAILFLPLPVSS D | 107 |
| EKFNLPPGNYKKPKLLYSSNGGHFLRILPDGTVDGTRDRSDQHIQLQLSAESVGEVYIKSTETGQYLCM DTDGLLYGSQTPNEECLFLERLEENHYNTYISKKHAEKNWFVGLKKNGSVKRGPRTHYGQKAILFLPLP VSSD | 108 |
| EKNLPPGNYKKPKLLYSSNGGHFLRILPDGTVDGTRDRSDQHIQLQLSAESVGEVYIKSTETGQYLCMD TDGLLYGSQTPNEECLFLERLEENHYNTYISKKHAEKNWFVGLKKNGSVKRGPRTHYGQKAILFLPLPV SSD | 109 |
| EKLPPGNYKKPKLLYSSNGGHFLRILPDGTVDGTRDRSDQHIQLQLSAESVGEVYIKSTETGQYLCMDT DGLLYGSQTPNEECLFLERLEENHYNTYISKKHAEKNWFVGLKKNGSVKRGPRTHYGQKAILFLPLPVS SD | 110 |
| EKPPGNYKKPKLLYSSNGGHFLRILPDGTVDGTRDRSDQHIQLQLSAESVGEVYIKSTETGQYLCMDTD GLLYGSQTPNEECLFLERLEENHYNTYISKKHAEKNWFVGLKKNGSVKRGPRTHYGQKAILFLPLPVSS D | 111 |
| EKGNYKKPKLLYSSNGGHFLRILPDGTVDGTRDRSDQHIQLQLSAESVGEVYIKSTETGQYLCMDTDG LLYGSQTPNEECLFLERLEENHYNTYISKKHAEKNWFVGLKKNGSVKRGPRTHYGQKAILFLPLPVSSD | 112 |
| KFNLPPGNYKKPKLLYSSNGGHFLRILPDGTVDGTRDRSDQHIQLQLSAESVGEVYIKSTETGQYLCMD TDGLLYGSQTPNEECLFLERLEENHYNTYISKKHAEKNWFVGLKKNGSVKRGPRTHYGQKAILFLPLPV SSD | 113 |
| KNLPPGNYKKPKLLYSSNGGHFLRILPDGTVDGTRDRSDQHIQLQLSAESVGEVYIKSTETGQYLCMDT DGLLYGSQTPNEECLFLERLEENHYNTYISKKHAEKNWFVGLKKNGSVKRGPRTHYGQKAILFLPLPVS SD | 114 |
| KLPPGNYKKPKLLYSSNGGHFLRILPDGTVDGTRDRSDQHIQLQLSAESVGEVYIKSTETGQYLCMDTD GLLYGSQTPNEECLFLERLEENHYNTYISKKHAEKNWFVGLKKNGSVKRGPRTHYGQKAILFLPLPVSS D | 115 |
| KPPGNYKKPKLLYSSNGGHFLRILPDGTVDGTRDRSDQHIQLQLSAESVGEVYIKSTETGQYLCMDTDG LLYGSQTPNEECLFLERLEENHYNTYISKKHAEKNWFVGLKKNGSVKRGPRTHYGQKAILFLPLPVSSD | 116 |
| KPGNYKKPKLLYSSNGGHFLRILPDGTVDGTRDRSDQHIQLQLSAESVGEVYIKSTETGQYLCMDTDGL LYGSQTPNEECLFLERLEENHYNTYISKKHAEKNWFVGLKKNGSVKRGPRTHYGQKAILFLPLPVSSD | 117 |

| SEQUENCES | |
|---|---|
| SEQUENCE | No. |
| MALTEKFNLPPGNYKKPKLLYSSNGGHFLRILPDGTVDGTRDRSDQHIQLQLSAESVGEVYIKSTETGQ YLCMDTDGLLYGSQTPNEECLFLERLEENHYNTYISKKHAEKNWFVGLKKNGSVKRGPRTHYGQKAILF LPLPVSSD | 118 |
| MALTEKNLPPGNYKKPKLLYSSNGGHFLRILPDGTVDGTRDRSDQHIQLQLSAESVGEVYIKSTETGQY LCMDTDGLLYGSQTPNEECLFLERLEENHYNTYISKKHAEKNWFVGLKKNGSVKRGPRTHYGQKAILEL PLPVSSD | 118 |
| MALTEKLPPGNYKKPKLLYSSNGGHFLRILPDGTVDGTRDRSDQHIQLQLSAESVGEVYIKSTETGQYL CMDTDGLLYGSQTPNEECLFLERLEENHYNTYISKKHAEKNWFVGLKKNGSVKRGPRTHYGQKAILFLP LPVSSD | 119 |
| MALTEKPPGNYKKPKLLYSSNGGHFLRILPDGTVDGTRDRSDQHIQLQLSAESVGEVYIKSTETGQYLC MDTDGLLYGSQTPNEECLFLERLEENHYNTYISKKHAEKNWFVGLKKNGSVKRGPRTHYGQKAILFLPL PVSSD | 120 |
| MALTEKPGNYKKPKLLYSSNGGHFLRILPDGTVDGTRDRSDQHIQLQLSAESVGEVYIKSTETGQYLCM DTDGLLYGSQTPNEECLFLERLEENHYNTYISKKHAEKNWFVGLKKNGSVKRGPRTHYGQKAILFLPLP VSSD | 121 |
| MLTEKFNLPPGNYKKPKLLYSSNGGHFLRILPDGTVDGTRDRSDQHIQLQLSAESVGEVYIKSTETGQY LCMDTDGLLYGSQTPNEECLFLERLEENHYNTYISKKHAEKNWFVGLKKNGSVKRGPRTHYGQKAILEL PLPVSSD | 122 |
| MLTEKNLPPGNYKKPKLLYSSNGGHFLRILPDGTVDGTRDRSDQHIQLQLSAESVGEVYIKSTETGQYL CMDTDGLLYGSQTPNEECLFLERLEENHYNTYISKKHAEKNWFVGLKKNGSVKRGPRTHYGQKAILFLP LPVSSD | 123 |
| MLTEKLPPGNYKKPKLLYSSNGGHFLRILPDGTVDGTRDRSDQHIQLQLSAESVGEVYIKSTETGQYLC MDTDGLLYGSQTPNEECLFLERLEENHYNTYISKKHAEKNWFVGLKKNGSVKRGPRTHYGQKAILFLPL PVSSD | 124 |
| MLTEKPPGNYKKPKLLYSSNGGHFLRILPDGTVDGTRDRSDQHIQLQLSAESVGEVYIKSTETGQYLCM DTDGLLYGSQTPNEECLFLERLEENHYNTYISKKHAEKNWFVGLKKNGSVKRGPRTHYGQKAILFLPLP VSSD | 125 |
| MLTEKPGNYKKPKLLYSSNGGHFLRILPDGTVDGTRDRSDQHIQLQLSAESVGEVYIKSTETGQYLCMD TDGLLYGSQTPNEECLFLERLEENHYNTYISKKHAEKNWFVGLKKNGSVKRGPRTHYGQKAILFLPLPV SSD | 126 |
| MTEKFNLPPGNYKKPKLLYSSNGGHFLRILPDGTVDGTRDRSDQHIQLQLSAESVGEVYIKSTETGQYL CMDTDGLLYGSQTPNEECLFLERLEENHYNTYISKKHAEKNWFVGLKKNGSVKRGPRTHYGQKAILFLP LPVSSD | 127 |
| MTEKNLPPGNYKKPKLLYSSNGGHFLRILPDGTVDGTRDRSDQHIQLQLSAESVGEVYIKSTETGQYLC MDTDGLLYGSQTPNEECLFLERLEENHYNTYISKKHAEKNWFVGLKKNGSVKRGPRTHYGQKAILFLPL PVSSD | 128 |
| MTEKLPPGNYKKPKLLYSSNGGHFLRILPDGTVDGTRDRSDQHIQLQLSAESVGEVYIKSTETGQYLCM DTDGLLYGSQTPNEECLFLERLEENHYNTYISKKHAEKNWFVGLKKNGSVKRGPRTHYGQKAILFLPLP VSSD | 129 |
| MTEKPPGNYKKPKLLYSSNGGHFLRILPDGTVDGTRDRSDQHIQLQLSAESVGEVYIKSTETGQYLCMD TDGLLYGSQTPNEECLFLERLEENHYNTYISKKHAEKNWFVGLKKNGSVKRGPRTHYGQKAILFLPLPV SSD | 130 |
| MTEKPGNYKKPKLLYSSNGGHFLRILPDGTVDGTRDRSDQHIQLQLSAESVGEVYIKSTETGQYLCMDT DGLLYGSQTPNEECLFLERLEENHYNTYISKKHAEKNWFVGLKKNGSVKRGPRTHYGQKAILFLPLPVS SD | 131 |
| MEKFNLPPGNYKKPKLLYSSNGGHFLRILPDGTVDGTRDRSDQHIQLQLSAESVGEVYIKSTETGQYLC MDTDGLLYGSQTPNEECLFLERLEENHYNTYISKKHAEKNWFVGLKKNGSVKRGPRTHYGQKAILFLPL PVSSD | 132 |
| MEKNLPPGNYKKPKLLYSSNGGHFLRILPDGTVDGTRDRSDQHIQLQLSAESVGEVYIKSTETGQYLCM DTDGLLYGSQTPNEECLFLERLEENHYNTYISKKHAEKNWFVGLKKNGSVKRGPRTHYGQKAILFLPLP VSSD | 133 |
| MEKLPPGNYKKPKLLYSSNGGHFLRILPDGTVDGTRDRSDQHIQLQLSAESVGEVYIKSTETGQYLCMD TDGLLYGSQTPNEECLFLERLEENHYNTYISKKHAEKNWFVGLKKNGSVKRGPRTHYGQKAILFLPLPV SSD | 134 |
| MEKPPGNYKKPKLLYSSNGGHFLRILPDGTVDGTRDRSDQHIQLQLSAESVGEVYIKSTETGQYLCMDT DGLLYGSQTPNEECLFLERLEENHYNTYISKKHAEKNWFVGLKKNGSVKRGPRTHYGQKAILFLPLPVS SD | 135 |

| SEQUENCE | No. |
|---|---|
| MEKPGNYKKPKLLYSSNGGHFLRILPDGTVDGTRDRSDQHIQLQLSAESVGEVYIKSTETGQYLCMDTD GLLYGSQTPNEECLFLERLEENHYNTYISKKHAEKNWFVGLKKNGSVKRGPRTHYGQKAILFLPLPVSS D | 136 |
| MKFNLPPGNYKKPKLLYSSNGGHFLRILPDGTVDGTRDRSDQHIQLQLSAESVGEVYIKSTETGQYLCM DTDGLLYGSQTPNEECLFLERLEENHYNTYISKKHAEKNWFVGLKKNGSVKRGPRTHYGQKAILFLPLP VSSD | 137 |
| MKNLPPGNYKKPKLLYSSNGGHFLRILPDGTVDGTRDRSDQHIQLQLSAESVGEVYIKSTETGQYLCMD TDGLLYGSQTPNEECLFLERLEENHYNTYISKKHAEKNWFVGLKKNGSVKRGPRTHYGQKAILFLPLPV SSD | 138 |
| MKLPPGNYKKPKLLYSSNGGHFLRILPDGTVDGTRDRSDQHIQLQLSAESVGEVYIKSTETGQYLCMDT DGLLYGSQTPNEECLFLERLEENHYNTYISKKHAEKNWFVGLKKNGSVKRGPRTHYGQKAILFLPLPVS SD | 139 |
| MKPPGNYKKPKLLYSSNGGHFLRILPDGTVDGTRDRSDQHIQLQLSAESVGEVYIKSTETGQYLCMDTD GLLYGSQTPNEECLFLERLEENHYNTYISKKHAEKNWFVGLKKNGSVKRGPRTHYGQKAILFLPLPVSS D | 140 |
| MKPGNYKKPKLLYSSNGGHFLRILPDGTVDGTRDRSDQHIQLQLSAESVGEVYIKSTETGQYLCMDTDG LLYGSQTPNEECLFLERLEENHYNTYISKKHAEKNWFVGLKKNGSVKRGPRTHYGQKAILFLPLPVSSD | 141 |
| FNLPPGNYKKPKLLYCSNGGHFLRILPDGTVDGTRDRSDQHIQLQLSAESVGEVY IKSTETGQYLAXDTDGLLYGSQTPNEECLFLERLEENHYNTYISKKHAEK NWFVGLKKNGSCKRGPRTHYGQKAILFLPLPVSSD | 142 |
| NLPPGNYKKPKLLYCSNGGHFLRILPDGTVDGTRDRSDQHIQLQLSAESVGEVY IKSTETGQYLAXDTDGLLYGSQTPNEECLFLERLEENHYNTYISKKHAEK NWFVGLKKNGSCKRGPRTHYGQKAILFLPLPVSSD | 143 |
| PPGNYKKPKLLYCSNGGHFLRILPDGTVDGTRDRSDQHIQLQLSAESVGEVY IKSTETGQYLAXDTDGLLYGSQTPNEECLFLERLEENHYNTYISKKHAEK NWFVGLKKNGSCKRGPRTHYGQKAILFLPLPVSSD | 144 |
| PGNYKKPKLLYCSNGGHFLRILPDGTVDGTRDRSDQHIQLQLSAESVGEVY IKSTETGQYLAXDTDGLLYGSQTPNEECLFLERLEENHYNTYISKKHAEK NWFVGLKKNGSCKRGPRTHYGQKAILFLPLPVSSD | 145 |
| FNLPPGNYKKPKLLYSSNGGHFLRILPDGTVDGTRDRSDQHIQLQLSAESVGEVYIKSTETGQYLCXDT DGLLYGSQTPNEECLFLERLEENHYNTYISKKHAEKNWFVGLKKNGSVKRGPRTHYGQKAILFLPLPVS SD | 146 |
| NLPPGNYKKPKLLYSSNGGHFLRILPDGTVDGTRDRSDQHIQLQLSAESVGEVYIKSTETGQYLCXDTD GLLYGSQTPNEECLFLERLEENHYNTYISKKHAEKNWFVGLKKNGSVKRGPRTHYGQKAILFLPLPVSS D | 147 |
| PPGNYKKPKLLYSSNGGHFLRILPDGTVDGTRDRSDQHIQLQLSAESVGEVYIKSTETGQYLCXDTDGL LYGSQTPNEECLFLERLEENHYNTYISKKHAEKNWFVGLKKNGSVKRGPRTHYGQKAILFLPLPVSSD | 148 |
| PGNYKKPKLLYSSNGGHFLRILPDGTVDGTRDRSDQHIQLQLSAESVGEVYIKSTETGQYLCXDTDGLL YGSQTPNEECLFLERLEENHYNTYISKKHAEKNWFVGLKKNGSVKRGPRTHYGQKAILFLPLPVSSD | 149 |
| ALTEKNLPPGNYKKPKLLYCSNGGHFLRILPDGTVDGTRDRSDQHIQLQLSAESVGEVY IKSTETGQYLAXDTDGLLYGSQTPNEECLFLERLEENHYNTYISKKHAEK NWFVGLKKNGSCKRGPRTHYGQKAILFLPLPVSSD | 150 |
| ALTEKLPPGNYKKPKLLYSSNGGHFLRILPDGTVDGTRDRSDQHIQLQLSAESVGEVYIKSTETGQYLC XDTDGLLYGSQTPNEECLFLERLEENHYNTYISKKHAEKNWFVGLKKNGSVKRGPRTHYGQKAILFLPL PVSSD | 151 |
| ALTEKPPGGNYKKPKLLYCSNGGHFLRILPDGTVDGTRDRSDQHIQLQLSAESVGEVY IKSTETGQYLAXDTDGLLYGSQTPNEECLFLERLEENHYNTYISKKHAEK NWFVGLKKNGSCKRGPRTHYGQKAILFLPLPVSSD | 152 |
| ALTEKPGNYKKPKLLYCSNGGHFLRILPDGTVDGTRDRSDQHIQLQLSAESVGEVY IKSTETGQYLAXDTDGLLYGSQTPNEECLFLERLEENHYNTYISKKHAEK NWFVGLKKNGSCKRGPRTHYGQKAILFLPLPVSSD | 153 |
| LTEKFNLPPGNYKKPKLLYCSNGGHFLRILPDGTVDGTRDRSDQHIQLQLSAESVGEVY IKSTETGQYLAXDTDGLLYGSQTPNEECLFLERLEENHYNTYISKKHAEK NWFVGLKKNGSCKRGPRTHYGQKAILFLPLPVSSD | 154 |

| SEQUENCES | |
|---|---|
| SEQUENCE | No. |
| LTEKNLPPGNYKKPKLLYCSNGGHFLRILPDGTVDGTRDRSDQHIQLQLSAESVGEVY IKSTETGQYLAXDTDGLLYGSQTPNEECLFLERLEENHYNTYISKKHAEK NWFVGLKKNGSCKRGPRTHYGQKAILFLPLPVSSD | 155 |
| LTEKLPPGNYKKPKLLYCSNGGHFLRILPDGTVDGTRDRSDQHIQLQLSAESVGEVY IKSTETGQYLAXDTDGLLYGSQTPNEECLFLERLEENHYNTYISKKHAEK NWFVGLKKNGSCKRGPRTHYGQKAILFLPLPVSSD | 156 |
| LTEKPPGNYKKPKLLYCSNGGHFLRILPDGTVDGTRDRSDQHIQLQLSAESVGEVY IKSTETGQYLAXDTDGLLYGSQTPNEECLFLERLEENHYNTYISKKHAEK NWFVGLKKNGSCKRGPRTHYGQKAILFLPLPVSSD | 157 |
| LTEKPGNYKKPKLLYCSNGGHFLRILPDGTVDGTRDRSDQHIQLQLSAESVGEVY IKSTETGQYLAXDTDGLLYGSQTPNEECLFLERLEENHYNTYISKKHAEK NWFVGLKKNGSCKRGPRTHYGQKAILFLPLPVSSD | 158 |
| TEKFNLPPGNYKKPKLLYCSNGGHFLRILPDGTVDGTRDRSDQHIQLQLSAESVGEVY IKSTETGQYLAXDTDGLLYGSQTPNEECLFLERLEENHYNTYISKKHAEK NWFVGLKKNGSCKRGPRTHYGQKAILFLPLPVSSD | 159 |
| TEKNLPPGNYKKPKLLYCSNGGHFLRILPDGTVDGTRDRSDQHIQLQLSAESVGEVY IKSTETGQYLAXDTDGLLYGSQTPNEECLFLERLEENHYNTYISKKHAEK NWFVGLKKNGSCKRGPRTHYGQKAILFLPLPVSSD | 160 |
| TEKLPPGNYKKPKLLYCSNGGHFLRILPDGTVDGTRDRSDQHIQLQLSAESVGEVY IKSTETGQYLAXDTDGLLYGSQTPNEECLFLERLEENHYNTYISKKHAEK NWFVGLKKNGSCKRGPRTHYGQKAILFLPLPVSSD | 161 |
| TEKPPGNYKKPKLLYCSNGGHFLRILPDGTVDGTRDRSDQHIQLQLSAESVGEVY IKSTETGQYLAXDTDGLLYGSQTPNEECLFLERLEENHYNTYISKKHAEK NWFVGLKKNGSCKRGPRTHYGQKAILFLPLPVSSD | 162 |
| TEKPGNYKKPKLLYCSNGGHFLRILPDGTVDGTRDRSDQHIQLQLSAESVGEVY IKSTETGQYLAXDTDGLLYGSQTPNEECLFLERLEENHYNTYISKKHAEK NWFVGLKKNGSCKRGPRTHYGQKAILFLPLPVSSD | 163 |
| EKFNLPPGNYKKPKLLYCSNGGHFLRILPDGTVDGTRDRSDQHIQLQLSAESVGEVY IKSTETGQYLAXDTDGLLYGSQTPNEECLFLERLEENHYNTYISKKHAEK NWFVGLKKNGSCKRGPRTHYGQKAILFLPLPVSSD | 164 |
| EKNLPPGNYKKPKLLYCSNGGHFLRILPDGTVDGTRDRSDQHIQLQLSAESVGEVY IKSTETGQYLAXDTDGLLYGSQTPNEECLFLERLEENHYNTYISKKHAEK NWFVGLKKNGSCKRGPRTHYGQKAILFLPLPVSSD | 165 |
| EKLPPGNYKKPKLLYCSNGGHFLRILPDGTVDGTRDRSDQHIQLQLSAESVGEVY IKSTETGQYLAXDTDGLLYGSQTPNEECLFLERLEENHYNTYISKKHAEK NWFVGLKKNGSCKRGPRTHYGQKAILFLPLPVSSD | 166 |
| EKPPGNYKKPKLLYCSNGGHFLRILPDGTVDGTRDRSDQHIQLQLSAESVGEVY IKSTETGQYLAXDTDGLLYGSQTPNEECLFLERLEENHYNTYISKKHAEK NWFVGLKKNGSCKRGPRTHYGQKAILFLPLPVSSD | 167 |
| EKPGNYKKPKLLYCSNGGHFLRILPDGTVDGTRDRSDQHIQLQLSAESVGEVY IKSTETGQYLAXDTDGLLYGSQTPNEECLFLERLEENHYNTYISKKHAEK NWFVGLKKNGSCKRGPRTHYGQKAILFLPLPVSSD | 168 |
| KFNLPPGNYKKPKLLYCSNGGHFLRILPDGTVDGTRDRSDQHIQLQLSAESVGEVY IKSTETGQYLAXDTDGLLYGSQTPNEECLFLERLEENHYNTYISKKHAEK NWFVGLKKNGSCKRGPRTHYGQKAILFLPLPVSSD | 169 |
| KNLPPGNYKKPKLLYCSNGGHFLRILPDGTVDGTRDRSDQHIQLQLSAESVGEVY IKSTETGQYLAXDTDGLLYGSQTPNEECLFLERLEENHYNTYISKKHAEK NWFVGLKKNGSCKRGPRTHYGQKAILFLPLPVSSD | 170 |
| KLPPGNYKKPKLLYCSNGGHFLRILPDGTVDGTRDRSDQHIQLQLSAESVGEVY IKSTETGQYLAXDTDGLLYGSQTPNEECLFLERLEENHYNTYISKKHAEK NWFVGLKKNGSCKRGPRTHYGQKAILFLPLPVSSD | 171 |
| KPPGNYKKPKLLYCSNGGHFLRILPDGTVDGTRDRSDQHIQLQLSAESVGEVY IKSTETGQYLAXDTDGLLYGSQTPNEECLFLERLEENHYNTYISKKHAEK NWFVGLKKNGSCKRGPRTHYGQKAILFLPLPVSSD | 172 |
| KPGNYKKPKLLYCSNGGHFLRILPDGTVDGTRDRSDQHIQLQLSAESVGEVY IKSTETGQYLAXDTDGLLYGSQTPNEECLFLERLEENHYNTYISKKHAEK NWFVGLKKNGSCKRGPRTHYGQKAILFLPLPVSSD | 173 |

| SEQUENCES | |
|---|---|
| SEQUENCE | No. |
| FNLPPGNYKKPKLLYSSNGGHFLRILPDGTVDGTRDRSDQHIQLQLSAESVGEVYIKSTETGQYLCXDT<br>DGLLYGSQTPNEECLFLERLEENHYNTYISKKHAEKNWFVGLKKNGSVKRGPRTHYGQKAILFLPLPVS<br>SD | 174 |
| ALTEKFNLPPGNYKKPKLLYSSNGGHFLRILPDGTVDGTRDRSDQHIQLQLSAESVGEVYIKSTETGQY<br>LCXDTDGLLYGSQTPNEECLFLERLEENHYNTYISKKHAEKNWFVGLKKNGSVKRGPRTHYGQKAILEL<br>PLPVSSD | 175 |
| LTEKFNLPPGNYKKPKLLYSSNGGHFLRILPDGTVDGTRDRSDQHIQLQLSAESVGEVYIKSTETGQYL<br>CXDTDGLLYGSQTPNEECLFLERLEENHYNTYISKKHAEKNWFVGLKKNGSVKRGPRTHYGQKAILFLP<br>LPVSSD | 176 |
| TEKFNLPPGNYKKPKLLYSSNGGHFLRILPDGTVDGTRDRSDQHIQLQLSAESVGEVYIKSTETGQYLC<br>XDTDGLLYGSQTPNEECLFLERLEENHYNTYISKKHAEKNWFVGLKKNGSVKRGPRTHYGQKAILFLPL<br>PVSSD | 177 |
| EKFNLPPGNYKKPKLLYSSNGGHFLRILPDGTVDGTRDRSDQHIQLQLSAESVGEVYIKSTETGQYLCX<br>DTDGLLYGSQTPNEECLFLERLEENHYNTYISKKHAEKNWFVGLKKNGSVKRGPRTHYGQKAILFLPLP<br>VSSD | 178 |
| KFNLPPGNYKKPKLLYSSNGGHFLRILPDGTVDGTRDRSDQHIQLQLSAESVGEVYIKSTETGQYLCXD<br>TDGLLYGSQTPNEECLFLERLEENHYNTYISKKHAEKNWFVGLKKNGSVKRGPRTHYGQKAILFLPLPV<br>SSD | 179 |
| KFNLPPGNYKKPKLLYSSNGGHFLRILPDGTVDGTRDRSDQHIQLQLSAESVGEVYIKSTETGQYLCXD<br>TDGLLYGSQTPNEECLFLERLEENHYNTYISKKHAEKNWFVGLKKNGSVKRGPRTHYGQKAILFLPLPV<br>SSD | 180 |
| ALTEKNLPPGNYKKPKLLYSSNGGHFLRILPDGTVDGTRDRSDQHIQLQLSAESVGEVYIKSTETGQYL<br>CXDTDGLLYGSQTPNEECLFLERLEENHYNTYISKKHAEKNWFVGLKKNGSVKRGPRTHYGQKAILFLP<br>LPVSSD | 181 |
| ALTEKLPPGNYKKPKLLYSSNGGHFLRILPDGTVDGTRDRSDQHIQLQLSAESVGEVYIKSTETGQYLC<br>XDTDGLLYGSQTPNEECLFLERLEENHYNTYISKKHAEKNWFVGLKKNGSVKRGPRTHYGQKAILFLPL<br>PVSSD | 182 |
| ALTEKPPGNYKKPKLLYSSNGGHFLRILPDGTVDGTRDRSDQHIQLQLSAESVGEVYIKSTETGQYLCX<br>DTDGLLYGSQTPNEECLFLERLEENHYNTYISKKHAEKNWFVGLKKNGSVKRGPRTHYGQKAILFLPLP<br>VSSD | 183 |
| ALTEKPGNYKKPKLLYSSNGGHFLRILPDGTVDGTRDRSDQHIQLQLSAESVGEVYIKSTETGQYLCXD<br>TDGLLYGSQTPNEECLFLERLEENHYNTYISKKHAEKNWFVGLKKNGSVKRGPRTHYGQKAILFLPLPV<br>SSD | 184 |
| LTEKFNLPPGNYKKPKLLYSSNGGHFLRILPDGTVDGTRDRSDQHIQLQLSAESVGEVYIKSTETGQYL<br>CXDTDGLLYGSQTPNEECLFLERLEENHYNTYISKKHAEKNWFVGLKKNGSVKRGPRTHYGQKAILFLP<br>LPVSSD | 185 |
| LTEKNLPPGNYKKPKLLYSSNGGHFLRILPDGTVDGTRDRSDQHIQLQLSAESVGEVYIKSTETGQYLC<br>XDTDGLLYGSQTPNEECLFLERLEENHYNTYISKKHAEKNWFVGLKKNGSVKRGPRTHYGQKAILFLPL<br>PVSSD | 186 |
| LTEKLPPGNYKKPKLLYSSNGGHFLRILPDGTVDGTRDRSDQHIQLQLSAESVGEVYIKSTETGQYLCX<br>DTDGLLYGSQTPNEECLFLERLEENHYNTYISKKHAEKNWFVGLKKNGSVKRGPRTHYGQKAILFLPLP<br>VSSD | 187 |
| LTEKPPGNYKKPKLLYSSNGGHFLRILPDGTVDGTRDRSDQHIQLQLSAESVGEVYIKSTETGQYLCXD<br>TDGLLYGSQTPNEECLFLERLEENHYNTYISKKHAEKNWFVGLKKNGSVKRGPRTHYGQKAILFLPLPV<br>SSD | 188 |
| LTEKPGNYKKPKLLYSSNGGHFLRILPDGTVDGTRDRSDQHIQLQLSAESVGEVYIKSTETGQYLCXDT<br>DGLLYGSQTPNEECLFLERLEENHYNTYISKKHAEKNWFVGLKKNGSVKRGPRTHYGQKAILFLPLPVS<br>SD | 189 |
| TEKFNLPPGNYKKPKLLYSSNGGHFLRILPDGTVDGTRDRSDQHIQLQLSAESVGEVYIKSTETGQYLC<br>XDTDGLLYGSQTPNEECLFLERLEENHYNTYISKKHAEKNWFVGLKKNGSVKRGPRTHYGQKAILFLPL<br>PVSSD | 190 |
| TEKNLPPGNYKKPKLLYSSNGGHFLRILPDGTVDGTRDRSDQHIQLQLSAESVGEVYIKSTETGQYLCX<br>DTDGLLYGSQTPNEECLFLERLEENHYNTYISKKHAEKNWFVGLKKNGSVKRGPRTHYGQKAILFLPLP<br>VSSD | 191 |

| SEQUENCE | No. |
|---|---|
| TEKLPPGNYKKPKLLYSSNGGHFLRILPDGTVDGTRDRSDQHIQLQLSAESVGEVYIKSTETGQYLCXDTDGLLYGSQTPNEECLFLERLEENHYNTYISKKHAEKNWFVGLKKNGSVKRGPRTHYGQKAILFLPLPVSSD | 192 |
| TEKPPGNYKKPKLLYSSNGGHFLRILPDGTVDGTRDRSDQHIQLQLSAESVGEVYIKSTETGQYLCXDTDGLLYGSQTPNEECLFLERLEENHYNTYISKKHAEKNWFVGLKKNGSVKRGPRTHYGQKAILFLPLPVSSD | 193 |
| TEKPGNYKKPKLLYSSNGGHFLRILPDGTVDGTRDRSDQHIQLQLSAESVGEVYIKSTETGQYLCXDTDGLLYGSQTPNEECLFLERLEENHYNTYISKKHAEKNWFVGLKKNGSVKRGPRTHYGQKAILFLPLPVSSD | 194 |
| EKFNLPPGNYKKPKLLYSSNGGHFLRILPDGTVDGTRDRSDQHIQLQLSAESVGEVYIKSTETGQYLCXDTDGLLYGSQTPNEECLFLERLEENHYNTYISKKHAEKNWFVGLKKNGSVKRGPRTHYGQKAILFLPLPVSSD | 195 |
| EKNLPPGNYKKPKLLYSSNGGHFLRILPDGTVDGTRDRSDQHIQLQLSAESVGEVYIKSTETGQYLCXDTDGLLYGSQTPNEECLFLERLEENHYNTYISKKHAEKNWFVGLKKNGSVKRGPRTHYGQKAILFLPLPVSSD | 196 |
| EKLPPGNYKKPKLLYSSNGGHFLRILPDGTVDGTRDRSDQHIQLQLSAESVGEVYIKSTETGQYLCXDTDGLLYGSQTPNEECLFLERLEENHYNTYISKKHAEKNWFVGLKKNGSVKRGPRTHYGQKAILFLPLPVSSD | 197 |
| EKPPGNYKKPKLLYSSNGGHFLRILPDGTVDGTRDRSDQHIQLQLSAESVGEVYIKSTETGQYLCXDTDGLLYGSQTPNEECLFLERLEENHYNTYISKKHAEKNWFVGLKKNGSVKRGPRTHYGQKAILFLPLPVSSD | 198 |
| EKPGNYKKPKLLYSSNGGHFLRILPDGTVDGTRDRSDQHIQLQLSAESVGEVYIKSTETGQYLCXDTDGLLYGSQTPNEECLFLERLEENHYNTYISKKHAEKNWFVGLKKNGSVKRGPRTHYGQKAILFLPLPVSSD | 199 |
| KFNLPPGNYKKPKLLYSSNGGHFLRILPDGTVDGTRDRSDQHIQLQLSAESVGEVYIKSTETGQYLCXDTDGLLYGSQTPNEECLFLERLEENHYNTYISKKHAEKNWFVGLKKNGSVKRGPRTHYGQKAILFLPLPVSSD | 200 |
| KNLPPGNYKKPKLLYSSNGGHFLRILPDGTVDGTRDRSDQHIQLQLSAESVGEVYIKSTETGQYLCXDTDGLLYGSQTPNEECLFLERLEENHYNTYISKKHAEKNWFVGLKKNGSVKRGPRTHYGQKAILFLPLPVSSD | 201 |
| KLPPGNYKKPKLLYSSNGGHFLRILPDGTVDGTRDRSDQHIQLQLSAESVGEVYIKSTETGQYLCXDTDGLLYGSQTPNEECLFLERLEENHYNTYISKKHAEKNWFVGLKKNGSVKRGPRTHYGQKAILFLPLPVSSD | 202 |
| KPPGNYKKPKLLYSSNGGHFLRILPDGTVDGTRDRSDQHIQLQLSAESVGEVYIKSTETGQYLCXDTDGLLYGSQTPNEECLFLERLEENHYNTYISKKHAEKNWFVGLKKNGSVKRGPRTHYGQKAILFLPLPVSSD | 203 |
| KPGNYKKPKLLYSSNGGHFLRILPDGTVDGTRDRSDQHIQLQLSAESVGEVYIKSTETGQYLCXDTDGLLYGSQTPNEECLFLERLEENHYNTYISKKHAEKNWFVGLKKNGSVKRGPRTHYGQKAILFLPLPVSSD | 204 |
| FNLPPGNYKKPVLLYCSNGGHFLRILPDGTVDGTRDRSDQHIQLQLSAESVGEVYIKSTETGQYLAMDTDGLLYGSQTPNEECLFLERLEENHYNTYISKKHAEKNWFVGLKKNGSVKRGPRTHYGQKAILFLVLPVSSD | 205 |
| FNLPPGNYKKPKLLYSSNGGHFLRILPDGTVDGTRDRSDQHIQLQLSAESVGEVYIKSTETGQYLCMDTDGLLYGSQTPNEECLFLERLEENHYNTYISKKHAEKNWFVGLKKNGSVKRGPRTHYGQKAILFLPLPVSSD | 206 |

What is claimed is:

1. A method of ameliorating a corneal herpetic keratopathy or suppressing reactivation of a latent herpes virus comprising administering to an eye of a mammal, a pharmaceutical composition comprising a recombinant modified FGF-1 polypeptide comprising a sequence comprising mutated residues compared to wild-type FGF-1 sequence of SEQ ID NO: 1, wherein the mutated residues comprise Cys16Ser, Ala66Cys, and Cys117Val, wherein the polypeptide comprises an N-terminal methionine residue positioned upstream to the first residue of SEQ ID NO: 1, wherein the corneal herpetic keratopathy is secondary to an infection by a herpes virus; and wherein administering the pharmaceutical composition comprising the recombinant modified FGF-1 polypeptide results in suppression of reactivation of the latent herpes virus in the mammal.

2. The method of claim 1, wherein the corneal herpetic keratopathy is a chronic or recurrent herpetic keratopathy.

3. The method of claim 1, wherein the corneal herpetic keratopathy comprises a neurotrophic keratopathy.

4. The method of claim 1, wherein the mammal is a human.

5. The method of claim 1, wherein the pharmaceutical composition comprises the recombinant modified FGF-1 polypeptide of SEQ ID NO: 2.

6. The method of claim 5, wherein the pharmaceutical composition comprises phosphate buffered saline, 0.3% propylene glycol, 0.4% polyethylene glycol 400, and 0.05% hydroxypropyl guar, wherein the phosphate buffered saline has a pH of 7.2.

7. The method of claim 6, wherein the pharmaceutical composition comprises at least about 50 pg/ml to about 500 pg/ml of the recombinant modified FGF-1 polypeptide.

8. The method of claim 1, wherein the administering comprises administering the pharmaceutical composition comprising the recombinant modified FGF-1 polypeptide for a duration of 30 days.

9. The method of claim 1, wherein the administering comprises administering the pharmaceutical composition comprising the recombinant modified FGF-1 polypeptide twice daily.

10. The method of claim 1, wherein the pharmaceutical composition is an aqueous ophthalmic formulation.

11. The method of claim 10, wherein the ophthalmic formulation is an eye drop.

12. The method of claim 1, wherein the pharmaceutical composition lacks heparin.

13. The method of claim 1, wherein the recombinant FGF-1 polypeptide comprises an amino acid sequence that is of at least 95% sequence identity to the recombinant modified FGF-1 polypeptide of SEQ ID NO:2.

14. The method of claim 1, wherein administering the pharmaceutical composition comprising the recombinant modified FGF-1 polypeptide reduces inflammation associated with the corneal herpetic keratopathy.

* * * * *

SEQUENCE LISTING

<160> NUMBER OF SEQ ID NOS: 207

<210> SEQ ID NO 1
<211> LENGTH: 140
<212> TYPE: PRT
<213> ORGANISM: Homo sapiens

<400> SEQUENCE: 1

Phe Asn Leu Pro Pro Gly Asn Tyr Lys Lys Pro Lys Leu Leu Tyr Cys
1               5                   10                  15

-continued

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
            100                 105                 110

Lys Asn Gly Ser Cys Lys Arg Gly Pro Arg Thr His Tyr Gly Gln Lys
        115                 120                 125

Ala Ile Leu Phe Leu Pro Leu Pro Val Ser Ser Asp
    130                 135                 140

<210> SEQ ID NO 2
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Phe Asn Leu Pro Pro Gly Asn Tyr Lys Lys Pro Lys Leu Leu Tyr
1               5                   10                  15

Ser Ser Asn Gly Gly His Phe Leu Arg Ile Leu Pro Asp Gly Thr Val
            20                  25                  30

Asp Gly Thr Arg Asp Arg Ser Asp Gln His Ile Gln Leu Gln Leu Ser
        35                  40                  45

Ala Glu Ser Val Gly Glu Val Tyr Ile Lys Ser Thr Glu Thr Gly Gln
    50                  55                  60

Tyr Leu Cys Met Asp Thr Asp Gly Leu Leu Tyr Gly Ser Gln Thr Pro
65                  70                  75                  80

Asn Glu Glu Cys Leu Phe Leu Glu Arg Leu Glu Glu Asn His Tyr Asn
                85                  90                  95

Thr Tyr Ile Ser Lys Lys His Ala Glu Lys Asn Trp Phe Val Gly Leu
            100                 105                 110

Lys Lys Asn Gly Ser Val Lys Arg Gly Pro Arg Thr His Tyr Gly Gln
        115                 120                 125

Lys Ala Ile Leu Phe Leu Pro Leu Pro Val Ser Ser Asp
    130                 135                 140

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Met Ala Glu Gly Glu Ile Thr Thr Phe Thr Ala Leu Thr Glu Lys
1               5                   10                  15

<210> SEQ ID NO 4
<211> LENGTH: 5

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Leu Thr Glu Lys
1               5

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Leu Thr Glu Lys
1

<210> SEQ ID NO 6
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Thr Glu Lys
1

<210> SEQ ID NO 7
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Glu Lys
1

<210> SEQ ID NO 8
<211> LENGTH: 1
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Lys
1

<210> SEQ ID NO 9
<211> LENGTH: 146
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Ala Leu Thr Glu Lys Phe Asn Leu Pro Pro Gly Asn Tyr Lys Lys
```

```
            1               5              10              15

Pro Lys Leu Leu Tyr Cys Ser Asn Gly Gly His Phe Leu Arg Ile Leu
                20              25              30

Pro Asp Gly Thr Val Asp Gly Thr Arg Asp Arg Ser Asp Gln His Ile
                35              40              45

Gln Leu Gln Leu Ser Ala Glu Ser Val Gly Glu Val Tyr Ile Lys Ser
                50              55              60

Thr Glu Thr Gly Gln Tyr Leu Ala Met Asp Thr Asp Gly Leu Leu Tyr
 65              70              75              80

Gly Ser Gln Thr Pro Asn Glu Glu Cys Leu Phe Leu Glu Arg Leu Glu
                85              90              95

Glu Asn His Tyr Asn Thr Tyr Ile Ser Lys Lys His Ala Glu Lys Asn
                100             105             110

Trp Phe Val Gly Leu Lys Lys Asn Gly Ser Cys Lys Arg Gly Pro Arg
                115             120             125

Thr His Tyr Gly Gln Lys Ala Ile Leu Phe Leu Pro Leu Pro Val Ser
                130             135             140

Ser Asp
145

<210> SEQ ID NO 10
<211> LENGTH: 145
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Leu Thr Glu Lys Phe Asn Leu Pro Pro Gly Asn Tyr Lys Lys Pro
 1               5              10              15

Lys Leu Leu Tyr Cys Ser Asn Gly Gly His Phe Leu Arg Ile Leu Pro
                20              25              30

Asp Gly Thr Val Asp Gly Thr Arg Asp Arg Ser Asp Gln His Ile Gln
                35              40              45

Leu Gln Leu Ser Ala Glu Ser Val Gly Glu Val Tyr Ile Lys Ser Thr
                50              55              60

Glu Thr Gly Gln Tyr Leu Ala Met Asp Thr Asp Gly Leu Leu Tyr Gly
 65              70              75              80

Ser Gln Thr Pro Asn Glu Glu Cys Leu Phe Leu Glu Arg Leu Glu Glu
                85              90              95

Asn His Tyr Asn Thr Tyr Ile Ser Lys Lys His Ala Glu Lys Asn Trp
                100             105             110

Phe Val Gly Leu Lys Lys Asn Gly Ser Cys Lys Arg Gly Pro Arg Thr
                115             120             125

His Tyr Gly Gln Lys Ala Ile Leu Phe Leu Pro Leu Pro Val Ser Ser
                130             135             140

Asp
145

<210> SEQ ID NO 11
<211> LENGTH: 144
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 11

Met Thr Glu Lys Phe Asn Leu Pro Pro Gly Asn Tyr Lys Lys Pro Lys
1               5                   10                  15

Leu Leu Tyr Cys Ser Asn Gly Gly His Phe Leu Arg Ile Leu Pro Asp
            20                  25                  30

Gly Thr Val Asp Gly Thr Arg Asp Arg Ser Asp Gln His Ile Gln Leu
        35                  40                  45

Gln Leu Ser Ala Glu Ser Val Gly Glu Val Tyr Ile Lys Ser Thr Glu
    50                  55                  60

Thr Gly Gln Tyr Leu Ala Met Asp Thr Asp Gly Leu Leu Tyr Gly Ser
65                  70                  75                  80

Gln Thr Pro Asn Glu Glu Cys Leu Phe Leu Glu Arg Leu Glu Glu Asn
            85                  90                  95

His Tyr Asn Thr Tyr Ile Ser Lys Lys His Ala Glu Lys Asn Trp Phe
        100                 105                 110

Val Gly Leu Lys Lys Asn Gly Ser Cys Lys Arg Gly Pro Arg Thr His
        115                 120                 125

Tyr Gly Gln Lys Ala Ile Leu Phe Leu Pro Leu Pro Val Ser Ser Asp
    130                 135                 140

<210> SEQ ID NO 12
<211> LENGTH: 143
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Glu Lys Phe Asn Leu Pro Pro Gly Asn Tyr Lys Lys Pro Lys Leu
1               5                   10                  15

Leu Tyr Cys Ser Asn Gly Gly His Phe Leu Arg Ile Leu Pro Asp Gly
            20                  25                  30

Thr Val Asp Gly Thr Arg Asp Arg Ser Asp Gln His Ile Gln Leu Gln
        35                  40                  45

Leu Ser Ala Glu Ser Val Gly Glu Val Tyr Ile Lys Ser Thr Glu Thr
    50                  55                  60

Gly Gln Tyr Leu Ala Met Asp Thr Asp Gly Leu Leu Tyr Gly Ser Gln
65                  70                  75                  80

Thr Pro Asn Glu Glu Cys Leu Phe Leu Glu Arg Leu Glu Glu Asn His
            85                  90                  95

Tyr Asn Thr Tyr Ile Ser Lys Lys His Ala Glu Lys Asn Trp Phe Val
        100                 105                 110

Gly Leu Lys Lys Asn Gly Ser Cys Lys Arg Gly Pro Arg Thr His Tyr
        115                 120                 125

Gly Gln Lys Ala Ile Leu Phe Leu Pro Leu Pro Val Ser Ser Asp
    130                 135                 140

<210> SEQ ID NO 13
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Lys Phe Asn Leu Pro Pro Gly Asn Tyr Lys Lys Pro Lys Leu Leu

```
                1               5                  10                 15
Tyr Cys Ser Asn Gly Gly His Phe Leu Arg Ile Leu Pro Asp Gly Thr
                    20                 25                 30

Val Asp Gly Thr Arg Asp Arg Ser Asp Gln His Ile Gln Leu Gln Leu
                    35                 40                 45

Ser Ala Glu Ser Val Gly Glu Val Tyr Ile Lys Ser Thr Glu Thr Gly
            50                 55                 60

Gln Tyr Leu Ala Met Asp Thr Asp Gly Leu Leu Tyr Gly Ser Gln Thr
65                      70                 75                 80

Pro Asn Glu Glu Cys Leu Phe Leu Glu Arg Leu Glu Glu Asn His Tyr
                        85                 90                 95

Asn Thr Tyr Ile Ser Lys Lys His Ala Glu Lys Asn Trp Phe Val Gly
                    100                105                110

Leu Lys Lys Asn Gly Ser Cys Lys Arg Gly Pro Arg Thr His Tyr Gly
                    115                120                125

Gln Lys Ala Ile Leu Phe Leu Pro Leu Pro Val Ser Ser Asp
            130                135                140
```

<210> SEQ ID NO 14
<211> LENGTH: 146
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

```
Met Ala Leu Thr Glu Lys Phe Asn Leu Pro Pro Gly Asn Tyr Lys Lys
1               5                  10                 15

Pro Lys Leu Leu Tyr Ser Ser Asn Gly Gly His Phe Leu Arg Ile Leu
                    20                 25                 30

Pro Asp Gly Thr Val Asp Gly Thr Arg Asp Arg Ser Asp Gln His Ile
            35                 40                 45

Gln Leu Gln Leu Ser Ala Glu Ser Val Gly Glu Val Tyr Ile Lys Ser
    50                 55                 60

Thr Glu Thr Gly Gln Tyr Leu Cys Met Asp Thr Asp Gly Leu Leu Tyr
65                  70                 75                 80

Gly Ser Gln Thr Pro Asn Glu Glu Cys Leu Phe Leu Glu Arg Leu Glu
                85                 90                 95

Glu Asn His Tyr Asn Thr Tyr Ile Ser Lys Lys His Ala Glu Lys Asn
            100                105                110

Trp Phe Val Gly Leu Lys Lys Asn Gly Ser Val Lys Arg Gly Pro Arg
        115                120                125

Thr His Tyr Gly Gln Lys Ala Ile Leu Phe Leu Pro Leu Pro Val Ser
    130                135                140

Ser Asp
145
```

<210> SEQ ID NO 15
<211> LENGTH: 145
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Leu Thr Glu Lys Phe Asn Leu Pro Pro Gly Asn Tyr Lys Lys Pro

```
                1               5                   10                  15
Lys Leu Leu Tyr Ser Ser Asn Gly Gly His Phe Leu Arg Ile Leu Pro
                20                  25                  30

Asp Gly Thr Val Asp Gly Thr Arg Asp Arg Ser Asp Gln His Ile Gln
                35                  40                  45

Leu Gln Leu Ser Ala Glu Ser Val Gly Glu Val Tyr Ile Lys Ser Thr
    50                  55                  60

Glu Thr Gly Gln Tyr Leu Cys Met Asp Thr Asp Gly Leu Leu Tyr Gly
65                  70                  75                  80

Ser Gln Thr Pro Asn Glu Glu Cys Leu Phe Leu Glu Arg Leu Glu Glu
                85                  90                  95

Asn His Tyr Asn Thr Tyr Ile Ser Lys Lys His Ala Glu Lys Asn Trp
                100                 105                 110

Phe Val Gly Leu Lys Lys Asn Gly Ser Val Lys Arg Gly Pro Arg Thr
                115                 120                 125

His Tyr Gly Gln Lys Ala Ile Leu Phe Leu Pro Leu Pro Val Ser Ser
                130                 135             140

Asp
145

<210> SEQ ID NO 16
<211> LENGTH: 144
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Thr Glu Lys Phe Asn Leu Pro Pro Gly Asn Tyr Lys Lys Pro Lys
1               5                   10                  15

Leu Leu Tyr Ser Ser Asn Gly Gly His Phe Leu Arg Ile Leu Pro Asp
                20                  25                  30

Gly Thr Val Asp Gly Thr Arg Asp Arg Ser Asp Gln His Ile Gln Leu
                35                  40                  45

Gln Leu Ser Ala Glu Ser Val Gly Glu Val Tyr Ile Lys Ser Thr Glu
    50                  55                  60

Thr Gly Gln Tyr Leu Cys Met Asp Thr Asp Gly Leu Leu Tyr Gly Ser
65                  70                  75                  80

Gln Thr Pro Asn Glu Glu Cys Leu Phe Leu Glu Arg Leu Glu Glu Asn
                85                  90                  95

His Tyr Asn Thr Tyr Ile Ser Lys Lys His Ala Glu Lys Asn Trp Phe
                100                 105                 110

Val Gly Leu Lys Lys Asn Gly Ser Val Lys Arg Gly Pro Arg Thr His
                115                 120                 125

Tyr Gly Gln Lys Ala Ile Leu Phe Leu Pro Leu Pro Val Ser Ser Asp
                130                 135             140

<210> SEQ ID NO 17
<211> LENGTH: 143
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Glu Lys Phe Asn Leu Pro Pro Gly Asn Tyr Lys Lys Pro Lys Leu
```

```
                1               5                  10                  15
Leu Tyr Ser Ser Asn Gly Gly His Phe Leu Arg Ile Leu Pro Asp Gly
            20                  25                  30

Thr Val Asp Gly Thr Arg Asp Arg Ser Asp Gln His Ile Gln Leu Gln
            35                  40                  45

Leu Ser Ala Glu Ser Val Gly Glu Val Tyr Ile Lys Ser Thr Glu Thr
            50                  55                  60

Gly Gln Tyr Leu Cys Met Asp Thr Asp Gly Leu Leu Tyr Gly Ser Gln
 65                 70                  75                  80

Thr Pro Asn Glu Glu Cys Leu Phe Leu Glu Arg Leu Glu Glu Asn His
                85                  90                  95

Tyr Asn Thr Tyr Ile Ser Lys Lys His Ala Glu Lys Asn Trp Phe Val
                100                 105                 110

Gly Leu Lys Lys Asn Gly Ser Val Lys Arg Gly Pro Arg Thr His Tyr
                115                 120                 125

Gly Gln Lys Ala Ile Leu Phe Leu Pro Leu Pro Val Ser Ser Asp
            130                 135                 140
```

<210> SEQ ID NO 18
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

```
Met Lys Phe Asn Leu Pro Pro Gly Asn Tyr Lys Lys Pro Lys Leu Leu
 1               5                  10                  15

Tyr Ser Ser Asn Gly Gly His Phe Leu Arg Ile Leu Pro Asp Gly Thr
            20                  25                  30

Val Asp Gly Thr Arg Asp Arg Ser Asp Gln His Ile Gln Leu Gln Leu
            35                  40                  45

Ser Ala Glu Ser Val Gly Glu Val Tyr Ile Lys Ser Thr Glu Thr Gly
            50                  55                  60

Gln Tyr Leu Cys Met Asp Thr Asp Gly Leu Leu Tyr Gly Ser Gln Thr
 65                 70                  75                  80

Pro Asn Glu Glu Cys Leu Phe Leu Glu Arg Leu Glu Glu Asn His Tyr
                85                  90                  95

Asn Thr Tyr Ile Ser Lys Lys His Ala Glu Lys Asn Trp Phe Val Gly
                100                 105                 110

Leu Lys Lys Asn Gly Ser Val Lys Arg Gly Pro Arg Thr His Tyr Gly
                115                 120                 125

Gln Lys Ala Ile Leu Phe Leu Pro Leu Pro Val Ser Ser Asp
            130                 135                 140
```

<210> SEQ ID NO 19
<211> LENGTH: 145
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

```
Ala Leu Thr Glu Lys Phe Asn Leu Pro Pro Gly Asn Tyr Lys Lys Pro
 1               5                  10                  15

Lys Leu Leu Tyr Cys Ser Asn Gly Gly His Phe Leu Arg Ile Leu Pro
```

```
                  20                  25                  30

Asp Gly Thr Val Asp Gly Thr Arg Asp Arg Ser Asp Gln His Ile Gln
         35                  40                  45

Leu Gln Leu Ser Ala Glu Ser Val Gly Glu Val Tyr Ile Lys Ser Thr
     50                  55                  60

Glu Thr Gly Gln Tyr Leu Ala Met Asp Thr Asp Gly Leu Leu Tyr Gly
 65                  70                  75                  80

Ser Gln Thr Pro Asn Glu Glu Cys Leu Phe Leu Glu Arg Leu Glu Glu
                 85                  90                  95

Asn His Tyr Asn Thr Tyr Ile Ser Lys Lys His Ala Glu Lys Asn Trp
             100                 105                 110

Phe Val Gly Leu Lys Lys Asn Gly Ser Cys Lys Arg Gly Pro Arg Thr
         115                 120                 125

His Tyr Gly Gln Lys Ala Ile Leu Phe Leu Pro Leu Pro Val Ser Ser
     130                 135                 140

Asp
145

<210> SEQ ID NO 20
<211> LENGTH: 144
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Leu Thr Glu Lys Phe Asn Leu Pro Pro Gly Asn Tyr Lys Lys Pro Lys
 1               5                  10                  15

Leu Leu Tyr Cys Ser Asn Gly Gly His Phe Leu Arg Ile Leu Pro Asp
             20                  25                  30

Gly Thr Val Asp Gly Thr Arg Asp Arg Ser Asp Gln His Ile Gln Leu
         35                  40                  45

Gln Leu Ser Ala Glu Ser Val Gly Glu Val Tyr Ile Lys Ser Thr Glu
     50                  55                  60

Thr Gly Gln Tyr Leu Ala Met Asp Thr Asp Gly Leu Leu Tyr Gly Ser
 65                  70                  75                  80

Gln Thr Pro Asn Glu Glu Cys Leu Phe Leu Glu Arg Leu Glu Glu Asn
                 85                  90                  95

His Tyr Asn Thr Tyr Ile Ser Lys Lys His Ala Glu Lys Asn Trp Phe
             100                 105                 110

Val Gly Leu Lys Lys Asn Gly Ser Cys Lys Arg Gly Pro Arg Thr His
         115                 120                 125

Tyr Gly Gln Lys Ala Ile Leu Phe Leu Pro Leu Pro Val Ser Ser Asp
     130                 135                 140

<210> SEQ ID NO 21
<211> LENGTH: 143
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Thr Glu Lys Phe Asn Leu Pro Pro Gly Asn Tyr Lys Lys Pro Lys Leu
 1               5                  10                  15

Leu Tyr Cys Ser Asn Gly Gly His Phe Leu Arg Ile Leu Pro Asp Gly
```

```
                    20                  25                  30
Thr Val Asp Gly Thr Arg Asp Arg Ser Asp Gln His Ile Gln Leu Gln
                35                  40                  45
Leu Ser Ala Glu Ser Val Gly Glu Val Tyr Ile Lys Ser Thr Glu Thr
            50                  55                  60
Gly Gln Tyr Leu Ala Met Asp Thr Asp Gly Leu Leu Tyr Gly Ser Gln
65                  70                  75                  80
Thr Pro Asn Glu Glu Cys Leu Phe Leu Glu Arg Leu Glu Glu Asn His
                85                  90                  95
Tyr Asn Thr Tyr Ile Ser Lys Lys His Ala Glu Lys Asn Trp Phe Val
            100                 105                 110
Gly Leu Lys Lys Asn Gly Ser Cys Lys Arg Gly Pro Arg Thr His Tyr
        115                 120                 125
Gly Gln Lys Ala Ile Leu Phe Leu Pro Leu Pro Val Ser Ser Asp
    130                 135                 140

<210> SEQ ID NO 22
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Glu Lys Phe Asn Leu Pro Pro Gly Asn Tyr Lys Lys Pro Lys Leu Leu
1               5                   10                  15
Tyr Cys Ser Asn Gly Gly His Phe Leu Arg Ile Leu Pro Asp Gly Thr
                20                  25                  30
Val Asp Gly Thr Arg Asp Arg Ser Asp Gln His Ile Gln Leu Gln Leu
            35                  40                  45
Ser Ala Glu Ser Val Gly Glu Val Tyr Ile Lys Ser Thr Glu Thr Gly
        50                  55                  60
Gln Tyr Leu Ala Met Asp Thr Asp Gly Leu Leu Tyr Gly Ser Gln Thr
65                  70                  75                  80
Pro Asn Glu Glu Cys Leu Phe Leu Glu Arg Leu Glu Glu Asn His Tyr
                85                  90                  95
Asn Thr Tyr Ile Ser Lys Lys His Ala Glu Lys Asn Trp Phe Val Gly
            100                 105                 110
Leu Lys Lys Asn Gly Ser Cys Lys Arg Gly Pro Arg Thr His Tyr Gly
        115                 120                 125
Gln Lys Ala Ile Leu Phe Leu Pro Leu Pro Val Ser Ser Asp
    130                 135                 140

<210> SEQ ID NO 23
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Lys Phe Asn Leu Pro Pro Gly Asn Tyr Lys Lys Pro Lys Leu Leu Tyr
1               5                   10                  15
Cys Ser Asn Gly Gly His Phe Leu Arg Ile Leu Pro Asp Gly Thr Val
                20                  25                  30
Asp Gly Thr Arg Asp Arg Ser Asp Gln His Ile Gln Leu Gln Leu Ser
```

```
            35                  40                  45

Ala Glu Ser Val Gly Glu Val Tyr Ile Lys Ser Thr Glu Thr Gly Gln
             50                  55                  60

Tyr Leu Ala Met Asp Thr Asp Gly Leu Leu Tyr Gly Ser Gln Thr Pro
 65                  70                  75                  80

Asn Glu Glu Cys Leu Phe Leu Glu Arg Leu Glu Asn His Tyr Asn
                 85                  90                  95

Thr Tyr Ile Ser Lys Lys His Ala Glu Lys Asn Trp Phe Val Gly Leu
                100                 105                 110

Lys Lys Asn Gly Ser Cys Lys Arg Gly Pro Arg Thr His Tyr Gly Gln
                115                 120                 125

Lys Ala Ile Leu Phe Leu Pro Leu Pro Val Ser Ser Asp
                130                 135                 140

<210> SEQ ID NO 24
<211> LENGTH: 145
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Ala Leu Thr Glu Lys Phe Asn Leu Pro Pro Gly Asn Tyr Lys Lys Pro
 1               5                  10                  15

Lys Leu Leu Tyr Ser Ser Asn Gly Gly His Phe Leu Arg Ile Leu Pro
                20                  25                  30

Asp Gly Thr Val Asp Gly Thr Arg Asp Arg Ser Asp Gln His Ile Gln
                35                  40                  45

Leu Gln Leu Ser Ala Glu Ser Val Gly Glu Val Tyr Ile Lys Ser Thr
 50                  55                  60

Glu Thr Gly Gln Tyr Leu Cys Met Asp Thr Asp Gly Leu Leu Tyr Gly
 65                  70                  75                  80

Ser Gln Thr Pro Asn Glu Glu Cys Leu Phe Leu Glu Arg Leu Glu Glu
                 85                  90                  95

Asn His Tyr Asn Thr Tyr Ile Ser Lys Lys His Ala Glu Lys Asn Trp
                100                 105                 110

Phe Val Gly Leu Lys Lys Asn Gly Ser Val Lys Arg Gly Pro Arg Thr
                115                 120                 125

His Tyr Gly Gln Lys Ala Ile Leu Phe Leu Pro Leu Pro Val Ser Ser
                130                 135                 140

Asp
145

<210> SEQ ID NO 25
<211> LENGTH: 144
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Leu Thr Glu Lys Phe Asn Leu Pro Pro Gly Asn Tyr Lys Lys Pro Lys
 1               5                  10                  15

Leu Leu Tyr Ser Ser Asn Gly Gly His Phe Leu Arg Ile Leu Pro Asp
                20                  25                  30

Gly Thr Val Asp Gly Thr Arg Asp Arg Ser Asp Gln His Ile Gln Leu
```

```
                35                  40                  45
Gln Leu Ser Ala Glu Ser Val Gly Glu Val Tyr Ile Lys Ser Thr Glu
         50                  55                  60
Thr Gly Gln Tyr Leu Cys Met Asp Thr Asp Gly Leu Leu Tyr Gly Ser
 65                  70                  75                  80
Gln Thr Pro Asn Glu Glu Cys Leu Phe Leu Glu Arg Leu Glu Glu Asn
                 85                  90                  95
His Tyr Asn Thr Tyr Ile Ser Lys Lys His Ala Glu Lys Asn Trp Phe
            100                 105                 110
Val Gly Leu Lys Lys Asn Gly Ser Val Lys Arg Gly Pro Arg Thr His
        115                 120                 125
Tyr Gly Gln Lys Ala Ile Leu Phe Leu Pro Leu Pro Val Ser Ser Asp
    130                 135                 140

<210> SEQ ID NO 26
<211> LENGTH: 143
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Thr Glu Lys Phe Asn Leu Pro Pro Gly Asn Tyr Lys Lys Pro Lys Leu
 1               5                  10                  15
Leu Tyr Ser Ser Asn Gly Gly His Phe Leu Arg Ile Leu Pro Asp Gly
             20                  25                  30
Thr Val Asp Gly Thr Arg Asp Arg Ser Asp Gln His Ile Gln Leu Gln
         35                  40                  45
Leu Ser Ala Glu Ser Val Gly Glu Val Tyr Ile Lys Ser Thr Glu Thr
     50                  55                  60
Gly Gln Tyr Leu Cys Met Asp Thr Asp Gly Leu Leu Tyr Gly Ser Gln
 65                  70                  75                  80
Thr Pro Asn Glu Glu Cys Leu Phe Leu Glu Arg Leu Glu Glu Asn His
                 85                  90                  95
Tyr Asn Thr Tyr Ile Ser Lys Lys His Ala Glu Lys Asn Trp Phe Val
            100                 105                 110
Gly Leu Lys Lys Asn Gly Ser Val Lys Arg Gly Pro Arg Thr His Tyr
        115                 120                 125
Gly Gln Lys Ala Ile Leu Phe Leu Pro Leu Pro Val Ser Ser Asp
    130                 135                 140

<210> SEQ ID NO 27
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Glu Lys Phe Asn Leu Pro Pro Gly Asn Tyr Lys Lys Pro Lys Leu Leu
 1               5                  10                  15
Tyr Ser Ser Asn Gly Gly His Phe Leu Arg Ile Leu Pro Asp Gly Thr
             20                  25                  30
Val Asp Gly Thr Arg Asp Arg Ser Asp Gln His Ile Gln Leu Gln Leu
         35                  40                  45
Ser Ala Glu Ser Val Gly Glu Val Tyr Ile Lys Ser Thr Glu Thr Gly
```

```
                    50                  55                  60
Gln Tyr Leu Cys Met Asp Thr Asp Gly Leu Leu Tyr Gly Ser Gln Thr
 65                  70                  75                  80

Pro Asn Glu Glu Cys Leu Phe Leu Glu Arg Leu Glu Glu Asn His Tyr
                 85                  90                  95

Asn Thr Tyr Ile Ser Lys Lys His Ala Glu Lys Asn Trp Phe Val Gly
            100                 105                 110

Leu Lys Lys Asn Gly Ser Val Lys Arg Gly Pro Arg Thr His Tyr Gly
        115                 120                 125

Gln Lys Ala Ile Leu Phe Leu Pro Leu Pro Val Ser Ser Asp
    130                 135                 140

<210> SEQ ID NO 28
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Lys Phe Asn Leu Pro Pro Gly Asn Tyr Lys Pro Lys Leu Leu Tyr
 1               5                  10                  15

Ser Ser Asn Gly Gly His Phe Leu Arg Ile Leu Pro Asp Gly Thr Val
             20                  25                  30

Asp Gly Thr Arg Asp Arg Ser Asp Gln His Ile Gln Leu Gln Leu Ser
         35                  40                  45

Ala Glu Ser Val Gly Glu Val Tyr Ile Lys Ser Thr Glu Thr Gly Gln
     50                  55                  60

Tyr Leu Cys Met Asp Thr Asp Gly Leu Leu Tyr Gly Ser Gln Thr Pro
 65                  70                  75                  80

Asn Glu Glu Cys Leu Phe Leu Glu Arg Leu Glu Glu Asn His Tyr Asn
                 85                  90                  95

Thr Tyr Ile Ser Lys Lys His Ala Glu Lys Asn Trp Phe Val Gly Leu
            100                 105                 110

Lys Lys Asn Gly Ser Val Lys Arg Gly Pro Arg Thr His Tyr Gly Gln
        115                 120                 125

Lys Ala Ile Leu Phe Leu Pro Leu Pro Val Ser Ser Asp
    130                 135                 140

<210> SEQ ID NO 29
<211> LENGTH: 139
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Asn Leu Pro Pro Gly Asn Tyr Lys Lys Pro Lys Leu Leu Tyr Cys Ser
 1               5                  10                  15

Asn Gly Gly His Phe Leu Arg Ile Leu Pro Asp Gly Thr Val Asp Gly
             20                  25                  30

Thr Arg Asp Arg Ser Asp Gln His Ile Gln Leu Gln Leu Ser Ala Glu
         35                  40                  45

Ser Val Gly Glu Val Tyr Ile Lys Ser Thr Glu Thr Gly Gln Tyr Leu
     50                  55                  60

Ala Met Asp Thr Asp Gly Leu Leu Tyr Gly Ser Gln Thr Pro Asn Glu
```

```
               65                  70                  75                  80
Glu Cys Leu Phe Leu Glu Arg Leu Glu Glu Asn His Tyr Asn Thr Tyr
                        85                  90                  95

Ile Ser Lys Lys His Ala Glu Lys Asn Trp Phe Val Gly Leu Lys Lys
                   100                 105                 110

Asn Gly Ser Cys Lys Arg Gly Pro Arg Thr His Tyr Gly Gln Lys Ala
               115                 120                 125

Ile Leu Phe Leu Pro Leu Pro Val Ser Ser Asp
           130                 135

<210> SEQ ID NO 30
<211> LENGTH: 138
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Leu Pro Pro Gly Asn Tyr Lys Lys Pro Lys Leu Leu Tyr Cys Ser Asn
1               5                   10                  15

Gly Gly His Phe Leu Arg Ile Leu Pro Asp Gly Thr Val Asp Gly Thr
                20                  25                  30

Arg Asp Arg Ser Asp Gln His Ile Gln Leu Gln Leu Ser Ala Glu Ser
            35                  40                  45

Val Gly Glu Val Tyr Ile Lys Ser Thr Glu Thr Gly Gln Tyr Leu Ala
        50                  55                  60

Met Asp Thr Asp Gly Leu Leu Tyr Gly Ser Gln Thr Pro Asn Glu Glu
65                  70                  75                  80

Cys Leu Phe Leu Glu Arg Leu Glu Glu Asn His Tyr Asn Thr Tyr Ile
                85                  90                  95

Ser Lys Lys His Ala Glu Lys Asn Trp Phe Val Gly Leu Lys Lys Asn
            100                 105                 110

Gly Ser Cys Lys Arg Gly Pro Arg Thr His Tyr Gly Gln Lys Ala Ile
        115                 120                 125

Leu Phe Leu Pro Leu Pro Val Ser Ser Asp
    130                 135

<210> SEQ ID NO 31
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Pro Pro Gly Asn Tyr Lys Lys Pro Lys Leu Leu Tyr Cys Ser Asn Gly
1               5                   10                  15

Gly His Phe Leu Arg Ile Leu Pro Asp Gly Thr Val Asp Gly Thr Arg
                20                  25                  30

Asp Arg Ser Asp Gln His Ile Gln Leu Gln Leu Ser Ala Glu Ser Val
            35                  40                  45

Gly Glu Val Tyr Ile Lys Ser Thr Glu Thr Gly Gln Tyr Leu Ala Met
        50                  55                  60

Asp Thr Asp Gly Leu Leu Tyr Gly Ser Gln Thr Pro Asn Glu Glu Cys
65                  70                  75                  80

Leu Phe Leu Glu Arg Leu Glu Glu Asn His Tyr Asn Thr Tyr Ile Ser
```

```
            85                  90                  95
Lys Lys His Ala Glu Lys Asn Trp Phe Val Gly Leu Lys Lys Asn Gly
            100                 105                 110

Ser Cys Lys Arg Gly Pro Arg Thr His Tyr Gly Gln Lys Ala Ile Leu
            115                 120                 125

Phe Leu Pro Leu Pro Val Ser Ser Asp
            130                 135

<210> SEQ ID NO 32
<211> LENGTH: 136
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Pro Gly Asn Tyr Lys Lys Pro Lys Leu Leu Tyr Cys Ser Asn Gly Gly
1               5                   10                  15

His Phe Leu Arg Ile Leu Pro Asp Gly Thr Val Asp Gly Thr Arg Asp
            20                  25                  30

Arg Ser Asp Gln His Ile Gln Leu Gln Leu Ser Ala Glu Ser Val Gly
        35                  40                  45

Glu Val Tyr Ile Lys Ser Thr Glu Thr Gly Gln Tyr Leu Ala Met Asp
    50                  55                  60

Thr Asp Gly Leu Leu Tyr Gly Ser Gln Thr Pro Asn Glu Glu Cys Leu
65                  70                  75                  80

Phe Leu Glu Arg Leu Glu Glu Asn His Tyr Asn Thr Tyr Ile Ser Lys
                85                  90                  95

Lys His Ala Glu Lys Asn Trp Phe Val Gly Leu Lys Lys Asn Gly Ser
            100                 105                 110

Cys Lys Arg Gly Pro Arg Thr His Tyr Gly Gln Lys Ala Ile Leu Phe
            115                 120                 125

Leu Pro Leu Pro Val Ser Ser Asp
            130                 135

<210> SEQ ID NO 33
<211> LENGTH: 139
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Asn Leu Pro Pro Gly Asn Tyr Lys Lys Pro Lys Leu Leu Tyr Ser Ser
1               5                   10                  15

Asn Gly Gly His Phe Leu Arg Ile Leu Pro Asp Gly Thr Val Asp Gly
            20                  25                  30

Thr Arg Asp Arg Ser Asp Gln His Ile Gln Leu Gln Leu Ser Ala Glu
        35                  40                  45

Ser Val Gly Glu Val Tyr Ile Lys Ser Thr Glu Thr Gly Gln Tyr Leu
    50                  55                  60

Cys Met Asp Thr Asp Gly Leu Leu Tyr Gly Ser Gln Thr Pro Asn Glu
65                  70                  75                  80

Glu Cys Leu Phe Leu Glu Arg Leu Glu Glu Asn His Tyr Asn Thr Tyr
                85                  90                  95

Ile Ser Lys Lys His Ala Glu Lys Asn Trp Phe Val Gly Leu Lys Lys
```

```
            100                 105                 110
Asn Gly Ser Val Lys Arg Gly Pro Arg Thr His Tyr Gly Gln Lys Ala
        115                 120                 125
Ile Leu Phe Leu Pro Leu Pro Val Ser Ser Asp
    130                 135
```

<210> SEQ ID NO 34
<211> LENGTH: 138
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

```
Leu Pro Pro Gly Asn Tyr Lys Lys Pro Lys Leu Leu Tyr Ser Ser Asn
1               5                   10                  15
Gly Gly His Phe Leu Arg Ile Leu Pro Asp Gly Thr Val Asp Gly Thr
            20                  25                  30
Arg Asp Arg Ser Asp Gln His Ile Gln Leu Gln Leu Ser Ala Glu Ser
        35                  40                  45
Val Gly Glu Val Tyr Ile Lys Ser Thr Glu Thr Gly Gln Tyr Leu Cys
    50                  55                  60
Met Asp Thr Asp Gly Leu Leu Tyr Gly Ser Gln Thr Pro Asn Glu Glu
65                  70                  75                  80
Cys Leu Phe Leu Glu Arg Leu Glu Glu Asn His Tyr Asn Thr Tyr Ile
                85                  90                  95
Ser Lys Lys His Ala Glu Lys Asn Trp Phe Val Gly Leu Lys Lys Asn
            100                 105                 110
Gly Ser Val Lys Arg Gly Pro Arg Thr His Tyr Gly Gln Lys Ala Ile
        115                 120                 125
Leu Phe Leu Pro Leu Pro Val Ser Ser Asp
    130                 135
```

<210> SEQ ID NO 35
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

```
Pro Pro Gly Asn Tyr Lys Lys Pro Lys Leu Leu Tyr Ser Ser Asn Gly
1               5                   10                  15
Gly His Phe Leu Arg Ile Leu Pro Asp Gly Thr Val Asp Gly Thr Arg
            20                  25                  30
Asp Arg Ser Asp Gln His Ile Gln Leu Gln Leu Ser Ala Glu Ser Val
        35                  40                  45
Gly Glu Val Tyr Ile Lys Ser Thr Glu Thr Gly Gln Tyr Leu Cys Met
    50                  55                  60
Asp Thr Asp Gly Leu Leu Tyr Gly Ser Gln Thr Pro Asn Glu Glu Cys
65                  70                  75                  80
Leu Phe Leu Glu Arg Leu Glu Glu Asn His Tyr Asn Thr Tyr Ile Ser
                85                  90                  95
Lys Lys His Ala Glu Lys Asn Trp Phe Val Gly Leu Lys Lys Asn Gly
            100                 105                 110
Ser Val Lys Arg Gly Pro Arg Thr His Tyr Gly Gln Lys Ala Ile Leu
```

```
            115                 120                 125
Phe Leu Pro Leu Pro Val Ser Ser Asp
    130                 135

<210> SEQ ID NO 36
<211> LENGTH: 136
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Pro Gly Asn Tyr Lys Lys Pro Lys Leu Leu Tyr Ser Ser Asn Gly Gly
1               5                   10                  15

His Phe Leu Arg Ile Leu Pro Asp Gly Thr Val Asp Gly Thr Arg Asp
            20                  25                  30

Arg Ser Asp Gln His Ile Gln Leu Gln Leu Ser Ala Glu Ser Val Gly
        35                  40                  45

Glu Val Tyr Ile Lys Ser Thr Glu Thr Gly Gln Tyr Leu Cys Met Asp
    50                  55                  60

Thr Asp Gly Leu Leu Tyr Gly Ser Gln Thr Pro Asn Glu Glu Cys Leu
65                  70                  75                  80

Phe Leu Glu Arg Leu Glu Glu Asn His Tyr Asn Thr Tyr Ile Ser Lys
                85                  90                  95

Lys His Ala Glu Lys Asn Trp Phe Val Gly Leu Lys Lys Asn Gly Ser
            100                 105                 110

Val Lys Arg Gly Pro Arg Thr His Tyr Gly Gln Lys Ala Ile Leu Phe
        115                 120                 125

Leu Pro Leu Pro Val Ser Ser Asp
    130                 135

<210> SEQ ID NO 37
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Met Asn Leu Pro Pro Gly Asn Tyr Lys Lys Pro Lys Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
            100                 105                 110

Lys Asn Gly Ser Cys Lys Arg Gly Pro Arg Thr His Tyr Gly Gln Lys
        115                 120                 125

Ala Ile Leu Phe Leu Pro Leu Pro Val Ser Ser Asp
```

130             135             140

<210> SEQ ID NO 38
<211> LENGTH: 139
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Met Leu Pro Pro Gly Asn Tyr Lys Lys Pro Lys Leu Leu Tyr Cys Ser
1               5                   10                  15

Asn Gly Gly His Phe Leu Arg Ile Leu Pro Asp Gly Thr Val Asp Gly
            20                  25                  30

Thr Arg Asp Arg Ser Asp Gln His Ile Gln Leu Gln Leu Ser Ala Glu
        35                  40                  45

Ser Val Gly Glu Val Tyr Ile Lys Ser Thr Glu Thr Gly Gln Tyr Leu
    50                  55                  60

Ala Met Asp Thr Asp Gly Leu Leu Tyr Gly Ser Gln Thr Pro Asn Glu
65                  70                  75                  80

Glu Cys Leu Phe Leu Glu Arg Leu Glu Glu Asn His Tyr Asn Thr Tyr
                85                  90                  95

Ile Ser Lys Lys His Ala Glu Lys Asn Trp Phe Val Gly Leu Lys Lys
            100                 105                 110

Asn Gly Ser Cys Lys Arg Gly Pro Arg Thr His Tyr Gly Gln Lys Ala
        115                 120                 125

Ile Leu Phe Leu Pro Leu Pro Val Ser Ser Asp
    130                 135

<210> SEQ ID NO 39
<211> LENGTH: 138
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Met Pro Pro Gly Asn Tyr Lys Lys Pro Lys Leu Leu Tyr Cys Ser Asn
1               5                   10                  15

Gly Gly His Phe Leu Arg Ile Leu Pro Asp Gly Thr Val Asp Gly Thr
            20                  25                  30

Arg Asp Arg Ser Asp Gln His Ile Gln Leu Gln Leu Ser Ala Glu Ser
        35                  40                  45

Val Gly Glu Val Tyr Ile Lys Ser Thr Glu Thr Gly Gln Tyr Leu Ala
    50                  55                  60

Met Asp Thr Asp Gly Leu Leu Tyr Gly Ser Gln Thr Pro Asn Glu Glu
65                  70                  75                  80

Cys Leu Phe Leu Glu Arg Leu Glu Glu Asn His Tyr Asn Thr Tyr Ile
                85                  90                  95

Ser Lys Lys His Ala Glu Lys Asn Trp Phe Val Gly Leu Lys Lys Asn
            100                 105                 110

Gly Ser Cys Lys Arg Gly Pro Arg Thr His Tyr Gly Gln Lys Ala Ile
        115                 120                 125

Leu Phe Leu Pro Leu Pro Val Ser Ser Asp
    130                 135

-continued

```
<210> SEQ ID NO 40
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Met Pro Gly Asn Tyr Lys Lys Pro Lys Leu Leu Tyr Cys Ser Asn Gly
1               5                   10                  15

Gly His Phe Leu Arg Ile Leu Pro Asp Gly Thr Val Asp Gly Thr Arg
            20                  25                  30

Asp Arg Ser Asp Gln His Ile Gln Leu Gln Leu Ser Ala Glu Ser Val
        35                  40                  45

Gly Glu Val Tyr Ile Lys Ser Thr Glu Thr Gly Gln Tyr Leu Ala Met
50                  55                  60

Asp Thr Asp Gly Leu Leu Tyr Gly Ser Gln Thr Pro Asn Glu Glu Cys
65                  70                  75                  80

Leu Phe Leu Glu Arg Leu Glu Glu Asn His Tyr Asn Thr Tyr Ile Ser
                85                  90                  95

Lys Lys His Ala Glu Lys Asn Trp Phe Val Gly Leu Lys Lys Asn Gly
            100                 105                 110

Ser Cys Lys Arg Gly Pro Arg Thr His Tyr Gly Gln Lys Ala Ile Leu
        115                 120                 125

Phe Leu Pro Leu Pro Val Ser Ser Asp
    130                 135

<210> SEQ ID NO 41
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Met Asn Leu Pro Pro Gly Asn Tyr Lys Lys Pro Lys Leu Leu Tyr Ser
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
50                  55                  60

Leu Cys Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
            100                 105                 110

Lys Asn Gly Ser Val Lys Arg Gly Pro Arg Thr His Tyr Gly Gln Lys
        115                 120                 125

Ala Ile Leu Phe Leu Pro Leu Pro Val Ser Ser Asp
    130                 135                 140

<210> SEQ ID NO 42
<211> LENGTH: 139
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 42

```
Met Leu Pro Pro Gly Asn Tyr Lys Lys Pro Lys Leu Leu Tyr Ser Ser
1               5                   10                  15

Asn Gly Gly His Phe Leu Arg Ile Leu Pro Asp Gly Thr Val Asp Gly
            20                  25                  30

Thr Arg Asp Arg Ser Asp Gln His Ile Gln Leu Gln Leu Ser Ala Glu
        35                  40                  45

Ser Val Gly Glu Val Tyr Ile Lys Ser Thr Glu Thr Gly Gln Tyr Leu
50                  55                  60

Cys Met Asp Thr Asp Gly Leu Leu Tyr Gly Ser Gln Thr Pro Asn Glu
65                  70                  75                  80

Glu Cys Leu Phe Leu Glu Arg Leu Glu Glu Asn His Tyr Asn Thr Tyr
                85                  90                  95

Ile Ser Lys Lys His Ala Glu Lys Asn Trp Phe Val Gly Leu Lys Lys
            100                 105                 110

Asn Gly Ser Val Lys Arg Gly Pro Arg Thr His Tyr Gly Gln Lys Ala
        115                 120                 125

Ile Leu Phe Leu Pro Leu Pro Val Ser Ser Asp
    130                 135
```

<210> SEQ ID NO 43
<211> LENGTH: 138
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 43

```
Met Pro Pro Gly Asn Tyr Lys Lys Pro Lys Leu Leu Tyr Ser Ser Asn
1               5                   10                  15

Gly Gly His Phe Leu Arg Ile Leu Pro Asp Gly Thr Val Asp Gly Thr
            20                  25                  30

Arg Asp Arg Ser Asp Gln His Ile Gln Leu Gln Leu Ser Ala Glu Ser
        35                  40                  45

Val Gly Glu Val Tyr Ile Lys Ser Thr Glu Thr Gly Gln Tyr Leu Cys
50                  55                  60

Met Asp Thr Asp Gly Leu Leu Tyr Gly Ser Gln Thr Pro Asn Glu Glu
65                  70                  75                  80

Cys Leu Phe Leu Glu Arg Leu Glu Glu Asn His Tyr Asn Thr Tyr Ile
                85                  90                  95

Ser Lys Lys His Ala Glu Lys Asn Trp Phe Val Gly Leu Lys Lys Asn
            100                 105                 110

Gly Ser Val Lys Arg Gly Pro Arg Thr His Tyr Gly Gln Lys Ala Ile
        115                 120                 125

Leu Phe Leu Pro Leu Pro Val Ser Ser Asp
    130                 135
```

<210> SEQ ID NO 44
<211> LENGTH: 137
<212> TYPE: PRT
<213> ORGANISM: Artificial Sequence
<220> FEATURE:
<223> OTHER INFORMATION: Description of Artificial Sequence: Synthetic

```
polypeptide

<400> SEQUENCE: 44

Met Pro Gly Asn Tyr Lys Lys Pro Lys Leu Tyr Ser Ser Asn Gly
1               5                   10                  15

Gly His Phe Leu Arg Ile Leu Pro Asp Gly Thr Val Asp Gly Thr Arg
            20                  25                  30

Asp Arg Ser Asp Gln His Ile Gln Leu Gln Leu Ser Ala Glu Ser Val
        35                  40                  45

Gly Glu Val Tyr Ile Lys Ser Thr Glu Thr Gly Gln Tyr Leu Cys Met
    50                  55                  60

Asp Thr Asp Gly Leu Leu Tyr Gly Ser Gln Thr Pro Asn Glu Glu Cys
65                  70                  75                  80

Leu Phe Leu Glu Arg Leu Glu Glu Asn His Tyr Asn Thr Tyr Ile Ser
                85                  90                  95

Lys Lys His Ala Glu Lys Asn Trp Phe Val Gly Leu Lys Lys Asn Gly
            100                 105                 110

Ser Val Lys Arg Gly Pro Arg Thr His Tyr Gly Gln Lys Ala Ile Leu
        115                 120                 125

Phe Leu Pro Leu Pro Val Ser Ser Asp
    130                 135

<210> SEQ ID NO 45
<211> LENGTH: 145
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Met Ala Leu Thr Glu Lys Asn Leu Pro Pro Gly Asn Tyr Lys Lys Pro
1               5                   10                  15

Lys Leu Leu Tyr Cys Ser Asn Gly Gly His Phe Leu Arg Ile Leu Pro
            20                  25                  30

Asp Gly Thr Val Asp Gly Thr Arg Asp Arg Ser Asp Gln His Ile Gln
        35                  40                  45

Leu Gln Leu Ser Ala Glu Ser Val Gly Glu Val Tyr Ile Lys Ser Thr
    50                  55                  60

Glu Thr Gly Gln Tyr Leu Ala Met Asp Thr Asp Gly Leu Leu Tyr Gly
65                  70                  75                  80

Ser Gln Thr Pro Asn Glu Glu Cys Leu Phe Leu Glu Arg Leu Glu Glu
                85                  90                  95

Asn His Tyr Asn Thr Tyr Ile Ser Lys Lys His Ala Glu Lys Asn Trp
            100                 105                 110

Phe Val Gly Leu Lys Lys Asn Gly Ser Cys Lys Arg Gly Pro Arg Thr
        115                 120                 125

His Tyr Gly Gln Lys Ala Ile Leu Phe Leu Pro Leu Pro Val Ser Ser
    130                 135                 140

Asp
145

<210> SEQ ID NO 46
<211> LENGTH: 144
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 46

Met Ala Leu Thr Glu Lys Leu Pro Pro Gly Asn Tyr Lys Lys Pro Lys
1               5                   10                  15

Leu Leu Tyr Ser Ser Asn Gly Gly His Phe Leu Arg Ile Leu Pro Asp
            20                  25                  30

Gly Thr Val Asp Gly Thr Arg Asp Arg Ser Asp Gln His Ile Gln Leu
        35                  40                  45

Gln Leu Ser Ala Glu Ser Val Gly Glu Val Tyr Ile Lys Ser Thr Glu
    50                  55                  60

Thr Gly Gln Tyr Leu Cys Met Asp Thr Asp Gly Leu Leu Tyr Gly Ser
65                  70                  75                  80

Gln Thr Pro Asn Glu Glu Cys Leu Phe Leu Glu Arg Leu Glu Glu Asn
                85                  90                  95

His Tyr Asn Thr Tyr Ile Ser Lys Lys His Ala Glu Lys Asn Trp Phe
            100                 105                 110

Val Gly Leu Lys Lys Asn Gly Ser Val Lys Arg Gly Pro Arg Thr His
        115                 120                 125

Tyr Gly Gln Lys Ala Ile Leu Phe Leu Pro Leu Pro Val Ser Ser Asp
    130                 135                 140

<210> SEQ ID NO 47
<211> LENGTH: 144
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Met Ala Leu Thr Glu Lys Pro Pro Gly Gly Asn Tyr Lys Lys Pro Lys
1               5                   10                  15

Leu Leu Tyr Cys Ser Asn Gly Gly His Phe Leu Arg Ile Leu Pro Asp
            20                  25                  30

Gly Thr Val Asp Gly Thr Arg Asp Arg Ser Asp Gln His Ile Gln Leu
        35                  40                  45

Gln Leu Ser Ala Glu Ser Val Gly Glu Val Tyr Ile Lys Ser Thr Glu
    50                  55                  60

Thr Gly Gln Tyr Leu Ala Met Asp Thr Asp Gly Leu Leu Tyr Gly Ser
65                  70                  75                  80

Gln Thr Pro Asn Glu Glu Cys Leu Phe Leu Glu Arg Leu Glu Glu Asn
                85                  90                  95

His Tyr Asn Thr Tyr Ile Ser Lys Lys His Ala Glu Lys Asn Trp Phe
            100                 105                 110

Val Gly Leu Lys Lys Asn Gly Ser Cys Lys Arg Gly Pro Arg Thr His
        115                 120                 125

Tyr Gly Gln Lys Ala Ile Leu Phe Leu Pro Leu Pro Val Ser Ser Asp
    130                 135                 140

<210> SEQ ID NO 48
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

```
Met Ala Leu Thr Glu Lys Pro Gly Asn Tyr Lys Lys Pro Lys Leu Leu
1               5                   10                  15

Tyr Cys Ser Asn Gly Gly His Phe Leu Arg Ile Leu Pro Asp Gly Thr
            20                  25                  30

Val Asp Gly Thr Arg Asp Arg Ser Asp Gln His Ile Gln Leu Gln Leu
        35                  40                  45

Ser Ala Glu Ser Val Gly Glu Val Tyr Ile Lys Ser Thr Glu Thr Gly
    50                  55                  60

Gln Tyr Leu Ala Met Asp Thr Asp Gly Leu Leu Tyr Gly Ser Gln Thr
65              70                  75                  80

Pro Asn Glu Glu Cys Leu Phe Leu Glu Arg Leu Glu Glu Asn His Tyr
                85                  90                  95

Asn Thr Tyr Ile Ser Lys Lys His Ala Glu Lys Asn Trp Phe Val Gly
            100                 105                 110

Leu Lys Lys Asn Gly Ser Cys Lys Arg Gly Pro Arg Thr His Tyr Gly
            115                 120                 125

Gln Lys Ala Ile Leu Phe Leu Pro Leu Pro Val Ser Ser Asp
        130                 135                 140
```

<210> SEQ ID NO 49
<211> LENGTH: 145
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

```
Met Leu Thr Glu Lys Phe Asn Leu Pro Pro Gly Asn Tyr Lys Lys Pro
1               5                   10                  15

Lys Leu Leu Tyr Cys Ser Asn Gly Gly His Phe Leu Arg Ile Leu Pro
            20                  25                  30

Asp Gly Thr Val Asp Gly Thr Arg Asp Arg Ser Asp Gln His Ile Gln
        35                  40                  45

Leu Gln Leu Ser Ala Glu Ser Val Gly Glu Val Tyr Ile Lys Ser Thr
    50                  55                  60

Glu Thr Gly Gln Tyr Leu Ala Met Asp Thr Asp Gly Leu Leu Tyr Gly
65              70                  75                  80

Ser Gln Thr Pro Asn Glu Glu Cys Leu Phe Leu Glu Arg Leu Glu Glu
                85                  90                  95

Asn His Tyr Asn Thr Tyr Ile Ser Lys Lys His Ala Glu Lys Asn Trp
            100                 105                 110

Phe Val Gly Leu Lys Lys Asn Gly Ser Cys Lys Arg Gly Pro Arg Thr
            115                 120                 125

His Tyr Gly Gln Lys Ala Ile Leu Phe Leu Pro Leu Pro Val Ser Ser
        130                 135                 140

Asp
145
```

<210> SEQ ID NO 50
<211> LENGTH: 144
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

```
Met Leu Thr Glu Lys Asn Leu Pro Pro Gly Asn Tyr Lys Pro Lys
1               5                   10                  15

Leu Leu Tyr Cys Ser Asn Gly Gly His Phe Leu Arg Ile Leu Pro Asp
                20                  25                  30

Gly Thr Val Asp Gly Thr Arg Asp Arg Ser Asp Gln His Ile Gln Leu
            35                  40                  45

Gln Leu Ser Ala Glu Ser Val Gly Glu Val Tyr Ile Lys Ser Thr Glu
    50                  55                  60

Thr Gly Gln Tyr Leu Ala Met Asp Thr Asp Gly Leu Leu Tyr Gly Ser
65                  70                  75                  80

Gln Thr Pro Asn Glu Glu Cys Leu Phe Leu Arg Leu Glu Glu Asn
                85                  90                  95

His Tyr Asn Thr Tyr Ile Ser Lys Lys His Ala Glu Lys Asn Trp Phe
                100                 105                 110

Val Gly Leu Lys Lys Asn Gly Ser Cys Lys Arg Gly Pro Arg Thr His
            115                 120                 125

Tyr Gly Gln Lys Ala Ile Leu Phe Leu Pro Leu Pro Val Ser Ser Asp
        130                 135                 140

<210> SEQ ID NO 51
<211> LENGTH: 143
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Met Leu Thr Glu Lys Leu Pro Pro Gly Asn Tyr Lys Lys Pro Lys Leu
1               5                   10                  15

Leu Tyr Cys Ser Asn Gly Gly His Phe Leu Arg Ile Leu Pro Asp Gly
                20                  25                  30

Thr Val Asp Gly Thr Arg Asp Arg Ser Asp Gln His Ile Gln Leu Gln
            35                  40                  45

Leu Ser Ala Glu Ser Val Gly Glu Val Tyr Ile Lys Ser Thr Glu Thr
    50                  55                  60

Gly Gln Tyr Leu Ala Met Asp Thr Asp Gly Leu Leu Tyr Gly Ser Gln
65                  70                  75                  80

Thr Pro Asn Glu Glu Cys Leu Phe Leu Glu Arg Leu Glu Glu Asn His
                85                  90                  95

Tyr Asn Thr Tyr Ile Ser Lys Lys His Ala Glu Lys Asn Trp Phe Val
                100                 105                 110

Gly Leu Lys Lys Asn Gly Ser Cys Lys Arg Gly Pro Arg Thr His Tyr
            115                 120                 125

Gly Gln Lys Ala Ile Leu Phe Leu Pro Leu Pro Val Ser Ser Asp
        130                 135                 140

<210> SEQ ID NO 52
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Met Leu Thr Glu Lys Pro Pro Gly Asn Tyr Lys Lys Pro Lys Leu Leu
1               5                   10                  15
```

-continued

```
Tyr Cys Ser Asn Gly Gly His Phe Leu Arg Ile Leu Pro Asp Gly Thr
            20                  25                  30

Val Asp Gly Thr Arg Asp Arg Ser Asp Gln His Ile Gln Leu Gln Leu
 35                  40                  45

Ser Ala Glu Ser Val Gly Glu Val Tyr Ile Lys Ser Thr Glu Thr Gly
 50                  55                  60

Gln Tyr Leu Ala Met Asp Thr Asp Gly Leu Leu Tyr Gly Ser Gln Thr
65                   70                  75                  80

Pro Asn Glu Glu Cys Leu Phe Leu Glu Arg Leu Glu Glu Asn His Tyr
                85                  90                  95

Asn Thr Tyr Ile Ser Lys Lys His Ala Glu Lys Asn Trp Phe Val Gly
            100                 105                 110

Leu Lys Lys Asn Gly Ser Cys Lys Arg Gly Pro Arg Thr His Tyr Gly
            115                 120                 125

Gln Lys Ala Ile Leu Phe Leu Pro Leu Pro Val Ser Ser Asp
        130                 135                 140
```

<210> SEQ ID NO 53
<211> LENGTH: 141
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 53

```
Met Leu Thr Glu Lys Pro Gly Asn Tyr Lys Lys Pro Lys Leu Leu Tyr
1               5                   10                  15

Cys Ser Asn Gly Gly His Phe Leu Arg Ile Leu Pro Asp Gly Thr Val
            20                  25                  30

Asp Gly Thr Arg Asp Arg Ser Asp Gln His Ile Gln Leu Gln Leu Ser
        35                  40                  45

Ala Glu Ser Val Gly Glu Val Tyr Ile Lys Ser Thr Glu Thr Gly Gln
    50                  55                  60

Tyr Leu Ala Met Asp Thr Asp Gly Leu Leu Tyr Gly Ser Gln Thr Pro
65                  70                  75                  80

Asn Glu Glu Cys Leu Phe Leu Glu Arg Leu Glu Glu Asn His Tyr Asn
                85                  90                  95

Thr Tyr Ile Ser Lys Lys His Ala Glu Lys Asn Trp Phe Val Gly Leu
            100                 105                 110

Lys Lys Asn Gly Ser Cys Lys Arg Gly Pro Arg Thr His Tyr Gly Gln
        115                 120                 125

Lys Ala Ile Leu Phe Leu Pro Leu Pro Val Ser Ser Asp
    130                 135                 140
```

<210> SEQ ID NO 54
<211> LENGTH: 144
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 54

```
Met Thr Glu Lys Phe Asn Leu Pro Pro Gly Asn Tyr Lys Lys Pro Lys
1               5                   10                  15

Leu Leu Tyr Cys Ser Asn Gly Gly His Phe Leu Arg Ile Leu Pro Asp
            20                  25                  30
```

Gly Thr Val Asp Gly Thr Arg Asp Arg Ser Asp Gln His Ile Gln Leu
                35                  40                  45

Gln Leu Ser Ala Glu Ser Val Gly Glu Val Tyr Ile Lys Ser Thr Glu
    50                  55                  60

Thr Gly Gln Tyr Leu Ala Met Asp Thr Asp Gly Leu Leu Tyr Gly Ser
65                  70                  75                  80

Gln Thr Pro Asn Glu Glu Cys Leu Phe Leu Glu Arg Leu Glu Glu Asn
                85                  90                  95

His Tyr Asn Thr Tyr Ile Ser Lys Lys His Ala Glu Lys Asn Trp Phe
            100                 105                 110

Val Gly Leu Lys Lys Asn Gly Ser Cys Lys Arg Gly Pro Arg Thr His
                115                 120                 125

Tyr Gly Gln Lys Ala Ile Leu Phe Leu Pro Leu Pro Val Ser Ser Asp
        130                 135                 140

<210> SEQ ID NO 55
<211> LENGTH: 143
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Met Thr Glu Lys Asn Leu Pro Pro Gly Asn Tyr Lys Lys Pro Lys Leu
1               5                   10                  15

Leu Tyr Cys Ser Asn Gly Gly His Phe Leu Arg Ile Leu Pro Asp Gly
                20                  25                  30

Thr Val Asp Gly Thr Arg Asp Arg Ser Asp Gln His Ile Gln Leu Gln
            35                  40                  45

Leu Ser Ala Glu Ser Val Gly Glu Val Tyr Ile Lys Ser Thr Glu Thr
        50                  55                  60

Gly Gln Tyr Leu Ala Met Asp Thr Asp Gly Leu Leu Tyr Gly Ser Gln
65                  70                  75                  80

Thr Pro Asn Glu Glu Cys Leu Phe Leu Glu Arg Leu Glu Glu Asn His
                85                  90                  95

Tyr Asn Thr Tyr Ile Ser Lys Lys His Ala Glu Lys Asn Trp Phe Val
            100                 105                 110

Gly Leu Lys Lys Asn Gly Ser Cys Lys Arg Gly Pro Arg Thr His Tyr
        115                 120                 125

Gly Gln Lys Ala Ile Leu Phe Leu Pro Leu Pro Val Ser Ser Asp
    130                 135                 140

<210> SEQ ID NO 56
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Met Thr Glu Lys Leu Pro Pro Gly Asn Tyr Lys Lys Pro Lys Leu Leu
1               5                   10                  15

Tyr Cys Ser Asn Gly Gly His Phe Leu Arg Ile Leu Pro Asp Gly Thr
                20                  25                  30

Val Asp Gly Thr Arg Asp Arg Ser Asp Gln His Ile Gln Leu Gln Leu
            35                  40                  45

Ser Ala Glu Ser Val Gly Glu Val Tyr Ile Lys Ser Thr Glu Thr Gly
 50                  55                  60

Gln Tyr Leu Ala Met Asp Thr Asp Gly Leu Leu Tyr Gly Ser Gln Thr
65                  70                  75                  80

Pro Asn Glu Glu Cys Leu Phe Leu Glu Arg Leu Glu Glu Asn His Tyr
             85                   90                  95

Asn Thr Tyr Ile Ser Lys Lys His Ala Glu Lys Asn Trp Phe Val Gly
            100                 105                 110

Leu Lys Lys Asn Gly Ser Cys Lys Arg Gly Pro Arg Thr His Tyr Gly
            115                 120                 125

Gln Lys Ala Ile Leu Phe Leu Pro Leu Pro Val Ser Ser Asp
        130                 135                 140

<210> SEQ ID NO 57
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Met Thr Glu Lys Pro Gly Asn Tyr Lys Lys Pro Lys Leu Leu Tyr
1               5                   10                  15

Cys Ser Asn Gly Gly His Phe Leu Arg Ile Leu Pro Asp Gly Thr Val
             20                  25                  30

Asp Gly Thr Arg Asp Arg Ser Asp Gln His Ile Gln Leu Gln Leu Ser
         35                  40                  45

Ala Glu Ser Val Gly Glu Val Tyr Ile Lys Ser Thr Glu Thr Gly Gln
 50                  55                  60

Tyr Leu Ala Met Asp Thr Asp Gly Leu Leu Tyr Gly Ser Gln Thr Pro
65                  70                  75                  80

Asn Glu Glu Cys Leu Phe Leu Glu Arg Leu Glu Glu Asn His Tyr Asn
                85                  90                  95

Thr Tyr Ile Ser Lys Lys His Ala Glu Lys Asn Trp Phe Val Gly Leu
            100                 105                 110

Lys Lys Asn Gly Ser Cys Lys Arg Gly Pro Arg Thr His Tyr Gly Gln
        115                 120                 125

Lys Ala Ile Leu Phe Leu Pro Leu Pro Val Ser Ser Asp
    130                 135                 140

<210> SEQ ID NO 58
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Met Thr Glu Lys Pro Gly Asn Tyr Lys Lys Pro Lys Leu Leu Tyr Cys
1               5                   10                  15

Ser Asn Gly Gly His Phe Leu Arg Ile Leu Pro Asp Gly Thr Val Asp
             20                  25                  30

Gly Thr Arg Asp Arg Ser Asp Gln His Ile Gln Leu Gln Leu Ser Ala
         35                  40                  45

Glu Ser Val Gly Glu Val Tyr Ile Lys Ser Thr Glu Thr Gly Gln Tyr
 50                  55                  60

```
Leu Ala Met Asp Thr Asp Gly Leu Leu Tyr Gly Ser Gln Thr Pro Asn
 65                  70                  75                  80

Glu Glu Cys Leu Phe Leu Glu Arg Leu Glu Glu Asn His Tyr Asn Thr
                 85                  90                  95

Tyr Ile Ser Lys Lys His Ala Glu Lys Asn Trp Phe Val Gly Leu Lys
            100                 105                 110

Lys Asn Gly Ser Cys Lys Arg Gly Pro Arg Thr His Tyr Gly Gln Lys
        115                 120                 125

Ala Ile Leu Phe Leu Pro Leu Pro Val Ser Ser Asp
130                 135                 140

<210> SEQ ID NO 59
<211> LENGTH: 143
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Met Glu Lys Phe Asn Leu Pro Pro Gly Asn Tyr Lys Lys Pro Lys Leu
1               5                   10                  15

Leu Tyr Cys Ser Asn Gly Gly His Phe Leu Arg Ile Leu Pro Asp Gly
            20                  25                  30

Thr Val Asp Gly Thr Arg Asp Arg Ser Asp Gln His Ile Gln Leu Gln
        35                  40                  45

Leu Ser Ala Glu Ser Val Gly Glu Val Tyr Ile Lys Ser Thr Glu Thr
50                  55                  60

Gly Gln Tyr Leu Ala Met Asp Thr Asp Gly Leu Leu Tyr Gly Ser Gln
65                  70                  75                  80

Thr Pro Asn Glu Glu Cys Leu Phe Leu Glu Arg Leu Glu Glu Asn His
                85                  90                  95

Tyr Asn Thr Tyr Ile Ser Lys Lys His Ala Glu Lys Asn Trp Phe Val
            100                 105                 110

Gly Leu Lys Lys Asn Gly Ser Cys Lys Arg Gly Pro Arg Thr His Tyr
        115                 120                 125

Gly Gln Lys Ala Ile Leu Phe Leu Pro Leu Pro Val Ser Ser Asp
130                 135                 140

<210> SEQ ID NO 60
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Met Glu Lys Asn Leu Pro Pro Gly Asn Tyr Lys Lys Pro Lys Leu Leu
1               5                   10                  15

Tyr Cys Ser Asn Gly Gly His Phe Leu Arg Ile Leu Pro Asp Gly Thr
            20                  25                  30

Val Asp Gly Thr Arg Asp Arg Ser Asp Gln His Ile Gln Leu Gln Leu
        35                  40                  45

Ser Ala Glu Ser Val Gly Glu Val Tyr Ile Lys Ser Thr Glu Thr Gly
50                  55                  60

Gln Tyr Leu Ala Met Asp Thr Asp Gly Leu Leu Tyr Gly Ser Gln Thr
65                  70                  75                  80
```

Pro Asn Glu Glu Cys Leu Phe Leu Glu Arg Leu Glu Glu Asn His Tyr
            85                  90                  95

Asn Thr Tyr Ile Ser Lys Lys His Ala Glu Lys Asn Trp Phe Val Gly
            100                 105                 110

Leu Lys Lys Asn Gly Ser Cys Lys Arg Gly Pro Arg Thr His Tyr Gly
        115                 120                 125

Gln Lys Ala Ile Leu Phe Leu Pro Leu Pro Val Ser Ser Asp
    130                 135                 140

<210> SEQ ID NO 61
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Met Glu Lys Leu Pro Pro Gly Asn Tyr Lys Pro Lys Leu Leu Tyr
1               5                   10                  15

Cys Ser Asn Gly Gly His Phe Leu Arg Ile Leu Pro Asp Gly Thr Val
            20                  25                  30

Asp Gly Thr Arg Asp Arg Ser Asp Gln His Ile Gln Leu Gln Leu Ser
        35                  40                  45

Ala Glu Ser Val Gly Glu Val Tyr Ile Lys Ser Thr Glu Thr Gly Gln
    50                  55                  60

Tyr Leu Ala Met Asp Thr Asp Gly Leu Leu Tyr Gly Ser Gln Thr Pro
65                  70                  75                  80

Asn Glu Glu Cys Leu Phe Leu Glu Arg Leu Glu Glu Asn His Tyr Asn
                85                  90                  95

Thr Tyr Ile Ser Lys Lys His Ala Glu Lys Asn Trp Phe Val Gly Leu
            100                 105                 110

Lys Lys Asn Gly Ser Cys Lys Arg Gly Pro Arg Thr His Tyr Gly Gln
        115                 120                 125

Lys Ala Ile Leu Phe Leu Pro Leu Pro Val Ser Ser Asp
    130                 135                 140

<210> SEQ ID NO 62
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Met Glu Lys Pro Pro Gly Asn Tyr Lys Pro Lys Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
            100                 105                 110

Lys Asn Gly Ser Cys Lys Arg Gly Pro Arg Thr His Tyr Gly Gln Lys
        115                 120                 125

Ala Ile Leu Phe Leu Pro Leu Pro Val Ser Ser Asp
    130                 135                 140

<210> SEQ ID NO 63
<211> LENGTH: 139
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Met Glu Lys Pro Gly Asn Tyr Lys Lys Pro Lys Leu Leu Tyr Cys Ser
1               5                   10                  15

Asn Gly Gly His Phe Leu Arg Ile Leu Pro Asp Gly Thr Val Asp Gly
            20                  25                  30

Thr Arg Asp Arg Ser Asp Gln His Ile Gln Leu Gln Leu Ser Ala Glu
        35                  40                  45

Ser Val Gly Glu Val Tyr Ile Lys Ser Thr Glu Thr Gly Gln Tyr Leu
    50                  55                  60

Ala Met Asp Thr Asp Gly Leu Leu Tyr Gly Ser Gln Thr Pro Asn Glu
65                  70                  75                  80

Glu Cys Leu Phe Leu Glu Arg Leu Glu Glu Asn His Tyr Asn Thr Tyr
                85                  90                  95

Ile Ser Lys Lys His Ala Glu Lys Asn Trp Phe Val Gly Leu Lys Lys
            100                 105                 110

Asn Gly Ser Cys Lys Arg Gly Pro Arg Thr His Tyr Gly Gln Lys Ala
        115                 120                 125

Ile Leu Phe Leu Pro Leu Pro Val Ser Ser Asp
    130                 135

<210> SEQ ID NO 64
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Met Lys Phe Asn Leu Pro Pro Gly Asn Tyr Lys Lys Pro Lys Leu Leu
1               5                   10                  15

Tyr Cys Ser Asn Gly Gly His Phe Leu Arg Ile Leu Pro Asp Gly Thr
            20                  25                  30

Val Asp Gly Thr Arg Asp Arg Ser Asp Gln His Ile Gln Leu Gln Leu
        35                  40                  45

Ser Ala Glu Ser Val Gly Glu Val Tyr Ile Lys Ser Thr Glu Thr Gly
    50                  55                  60

Gln Tyr Leu Ala Met Asp Thr Asp Gly Leu Leu Tyr Gly Ser Gln Thr
65                  70                  75                  80

Pro Asn Glu Glu Cys Leu Phe Leu Glu Arg Leu Glu Glu Asn His Tyr
                85                  90                  95

Asn Thr Tyr Ile Ser Lys Lys His Ala Glu Lys Asn Trp Phe Val Gly
            100                 105                 110

```
Leu Lys Lys Asn Gly Ser Cys Lys Arg Gly Pro Arg Thr His Tyr Gly
        115                 120                 125

Gln Lys Ala Ile Leu Phe Leu Pro Leu Pro Val Ser Ser Asp
    130                 135                 140

<210> SEQ ID NO 65
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Met Lys Asn Leu Pro Pro Gly Asn Tyr Lys Lys Pro Lys Leu Leu Tyr
1               5                   10                  15

Cys Ser Asn Gly Gly His Phe Leu Arg Ile Leu Pro Asp Gly Thr Val
            20                  25                  30

Asp Gly Thr Arg Asp Arg Ser Asp Gln His Ile Gln Leu Gln Leu Ser
        35                  40                  45

Ala Glu Ser Val Gly Glu Val Tyr Ile Lys Ser Thr Glu Thr Gly Gln
    50                  55                  60

Tyr Leu Ala Met Asp Thr Asp Gly Leu Leu Tyr Gly Ser Gln Thr Pro
65                  70                  75                  80

Asn Glu Glu Cys Leu Phe Leu Glu Arg Leu Glu Glu Asn His Tyr Asn
                85                  90                  95

Thr Tyr Ile Ser Lys Lys His Ala Glu Lys Asn Trp Phe Val Gly Leu
            100                 105                 110

Lys Lys Asn Gly Ser Cys Lys Arg Gly Pro Arg Thr His Tyr Gly Gln
        115                 120                 125

Lys Ala Ile Leu Phe Leu Pro Leu Pro Val Ser Ser Asp
    130                 135                 140

<210> SEQ ID NO 66
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Met Lys Leu Pro Pro Gly Asn Tyr Lys Lys Pro Lys Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
            100                 105                 110

Lys Asn Gly Ser Cys Lys Arg Gly Pro Arg Thr His Tyr Gly Gln Lys
        115                 120                 125
```

```
Ala Ile Leu Phe Leu Pro Leu Pro Val Ser Ser Asp
        130                 135                 140

<210> SEQ ID NO 67
<211> LENGTH: 139
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Met Lys Pro Pro Gly Asn Tyr Lys Lys Pro Lys Leu Leu Tyr Cys Ser
1               5                   10                  15

Asn Gly Gly His Phe Leu Arg Ile Leu Pro Asp Gly Thr Val Asp Gly
                20                  25                  30

Thr Arg Asp Arg Ser Asp Gln His Ile Gln Leu Gln Leu Ser Ala Glu
            35                  40                  45

Ser Val Gly Glu Val Tyr Ile Lys Ser Thr Glu Thr Gly Gln Tyr Leu
    50                  55                  60

Ala Met Asp Thr Asp Gly Leu Leu Tyr Gly Ser Gln Thr Pro Asn Glu
65                  70                  75                  80

Glu Cys Leu Phe Leu Glu Arg Leu Glu Glu Asn His Tyr Asn Thr Tyr
                85                  90                  95

Ile Ser Lys Lys His Ala Glu Lys Asn Trp Phe Val Gly Leu Lys Lys
            100                 105                 110

Asn Gly Ser Cys Lys Arg Gly Pro Arg Thr His Tyr Gly Gln Lys Ala
        115                 120                 125

Ile Leu Phe Leu Pro Leu Pro Val Ser Ser Asp
    130                 135

<210> SEQ ID NO 68
<211> LENGTH: 138
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Met Lys Pro Gly Asn Tyr Lys Lys Pro Lys Leu Leu Tyr Cys Ser Asn
1               5                   10                  15

Gly Gly His Phe Leu Arg Ile Leu Pro Asp Gly Thr Val Asp Gly Thr
                20                  25                  30

Arg Asp Arg Ser Asp Gln His Ile Gln Leu Gln Leu Ser Ala Glu Ser
            35                  40                  45

Val Gly Glu Val Tyr Ile Lys Ser Thr Glu Thr Gly Gln Tyr Leu Ala
    50                  55                  60

Met Asp Thr Asp Gly Leu Leu Tyr Gly Ser Gln Thr Pro Asn Glu Glu
65                  70                  75                  80

Cys Leu Phe Leu Glu Arg Leu Glu Glu Asn His Tyr Asn Thr Tyr Ile
                85                  90                  95

Ser Lys Lys His Ala Glu Lys Asn Trp Phe Val Gly Leu Lys Lys Asn
            100                 105                 110

Gly Ser Cys Lys Arg Gly Pro Arg Thr His Tyr Gly Gln Lys Ala Ile
        115                 120                 125

Leu Phe Leu Pro Leu Pro Val Ser Ser Asp
    130                 135
```

<210> SEQ ID NO 69
<211> LENGTH: 144
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Ala Leu Thr Glu Lys Asn Leu Pro Pro Gly Asn Tyr Lys Lys Pro Lys
1               5                   10                  15

Leu Leu Tyr Cys Ser Asn Gly Gly His Phe Leu Arg Ile Leu Pro Asp
            20                  25                  30

Gly Thr Val Asp Gly Thr Arg Asp Arg Ser Asp Gln His Ile Gln Leu
        35                  40                  45

Gln Leu Ser Ala Glu Ser Val Gly Glu Val Tyr Ile Lys Ser Thr Glu
    50                  55                  60

Thr Gly Gln Tyr Leu Ala Met Asp Thr Asp Gly Leu Leu Tyr Gly Ser
65                  70                  75                  80

Gln Thr Pro Asn Glu Glu Cys Leu Phe Leu Glu Arg Leu Glu Glu Asn
                85                  90                  95

His Tyr Asn Thr Tyr Ile Ser Lys Lys His Ala Glu Lys Asn Trp Phe
            100                 105                 110

Val Gly Leu Lys Lys Asn Gly Ser Cys Lys Arg Gly Pro Arg Thr His
        115                 120                 125

Tyr Gly Gln Lys Ala Ile Leu Phe Leu Pro Leu Pro Val Ser Ser Asp
    130                 135                 140

<210> SEQ ID NO 70
<211> LENGTH: 143
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Ala Leu Thr Glu Lys Leu Pro Pro Gly Asn Tyr Lys Lys Pro Lys Leu
1               5                   10                  15

Leu Tyr Cys Ser Asn Gly Gly His Phe Leu Arg Ile Leu Pro Asp Gly
            20                  25                  30

Thr Val Asp Gly Thr Arg Asp Arg Ser Asp Gln His Ile Gln Leu Gln
        35                  40                  45

Leu Ser Ala Glu Ser Val Gly Glu Val Tyr Ile Lys Ser Thr Glu Thr
    50                  55                  60

Gly Gln Tyr Leu Ala Met Asp Thr Asp Gly Leu Leu Tyr Gly Ser Gln
65                  70                  75                  80

Thr Pro Asn Glu Glu Cys Leu Phe Leu Glu Arg Leu Glu Glu Asn His
                85                  90                  95

Tyr Asn Thr Tyr Ile Ser Lys Lys His Ala Glu Lys Asn Trp Phe Val
            100                 105                 110

Gly Leu Lys Lys Asn Gly Ser Cys Lys Arg Gly Pro Arg Thr His Tyr
        115                 120                 125

Gly Gln Lys Ala Ile Leu Phe Leu Pro Leu Pro Val Ser Ser Asp
    130                 135                 140

<210> SEQ ID NO 71

<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Ala Leu Thr Glu Lys Pro Pro Gly Asn Tyr Lys Lys Pro Lys Leu Leu
1               5                   10                  15
Tyr Cys Ser Asn Gly Gly His Phe Leu Arg Ile Leu Pro Asp Gly Thr
            20                  25                  30
Val Asp Gly Thr Arg Asp Arg Ser Asp Gln His Ile Gln Leu Gln Leu
        35                  40                  45
Ser Ala Glu Ser Val Gly Glu Val Tyr Ile Lys Ser Thr Glu Thr Gly
50                  55                  60
Gln Tyr Leu Ala Met Asp Thr Asp Gly Leu Leu Tyr Gly Ser Gln Thr
65                  70                  75                  80
Pro Asn Glu Glu Cys Leu Phe Leu Glu Arg Leu Glu Glu Asn His Tyr
                85                  90                  95
Asn Thr Tyr Ile Ser Lys Lys His Ala Glu Lys Asn Trp Phe Val Gly
            100                 105                 110
Leu Lys Lys Asn Gly Ser Cys Lys Arg Gly Pro Arg Thr His Tyr Gly
        115                 120                 125
Gln Lys Ala Ile Leu Phe Leu Pro Leu Pro Val Ser Ser Asp
    130                 135                 140

<210> SEQ ID NO 72
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Ala Leu Thr Glu Lys Pro Gly Asn Tyr Lys Lys Pro Lys Leu Leu Tyr
1               5                   10                  15
Cys Ser Asn Gly Gly His Phe Leu Arg Ile Leu Pro Asp Gly Thr Val
            20                  25                  30
Asp Gly Thr Arg Asp Arg Ser Asp Gln His Ile Gln Leu Gln Leu Ser
        35                  40                  45
Ala Glu Ser Val Gly Glu Val Tyr Ile Lys Ser Thr Glu Thr Gly Gln
50                  55                  60
Tyr Leu Ala Met Asp Thr Asp Gly Leu Leu Tyr Gly Ser Gln Thr Pro
65                  70                  75                  80
Asn Glu Glu Cys Leu Phe Leu Glu Arg Leu Glu Glu Asn His Tyr Asn
                85                  90                  95
Thr Tyr Ile Ser Lys Lys His Ala Glu Lys Asn Trp Phe Val Gly Leu
            100                 105                 110
Lys Lys Asn Gly Ser Cys Lys Arg Gly Pro Arg Thr His Tyr Gly Gln
        115                 120                 125
Lys Ala Ile Leu Phe Leu Pro Leu Pro Val Ser Ser Asp
    130                 135                 140

<210> SEQ ID NO 73
<211> LENGTH: 144
<212> TYPE: PRT
<213> ORGANISM: Artificial Sequence -continued

```
<220> FEATURE:
<223> OTHER INFORMATION: Description of Artificial Sequence: Synthetic
      polypeptide

<400> SEQUENCE: 73

Leu Thr Glu Lys Phe Asn Leu Pro Pro Gly Asn Tyr Lys Lys Pro Lys
1               5                   10                  15

Leu Leu Tyr Cys Ser Asn Gly Gly His Phe Leu Arg Ile Leu Pro Asp
            20                  25                  30

Gly Thr Val Asp Gly Thr Arg Asp Arg Ser Asp Gln His Ile Gln Leu
        35                  40                  45

Gln Leu Ser Ala Glu Ser Val Gly Glu Val Tyr Ile Lys Ser Thr Glu
50                  55                  60

Thr Gly Gln Tyr Leu Ala Met Asp Thr Asp Gly Leu Leu Tyr Gly Ser
65                  70                  75                  80

Gln Thr Pro Asn Glu Glu Cys Leu Phe Leu Glu Arg Leu Glu Glu Asn
                85                  90                  95

His Tyr Asn Thr Tyr Ile Ser Lys Lys His Ala Glu Lys Asn Trp Phe
            100                 105                 110

Val Gly Leu Lys Lys Asn Gly Ser Cys Lys Arg Gly Pro Arg Thr His
        115                 120                 125

Tyr Gly Gln Lys Ala Ile Leu Phe Leu Pro Leu Pro Val Ser Ser Asp
    130                 135                 140

<210> SEQ ID NO 74
<211> LENGTH: 143
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Leu Thr Glu Lys Asn Leu Pro Pro Gly Asn Tyr Lys Lys Pro Lys Leu
1               5                   10                  15

Leu Tyr Cys Ser Asn Gly Gly His Phe Leu Arg Ile Leu Pro Asp Gly
            20                  25                  30

Thr Val Asp Gly Thr Arg Asp Arg Ser Asp Gln His Ile Gln Leu Gln
        35                  40                  45

Leu Ser Ala Glu Ser Val Gly Glu Val Tyr Ile Lys Ser Thr Glu Thr
    50                  55                  60

Gly Gln Tyr Leu Ala Met Asp Thr Asp Gly Leu Leu Tyr Gly Ser Gln
65                  70                  75                  80

Thr Pro Asn Glu Glu Cys Leu Phe Leu Glu Arg Leu Glu Glu Asn His
                85                  90                  95

Tyr Asn Thr Tyr Ile Ser Lys Lys His Ala Glu Lys Asn Trp Phe Val
            100                 105                 110

Gly Leu Lys Lys Asn Gly Ser Cys Lys Arg Gly Pro Arg Thr His Tyr
        115                 120                 125

Gly Gln Lys Ala Ile Leu Phe Leu Pro Leu Pro Val Ser Ser Asp
    130                 135                 140

<210> SEQ ID NO 75
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 75

Leu Thr Glu Lys Leu Pro Pro Gly Asn Tyr Lys Pro Lys Leu Leu
1               5                   10                  15

Tyr Cys Ser Asn Gly Gly His Phe Leu Arg Ile Leu Pro Asp Gly Thr
            20                  25                  30

Val Asp Gly Thr Arg Asp Arg Ser Asp Gln His Ile Gln Leu Gln Leu
            35                  40                  45

Ser Ala Glu Ser Val Gly Glu Val Tyr Ile Lys Ser Thr Glu Thr Gly
50                  55                  60

Gln Tyr Leu Ala Met Asp Thr Asp Gly Leu Leu Tyr Gly Ser Gln Thr
65                  70                  75                  80

Pro Asn Glu Glu Cys Leu Phe Leu Glu Arg Leu Glu Glu Asn His Tyr
                85                  90                  95

Asn Thr Tyr Ile Ser Lys Lys His Ala Glu Lys Asn Trp Phe Val Gly
                100                 105                 110

Leu Lys Lys Asn Gly Ser Cys Lys Arg Gly Pro Arg Thr His Tyr Gly
            115                 120                 125

Gln Lys Ala Ile Leu Phe Leu Pro Leu Pro Val Ser Ser Asp
130                 135                 140

<210> SEQ ID NO 76
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Leu Thr Glu Lys Pro Pro Gly Asn Tyr Lys Pro Lys Leu Leu Tyr
1               5                   10                  15

Cys Ser Asn Gly Gly His Phe Leu Arg Ile Leu Pro Asp Gly Thr Val
            20                  25                  30

Asp Gly Thr Arg Asp Arg Ser Asp Gln His Ile Gln Leu Gln Leu Ser
            35                  40                  45

Ala Glu Ser Val Gly Glu Val Tyr Ile Lys Ser Thr Glu Thr Gly Gln
50                  55                  60

Tyr Leu Ala Met Asp Thr Asp Gly Leu Leu Tyr Gly Ser Gln Thr Pro
65                  70                  75                  80

Asn Glu Glu Cys Leu Phe Leu Glu Arg Leu Glu Glu Asn His Tyr Asn
                85                  90                  95

Thr Tyr Ile Ser Lys Lys His Ala Glu Lys Asn Trp Phe Val Gly Leu
                100                 105                 110

Lys Lys Asn Gly Ser Cys Lys Arg Gly Pro Arg Thr His Tyr Gly Gln
            115                 120                 125

Lys Ala Ile Leu Phe Leu Pro Leu Pro Val Ser Ser Asp
130                 135                 140

<210> SEQ ID NO 77
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

```
Leu Thr Glu Lys Pro Gly Asn Tyr Lys Lys Pro Lys Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
            100                 105                 110

Lys Asn Gly Ser Cys Lys Arg Gly Pro Arg Thr His Tyr Gly Gln Lys
        115                 120                 125

Ala Ile Leu Phe Leu Pro Leu Pro Val Ser Ser Asp
    130                 135                 140

<210> SEQ ID NO 78
<211> LENGTH: 143
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Thr Glu Lys Phe Asn Leu Pro Pro Gly Asn Tyr Lys Lys Pro Lys Leu
1               5                   10                  15

Leu Tyr Cys Ser Asn Gly Gly His Phe Leu Arg Ile Leu Pro Asp Gly
            20                  25                  30

Thr Val Asp Gly Thr Arg Asp Arg Ser Asp Gln His Ile Gln Leu Gln
        35                  40                  45

Leu Ser Ala Glu Ser Val Gly Glu Val Tyr Ile Lys Ser Thr Glu Thr
50                  55                  60

Gly Gln Tyr Leu Ala Met Asp Thr Asp Gly Leu Leu Tyr Gly Ser Gln
65                  70                  75                  80

Thr Pro Asn Glu Glu Cys Leu Phe Leu Glu Arg Leu Glu Glu Asn His
                85                  90                  95

Tyr Asn Thr Tyr Ile Ser Lys Lys His Ala Glu Lys Asn Trp Phe Val
            100                 105                 110

Gly Leu Lys Lys Asn Gly Ser Cys Lys Arg Gly Pro Arg Thr His Tyr
        115                 120                 125

Gly Gln Lys Ala Ile Leu Phe Leu Pro Leu Pro Val Ser Ser Asp
    130                 135                 140

<210> SEQ ID NO 79
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Thr Glu Lys Asn Leu Pro Pro Gly Asn Tyr Lys Lys Pro Lys Leu Leu
1               5                   10                  15
```

```
Tyr Cys Ser Asn Gly Gly His Phe Leu Arg Ile Leu Pro Asp Gly Thr
                20                  25                  30

Val Asp Gly Thr Arg Asp Arg Ser Asp Gln His Ile Gln Leu Gln Leu
             35                  40                  45

Ser Ala Glu Ser Val Gly Glu Val Tyr Ile Lys Ser Thr Glu Thr Gly
 50                  55                  60

Gln Tyr Leu Ala Met Asp Thr Asp Gly Leu Leu Tyr Gly Ser Gln Thr
 65                  70                  75                  80

Pro Asn Glu Glu Cys Leu Phe Leu Glu Arg Leu Glu Glu Asn His Tyr
                 85                  90                  95

Asn Thr Tyr Ile Ser Lys Lys His Ala Glu Lys Asn Trp Phe Val Gly
            100                 105                 110

Leu Lys Lys Asn Gly Ser Cys Lys Arg Gly Pro Arg Thr His Tyr Gly
            115                 120                 125

Gln Lys Ala Ile Leu Phe Leu Pro Leu Pro Val Ser Ser Asp
        130                 135                 140

<210> SEQ ID NO 80
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Thr Glu Lys Leu Pro Pro Gly Asn Tyr Lys Lys Pro Lys Leu Leu Tyr
 1               5                  10                  15

Cys Ser Asn Gly Gly His Phe Leu Arg Ile Leu Pro Asp Gly Thr Val
                20                  25                  30

Asp Gly Thr Arg Asp Arg Ser Asp Gln His Ile Gln Leu Gln Leu Ser
             35                  40                  45

Ala Glu Ser Val Gly Glu Val Tyr Ile Lys Ser Thr Glu Thr Gly Gln
 50                  55                  60

Tyr Leu Ala Met Asp Thr Asp Gly Leu Leu Tyr Gly Ser Gln Thr Pro
 65                  70                  75                  80

Asn Glu Glu Cys Leu Phe Leu Glu Arg Leu Glu Glu Asn His Tyr Asn
                 85                  90                  95

Thr Tyr Ile Ser Lys Lys His Ala Glu Lys Asn Trp Phe Val Gly Leu
            100                 105                 110

Lys Lys Asn Gly Ser Cys Lys Arg Gly Pro Arg Thr His Tyr Gly Gln
            115                 120                 125

Lys Ala Ile Leu Phe Leu Pro Leu Pro Val Ser Ser Asp
        130                 135                 140

<210> SEQ ID NO 81
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Thr Glu Lys Pro Pro Gly Asn Tyr Lys Lys Pro Lys Leu Leu Tyr Cys
 1               5                  10                  15

Ser Asn Gly Gly His Phe Leu Arg Ile Leu Pro Asp Gly Thr Val Asp
                20                  25                  30
```

Gly Thr Arg Asp Arg Ser Asp Gln His Ile Gln Leu Gln Leu Ser Ala
                35                  40                  45

Glu Ser Val Gly Glu Val Tyr Ile Lys Ser Thr Glu Thr Gly Gln Tyr
 50                  55                  60

Leu Ala Met Asp Thr Asp Gly Leu Leu Tyr Gly Ser Gln Thr Pro Asn
 65                  70                  75                  80

Glu Glu Cys Leu Phe Leu Glu Arg Leu Glu Glu Asn His Tyr Asn Thr
                 85                  90                  95

Tyr Ile Ser Lys Lys His Ala Glu Lys Asn Trp Phe Val Gly Leu Lys
                100                 105                 110

Lys Asn Gly Ser Cys Lys Arg Gly Pro Arg Thr His Tyr Gly Gln Lys
                115                 120                 125

Ala Ile Leu Phe Leu Pro Leu Pro Val Ser Ser Asp
            130                 135                 140

<210> SEQ ID NO 82
<211> LENGTH: 139
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Thr Glu Lys Pro Gly Asn Tyr Lys Lys Pro Lys Leu Leu Tyr Cys Ser
 1               5                  10                  15

Asn Gly Gly His Phe Leu Arg Ile Leu Pro Asp Gly Thr Val Asp Gly
                20                  25                  30

Thr Arg Asp Arg Ser Asp Gln His Ile Gln Leu Gln Leu Ser Ala Glu
             35                  40                  45

Ser Val Gly Glu Val Tyr Ile Lys Ser Thr Glu Thr Gly Gln Tyr Leu
 50                  55                  60

Ala Met Asp Thr Asp Gly Leu Leu Tyr Gly Ser Gln Thr Pro Asn Glu
 65                  70                  75                  80

Glu Cys Leu Phe Leu Glu Arg Leu Glu Glu Asn His Tyr Asn Thr Tyr
                 85                  90                  95

Ile Ser Lys Lys His Ala Glu Lys Asn Trp Phe Val Gly Leu Lys Lys
                100                 105                 110

Asn Gly Ser Cys Lys Arg Gly Pro Arg Thr His Tyr Gly Gln Lys Ala
                115                 120                 125

Ile Leu Phe Leu Pro Leu Pro Val Ser Ser Asp
            130                 135

<210> SEQ ID NO 83
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Glu Lys Phe Asn Leu Pro Pro Gly Asn Tyr Lys Lys Pro Lys Leu Leu
 1               5                  10                  15

Tyr Cys Ser Asn Gly Gly His Phe Leu Arg Ile Leu Pro Asp Gly Thr
                20                  25                  30

Val Asp Gly Thr Arg Asp Arg Ser Asp Gln His Ile Gln Leu Gln Leu
             35                  40                  45

-continued

```
Ser Ala Glu Ser Val Gly Glu Val Tyr Ile Lys Ser Thr Glu Thr Gly
 50                  55                  60

Gln Tyr Leu Ala Met Asp Thr Asp Gly Leu Leu Tyr Gly Ser Gln Thr
 65                  70                  75                  80

Pro Asn Glu Glu Cys Leu Phe Leu Glu Arg Leu Glu Glu Asn His Tyr
                 85                  90                  95

Asn Thr Tyr Ile Ser Lys Lys His Ala Glu Lys Asn Trp Phe Val Gly
            100                 105                 110

Leu Lys Lys Asn Gly Ser Cys Lys Arg Gly Pro Arg Thr His Tyr Gly
        115                 120                 125

Gln Lys Ala Ile Leu Phe Leu Pro Leu Pro Val Ser Ser Asp
    130                 135                 140

<210> SEQ ID NO 84
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Glu Lys Asn Leu Pro Pro Gly Asn Tyr Lys Lys Pro Lys Leu Leu Tyr
  1               5                  10                  15

Cys Ser Asn Gly Gly His Phe Leu Arg Ile Leu Pro Asp Gly Thr Val
                 20                  25                  30

Asp Gly Thr Arg Asp Arg Ser Asp Gln His Ile Gln Leu Gln Leu Ser
             35                  40                  45

Ala Glu Ser Val Gly Glu Val Tyr Ile Lys Ser Thr Glu Thr Gly Gln
 50                  55                  60

Tyr Leu Ala Met Asp Thr Asp Gly Leu Leu Tyr Gly Ser Gln Thr Pro
 65                  70                  75                  80

Asn Glu Glu Cys Leu Phe Leu Glu Arg Leu Glu Glu Asn His Tyr Asn
                 85                  90                  95

Thr Tyr Ile Ser Lys Lys His Ala Glu Lys Asn Trp Phe Val Gly Leu
            100                 105                 110

Lys Lys Asn Gly Ser Cys Lys Arg Gly Pro Arg Thr His Tyr Gly Gln
        115                 120                 125

Lys Ala Ile Leu Phe Leu Pro Leu Pro Val Ser Ser Asp
    130                 135                 140

<210> SEQ ID NO 85
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Glu Lys Leu Pro Pro Gly Asn Tyr Lys Lys Pro Lys Leu Leu Tyr Cys
  1               5                  10                  15

Ser Asn Gly Gly His Phe Leu Arg Ile Leu Pro Asp Gly Thr Val Asp
                 20                  25                  30

Gly Thr Arg Asp Arg Ser Asp Gln His Ile Gln Leu Gln Leu Ser Ala
             35                  40                  45

Glu Ser Val Gly Glu Val Tyr Ile Lys Ser Thr Glu Thr Gly Gln Tyr
 50                  55                  60
```

```
Leu Ala Met Asp Thr Asp Gly Leu Leu Tyr Gly Ser Gln Thr Pro Asn
 65                  70                  75                  80

Glu Glu Cys Leu Phe Leu Glu Arg Leu Glu Glu Asn His Tyr Asn Thr
                 85                  90                  95

Tyr Ile Ser Lys Lys His Ala Glu Lys Asn Trp Phe Val Gly Leu Lys
            100                 105                 110

Lys Asn Gly Ser Cys Lys Arg Gly Pro Arg Thr His Tyr Gly Gln Lys
        115                 120                 125

Ala Ile Leu Phe Leu Pro Leu Pro Val Ser Ser Asp
        130                 135                 140

<210> SEQ ID NO 86
<211> LENGTH: 139
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Glu Lys Pro Pro Gly Asn Tyr Lys Lys Pro Lys Leu Leu Tyr Cys Ser
  1               5                  10                  15

Asn Gly Gly His Phe Leu Arg Ile Leu Pro Asp Gly Thr Val Asp Gly
                 20                  25                  30

Thr Arg Asp Arg Ser Asp Gln His Ile Gln Leu Gln Leu Ser Ala Glu
             35                  40                  45

Ser Val Gly Glu Val Tyr Ile Lys Ser Thr Glu Thr Gly Gln Tyr Leu
 50                  55                  60

Ala Met Asp Thr Asp Gly Leu Leu Tyr Gly Ser Gln Thr Pro Asn Glu
 65                  70                  75                  80

Glu Cys Leu Phe Leu Glu Arg Leu Glu Glu Asn His Tyr Asn Thr Tyr
                 85                  90                  95

Ile Ser Lys Lys His Ala Glu Lys Asn Trp Phe Val Gly Leu Lys Lys
            100                 105                 110

Asn Gly Ser Cys Lys Arg Gly Pro Arg Thr His Tyr Gly Gln Lys Ala
        115                 120                 125

Ile Leu Phe Leu Pro Leu Pro Val Ser Ser Asp
        130                 135

<210> SEQ ID NO 87
<211> LENGTH: 138
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Glu Lys Pro Gly Asn Tyr Lys Lys Pro Lys Leu Leu Tyr Cys Ser Asn
  1               5                  10                  15

Gly Gly His Phe Leu Arg Ile Leu Pro Asp Gly Thr Val Asp Gly Thr
                 20                  25                  30

Arg Asp Arg Ser Asp Gln His Ile Gln Leu Gln Leu Ser Ala Glu Ser
             35                  40                  45

Val Gly Glu Val Tyr Ile Lys Ser Thr Glu Thr Gly Gln Tyr Leu Ala
 50                  55                  60

Met Asp Thr Asp Gly Leu Leu Tyr Gly Ser Gln Thr Pro Asn Glu Glu
 65                  70                  75                  80
```

```
Cys Leu Phe Leu Glu Arg Leu Glu Glu Asn His Tyr Asn Thr Tyr Ile
             85                  90                  95

Ser Lys Lys His Ala Glu Lys Asn Trp Phe Val Gly Leu Lys Lys Asn
            100                 105                 110

Gly Ser Cys Lys Arg Gly Pro Arg Thr His Tyr Gly Gln Lys Ala Ile
        115                 120                 125

Leu Phe Leu Pro Leu Pro Val Ser Ser Asp
    130                 135
```

<210> SEQ ID NO 88
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

```
Lys Phe Asn Leu Pro Pro Gly Asn Tyr Lys Lys Pro Lys Leu Leu Tyr
1               5                   10                  15

Cys Ser Asn Gly Gly His Phe Leu Arg Ile Leu Pro Asp Gly Thr Val
            20                  25                  30

Asp Gly Thr Arg Asp Arg Ser Asp Gln His Ile Gln Leu Gln Leu Ser
        35                  40                  45

Ala Glu Ser Val Gly Glu Val Tyr Ile Lys Ser Thr Glu Thr Gly Gln
    50                  55                  60

Tyr Leu Ala Met Asp Thr Asp Gly Leu Leu Tyr Gly Ser Gln Thr Pro
65                  70                  75                  80

Asn Glu Glu Cys Leu Phe Leu Glu Arg Leu Glu Glu Asn His Tyr Asn
                85                  90                  95

Thr Tyr Ile Ser Lys Lys His Ala Glu Lys Asn Trp Phe Val Gly Leu
            100                 105                 110

Lys Lys Asn Gly Ser Cys Lys Arg Gly Pro Arg Thr His Tyr Gly Gln
        115                 120                 125

Lys Ala Ile Leu Phe Leu Pro Leu Pro Val Ser Ser Asp
    130                 135                 140
```

<210> SEQ ID NO 89
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

```
Lys Asn Leu Pro Pro Gly Asn Tyr Lys Lys Pro Lys Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95
```

-continued

Tyr Ile Ser Lys Lys His Ala Glu Lys Asn Trp Phe Val Gly Leu Lys
            100                 105                 110

Lys Asn Gly Ser Cys Lys Arg Gly Pro Arg Thr His Tyr Gly Gln Lys
        115                 120                 125

Ala Ile Leu Phe Leu Pro Leu Pro Val Ser Ser Asp
    130                 135                 140

<210> SEQ ID NO 90
<211> LENGTH: 139
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Lys Leu Pro Pro Gly Asn Tyr Lys Lys Pro Leu Leu Tyr Cys Ser
1               5                   10                  15

Asn Gly Gly His Phe Leu Arg Ile Leu Pro Asp Gly Thr Val Asp Gly
            20                  25                  30

Thr Arg Asp Arg Ser Asp Gln His Ile Gln Leu Gln Leu Ser Ala Glu
        35                  40                  45

Ser Val Gly Glu Val Tyr Ile Lys Ser Thr Glu Thr Gly Gln Tyr Leu
    50                  55                  60

Ala Met Asp Thr Asp Gly Leu Leu Tyr Gly Ser Gln Thr Pro Asn Glu
65                  70                  75                  80

Glu Cys Leu Phe Leu Glu Arg Leu Glu Glu Asn His Tyr Asn Thr Tyr
                85                  90                  95

Ile Ser Lys Lys His Ala Glu Lys Asn Trp Phe Val Gly Leu Lys Lys
            100                 105                 110

Asn Gly Ser Cys Lys Arg Gly Pro Arg Thr His Tyr Gly Gln Lys Ala
        115                 120                 125

Ile Leu Phe Leu Pro Leu Pro Val Ser Ser Asp
    130                 135

<210> SEQ ID NO 91
<211> LENGTH: 138
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Lys Pro Pro Gly Asn Tyr Lys Lys Pro Leu Leu Tyr Cys Ser Asn
1               5                   10                  15

Gly Gly His Phe Leu Arg Ile Leu Pro Asp Gly Thr Val Asp Gly Thr
            20                  25                  30

Arg Asp Arg Ser Asp Gln His Ile Gln Leu Gln Leu Ser Ala Glu Ser
        35                  40                  45

Val Gly Glu Val Tyr Ile Lys Ser Thr Glu Thr Gly Gln Tyr Leu Ala
    50                  55                  60

Met Asp Thr Asp Gly Leu Leu Tyr Gly Ser Gln Thr Pro Asn Glu Glu
65                  70                  75                  80

Cys Leu Phe Leu Glu Arg Leu Glu Glu Asn His Tyr Asn Thr Tyr Ile
                85                  90                  95

Ser Lys Lys His Ala Glu Lys Asn Trp Phe Val Gly Leu Lys Lys Asn
            100                 105                 110

Gly Ser Cys Lys Arg Gly Pro Arg Thr His Tyr Gly Gln Lys Ala Ile
            115                 120                 125

Leu Phe Leu Pro Leu Pro Val Ser Ser Asp
    130                 135

<210> SEQ ID NO 92
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Lys Pro Gly Asn Tyr Lys Lys Pro Lys Leu Leu Tyr Cys Ser Asn Gly
1               5                   10                  15

Gly His Phe Leu Arg Ile Leu Pro Asp Gly Thr Val Asp Gly Thr Arg
            20                  25                  30

Asp Arg Ser Asp Gln His Ile Gln Leu Gln Leu Ser Ala Glu Ser Val
        35                  40                  45

Gly Glu Val Tyr Ile Lys Ser Thr Glu Thr Gly Gln Tyr Leu Ala Met
    50                  55                  60

Asp Thr Asp Gly Leu Leu Tyr Gly Ser Gln Thr Pro Asn Glu Glu Cys
65                  70                  75                  80

Leu Phe Leu Glu Arg Leu Glu Glu Asn His Tyr Asn Thr Tyr Ile Ser
                85                  90                  95

Lys Lys His Ala Glu Lys Asn Trp Phe Val Gly Leu Lys Lys Asn Gly
            100                 105                 110

Ser Cys Lys Arg Gly Pro Arg Thr His Tyr Gly Gln Lys Ala Ile Leu
        115                 120                 125

Phe Leu Pro Leu Pro Val Ser Ser Asp
    130                 135

<210> SEQ ID NO 93
<211> LENGTH: 144
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Ala Leu Thr Glu Lys Asn Leu Pro Pro Gly Asn Tyr Lys Lys Pro Lys
1               5                   10                  15

Leu Leu Tyr Ser Ser Asn Gly Gly His Phe Leu Arg Ile Leu Pro Asp
            20                  25                  30

Gly Thr Val Asp Gly Thr Arg Asp Arg Ser Asp Gln His Ile Gln Leu
        35                  40                  45

Gln Leu Ser Ala Glu Ser Val Gly Glu Val Tyr Ile Lys Ser Thr Glu
    50                  55                  60

Thr Gly Gln Tyr Leu Cys Met Asp Thr Asp Gly Leu Leu Tyr Gly Ser
65                  70                  75                  80

Gln Thr Pro Asn Glu Glu Cys Leu Phe Leu Glu Arg Leu Glu Glu Asn
                85                  90                  95

His Tyr Asn Thr Tyr Ile Ser Lys Lys His Ala Glu Lys Asn Trp Phe
            100                 105                 110

Val Gly Leu Lys Lys Asn Gly Ser Val Lys Arg Gly Pro Arg Thr His
        115                 120                 125

```
Tyr Gly Gln Lys Ala Ile Leu Phe Leu Pro Leu Pro Val Ser Ser Asp
        130                 135                 140

<210> SEQ ID NO 94
<211> LENGTH: 143
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Ala Leu Thr Glu Lys Leu Pro Pro Gly Asn Tyr Lys Lys Pro Lys Leu
1               5                   10                  15

Leu Tyr Ser Ser Asn Gly Gly His Phe Leu Arg Ile Leu Pro Asp Gly
            20                  25                  30

Thr Val Asp Gly Thr Arg Asp Arg Ser Asp Gln His Ile Gln Leu Gln
        35                  40                  45

Leu Ser Ala Glu Ser Val Gly Glu Val Tyr Ile Lys Ser Thr Glu Thr
    50                  55                  60

Gly Gln Tyr Leu Cys Met Asp Thr Asp Gly Leu Leu Tyr Gly Ser Gln
65                  70                  75                  80

Thr Pro Asn Glu Glu Cys Leu Phe Leu Glu Arg Leu Glu Glu Asn His
                85                  90                  95

Tyr Asn Thr Tyr Ile Ser Lys Lys His Ala Glu Lys Asn Trp Phe Val
            100                 105                 110

Gly Leu Lys Lys Asn Gly Ser Val Lys Arg Gly Pro Arg Thr His Tyr
        115                 120                 125

Gly Gln Lys Ala Ile Leu Phe Leu Pro Leu Pro Val Ser Ser Asp
    130                 135                 140

<210> SEQ ID NO 95

<400> SEQUENCE: 95

000

<210> SEQ ID NO 96
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Ala Leu Thr Glu Lys Pro Pro Gly Asn Tyr Lys Lys Pro Lys Leu Leu
1               5                   10                  15

Tyr Ser Ser Asn Gly Gly His Phe Leu Arg Ile Leu Pro Asp Gly Thr
            20                  25                  30

Val Asp Gly Thr Arg Asp Arg Ser Asp Gln His Ile Gln Leu Gln Leu
        35                  40                  45

Ser Ala Glu Ser Val Gly Glu Val Tyr Ile Lys Ser Thr Glu Thr Gly
    50                  55                  60

Gln Tyr Leu Cys Met Asp Thr Asp Gly Leu Leu Tyr Gly Ser Gln Thr
65                  70                  75                  80

Pro Asn Glu Glu Cys Leu Phe Leu Glu Arg Leu Glu Glu Asn His Tyr
                85                  90                  95

Asn Thr Tyr Ile Ser Lys Lys His Ala Glu Lys Asn Trp Phe Val Gly
            100                 105                 110
```

```
Leu Lys Lys Asn Gly Ser Val Lys Arg Gly Pro Arg Thr His Tyr Gly
        115                 120                 125

Gln Lys Ala Ile Leu Phe Leu Pro Leu Pro Val Ser Ser Asp
    130                 135                 140

<210> SEQ ID NO 97
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Ala Leu Thr Glu Lys Pro Gly Asn Tyr Lys Pro Lys Leu Leu Tyr
1               5                  10                  15

Ser Ser Asn Gly Gly His Phe Leu Arg Ile Leu Pro Asp Gly Thr Val
            20                  25                  30

Asp Gly Thr Arg Asp Arg Ser Asp Gln His Ile Gln Leu Gln Leu Ser
        35                  40                  45

Ala Glu Ser Val Gly Glu Val Tyr Ile Lys Ser Thr Glu Thr Gly Gln
    50                  55                  60

Tyr Leu Cys Met Asp Thr Asp Gly Leu Leu Tyr Gly Ser Gln Thr Pro
65                  70                  75                  80

Asn Glu Glu Cys Leu Phe Leu Glu Arg Leu Glu Glu Asn His Tyr Asn
                85                  90                  95

Thr Tyr Ile Ser Lys Lys His Ala Glu Lys Asn Trp Phe Val Gly Leu
            100                 105                 110

Lys Lys Asn Gly Ser Val Lys Arg Gly Pro Arg Thr His Tyr Gly Gln
        115                 120                 125

Lys Ala Ile Leu Phe Leu Pro Leu Pro Val Ser Ser Asp
    130                 135                 140

<210> SEQ ID NO 98
<211> LENGTH: 144
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Leu Thr Glu Lys Phe Asn Leu Pro Pro Gly Asn Tyr Lys Lys Pro Lys
1               5                   10                  15

Leu Leu Tyr Ser Ser Asn Gly Gly His Phe Leu Arg Ile Leu Pro Asp
            20                  25                  30

Gly Thr Val Asp Gly Thr Arg Asp Arg Ser Asp Gln His Ile Gln Leu
        35                  40                  45

Gln Leu Ser Ala Glu Ser Val Gly Glu Val Tyr Ile Lys Ser Thr Glu
    50                  55                  60

Thr Gly Gln Tyr Leu Cys Met Asp Thr Asp Gly Leu Leu Tyr Gly Ser
65                  70                  75                  80

Gln Thr Pro Asn Glu Glu Cys Leu Phe Leu Glu Arg Leu Glu Glu Asn
                85                  90                  95

His Tyr Asn Thr Tyr Ile Ser Lys Lys His Ala Glu Lys Asn Trp Phe
            100                 105                 110

Val Gly Leu Lys Lys Asn Gly Ser Val Lys Arg Gly Pro Arg Thr His
        115                 120                 125
```

```
Tyr Gly Gln Lys Ala Ile Leu Phe Leu Pro Leu Pro Val Ser Ser Asp
            130                 135                 140
```

<210> SEQ ID NO 99
<211> LENGTH: 143
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

```
Leu Thr Glu Lys Asn Leu Pro Pro Gly Asn Tyr Lys Lys Pro Lys Leu
1               5                  10                  15

Leu Tyr Ser Ser Asn Gly Gly His Phe Leu Arg Ile Leu Pro Asp Gly
            20                  25                  30

Thr Val Asp Gly Thr Arg Asp Arg Ser Asp Gln His Ile Gln Leu Gln
        35                  40                  45

Leu Ser Ala Glu Ser Val Gly Glu Val Tyr Ile Lys Ser Thr Glu Thr
50                  55                  60

Gly Gln Tyr Leu Cys Met Asp Thr Asp Gly Leu Leu Tyr Gly Ser Gln
65                  70                  75                  80

Thr Pro Asn Glu Glu Cys Leu Phe Leu Glu Arg Leu Glu Glu Asn His
                85                  90                  95

Tyr Asn Thr Tyr Ile Ser Lys Lys His Ala Glu Lys Asn Trp Phe Val
            100                 105                 110

Gly Leu Lys Lys Asn Gly Ser Val Lys Arg Gly Pro Arg Thr His Tyr
        115                 120                 125

Gly Gln Lys Ala Ile Leu Phe Leu Pro Leu Pro Val Ser Ser Asp
    130                 135                 140
```

<210> SEQ ID NO 100
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

```
Leu Thr Glu Lys Leu Pro Pro Gly Asn Tyr Lys Lys Pro Lys Leu Leu
1               5                  10                  15

Tyr Ser Ser Asn Gly Gly His Phe Leu Arg Ile Leu Pro Asp Gly Thr
            20                  25                  30

Val Asp Gly Thr Arg Asp Arg Ser Asp Gln His Ile Gln Leu Gln Leu
        35                  40                  45

Ser Ala Glu Ser Val Gly Glu Val Tyr Ile Lys Ser Thr Glu Thr Gly
    50                  55                  60

Gln Tyr Leu Cys Met Asp Thr Asp Gly Leu Leu Tyr Gly Ser Gln Thr
65                  70                  75                  80

Pro Asn Glu Glu Cys Leu Phe Leu Glu Arg Leu Glu Glu Asn His Tyr
                85                  90                  95

Asn Thr Tyr Ile Ser Lys Lys His Ala Glu Lys Asn Trp Phe Val Gly
            100                 105                 110

Leu Lys Lys Asn Gly Ser Val Lys Arg Gly Pro Arg Thr His Tyr Gly
        115                 120                 125

Gln Lys Ala Ile Leu Phe Leu Pro Leu Pro Val Ser Ser Asp
    130                 135                 140
```

<210> SEQ ID NO 101
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Leu Thr Glu Lys Pro Pro Gly Asn Tyr Lys Lys Pro Lys Leu Leu Tyr
1               5                   10                  15

Ser Ser Asn Gly Gly His Phe Leu Arg Ile Leu Pro Asp Gly Thr Val
                20                  25                  30

Asp Gly Thr Arg Asp Arg Ser Asp Gln His Ile Gln Leu Gln Leu Ser
            35                  40                  45

Ala Glu Ser Val Gly Glu Val Tyr Ile Lys Ser Thr Glu Thr Gly Gln
        50                  55                  60

Tyr Leu Cys Met Asp Thr Asp Gly Leu Leu Tyr Gly Ser Gln Thr Pro
65                  70                  75                  80

Asn Glu Glu Cys Leu Phe Leu Glu Arg Leu Glu Glu Asn His Tyr Asn
                85                  90                  95

Thr Tyr Ile Ser Lys Lys His Ala Glu Lys Asn Trp Phe Val Gly Leu
                100                 105                 110

Lys Lys Asn Gly Ser Val Lys Arg Gly Pro Arg Thr His Tyr Gly Gln
            115                 120                 125

Lys Ala Ile Leu Phe Leu Pro Leu Pro Val Ser Ser Asp
        130                 135                 140

<210> SEQ ID NO 102
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Leu Thr Glu Lys Pro Pro Gly Asn Tyr Lys Lys Pro Lys Leu Leu Tyr Ser
1               5                   10                  15

Ser Asn Gly Gly His Phe Leu Arg Ile Leu Pro Asp Gly Thr Val Asp
                20                  25                  30

Gly Thr Arg Asp Arg Ser Asp Gln His Ile Gln Leu Gln Leu Ser Ala
            35                  40                  45

Glu Ser Val Gly Glu Val Tyr Ile Lys Ser Thr Glu Thr Gly Gln Tyr
        50                  55                  60

Leu Cys Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
                100                 105                 110

Lys Asn Gly Ser Val Lys Arg Gly Pro Arg Thr His Tyr Gly Gln Lys
            115                 120                 125

Ala Ile Leu Phe Leu Pro Leu Pro Val Ser Ser Asp
        130                 135                 140

<210> SEQ ID NO 103

<211> LENGTH: 143
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Thr Glu Lys Phe Asn Leu Pro Pro Gly Asn Tyr Lys Lys Pro Lys Leu
1               5                   10                  15

Leu Tyr Ser Ser Asn Gly Gly His Phe Leu Arg Ile Leu Pro Asp Gly
            20                  25                  30

Thr Val Asp Gly Thr Arg Asp Arg Ser Asp Gln His Ile Gln Leu Gln
        35                  40                  45

Leu Ser Ala Glu Ser Val Gly Glu Val Tyr Ile Lys Ser Thr Glu Thr
    50                  55                  60

Gly Gln Tyr Leu Cys Met Asp Thr Asp Gly Leu Leu Tyr Gly Ser Gln
65                  70                  75                  80

Thr Pro Asn Glu Glu Cys Leu Phe Leu Glu Arg Leu Glu Glu Asn His
                85                  90                  95

Tyr Asn Thr Tyr Ile Ser Lys Lys His Ala Glu Lys Asn Trp Phe Val
            100                 105                 110

Gly Leu Lys Lys Asn Gly Ser Val Lys Arg Gly Pro Arg Thr His Tyr
        115                 120                 125

Gly Gln Lys Ala Ile Leu Phe Leu Pro Leu Pro Val Ser Ser Asp
    130                 135                 140

<210> SEQ ID NO 104
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Thr Glu Lys Asn Leu Pro Pro Gly Asn Tyr Lys Lys Pro Lys Leu Leu
1               5                   10                  15

Tyr Ser Ser Asn Gly Gly His Phe Leu Arg Ile Leu Pro Asp Gly Thr
            20                  25                  30

Val Asp Gly Thr Arg Asp Arg Ser Asp Gln His Ile Gln Leu Gln Leu
        35                  40                  45

Ser Ala Glu Ser Val Gly Glu Val Tyr Ile Lys Ser Thr Glu Thr Gly
    50                  55                  60

Gln Tyr Leu Cys Met Asp Thr Asp Gly Leu Leu Tyr Gly Ser Gln Thr
65                  70                  75                  80

Pro Asn Glu Glu Cys Leu Phe Leu Glu Arg Leu Glu Glu Asn His Tyr
                85                  90                  95

Asn Thr Tyr Ile Ser Lys Lys His Ala Glu Lys Asn Trp Phe Val Gly
            100                 105                 110

Leu Lys Lys Asn Gly Ser Val Lys Arg Gly Pro Arg Thr His Tyr Gly
        115                 120                 125

Gln Lys Ala Ile Leu Phe Leu Pro Leu Pro Val Ser Ser Asp
    130                 135                 140

<210> SEQ ID NO 105
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

```
Thr Glu Lys Leu Pro Pro Gly Asn Tyr Lys Lys Pro Lys Leu Leu Tyr
1               5                   10                  15
Ser Ser Asn Gly Gly His Phe Leu Arg Ile Leu Pro Asp Gly Thr Val
            20                  25                  30
Asp Gly Thr Arg Asp Arg Ser Asp Gln His Ile Gln Leu Gln Leu Ser
        35                  40                  45
Ala Glu Ser Val Gly Glu Val Tyr Ile Lys Ser Thr Glu Thr Gly Gln
    50                  55                  60
Tyr Leu Cys Met Asp Thr Asp Gly Leu Leu Tyr Gly Ser Gln Thr Pro
65                  70                  75                  80
Asn Glu Glu Cys Leu Phe Leu Glu Arg Leu Glu Glu Asn His Tyr Asn
                85                  90                  95
Thr Tyr Ile Ser Lys Lys His Ala Glu Lys Asn Trp Phe Val Gly Leu
            100                 105                 110
Lys Lys Asn Gly Ser Val Lys Arg Gly Pro Arg Thr His Tyr Gly Gln
        115                 120                 125
Lys Ala Ile Leu Phe Leu Pro Leu Pro Val Ser Ser Asp
    130                 135                 140
```

<210> SEQ ID NO 106
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

```
Thr Glu Lys Pro Pro Gly Asn Tyr Lys Lys Pro Lys Leu Leu Tyr Ser
1               5                   10                  15
Ser Asn Gly Gly His Phe Leu Arg Ile Leu Pro Asp Gly Thr Val Asp
            20                  25                  30
Gly Thr Arg Asp Arg Ser Asp Gln His Ile Gln Leu Gln Leu Ser Ala
        35                  40                  45
Glu Ser Val Gly Glu Val Tyr Ile Lys Ser Thr Glu Thr Gly Gln Tyr
    50                  55                  60
Leu Cys Met Asp Thr Asp Gly Leu Leu Tyr Gly Ser Gln Thr Pro Asn
65                  70                  75                  80
Glu Glu Cys Leu Phe Leu Glu Arg Leu Glu Glu Asn His Tyr Asn Thr
                85                  90                  95
Tyr Ile Ser Lys Lys His Ala Glu Lys Asn Trp Phe Val Gly Leu Lys
            100                 105                 110
Lys Asn Gly Ser Val Lys Arg Gly Pro Arg Thr His Tyr Gly Gln Lys
        115                 120                 125
Ala Ile Leu Phe Leu Pro Leu Pro Val Ser Ser Asp
    130                 135                 140
```

<210> SEQ ID NO 107
<211> LENGTH: 139
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Thr Glu Lys Pro Gly Asn Tyr Lys Lys Pro Lys Leu Leu Tyr Ser Ser
1               5                   10                  15

Asn Gly Gly His Phe Leu Arg Ile Leu Pro Asp Gly Thr Val Asp Gly
            20                  25                  30

Thr Arg Asp Arg Ser Asp Gln His Ile Gln Leu Gln Leu Ser Ala Glu
        35                  40                  45

Ser Val Gly Glu Val Tyr Ile Lys Ser Thr Glu Thr Gly Gln Tyr Leu
50                  55                  60

Cys Met Asp Thr Asp Gly Leu Leu Tyr Gly Ser Gln Thr Pro Asn Glu
65                  70                  75                  80

Glu Cys Leu Phe Leu Glu Arg Leu Glu Glu Asn His Tyr Asn Thr Tyr
                85                  90                  95

Ile Ser Lys Lys His Ala Glu Lys Asn Trp Phe Val Gly Leu Lys Lys
            100                 105                 110

Asn Gly Ser Val Lys Arg Gly Pro Arg Thr His Tyr Gly Gln Lys Ala
        115                 120                 125

Ile Leu Phe Leu Pro Leu Pro Val Ser Ser Asp
    130                 135

<210> SEQ ID NO 108
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Glu Lys Phe Asn Leu Pro Pro Gly Asn Tyr Lys Lys Pro Lys Leu Leu
1               5                   10                  15

Tyr Ser Ser Asn Gly Gly His Phe Leu Arg Ile Leu Pro Asp Gly Thr
            20                  25                  30

Val Asp Gly Thr Arg Asp Arg Ser Asp Gln His Ile Gln Leu Gln Leu
        35                  40                  45

Ser Ala Glu Ser Val Gly Glu Val Tyr Ile Lys Ser Thr Glu Thr Gly
50                  55                  60

Gln Tyr Leu Cys Met Asp Thr Asp Gly Leu Leu Tyr Gly Ser Gln Thr
65                  70                  75                  80

Pro Asn Glu Glu Cys Leu Phe Leu Glu Arg Leu Glu Glu Asn His Tyr
                85                  90                  95

Asn Thr Tyr Ile Ser Lys Lys His Ala Glu Lys Asn Trp Phe Val Gly
            100                 105                 110

Leu Lys Lys Asn Gly Ser Val Lys Arg Gly Pro Arg Thr His Tyr Gly
        115                 120                 125

Gln Lys Ala Ile Leu Phe Leu Pro Leu Pro Val Ser Ser Asp
    130                 135                 140

<210> SEQ ID NO 109
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

```
Glu Lys Asn Leu Pro Pro Gly Asn Tyr Lys Pro Lys Leu Leu Tyr
1               5                   10                  15

Ser Ser Asn Gly Gly His Phe Leu Arg Ile Leu Pro Asp Gly Thr Val
            20                  25                  30

Asp Gly Thr Arg Asp Arg Ser Asp Gln His Ile Gln Leu Gln Leu Ser
            35                  40                  45

Ala Glu Ser Val Gly Glu Val Tyr Ile Lys Ser Thr Glu Thr Gly Gln
50                  55                  60

Tyr Leu Cys Met Asp Thr Asp Gly Leu Leu Tyr Gly Ser Gln Thr Pro
65                  70                  75                  80

Asn Glu Glu Cys Leu Phe Leu Glu Arg Leu Glu Glu Asn His Tyr Asn
                85                  90                  95

Thr Tyr Ile Ser Lys Lys His Ala Glu Lys Asn Trp Phe Val Gly Leu
            100                 105                 110

Lys Lys Asn Gly Ser Val Lys Arg Gly Pro Arg Thr His Tyr Gly Gln
            115                 120                 125

Lys Ala Ile Leu Phe Leu Pro Leu Pro Val Ser Ser Asp
    130                 135                 140
```

<210> SEQ ID NO 110
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

```
Glu Lys Leu Pro Pro Gly Asn Tyr Lys Lys Pro Lys Leu Leu Tyr Ser
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
            35                  40                  45

Glu Ser Val Gly Glu Val Tyr Ile Lys Ser Thr Glu Thr Gly Gln Tyr
50                  55                  60

Leu Cys Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
            100                 105                 110

Lys Asn Gly Ser Val Lys Arg Gly Pro Arg Thr His Tyr Gly Gln Lys
            115                 120                 125

Ala Ile Leu Phe Leu Pro Leu Pro Val Ser Ser Asp
    130                 135                 140
```

<210> SEQ ID NO 111
<211> LENGTH: 139
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

```
Glu Lys Pro Pro Gly Asn Tyr Lys Lys Pro Lys Leu Leu Tyr Ser Ser
1               5                   10                  15
```

```
Asn Gly Gly His Phe Leu Arg Ile Leu Pro Asp Gly Thr Val Asp Gly
            20                  25                  30

Thr Arg Asp Arg Ser Asp Gln His Ile Gln Leu Gln Leu Ser Ala Glu
                35                  40                  45

Ser Val Gly Glu Val Tyr Ile Lys Ser Thr Glu Thr Gly Gln Tyr Leu
 50                  55                  60

Cys Met Asp Thr Asp Gly Leu Leu Tyr Gly Ser Gln Thr Pro Asn Glu
 65                  70                  75                  80

Glu Cys Leu Phe Leu Glu Arg Leu Glu Glu Asn His Tyr Asn Thr Tyr
                85                  90                  95

Ile Ser Lys Lys His Ala Glu Lys Asn Trp Phe Val Gly Leu Lys Lys
                100                 105                 110

Asn Gly Ser Val Lys Arg Gly Pro Arg Thr His Tyr Gly Gln Lys Ala
            115                 120                 125

Ile Leu Phe Leu Pro Leu Pro Val Ser Ser Asp
            130                 135
```

<210> SEQ ID NO 112
<211> LENGTH: 138
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

```
Glu Lys Pro Gly Asn Tyr Lys Lys Pro Lys Leu Leu Tyr Ser Ser Asn
 1               5                  10                  15

Gly Gly His Phe Leu Arg Ile Leu Pro Asp Gly Thr Val Asp Gly Thr
            20                  25                  30

Arg Asp Arg Ser Asp Gln His Ile Gln Leu Gln Leu Ser Ala Glu Ser
        35                  40                  45

Val Gly Glu Val Tyr Ile Lys Ser Thr Glu Thr Gly Gln Tyr Leu Cys
 50                  55                  60

Met Asp Thr Asp Gly Leu Leu Tyr Gly Ser Gln Thr Pro Asn Glu Glu
65                  70                  75                  80

Cys Leu Phe Leu Glu Arg Leu Glu Glu Asn His Tyr Asn Thr Tyr Ile
                85                  90                  95

Ser Lys Lys His Ala Glu Lys Asn Trp Phe Val Gly Leu Lys Lys Asn
                100                 105                 110

Gly Ser Val Lys Arg Gly Pro Arg Thr His Tyr Gly Gln Lys Ala Ile
            115                 120                 125

Leu Phe Leu Pro Leu Pro Val Ser Ser Asp
            130                 135
```

<210> SEQ ID NO 113
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

```
Lys Phe Asn Leu Pro Pro Gly Asn Tyr Lys Lys Pro Lys Leu Leu Tyr
 1               5                  10                  15

Ser Ser Asn Gly Gly His Phe Leu Arg Ile Leu Pro Asp Gly Thr Val
            20                  25                  30
```

```
Asp Gly Thr Arg Asp Arg Ser Asp Gln His Ile Gln Leu Gln Leu Ser
            35                  40                  45

Ala Glu Ser Val Gly Glu Val Tyr Ile Lys Ser Thr Glu Thr Gly Gln
 50                  55                  60

Tyr Leu Cys Met Asp Thr Asp Gly Leu Leu Tyr Gly Ser Gln Thr Pro
 65                  70                  75                  80

Asn Glu Glu Cys Leu Phe Leu Glu Arg Leu Glu Glu Asn His Tyr Asn
                 85                  90                  95

Thr Tyr Ile Ser Lys Lys His Ala Glu Lys Asn Trp Phe Val Gly Leu
            100                 105                 110

Lys Lys Asn Gly Ser Val Lys Arg Gly Pro Arg Thr His Tyr Gly Gln
            115                 120                 125

Lys Ala Ile Leu Phe Leu Pro Leu Pro Val Ser Ser Asp
            130                 135                 140

<210> SEQ ID NO 114
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Lys Asn Leu Pro Pro Gly Asn Tyr Lys Lys Pro Lys Leu Leu Tyr Ser
 1               5                  10                  15

Ser Asn Gly Gly His Phe Leu Arg Ile Leu Pro Asp Gly Thr Val Asp
             20                  25                  30

Gly Thr Arg Asp Arg Ser Asp Gln His Ile Gln Leu Gln Leu Ser Ala
            35                  40                  45

Glu Ser Val Gly Glu Val Tyr Ile Lys Ser Thr Glu Thr Gly Gln Tyr
 50                  55                  60

Leu Cys Met Asp Thr Asp Gly Leu Leu Tyr Gly Ser Gln Thr Pro Asn
 65                  70                  75                  80

Glu Glu Cys Leu Phe Leu Glu Arg Leu Glu Glu Asn His Tyr Asn Thr
                 85                  90                  95

Tyr Ile Ser Lys Lys His Ala Glu Lys Asn Trp Phe Val Gly Leu Lys
            100                 105                 110

Lys Asn Gly Ser Val Lys Arg Gly Pro Arg Thr His Tyr Gly Gln Lys
            115                 120                 125

Ala Ile Leu Phe Leu Pro Leu Pro Val Ser Ser Asp
            130                 135                 140

<210> SEQ ID NO 115
<211> LENGTH: 139
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Lys Leu Pro Pro Gly Asn Tyr Lys Lys Pro Lys Leu Leu Tyr Ser Ser
 1               5                  10                  15

Asn Gly Gly His Phe Leu Arg Ile Leu Pro Asp Gly Thr Val Asp Gly
             20                  25                  30

Thr Arg Asp Arg Ser Asp Gln His Ile Gln Leu Gln Leu Ser Ala Glu
            35                  40                  45
```

```
Ser Val Gly Glu Val Tyr Ile Lys Ser Thr Glu Thr Gly Gln Tyr Leu
 50                  55                  60

Cys Met Asp Thr Asp Gly Leu Leu Tyr Gly Ser Gln Thr Pro Asn Glu
 65                  70                  75                  80

Glu Cys Leu Phe Leu Glu Arg Leu Glu Glu Asn His Tyr Asn Thr Tyr
                     85                  90                  95

Ile Ser Lys Lys His Ala Glu Lys Asn Trp Phe Val Gly Leu Lys Lys
                100                 105                 110

Asn Gly Ser Val Lys Arg Gly Pro Arg Thr His Tyr Gly Gln Lys Ala
            115                 120                 125

Ile Leu Phe Leu Pro Leu Pro Val Ser Ser Asp
        130                 135
```

<210> SEQ ID NO 116
<211> LENGTH: 138
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

```
Lys Pro Pro Gly Asn Tyr Lys Lys Pro Lys Leu Leu Tyr Ser Ser Asn
 1                   5                  10                  15

Gly Gly His Phe Leu Arg Ile Leu Pro Asp Gly Thr Val Asp Gly Thr
                 20                  25                  30

Arg Asp Arg Ser Asp Gln His Ile Gln Leu Gln Leu Ser Ala Glu Ser
             35                  40                  45

Val Gly Glu Val Tyr Ile Lys Ser Thr Glu Thr Gly Gln Tyr Leu Cys
 50                  55                  60

Met Asp Thr Asp Gly Leu Leu Tyr Gly Ser Gln Thr Pro Asn Glu Glu
 65                  70                  75                  80

Cys Leu Phe Leu Glu Arg Leu Glu Glu Asn His Tyr Asn Thr Tyr Ile
                 85                  90                  95

Ser Lys Lys His Ala Glu Lys Asn Trp Phe Val Gly Leu Lys Lys Asn
            100                 105                 110

Gly Ser Val Lys Arg Gly Pro Arg Thr His Tyr Gly Gln Lys Ala Ile
        115                 120                 125

Leu Phe Leu Pro Leu Pro Val Ser Ser Asp
    130                 135
```

<210> SEQ ID NO 117
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

```
Lys Pro Gly Asn Tyr Lys Lys Pro Lys Leu Leu Tyr Ser Ser Asn Gly
 1                   5                  10                  15

Gly His Phe Leu Arg Ile Leu Pro Asp Gly Thr Val Asp Gly Thr Arg
                 20                  25                  30

Asp Arg Ser Asp Gln His Ile Gln Leu Gln Leu Ser Ala Glu Ser Val
             35                  40                  45

Gly Glu Val Tyr Ile Lys Ser Thr Glu Thr Gly Gln Tyr Leu Cys Met
 50                  55                  60
```

```
Asp Thr Asp Gly Leu Leu Tyr Gly Ser Gln Thr Pro Asn Glu Glu Cys
 65                  70                  75                  80

Leu Phe Leu Glu Arg Leu Glu Glu Asn His Tyr Asn Thr Tyr Ile Ser
                 85                  90                  95

Lys Lys His Ala Glu Lys Asn Trp Phe Val Gly Leu Lys Lys Asn Gly
            100                 105                 110

Ser Val Lys Arg Gly Pro Arg Thr His Tyr Gly Gln Lys Ala Ile Leu
        115                 120                 125

Phe Leu Pro Leu Pro Val Ser Ser Asp
        130                 135
```

<210> SEQ ID NO 118
<211> LENGTH: 146
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

```
Met Ala Leu Thr Glu Lys Phe Asn Leu Pro Pro Gly Asn Tyr Lys Lys
 1               5                  10                  15

Pro Lys Leu Leu Tyr Ser Ser Asn Gly Gly His Phe Leu Arg Ile Leu
                20                  25                  30

Pro Asp Gly Thr Val Asp Gly Thr Arg Asp Arg Ser Asp Gln His Ile
            35                  40                  45

Gln Leu Gln Leu Ser Ala Glu Ser Val Gly Glu Val Tyr Ile Lys Ser
        50                  55                  60

Thr Glu Thr Gly Gln Tyr Leu Cys Met Asp Thr Asp Gly Leu Leu Tyr
 65                  70                  75                  80

Gly Ser Gln Thr Pro Asn Glu Glu Cys Leu Phe Leu Glu Arg Leu Glu
                 85                  90                  95

Glu Asn His Tyr Asn Thr Tyr Ile Ser Lys Lys His Ala Glu Lys Asn
            100                 105                 110

Trp Phe Val Gly Leu Lys Lys Asn Gly Ser Val Lys Arg Gly Pro Arg
        115                 120                 125

Thr His Tyr Gly Gln Lys Ala Ile Leu Phe Leu Pro Leu Pro Val Ser
130                 135                 140

Ser Asp
145
```

<210> SEQ ID NO 119
<211> LENGTH: 144
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

```
Met Ala Leu Thr Glu Lys Leu Pro Pro Gly Asn Tyr Lys Lys Pro Lys
 1               5                  10                  15

Leu Leu Tyr Ser Ser Asn Gly Gly His Phe Leu Arg Ile Leu Pro Asp
                20                  25                  30

Gly Thr Val Asp Gly Thr Arg Asp Arg Ser Asp Gln His Ile Gln Leu
            35                  40                  45

Gln Leu Ser Ala Glu Ser Val Gly Glu Val Tyr Ile Lys Ser Thr Glu
        50                  55                  60
```

```
Thr Gly Gln Tyr Leu Cys Met Asp Thr Asp Gly Leu Leu Tyr Gly Ser
 65                  70                  75                  80

Gln Thr Pro Asn Glu Glu Cys Leu Phe Leu Glu Arg Leu Glu Glu Asn
                 85                  90                  95

His Tyr Asn Thr Tyr Ile Ser Lys Lys His Ala Glu Lys Asn Trp Phe
            100                 105                 110

Val Gly Leu Lys Lys Asn Gly Ser Val Lys Arg Gly Pro Arg Thr His
        115                 120                 125

Tyr Gly Gln Lys Ala Ile Leu Phe Leu Pro Leu Pro Val Ser Ser Asp
    130                 135                 140

<210> SEQ ID NO 120
<211> LENGTH: 143
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Met Ala Leu Thr Glu Lys Pro Pro Gly Asn Tyr Lys Lys Pro Lys Leu
 1               5                  10                  15

Leu Tyr Ser Ser Asn Gly Gly His Phe Leu Arg Ile Leu Pro Asp Gly
                20                  25                  30

Thr Val Asp Gly Thr Arg Asp Arg Ser Asp Gln His Ile Gln Leu Gln
            35                  40                  45

Leu Ser Ala Glu Ser Val Gly Glu Val Tyr Ile Lys Ser Thr Glu Thr
        50                  55                  60

Gly Gln Tyr Leu Cys Met Asp Thr Asp Gly Leu Leu Tyr Gly Ser Gln
 65                  70                  75                  80

Thr Pro Asn Glu Glu Cys Leu Phe Leu Glu Arg Leu Glu Glu Asn His
                 85                  90                  95

Tyr Asn Thr Tyr Ile Ser Lys Lys His Ala Glu Lys Asn Trp Phe Val
            100                 105                 110

Gly Leu Lys Lys Asn Gly Ser Val Lys Arg Gly Pro Arg Thr His Tyr
        115                 120                 125

Gly Gln Lys Ala Ile Leu Phe Leu Pro Leu Pro Val Ser Ser Asp
    130                 135                 140

<210> SEQ ID NO 121
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Met Ala Leu Thr Glu Lys Pro Gly Asn Tyr Lys Lys Pro Lys Leu Leu
 1               5                  10                  15

Tyr Ser Ser Asn Gly Gly His Phe Leu Arg Ile Leu Pro Asp Gly Thr
                20                  25                  30

Val Asp Gly Thr Arg Asp Arg Ser Asp Gln His Ile Gln Leu Gln Leu
            35                  40                  45

Ser Ala Glu Ser Val Gly Glu Val Tyr Ile Lys Ser Thr Glu Thr Gly
        50                  55                  60

Gln Tyr Leu Cys Met Asp Thr Asp Gly Leu Leu Tyr Gly Ser Gln Thr
 65                  70                  75                  80
```

```
Pro Asn Glu Glu Cys Leu Phe Leu Glu Arg Leu Glu Asn His Tyr
            85                  90                  95

Asn Thr Tyr Ile Ser Lys Lys His Ala Glu Lys Asn Trp Phe Val Gly
            100                 105                 110

Leu Lys Lys Asn Gly Ser Val Lys Arg Gly Pro Arg Thr His Tyr Gly
        115                 120                 125

Gln Lys Ala Ile Leu Phe Leu Pro Leu Pro Val Ser Ser Asp
    130                 135                 140
```

<210> SEQ ID NO 122
<211> LENGTH: 145
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 122

```
Met Leu Thr Glu Lys Phe Asn Leu Pro Pro Gly Asn Tyr Lys Lys Pro
1               5                   10                  15

Lys Leu Leu Tyr Ser Ser Asn Gly Gly His Phe Leu Arg Ile Leu Pro
            20                  25                  30

Asp Gly Thr Val Asp Gly Thr Arg Asp Arg Ser Asp Gln His Ile Gln
        35                  40                  45

Leu Gln Leu Ser Ala Glu Ser Val Gly Glu Val Tyr Ile Lys Ser Thr
    50                  55                  60

Glu Thr Gly Gln Tyr Leu Cys Met Asp Thr Asp Gly Leu Leu Tyr Gly
65                  70                  75                  80

Ser Gln Thr Pro Asn Glu Glu Cys Leu Phe Leu Glu Arg Leu Glu Glu
                85                  90                  95

Asn His Tyr Asn Thr Tyr Ile Ser Lys Lys His Ala Glu Lys Asn Trp
            100                 105                 110

Phe Val Gly Leu Lys Lys Asn Gly Ser Val Lys Arg Gly Pro Arg Thr
        115                 120                 125

His Tyr Gly Gln Lys Ala Ile Leu Phe Leu Pro Leu Pro Val Ser Ser
    130                 135                 140

Asp
145
```

<210> SEQ ID NO 123
<211> LENGTH: 144
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 123

```
Met Leu Thr Glu Lys Asn Leu Pro Pro Gly Asn Tyr Lys Lys Pro Lys
1               5                   10                  15

Leu Leu Tyr Ser Ser Asn Gly Gly His Phe Leu Arg Ile Leu Pro Asp
            20                  25                  30

Gly Thr Val Asp Gly Thr Arg Asp Arg Ser Asp Gln His Ile Gln Leu
        35                  40                  45

Gln Leu Ser Ala Glu Ser Val Gly Glu Val Tyr Ile Lys Ser Thr Glu
    50                  55                  60

Thr Gly Gln Tyr Leu Cys Met Asp Thr Asp Gly Leu Leu Tyr Gly Ser
65                  70                  75                  80
```

```
Gln Thr Pro Asn Glu Glu Cys Leu Phe Leu Glu Arg Leu Glu Glu Asn
                85                  90                  95

His Tyr Asn Thr Tyr Ile Ser Lys Lys His Ala Glu Lys Asn Trp Phe
            100                 105                 110

Val Gly Leu Lys Lys Asn Gly Ser Val Lys Arg Gly Pro Arg Thr His
        115                 120                 125

Tyr Gly Gln Lys Ala Ile Leu Phe Leu Pro Leu Pro Val Ser Ser Asp
    130                 135                 140

<210> SEQ ID NO 124
<211> LENGTH: 143
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Met Leu Thr Glu Lys Leu Pro Pro Gly Asn Tyr Lys Lys Pro Lys Leu
1               5                   10                  15

Leu Tyr Ser Ser Asn Gly Gly His Phe Leu Arg Ile Leu Pro Asp Gly
            20                  25                  30

Thr Val Asp Gly Thr Arg Asp Arg Ser Asp Gln His Ile Gln Leu Gln
        35                  40                  45

Leu Ser Ala Glu Ser Val Gly Glu Val Tyr Ile Lys Ser Thr Glu Thr
    50                  55                  60

Gly Gln Tyr Leu Cys Met Asp Thr Asp Gly Leu Leu Tyr Gly Ser Gln
65                  70                  75                  80

Thr Pro Asn Glu Glu Cys Leu Phe Leu Glu Arg Leu Glu Glu Asn His
                85                  90                  95

Tyr Asn Thr Tyr Ile Ser Lys Lys His Ala Glu Lys Asn Trp Phe Val
            100                 105                 110

Gly Leu Lys Lys Asn Gly Ser Val Lys Arg Gly Pro Arg Thr His Tyr
        115                 120                 125

Gly Gln Lys Ala Ile Leu Phe Leu Pro Leu Pro Val Ser Ser Asp
    130                 135                 140

<210> SEQ ID NO 125
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Met Leu Thr Glu Lys Pro Pro Gly Asn Tyr Lys Lys Pro Lys Leu Leu
1               5                   10                  15

Tyr Ser Ser Asn Gly Gly His Phe Leu Arg Ile Leu Pro Asp Gly Thr
            20                  25                  30

Val Asp Gly Thr Arg Asp Arg Ser Asp Gln His Ile Gln Leu Gln Leu
        35                  40                  45

Ser Ala Glu Ser Val Gly Glu Val Tyr Ile Lys Ser Thr Glu Thr Gly
    50                  55                  60

Gln Tyr Leu Cys Met Asp Thr Asp Gly Leu Leu Tyr Gly Ser Gln Thr
65                  70                  75                  80

Pro Asn Glu Glu Cys Leu Phe Leu Glu Arg Leu Glu Glu Asn His Tyr
                85                  90                  95
```

```
Asn Thr Tyr Ile Ser Lys Lys His Ala Glu Lys Asn Trp Phe Val Gly
                100                 105                 110

Leu Lys Lys Asn Gly Ser Val Lys Arg Gly Pro Arg Thr His Tyr Gly
        115                 120                 125

Gln Lys Ala Ile Leu Phe Leu Pro Leu Pro Val Ser Ser Asp
    130                 135                 140

<210> SEQ ID NO 126
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Met Leu Thr Glu Lys Pro Gly Asn Tyr Lys Pro Lys Leu Leu Tyr
1               5                   10                  15

Ser Ser Asn Gly Gly His Phe Leu Arg Ile Leu Pro Asp Gly Thr Val
            20                  25                  30

Asp Gly Thr Arg Asp Arg Ser Asp Gln His Ile Gln Leu Gln Leu Ser
        35                  40                  45

Ala Glu Ser Val Gly Glu Val Tyr Ile Lys Ser Thr Glu Thr Gly Gln
    50                  55                  60

Tyr Leu Cys Met Asp Thr Asp Gly Leu Leu Tyr Gly Ser Gln Thr Pro
65                  70                  75                  80

Asn Glu Glu Cys Leu Phe Leu Glu Arg Leu Glu Glu Asn His Tyr Asn
                85                  90                  95

Thr Tyr Ile Ser Lys Lys His Ala Glu Lys Asn Trp Phe Val Gly Leu
                100                 105                 110

Lys Lys Asn Gly Ser Val Lys Arg Gly Pro Arg Thr His Tyr Gly Gln
        115                 120                 125

Lys Ala Ile Leu Phe Leu Pro Leu Pro Val Ser Ser Asp
    130                 135                 140

<210> SEQ ID NO 127
<211> LENGTH: 144
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Met Thr Glu Lys Phe Asn Leu Pro Pro Gly Asn Tyr Lys Lys Pro Lys
1               5                   10                  15

Leu Leu Tyr Ser Ser Asn Gly Gly His Phe Leu Arg Ile Leu Pro Asp
            20                  25                  30

Gly Thr Val Asp Gly Thr Arg Asp Arg Ser Asp Gln His Ile Gln Leu
        35                  40                  45

Gln Leu Ser Ala Glu Ser Val Gly Glu Val Tyr Ile Lys Ser Thr Glu
    50                  55                  60

Thr Gly Gln Tyr Leu Cys Met Asp Thr Asp Gly Leu Leu Tyr Gly Ser
65                  70                  75                  80

Gln Thr Pro Asn Glu Glu Cys Leu Phe Leu Glu Arg Leu Glu Glu Asn
                85                  90                  95

His Tyr Asn Thr Tyr Ile Ser Lys Lys His Ala Glu Lys Asn Trp Phe
                100                 105                 110
```

Val Gly Leu Lys Lys Asn Gly Ser Val Lys Arg Gly Pro Arg Thr His
            115                 120                 125

Tyr Gly Gln Lys Ala Ile Leu Phe Leu Pro Leu Pro Val Ser Ser Asp
        130                 135                 140

<210> SEQ ID NO 128
<211> LENGTH: 143
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Met Thr Glu Lys Asn Leu Pro Pro Gly Asn Tyr Lys Pro Lys Leu
1               5                   10                  15

Leu Tyr Ser Ser Asn Gly Gly His Phe Leu Arg Ile Leu Pro Asp Gly
                20                  25                  30

Thr Val Asp Gly Thr Arg Asp Arg Ser Asp Gln His Ile Gln Leu Gln
            35                  40                  45

Leu Ser Ala Glu Ser Val Gly Glu Val Tyr Ile Lys Ser Thr Glu Thr
    50                  55                  60

Gly Gln Tyr Leu Cys Met Asp Thr Asp Gly Leu Leu Tyr Gly Ser Gln
65                  70                  75                  80

Thr Pro Asn Glu Glu Cys Leu Phe Leu Glu Arg Leu Glu Glu Asn His
                85                  90                  95

Tyr Asn Thr Tyr Ile Ser Lys Lys His Ala Glu Lys Asn Trp Phe Val
            100                 105                 110

Gly Leu Lys Lys Asn Gly Ser Val Lys Arg Gly Pro Arg Thr His Tyr
        115                 120                 125

Gly Gln Lys Ala Ile Leu Phe Leu Pro Leu Pro Val Ser Ser Asp
    130                 135                 140

<210> SEQ ID NO 129
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Met Thr Glu Lys Leu Pro Pro Gly Asn Tyr Lys Lys Pro Lys Leu Leu
1               5                   10                  15

Tyr Ser Ser Asn Gly Gly His Phe Leu Arg Ile Leu Pro Asp Gly Thr
                20                  25                  30

Val Asp Gly Thr Arg Asp Arg Ser Asp Gln His Ile Gln Leu Gln Leu
            35                  40                  45

Ser Ala Glu Ser Val Gly Glu Val Tyr Ile Lys Ser Thr Glu Thr Gly
    50                  55                  60

Gln Tyr Leu Cys Met Asp Thr Asp Gly Leu Leu Tyr Gly Ser Gln Thr
65                  70                  75                  80

Pro Asn Glu Glu Cys Leu Phe Leu Glu Arg Leu Glu Glu Asn His Tyr
                85                  90                  95

Asn Thr Tyr Ile Ser Lys Lys His Ala Glu Lys Asn Trp Phe Val Gly
            100                 105                 110

Leu Lys Lys Asn Gly Ser Val Lys Arg Gly Pro Arg Thr His Tyr Gly
        115                 120                 125

```
Gln Lys Ala Ile Leu Phe Leu Pro Leu Pro Val Ser Ser Asp
    130                 135                 140
```

<210> SEQ ID NO 130
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

```
Met Thr Glu Lys Pro Gly Asn Tyr Lys Lys Pro Lys Leu Leu Tyr
1               5                   10                  15

Ser Ser Asn Gly Gly His Phe Leu Arg Ile Leu Pro Asp Gly Thr Val
                20                  25                  30

Asp Gly Thr Arg Asp Arg Ser Asp Gln His Ile Gln Leu Gln Leu Ser
            35                  40                  45

Ala Glu Ser Val Gly Glu Val Tyr Ile Lys Ser Thr Glu Thr Gly Gln
        50                  55                  60

Tyr Leu Cys Met Asp Thr Asp Gly Leu Leu Tyr Gly Ser Gln Thr Pro
65                  70                  75                  80

Asn Glu Glu Cys Leu Phe Leu Glu Arg Leu Glu Glu Asn His Tyr Asn
                85                  90                  95

Thr Tyr Ile Ser Lys Lys His Ala Glu Lys Asn Trp Phe Val Gly Leu
            100                 105                 110

Lys Lys Asn Gly Ser Val Lys Arg Gly Pro Arg Thr His Tyr Gly Gln
        115                 120                 125

Lys Ala Ile Leu Phe Leu Pro Leu Pro Val Ser Ser Asp
    130                 135                 140
```

<210> SEQ ID NO 131
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

```
Met Thr Glu Lys Pro Gly Asn Tyr Lys Lys Pro Lys Leu Leu Tyr Ser
1               5                   10                  15

Ser Asn Gly Gly His Phe Leu Arg Ile Leu Pro Asp Gly Thr Val Asp
                20                  25                  30

Gly Thr Arg Asp Arg Ser Asp Gln His Ile Gln Leu Gln Leu Ser Ala
            35                  40                  45

Glu Ser Val Gly Glu Val Tyr Ile Lys Ser Thr Glu Thr Gly Gln Tyr
        50                  55                  60

Leu Cys Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
            100                 105                 110

Lys Asn Gly Ser Val Lys Arg Gly Pro Arg Thr His Tyr Gly Gln Lys
        115                 120                 125

Ala Ile Leu Phe Leu Pro Leu Pro Val Ser Ser Asp
    130                 135                 140
```

<210> SEQ ID NO 132
<211> LENGTH: 143
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 132

```
Met Glu Lys Phe Asn Leu Pro Pro Gly Asn Tyr Lys Lys Pro Lys Leu
1               5                   10                  15

Leu Tyr Ser Ser Asn Gly Gly His Phe Leu Arg Ile Leu Pro Asp Gly
            20                  25                  30

Thr Val Asp Gly Thr Arg Asp Arg Ser Asp Gln His Ile Gln Leu Gln
        35                  40                  45

Leu Ser Ala Glu Ser Val Gly Glu Val Tyr Ile Lys Ser Thr Glu Thr
    50                  55                  60

Gly Gln Tyr Leu Cys Met Asp Thr Asp Gly Leu Leu Tyr Gly Ser Gln
65                  70                  75                  80

Thr Pro Asn Glu Glu Cys Leu Phe Leu Glu Arg Leu Glu Glu Asn His
                85                  90                  95

Tyr Asn Thr Tyr Ile Ser Lys Lys His Ala Glu Lys Asn Trp Phe Val
            100                 105                 110

Gly Leu Lys Lys Asn Gly Ser Val Lys Arg Gly Pro Arg Thr His Tyr
        115                 120                 125

Gly Gln Lys Ala Ile Leu Phe Leu Pro Leu Pro Val Ser Ser Asp
    130                 135                 140
```

<210> SEQ ID NO 133
<211> LENGTH: 142
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 133

```
Met Glu Lys Asn Leu Pro Pro Gly Asn Tyr Lys Lys Pro Lys Leu Leu
1               5                   10                  15

Tyr Ser Ser Asn Gly Gly His Phe Leu Arg Ile Leu Pro Asp Gly Thr
            20                  25                  30

Val Asp Gly Thr Arg Asp Arg Ser Asp Gln His Ile Gln Leu Gln Leu
        35                  40                  45

Ser Ala Glu Ser Val Gly Glu Val Tyr Ile Lys Ser Thr Glu Thr Gly
    50                  55                  60

Gln Tyr Leu Cys Met Asp Thr Asp Gly Leu Leu Tyr Gly Ser Gln Thr
65                  70                  75                  80

Pro Asn Glu Glu Cys Leu Phe Leu Glu Arg Leu Glu Glu Asn His Tyr
                85                  90                  95

Asn Thr Tyr Ile Ser Lys Lys His Ala Glu Lys Asn Trp Phe Val Gly
            100                 105                 110

Leu Lys Lys Asn Gly Ser Val Lys Arg Gly Pro Arg Thr His Tyr Gly
        115                 120                 125

Gln Lys Ala Ile Leu Phe Leu Pro Leu Pro Val Ser Ser Asp
    130                 135                 140
```

<210> SEQ ID NO 134
<211> LENGTH: 141

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Met Glu Lys Leu Pro Pro Gly Asn Tyr Lys Lys Pro Lys Leu Leu Tyr
1               5                   10                  15

Ser Ser Asn Gly Gly His Phe Leu Arg Ile Leu Pro Asp Gly Thr Val
            20                  25                  30

Asp Gly Thr Arg Asp Arg Ser Asp Gln His Ile Gln Leu Gln Leu Ser
        35                  40                  45

Ala Glu Ser Val Gly Glu Val Tyr Ile Lys Ser Thr Glu Thr Gly Gln
    50                  55                  60

Tyr Leu Cys Met Asp Thr Asp Gly Leu Leu Tyr Gly Ser Gln Thr Pro
65                  70                  75                  80

Asn Glu Glu Cys Leu Phe Leu Glu Arg Leu Glu Glu Asn His Tyr Asn
                85                  90                  95

Thr Tyr Ile Ser Lys Lys His Ala Glu Lys Asn Trp Phe Val Gly Leu
            100                 105                 110

Lys Lys Asn Gly Ser Val Lys Arg Gly Pro Arg Thr His Tyr Gly Gln
        115                 120                 125

Lys Ala Ile Leu Phe Leu Pro Leu Pro Val Ser Ser Asp
    130                 135                 140

<210> SEQ ID NO 135
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Met Glu Lys Pro Pro Gly Asn Tyr Lys Lys Pro Lys Leu Leu Tyr Ser
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
    50                  55                  60

Leu Cys Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
            100                 105                 110

Lys Asn Gly Ser Val Lys Arg Gly Pro Arg Thr His Tyr Gly Gln Lys
        115                 120                 125

Ala Ile Leu Phe Leu Pro Leu Pro Val Ser Ser Asp
    130                 135                 140

<210> SEQ ID NO 136
<211> LENGTH: 139
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 136

Met Glu Lys Pro Gly Asn Tyr Lys Lys Pro Lys Leu Leu Tyr Ser Ser
1               5                   10                  15

Asn Gly Gly His Phe Leu Arg Ile Leu Pro Asp Gly Thr Val Asp Gly
            20                  25                  30

Thr Arg Asp Arg Ser Asp Gln His Ile Gln Leu Gln Leu Ser Ala Glu
        35                  40                  45

Ser Val Gly Glu Val Tyr Ile Lys Ser Thr Glu Thr Gly Gln Tyr Leu
    50                  55                  60

Cys Met Asp Thr Asp Gly Leu Leu Tyr Gly Ser Gln Thr Pro Asn Glu
65                  70                  75                  80

Glu Cys Leu Phe Leu Glu Arg Leu Glu Glu Asn His Tyr Asn Thr Tyr
                85                  90                  95

Ile Ser Lys Lys His Ala Glu Lys Asn Trp Phe Val Gly Leu Lys Lys
            100                 105                 110

Asn Gly Ser Val Lys Arg Gly Pro Arg Thr His Tyr Gly Gln Lys Ala
        115                 120                 125

Ile Leu Phe Leu Pro Leu Pro Val Ser Ser Asp
    130                 135

<210> SEQ ID NO 137
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Met Lys Phe Asn Leu Pro Pro Gly Asn Tyr Lys Lys Pro Lys Leu Leu
1               5                   10                  15

Tyr Ser Ser Asn Gly Gly His Phe Leu Arg Ile Leu Pro Asp Gly Thr
            20                  25                  30

Val Asp Gly Thr Arg Asp Arg Ser Asp Gln His Ile Gln Leu Gln Leu
        35                  40                  45

Ser Ala Glu Ser Val Gly Glu Val Tyr Ile Lys Ser Thr Glu Thr Gly
    50                  55                  60

Gln Tyr Leu Cys Met Asp Thr Asp Gly Leu Leu Tyr Gly Ser Gln Thr
65                  70                  75                  80

Pro Asn Glu Glu Cys Leu Phe Leu Glu Arg Leu Glu Glu Asn His Tyr
                85                  90                  95

Asn Thr Tyr Ile Ser Lys Lys His Ala Glu Lys Asn Trp Phe Val Gly
            100                 105                 110

Leu Lys Lys Asn Gly Ser Val Lys Arg Gly Pro Arg Thr His Tyr Gly
        115                 120                 125

Gln Lys Ala Ile Leu Phe Leu Pro Leu Pro Val Ser Ser Asp
    130                 135                 140

<210> SEQ ID NO 138
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Met Lys Asn Leu Pro Pro Gly Asn Tyr Lys Pro Lys Leu Leu Tyr
1               5                   10                  15

Ser Ser Asn Gly Gly His Phe Leu Arg Ile Leu Pro Asp Gly Thr Val
            20                  25                  30

Asp Gly Thr Arg Asp Arg Ser Asp Gln His Ile Gln Leu Gln Leu Ser
        35                  40                  45

Ala Glu Ser Val Gly Glu Val Tyr Ile Lys Ser Thr Glu Thr Gly Gln
50                  55                  60

Tyr Leu Cys Met Asp Thr Asp Gly Leu Leu Tyr Gly Ser Gln Thr Pro
65                  70                  75                  80

Asn Glu Glu Cys Leu Phe Leu Glu Arg Leu Glu Glu Asn His Tyr Asn
                85                  90                  95

Thr Tyr Ile Ser Lys Lys His Ala Glu Lys Asn Trp Phe Val Gly Leu
            100                 105                 110

Lys Lys Asn Gly Ser Val Lys Arg Gly Pro Arg Thr His Tyr Gly Gln
            115                 120                 125

Lys Ala Ile Leu Phe Leu Pro Leu Pro Val Ser Ser Asp
130                 135                 140

<210> SEQ ID NO 139
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Met Lys Leu Pro Pro Gly Asn Tyr Lys Lys Pro Lys Leu Leu Tyr Ser
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
50                  55                  60

Leu Cys Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
            100                 105                 110

Lys Asn Gly Ser Val Lys Arg Gly Pro Arg Thr His Tyr Gly Gln Lys
            115                 120                 125

Ala Ile Leu Phe Leu Pro Leu Pro Val Ser Ser Asp
130                 135                 140

<210> SEQ ID NO 140
<211> LENGTH: 139
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Met Lys Pro Pro Gly Asn Tyr Lys Lys Pro Lys Leu Leu Tyr Ser Ser

```
                1               5                   10                  15
Asn Gly Gly His Phe Leu Arg Ile Leu Pro Asp Gly Thr Val Asp Gly
                    20                  25                  30

Thr Arg Asp Arg Ser Asp Gln His Ile Gln Leu Gln Leu Ser Ala Glu
                    35                  40                  45

Ser Val Gly Glu Val Tyr Ile Lys Ser Thr Glu Thr Gly Gln Tyr Leu
        50                  55                  60

Cys Met Asp Thr Asp Gly Leu Leu Tyr Gly Ser Gln Thr Pro Asn Glu
65                  70                  75                  80

Glu Cys Leu Phe Leu Glu Arg Leu Glu Glu Asn His Tyr Asn Thr Tyr
                    85                  90                  95

Ile Ser Lys Lys His Ala Glu Lys Asn Trp Phe Val Gly Leu Lys Lys
                    100                 105                 110

Asn Gly Ser Val Lys Arg Gly Pro Arg Thr His Tyr Gly Gln Lys Ala
                    115                 120                 125

Ile Leu Phe Leu Pro Leu Pro Val Ser Ser Asp
                    130                 135
```

<210> SEQ ID NO 141
<211> LENGTH: 138
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 141

```
Met Lys Pro Gly Asn Tyr Lys Lys Pro Lys Leu Leu Tyr Ser Ser Asn
1               5                   10                  15

Gly Gly His Phe Leu Arg Ile Leu Pro Asp Gly Thr Val Asp Gly Thr
                    20                  25                  30

Arg Asp Arg Ser Asp Gln His Ile Gln Leu Gln Leu Ser Ala Glu Ser
                    35                  40                  45

Val Gly Glu Val Tyr Ile Lys Ser Thr Glu Thr Gly Gln Tyr Leu Cys
        50                  55                  60

Met Asp Thr Asp Gly Leu Leu Tyr Gly Ser Gln Thr Pro Asn Glu Glu
65                  70                  75                  80

Cys Leu Phe Leu Glu Arg Leu Glu Glu Asn His Tyr Asn Thr Tyr Ile
                    85                  90                  95

Ser Lys Lys His Ala Glu Lys Asn Trp Phe Val Gly Leu Lys Lys Asn
                    100                 105                 110

Gly Ser Val Lys Arg Gly Pro Arg Thr His Tyr Gly Gln Lys Ala Ile
                    115                 120                 125

Leu Phe Leu Pro Leu Pro Val Ser Ser Asp
                    130                 135
```

<210> SEQ ID NO 142
<211> LENGTH: 140
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<221> NAME/KEY: MOD_RES
<222> LOCATION: (67)..(67)
<223> OTHER INFORMATION: Any amino acid

<400> SEQUENCE: 142

```
Phe Asn Leu Pro Pro Gly Asn Tyr Lys Lys Pro Lys Leu Leu Tyr Cys
 1               5                  10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
 50                  55                  60

Leu Ala Xaa Asp Thr Asp Gly Leu Leu Tyr Gly Ser Gln Thr Pro Asn
 65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
                100                 105                 110

Lys Asn Gly Ser Cys Lys Arg Gly Pro Arg Thr His Tyr Gly Gln Lys
            115                 120                 125

Ala Ile Leu Phe Leu Pro Leu Pro Val Ser Ser Asp
            130                 135                 140

<210> SEQ ID NO 143
<211> LENGTH: 139
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (66)..(66)
<223> OTHER INFORMATION: Any amino acid

<400> SEQUENCE: 143

Asn Leu Pro Pro Gly Asn Tyr Lys Lys Pro Lys Leu Leu Tyr Cys Ser
 1               5                  10                  15

Asn Gly Gly His Phe Leu Arg Ile Leu Pro Asp Gly Thr Val Asp Gly
            20                  25                  30

Thr Arg Asp Arg Ser Asp Gln His Ile Gln Leu Gln Leu Ser Ala Glu
        35                  40                  45

Ser Val Gly Glu Val Tyr Ile Lys Ser Thr Glu Thr Gly Gln Tyr Leu
 50                  55                  60

Ala Xaa Asp Thr Asp Gly Leu Leu Tyr Gly Ser Gln Thr Pro Asn Glu
 65                  70                  75                  80

Glu Cys Leu Phe Leu Glu Arg Leu Glu Glu Asn His Tyr Asn Thr Tyr
                85                  90                  95

Ile Ser Lys Lys His Ala Glu Lys Asn Trp Phe Val Gly Leu Lys Lys
                100                 105                 110

Asn Gly Ser Cys Lys Arg Gly Pro Arg Thr His Tyr Gly Gln Lys Ala
            115                 120                 125

Ile Leu Phe Leu Pro Leu Pro Val Ser Ser Asp
            130                 135

<210> SEQ ID NO 144
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
```

<222> LOCATION: (64)..(64)
<223> OTHER INFORMATION: Any amino acid

<400> SEQUENCE: 144

```
Pro Pro Gly Asn Tyr Lys Lys Pro Lys Leu Leu Tyr Cys Ser Asn Gly
1               5                   10                  15
Gly His Phe Leu Arg Ile Leu Pro Asp Gly Thr Val Asp Gly Thr Arg
            20                  25                  30
Asp Arg Ser Asp Gln His Ile Gln Leu Gln Leu Ser Ala Glu Ser Val
        35                  40                  45
Gly Glu Val Tyr Ile Lys Ser Thr Glu Thr Gly Gln Tyr Leu Ala Xaa
50                  55                  60
Asp Thr Asp Gly Leu Leu Tyr Gly Ser Gln Thr Pro Asn Glu Glu Cys
65                  70                  75                  80
Leu Phe Leu Glu Arg Leu Glu Glu Asn His Tyr Asn Thr Tyr Ile Ser
                85                  90                  95
Lys Lys His Ala Glu Lys Asn Trp Phe Val Gly Leu Lys Lys Asn Gly
            100                 105                 110
Ser Cys Lys Arg Gly Pro Arg Thr His Tyr Gly Gln Lys Ala Ile Leu
        115                 120                 125
Phe Leu Pro Leu Pro Val Ser Ser Asp
    130                 135
```

<210> SEQ ID NO 145
<211> LENGTH: 136
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (63)..(63)
<223> OTHER INFORMATION: Any amino acid

<400> SEQUENCE: 145

```
Pro Gly Asn Tyr Lys Lys Pro Lys Leu Leu Tyr Cys Ser Asn Gly Gly
1               5                   10                  15
His Phe Leu Arg Ile Leu Pro Asp Gly Thr Val Asp Gly Thr Arg Asp
            20                  25                  30
Arg Ser Asp Gln His Ile Gln Leu Gln Leu Ser Ala Glu Ser Val Gly
        35                  40                  45
Glu Val Tyr Ile Lys Ser Thr Glu Thr Gly Gln Tyr Leu Ala Xaa Asp
50                  55                  60
Thr Asp Gly Leu Leu Tyr Gly Ser Gln Thr Pro Asn Glu Glu Cys Leu
65                  70                  75                  80
Phe Leu Glu Arg Leu Glu Glu Asn His Tyr Asn Thr Tyr Ile Ser Lys
                85                  90                  95
Lys His Ala Glu Lys Asn Trp Phe Val Gly Leu Lys Lys Asn Gly Ser
            100                 105                 110
Cys Lys Arg Gly Pro Arg Thr His Tyr Gly Gln Lys Ala Ile Leu Phe
        115                 120                 125
Leu Pro Leu Pro Val Ser Ser Asp
    130                 135
```

<210> SEQ ID NO 146
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (67)..(67)
<223> OTHER INFORMATION: Any amino acid

<400> SEQUENCE: 146

Phe Asn Leu Pro Pro Gly Asn Tyr Lys Lys Pro Lys Leu Leu Tyr Ser
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
    50                  55                  60

Leu Cys Xaa Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
            100                 105                 110

Lys Asn Gly Ser Val Lys Arg Gly Pro Arg Thr His Tyr Gly Gln Lys
        115                 120                 125

Ala Ile Leu Phe Leu Pro Leu Pro Val Ser Ser Asp
    130                 135                 140

<210> SEQ ID NO 147
<211> LENGTH: 139
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (66)..(66)
<223> OTHER INFORMATION: Any amino acid

<400> SEQUENCE: 147

Asn Leu Pro Pro Gly Asn Tyr Lys Lys Pro Lys Leu Leu Tyr Ser Ser
1               5                   10                  15

Asn Gly Gly His Phe Leu Arg Ile Leu Pro Asp Gly Thr Val Asp Gly
            20                  25                  30

Thr Arg Asp Arg Ser Asp Gln His Ile Gln Leu Gln Leu Ser Ala Glu
        35                  40                  45

Ser Val Gly Glu Val Tyr Ile Lys Ser Thr Glu Thr Gly Gln Tyr Leu
    50                  55                  60

Cys Xaa Asp Thr Asp Gly Leu Leu Tyr Gly Ser Gln Thr Pro Asn Glu
65                  70                  75                  80

Glu Cys Leu Phe Leu Glu Arg Leu Glu Glu Asn His Tyr Asn Thr Tyr
                85                  90                  95

Ile Ser Lys Lys His Ala Glu Lys Asn Trp Phe Val Gly Leu Lys Lys
            100                 105                 110

Asn Gly Ser Val Lys Arg Gly Pro Arg Thr His Tyr Gly Gln Lys Ala
        115                 120                 125

Ile Leu Phe Leu Pro Leu Pro Val Ser Ser Asp
    130                 135

```
<210> SEQ ID NO 148
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (64)..(64)
<223> OTHER INFORMATION: Any amino acid

<400> SEQUENCE: 148

Pro Pro Gly Asn Tyr Lys Lys Pro Lys Leu Leu Tyr Ser Ser Asn Gly
1               5                   10                  15

Gly His Phe Leu Arg Ile Leu Pro Asp Gly Thr Val Asp Gly Thr Arg
            20                  25                  30

Asp Arg Ser Asp Gln His Ile Gln Leu Gln Leu Ser Ala Glu Ser Val
        35                  40                  45

Gly Glu Val Tyr Ile Lys Ser Thr Glu Thr Gly Gln Tyr Leu Cys Xaa
50                  55                  60

Asp Thr Asp Gly Leu Leu Tyr Gly Ser Gln Thr Pro Asn Glu Glu Cys
65                  70                  75                  80

Leu Phe Leu Glu Arg Leu Glu Glu Asn His Tyr Asn Thr Tyr Ile Ser
                85                  90                  95

Lys Lys His Ala Glu Lys Asn Trp Phe Val Gly Leu Lys Lys Asn Gly
            100                 105                 110

Ser Val Lys Arg Gly Pro Arg Thr His Tyr Gly Gln Lys Ala Ile Leu
        115                 120                 125

Phe Leu Pro Leu Pro Val Ser Ser Asp
    130                 135

<210> SEQ ID NO 149
<211> LENGTH: 136
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (63)..(63)
<223> OTHER INFORMATION: Any amino acid

<400> SEQUENCE: 149

Pro Gly Asn Tyr Lys Lys Pro Lys Leu Leu Tyr Ser Ser Asn Gly Gly
1               5                   10                  15

His Phe Leu Arg Ile Leu Pro Asp Gly Thr Val Asp Gly Thr Arg Asp
            20                  25                  30

Arg Ser Asp Gln His Ile Gln Leu Gln Leu Ser Ala Glu Ser Val Gly
        35                  40                  45

Glu Val Tyr Ile Lys Ser Thr Glu Thr Gly Gln Tyr Leu Cys Xaa Asp
    50                  55                  60

Thr Asp Gly Leu Leu Tyr Gly Ser Gln Thr Pro Asn Glu Glu Cys Leu
65                  70                  75                  80

Phe Leu Glu Arg Leu Glu Glu Asn His Tyr Asn Thr Tyr Ile Ser Lys
                85                  90                  95

Lys His Ala Glu Lys Asn Trp Phe Val Gly Leu Lys Lys Asn Gly Ser
            100                 105                 110

Val Lys Arg Gly Pro Arg Thr His Tyr Gly Gln Lys Ala Ile Leu Phe
```

```
                    115                 120                 125

Leu Pro Leu Pro Val Ser Ser Asp
    130                 135

<210> SEQ ID NO 150
<211> LENGTH: 144
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (71)..(71)
<223> OTHER INFORMATION: Any amino acid

<400> SEQUENCE: 150

Ala Leu Thr Glu Lys Asn Leu Pro Pro Gly Asn Tyr Lys Lys Pro Lys
1               5                   10                  15

Leu Leu Tyr Cys Ser Asn Gly Gly His Phe Leu Arg Ile Leu Pro Asp
            20                  25                  30

Gly Thr Val Asp Gly Thr Arg Asp Arg Ser Asp Gln His Ile Gln Leu
        35                  40                  45

Gln Leu Ser Ala Glu Ser Val Gly Glu Val Tyr Ile Lys Ser Thr Glu
    50                  55                  60

Thr Gly Gln Tyr Leu Ala Xaa Asp Thr Asp Gly Leu Leu Tyr Gly Ser
65                  70                  75                  80

Gln Thr Pro Asn Glu Glu Cys Leu Phe Leu Glu Arg Leu Glu Glu Asn
                85                  90                  95

His Tyr Asn Thr Tyr Ile Ser Lys Lys His Ala Glu Lys Asn Trp Phe
            100                 105                 110

Val Gly Leu Lys Lys Asn Gly Ser Cys Lys Arg Gly Pro Arg Thr His
        115                 120                 125

Tyr Gly Gln Lys Ala Ile Leu Phe Leu Pro Leu Pro Val Ser Ser Asp
    130                 135                 140

<210> SEQ ID NO 151
<211> LENGTH: 143
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (70)..(70)
<223> OTHER INFORMATION: Any amino acid

<400> SEQUENCE: 151

Ala Leu Thr Glu Lys Leu Pro Pro Gly Asn Tyr Lys Lys Pro Lys Leu
1               5                   10                  15

Leu Tyr Ser Ser Asn Gly Gly His Phe Leu Arg Ile Leu Pro Asp Gly
            20                  25                  30

Thr Val Asp Gly Thr Arg Asp Arg Ser Asp Gln His Ile Gln Leu Gln
        35                  40                  45

Leu Ser Ala Glu Ser Val Gly Glu Val Tyr Ile Lys Ser Thr Glu Thr
    50                  55                  60

Gly Gln Tyr Leu Cys Xaa Asp Thr Asp Gly Leu Leu Tyr Gly Ser Gln
65                  70                  75                  80

Thr Pro Asn Glu Glu Cys Leu Phe Leu Glu Arg Leu Glu Glu Asn His
                85                  90                  95
```

```
Tyr Asn Thr Tyr Ile Ser Lys Lys His Ala Glu Lys Asn Trp Phe Val
            100                 105                 110

Gly Leu Lys Lys Asn Gly Ser Val Lys Arg Gly Pro Arg Thr His Tyr
        115                 120                 125

Gly Gln Lys Ala Ile Leu Phe Leu Pro Leu Pro Val Ser Ser Asp
    130                 135                 140

<210> SEQ ID NO 152
<211> LENGTH: 143
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (70)..(70)
<223> OTHER INFORMATION: Any amino acid

<400> SEQUENCE: 152

Ala Leu Thr Glu Lys Pro Pro Gly Gly Asn Tyr Lys Lys Pro Lys Leu
1               5                   10                  15

Leu Tyr Cys Ser Asn Gly Gly His Phe Leu Arg Ile Leu Pro Asp Gly
            20                  25                  30

Thr Val Asp Gly Thr Arg Asp Arg Ser Asp Gln His Ile Gln Leu Gln
        35                  40                  45

Leu Ser Ala Glu Ser Val Gly Glu Val Tyr Ile Lys Ser Thr Glu Thr
    50                  55                  60

Gly Gln Tyr Leu Ala Xaa Asp Thr Asp Gly Leu Leu Tyr Gly Ser Gln
65                  70                  75                  80

Thr Pro Asn Glu Glu Cys Leu Phe Leu Glu Arg Leu Glu Glu Asn His
                85                  90                  95

Tyr Asn Thr Tyr Ile Ser Lys Lys His Ala Glu Lys Asn Trp Phe Val
            100                 105                 110

Gly Leu Lys Lys Asn Gly Ser Cys Lys Arg Gly Pro Arg Thr His Tyr
        115                 120                 125

Gly Gln Lys Ala Ile Leu Phe Leu Pro Leu Pro Val Ser Ser Asp
    130                 135                 140

<210> SEQ ID NO 153
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (68)..(68)
<223> OTHER INFORMATION: Any amino acid

<400> SEQUENCE: 153

Ala Leu Thr Glu Lys Pro Gly Asn Tyr Lys Lys Pro Lys Leu Leu Tyr
1               5                   10                  15

Cys Ser Asn Gly Gly His Phe Leu Arg Ile Leu Pro Asp Gly Thr Val
            20                  25                  30

Asp Gly Thr Arg Asp Arg Ser Asp Gln His Ile Gln Leu Gln Leu Ser
        35                  40                  45

Ala Glu Ser Val Gly Glu Val Tyr Ile Lys Ser Thr Glu Thr Gly Gln
    50                  55                  60
```

```
Tyr Leu Ala Xaa Asp Thr Asp Gly Leu Leu Tyr Gly Ser Gln Thr Pro
 65                  70                  75                  80

Asn Glu Glu Cys Leu Phe Leu Glu Arg Leu Glu Glu Asn His Tyr Asn
                 85                  90                  95

Thr Tyr Ile Ser Lys Lys His Ala Glu Lys Asn Trp Phe Val Gly Leu
            100                 105                 110

Lys Lys Asn Gly Ser Cys Lys Arg Gly Pro Arg Thr His Tyr Gly Gln
        115                 120                 125

Lys Ala Ile Leu Phe Leu Pro Leu Pro Val Ser Ser Asp
    130                 135                 140

<210> SEQ ID NO 154
<211> LENGTH: 144
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (71)..(71)
<223> OTHER INFORMATION: Any amino acid

<400> SEQUENCE: 154

Leu Thr Glu Lys Phe Asn Leu Pro Pro Gly Asn Tyr Lys Lys Pro Lys
 1               5                  10                  15

Leu Leu Tyr Cys Ser Asn Gly Gly His Phe Leu Arg Ile Leu Pro Asp
            20                  25                  30

Gly Thr Val Asp Gly Thr Arg Asp Arg Ser Asp Gln His Ile Gln Leu
        35                  40                  45

Gln Leu Ser Ala Glu Ser Val Gly Glu Val Tyr Ile Lys Ser Thr Glu
    50                  55                  60

Thr Gly Gln Tyr Leu Ala Xaa Asp Thr Asp Gly Leu Leu Tyr Gly Ser
 65                  70                  75                  80

Gln Thr Pro Asn Glu Glu Cys Leu Phe Leu Glu Arg Leu Glu Glu Asn
                 85                  90                  95

His Tyr Asn Thr Tyr Ile Ser Lys Lys His Ala Glu Lys Asn Trp Phe
            100                 105                 110

Val Gly Leu Lys Lys Asn Gly Ser Cys Lys Arg Gly Pro Arg Thr His
        115                 120                 125

Tyr Gly Gln Lys Ala Ile Leu Phe Leu Pro Leu Pro Val Ser Ser Asp
    130                 135                 140

<210> SEQ ID NO 155
<211> LENGTH: 143
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (70)..(70)
<223> OTHER INFORMATION: Any amino acid

<400> SEQUENCE: 155

Leu Thr Glu Lys Asn Leu Pro Pro Gly Asn Tyr Lys Lys Pro Lys Leu
 1               5                  10                  15

Leu Tyr Cys Ser Asn Gly Gly His Phe Leu Arg Ile Leu Pro Asp Gly
            20                  25                  30

Thr Val Asp Gly Thr Arg Asp Arg Ser Asp Gln His Ile Gln Leu Gln
```

```
                    35                  40                  45
Leu Ser Ala Glu Ser Val Gly Glu Val Tyr Ile Lys Ser Thr Glu Thr
 50                  55                  60

Gly Gln Tyr Leu Ala Xaa Asp Thr Asp Gly Leu Leu Tyr Gly Ser Gln
 65                  70                  75                  80

Thr Pro Asn Glu Glu Cys Leu Phe Leu Glu Arg Leu Glu Glu Asn His
                 85                  90                  95

Tyr Asn Thr Tyr Ile Ser Lys Lys His Ala Glu Lys Asn Trp Phe Val
                100                 105                 110

Gly Leu Lys Lys Asn Gly Ser Cys Lys Arg Gly Pro Arg Thr His Tyr
                115                 120                 125

Gly Gln Lys Ala Ile Leu Phe Leu Pro Leu Pro Val Ser Ser Asp
    130                 135                 140
```

<210> SEQ ID NO 156
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (69)..(69)
<223> OTHER INFORMATION: Any amino acid

<400> SEQUENCE: 156

```
Leu Thr Glu Lys Leu Pro Pro Gly Asn Tyr Lys Lys Pro Lys Leu Leu
 1               5                  10                  15

Tyr Cys Ser Asn Gly Gly His Phe Leu Arg Ile Leu Pro Asp Gly Thr
                20                  25                  30

Val Asp Gly Thr Arg Asp Arg Ser Asp Gln His Ile Gln Leu Gln Leu
                35                  40                  45

Ser Ala Glu Ser Val Gly Glu Val Tyr Ile Lys Ser Thr Glu Thr Gly
 50                  55                  60

Gln Tyr Leu Ala Xaa Asp Thr Asp Gly Leu Leu Tyr Gly Ser Gln Thr
 65                  70                  75                  80

Pro Asn Glu Glu Cys Leu Phe Leu Glu Arg Leu Glu Glu Asn His Tyr
                 85                  90                  95

Asn Thr Tyr Ile Ser Lys Lys His Ala Glu Lys Asn Trp Phe Val Gly
                100                 105                 110

Leu Lys Lys Asn Gly Ser Cys Lys Arg Gly Pro Arg Thr His Tyr Gly
                115                 120                 125

Gln Lys Ala Ile Leu Phe Leu Pro Leu Pro Val Ser Ser Asp
    130                 135                 140
```

<210> SEQ ID NO 157
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (68)..(68)
<223> OTHER INFORMATION: Any amino acid

<400> SEQUENCE: 157

```
Leu Thr Glu Lys Pro Pro Gly Asn Tyr Lys Lys Pro Lys Leu Leu Tyr
 1               5                  10                  15
```

```
Cys Ser Asn Gly Gly His Phe Leu Arg Ile Leu Pro Asp Gly Thr Val
             20                  25                  30

Asp Gly Thr Arg Asp Arg Ser Asp Gln His Ile Gln Leu Gln Leu Ser
         35                  40                  45

Ala Glu Ser Val Gly Glu Val Tyr Ile Lys Ser Thr Glu Thr Gly Gln
 50                  55                  60

Tyr Leu Ala Xaa Asp Thr Asp Gly Leu Leu Tyr Gly Ser Gln Thr Pro
 65                  70                  75                  80

Asn Glu Glu Cys Leu Phe Leu Glu Arg Leu Glu Glu Asn His Tyr Asn
                 85                  90                  95

Thr Tyr Ile Ser Lys Lys His Ala Glu Lys Asn Trp Phe Val Gly Leu
            100                 105                 110

Lys Lys Asn Gly Ser Cys Lys Arg Gly Pro Arg Thr His Tyr Gly Gln
            115                 120                 125

Lys Ala Ile Leu Phe Leu Pro Leu Pro Val Ser Ser Asp
        130                 135                 140
```

<210> SEQ ID NO 158
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (67)..(67)
<223> OTHER INFORMATION: Any amino acid

<400> SEQUENCE: 158

```
Leu Thr Glu Lys Pro Gly Asn Tyr Lys Lys Pro Lys Leu Leu Tyr Cys
 1               5                  10                  15

Ser Asn Gly Gly His Phe Leu Arg Ile Leu Pro Asp Gly Thr Val Asp
             20                  25                  30

Gly Thr Arg Asp Arg Ser Asp Gln His Ile Gln Leu Gln Leu Ser Ala
         35                  40                  45

Glu Ser Val Gly Glu Val Tyr Ile Lys Ser Thr Glu Thr Gly Gln Tyr
 50                  55                  60

Leu Ala Xaa Asp Thr Asp Gly Leu Leu Tyr Gly Ser Gln Thr Pro Asn
 65                  70                  75                  80

Glu Glu Cys Leu Phe Leu Glu Arg Leu Glu Glu Asn His Tyr Asn Thr
                 85                  90                  95

Tyr Ile Ser Lys Lys His Ala Glu Lys Asn Trp Phe Val Gly Leu Lys
            100                 105                 110

Lys Asn Gly Ser Cys Lys Arg Gly Pro Arg Thr His Tyr Gly Gln Lys
            115                 120                 125

Ala Ile Leu Phe Leu Pro Leu Pro Val Ser Ser Asp
        130                 135                 140
```

<210> SEQ ID NO 159
<211> LENGTH: 143
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (70)..(70)
<223> OTHER INFORMATION: Any amino acid

<400> SEQUENCE: 159

Thr Glu Lys Phe Asn Leu Pro Pro Gly Asn Tyr Lys Lys Pro Lys Leu
1               5                   10                  15

Leu Tyr Cys Ser Asn Gly Gly His Phe Leu Arg Ile Leu Pro Asp Gly
                20                  25                  30

Thr Val Asp Gly Thr Arg Asp Arg Ser Asp Gln His Ile Gln Leu Gln
            35                  40                  45

Leu Ser Ala Glu Ser Val Gly Glu Val Tyr Ile Lys Ser Thr Glu Thr
    50                  55                  60

Gly Gln Tyr Leu Ala Xaa Asp Thr Asp Gly Leu Leu Tyr Gly Ser Gln
65                  70                  75                  80

Thr Pro Asn Glu Glu Cys Leu Phe Leu Glu Arg Leu Glu Glu Asn His
                85                  90                  95

Tyr Asn Thr Tyr Ile Ser Lys Lys His Ala Glu Lys Asn Trp Phe Val
                100                 105                 110

Gly Leu Lys Lys Asn Gly Ser Cys Lys Arg Gly Pro Arg Thr His Tyr
            115                 120                 125

Gly Gln Lys Ala Ile Leu Phe Leu Pro Leu Pro Val Ser Ser Asp
    130                 135                 140

<210> SEQ ID NO 160
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (69)..(69)
<223> OTHER INFORMATION: Any amino acid

<400> SEQUENCE: 160

Thr Glu Lys Asn Leu Pro Pro Gly Asn Tyr Lys Lys Pro Lys Leu Leu
1               5                   10                  15

Tyr Cys Ser Asn Gly Gly His Phe Leu Arg Ile Leu Pro Asp Gly Thr
                20                  25                  30

Val Asp Gly Thr Arg Asp Arg Ser Asp Gln His Ile Gln Leu Gln Leu
            35                  40                  45

Ser Ala Glu Ser Val Gly Glu Val Tyr Ile Lys Ser Thr Glu Thr Gly
    50                  55                  60

Gln Tyr Leu Ala Xaa Asp Thr Asp Gly Leu Leu Tyr Gly Ser Gln Thr
65                  70                  75                  80

Pro Asn Glu Glu Cys Leu Phe Leu Glu Arg Leu Glu Glu Asn His Tyr
                85                  90                  95

Asn Thr Tyr Ile Ser Lys Lys His Ala Glu Lys Asn Trp Phe Val Gly
                100                 105                 110

Leu Lys Lys Asn Gly Ser Cys Lys Arg Gly Pro Arg Thr His Tyr Gly
            115                 120                 125

Gln Lys Ala Ile Leu Phe Leu Pro Leu Pro Val Ser Ser Asp
    130                 135                 140

<210> SEQ ID NO 161
<211> LENGTH: 141
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (68)..(68)
<223> OTHER INFORMATION: Any amino acid

<400> SEQUENCE: 161

Thr Glu Lys Leu Pro Pro Gly Asn Tyr Lys Lys Pro Lys Leu Leu Tyr
1               5                   10                  15

Cys Ser Asn Gly Gly His Phe Leu Arg Ile Leu Pro Asp Gly Thr Val
            20                  25                  30

Asp Gly Thr Arg Asp Arg Ser Asp Gln His Ile Gln Leu Gln Leu Ser
        35                  40                  45

Ala Glu Ser Val Gly Glu Val Tyr Ile Lys Ser Thr Glu Thr Gly Gln
    50                  55                  60

Tyr Leu Ala Xaa Asp Thr Asp Gly Leu Leu Tyr Gly Ser Gln Thr Pro
65                  70                  75                  80

Asn Glu Glu Cys Leu Phe Leu Glu Arg Leu Glu Glu Asn His Tyr Asn
                85                  90                  95

Thr Tyr Ile Ser Lys Lys His Ala Glu Lys Asn Trp Phe Val Gly Leu
            100                 105                 110

Lys Lys Asn Gly Ser Cys Lys Arg Gly Pro Arg Thr His Tyr Gly Gln
        115                 120                 125

Lys Ala Ile Leu Phe Leu Pro Leu Pro Val Ser Ser Asp
    130                 135                 140

<210> SEQ ID NO 162
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (67)..(67)
<223> OTHER INFORMATION: Any amino acid

<400> SEQUENCE: 162

Thr Glu Lys Pro Pro Gly Asn Tyr Lys Lys Pro Lys Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
    50                  55                  60

Leu Ala Xaa Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
            100                 105                 110

Lys Asn Gly Ser Cys Lys Arg Gly Pro Arg Thr His Tyr Gly Gln Lys
        115                 120                 125

Ala Ile Leu Phe Leu Pro Leu Pro Val Ser Ser Asp
    130                 135                 140

<210> SEQ ID NO 163

```
<211> LENGTH: 139
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (66)..(66)
<223> OTHER INFORMATION: Any amino acid

<400> SEQUENCE: 163

Thr Glu Lys Pro Gly Asn Tyr Lys Lys Pro Lys Leu Leu Tyr Cys Ser
1               5                   10                  15

Asn Gly Gly His Phe Leu Arg Ile Leu Pro Asp Gly Thr Val Asp Gly
            20                  25                  30

Thr Arg Asp Arg Ser Asp Gln His Ile Gln Leu Gln Leu Ser Ala Glu
        35                  40                  45

Ser Val Gly Glu Val Tyr Ile Lys Ser Thr Glu Thr Gly Gln Tyr Leu
    50                  55                  60

Ala Xaa Asp Thr Asp Gly Leu Leu Tyr Gly Ser Gln Thr Pro Asn Glu
65                  70                  75                  80

Glu Cys Leu Phe Leu Glu Arg Leu Glu Glu Asn His Tyr Asn Thr Tyr
                85                  90                  95

Ile Ser Lys Lys His Ala Glu Lys Asn Trp Phe Val Gly Leu Lys Lys
            100                 105                 110

Asn Gly Ser Cys Lys Arg Gly Pro Arg Thr His Tyr Gly Gln Lys Ala
        115                 120                 125

Ile Leu Phe Leu Pro Leu Pro Val Ser Ser Asp
    130                 135

<210> SEQ ID NO 164
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (69)..(69)
<223> OTHER INFORMATION: Any amino acid

<400> SEQUENCE: 164

Glu Lys Phe Asn Leu Pro Pro Gly Asn Tyr Lys Lys Pro Lys Leu Leu
1               5                   10                  15

Tyr Cys Ser Asn Gly Gly His Phe Leu Arg Ile Leu Pro Asp Gly Thr
            20                  25                  30

Val Asp Gly Thr Arg Asp Arg Ser Asp Gln His Ile Gln Leu Gln Leu
        35                  40                  45

Ser Ala Glu Ser Val Gly Glu Val Tyr Ile Lys Ser Thr Glu Thr Gly
    50                  55                  60

Gln Tyr Leu Ala Xaa Asp Thr Asp Gly Leu Leu Tyr Gly Ser Gln Thr
65                  70                  75                  80

Pro Asn Glu Glu Cys Leu Phe Leu Glu Arg Leu Glu Glu Asn His Tyr
                85                  90                  95

Asn Thr Tyr Ile Ser Lys Lys His Ala Glu Lys Asn Trp Phe Val Gly
            100                 105                 110

Leu Lys Lys Asn Gly Ser Cys Lys Arg Gly Pro Arg Thr His Tyr Gly
        115                 120                 125
```

Gln Lys Ala Ile Leu Phe Leu Pro Leu Pro Val Ser Ser Asp
        130                 135                 140

<210> SEQ ID NO 165
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (68)..(68)
<223> OTHER INFORMATION: Any amino acid

<400> SEQUENCE: 165

Glu Lys Asn Leu Pro Pro Gly Asn Tyr Lys Pro Lys Leu Leu Tyr
1               5                   10                  15

Cys Ser Asn Gly Gly His Phe Leu Arg Ile Leu Pro Asp Gly Thr Val
            20                  25                  30

Asp Gly Thr Arg Asp Arg Ser Asp Gln His Ile Gln Leu Gln Leu Ser
        35                  40                  45

Ala Glu Ser Val Gly Glu Val Tyr Ile Lys Ser Thr Glu Thr Gly Gln
50                  55                  60

Tyr Leu Ala Xaa Asp Thr Asp Gly Leu Leu Tyr Gly Ser Gln Thr Pro
65                  70                  75                  80

Asn Glu Glu Cys Leu Phe Leu Glu Arg Leu Glu Glu Asn His Tyr Asn
                85                  90                  95

Thr Tyr Ile Ser Lys Lys His Ala Glu Lys Asn Trp Phe Val Gly Leu
            100                 105                 110

Lys Lys Asn Gly Ser Cys Lys Arg Gly Pro Arg Thr His Tyr Gly Gln
        115                 120                 125

Lys Ala Ile Leu Phe Leu Pro Leu Pro Val Ser Ser Asp
    130                 135                 140

<210> SEQ ID NO 166
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (67)..(67)
<223> OTHER INFORMATION: Any amino acid

<400> SEQUENCE: 166

Glu Lys Leu Pro Pro Gly Asn Tyr Lys Pro Lys Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
50                  55                  60

Leu Ala Xaa Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys

```
                    100                 105                 110
Lys Asn Gly Ser Cys Lys Arg Gly Pro Arg Thr His Tyr Gly Gln Lys
            115                 120                 125

Ala Ile Leu Phe Leu Pro Leu Pro Val Ser Ser Asp
        130                 135                 140

<210> SEQ ID NO 167
<211> LENGTH: 139
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (66)..(66)
<223> OTHER INFORMATION: Any amino acid

<400> SEQUENCE: 167

Glu Lys Pro Pro Gly Asn Tyr Lys Lys Pro Lys Leu Leu Tyr Cys Ser
1               5                   10                  15

Asn Gly Gly His Phe Leu Arg Ile Leu Pro Asp Gly Thr Val Asp Gly
            20                  25                  30

Thr Arg Asp Arg Ser Asp Gln His Ile Gln Leu Gln Leu Ser Ala Glu
        35                  40                  45

Ser Val Gly Glu Val Tyr Ile Lys Ser Thr Glu Thr Gly Gln Tyr Leu
    50                  55                  60

Ala Xaa Asp Thr Asp Gly Leu Leu Tyr Gly Ser Gln Thr Pro Asn Glu
65                  70                  75                  80

Glu Cys Leu Phe Leu Glu Arg Leu Glu Glu Asn His Tyr Asn Thr Tyr
                85                  90                  95

Ile Ser Lys Lys His Ala Glu Lys Asn Trp Phe Val Gly Leu Lys Lys
            100                 105                 110

Asn Gly Ser Cys Lys Arg Gly Pro Arg Thr His Tyr Gly Gln Lys Ala
        115                 120                 125

Ile Leu Phe Leu Pro Leu Pro Val Ser Ser Asp
    130                 135

<210> SEQ ID NO 168
<211> LENGTH: 138
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (65)..(65)
<223> OTHER INFORMATION: Any amino acid

<400> SEQUENCE: 168

Glu Lys Pro Gly Asn Tyr Lys Lys Pro Lys Leu Leu Tyr Cys Ser Asn
1               5                   10                  15

Gly Gly His Phe Leu Arg Ile Leu Pro Asp Gly Thr Val Asp Gly Thr
            20                  25                  30

Arg Asp Arg Ser Asp Gln His Ile Gln Leu Gln Leu Ser Ala Glu Ser
        35                  40                  45

Val Gly Glu Val Tyr Ile Lys Ser Thr Glu Thr Gly Gln Tyr Leu Ala
    50                  55                  60

Xaa Asp Thr Asp Gly Leu Leu Tyr Gly Ser Gln Thr Pro Asn Glu Glu
65                  70                  75                  80
```

-continued

Cys Leu Phe Leu Glu Arg Leu Glu Glu Asn His Tyr Asn Thr Tyr Ile
                85                  90                  95

Ser Lys Lys His Ala Glu Lys Asn Trp Phe Val Gly Leu Lys Lys Asn
            100                 105                 110

Gly Ser Cys Lys Arg Gly Pro Arg Thr His Tyr Gly Gln Lys Ala Ile
        115                 120                 125

Leu Phe Leu Pro Leu Pro Val Ser Ser Asp
    130                 135

<210> SEQ ID NO 169
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (68)..(68)
<223> OTHER INFORMATION: Any amino acid

<400> SEQUENCE: 169

Lys Phe Asn Leu Pro Pro Gly Asn Tyr Lys Lys Pro Lys Leu Leu Tyr
1               5                   10                  15

Cys Ser Asn Gly Gly His Phe Leu Arg Ile Leu Pro Asp Gly Thr Val
            20                  25                  30

Asp Gly Thr Arg Asp Arg Ser Asp Gln His Ile Gln Leu Gln Leu Ser
        35                  40                  45

Ala Glu Ser Val Gly Glu Val Tyr Ile Lys Ser Thr Glu Thr Gly Gln
    50                  55                  60

Tyr Leu Ala Xaa Asp Thr Asp Gly Leu Leu Tyr Gly Ser Gln Thr Pro
65                  70                  75                  80

Asn Glu Glu Cys Leu Phe Leu Glu Arg Leu Glu Glu Asn His Tyr Asn
                85                  90                  95

Thr Tyr Ile Ser Lys Lys His Ala Glu Lys Asn Trp Phe Val Gly Leu
            100                 105                 110

Lys Lys Asn Gly Ser Cys Lys Arg Gly Pro Arg Thr His Tyr Gly Gln
        115                 120                 125

Lys Ala Ile Leu Phe Leu Pro Leu Pro Val Ser Ser Asp
    130                 135                 140

<210> SEQ ID NO 170
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (67)..(67)
<223> OTHER INFORMATION: Any amino acid

<400> SEQUENCE: 170

Lys Asn Leu Pro Pro Gly Asn Tyr Lys Lys Pro Lys Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

```
Glu Ser Val Gly Glu Val Tyr Ile Lys Ser Thr Glu Thr Gly Gln Tyr
 50                  55                  60

Leu Ala Xaa Asp Thr Asp Gly Leu Leu Tyr Gly Ser Gln Thr Pro Asn
 65                  70                  75                  80

Glu Glu Cys Leu Phe Leu Glu Arg Leu Glu Glu Asn His Tyr Asn Thr
                 85                  90                  95

Tyr Ile Ser Lys Lys His Ala Glu Lys Asn Trp Phe Val Gly Leu Lys
                100                 105                 110

Lys Asn Gly Ser Cys Lys Arg Gly Pro Arg Thr His Tyr Gly Gln Lys
            115                 120                 125

Ala Ile Leu Phe Leu Pro Leu Pro Val Ser Ser Asp
130                 135                 140
```

<210> SEQ ID NO 171
<211> LENGTH: 139
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (66)..(66)
<223> OTHER INFORMATION: Any amino acid

<400> SEQUENCE: 171

```
Lys Leu Pro Pro Gly Asn Tyr Lys Lys Pro Lys Leu Leu Tyr Cys Ser
  1               5                  10                  15

Asn Gly Gly His Phe Leu Arg Ile Leu Pro Asp Gly Thr Val Asp Gly
                 20                  25                  30

Thr Arg Asp Arg Ser Asp Gln His Ile Gln Leu Gln Leu Ser Ala Glu
             35                  40                  45

Ser Val Gly Glu Val Tyr Ile Lys Ser Thr Glu Thr Gly Gln Tyr Leu
 50                  55                  60

Ala Xaa Asp Thr Asp Gly Leu Leu Tyr Gly Ser Gln Thr Pro Asn Glu
 65                  70                  75                  80

Glu Cys Leu Phe Leu Glu Arg Leu Glu Glu Asn His Tyr Asn Thr Tyr
                 85                  90                  95

Ile Ser Lys Lys His Ala Glu Lys Asn Trp Phe Val Gly Leu Lys Lys
                100                 105                 110

Asn Gly Ser Cys Lys Arg Gly Pro Arg Thr His Tyr Gly Gln Lys Ala
            115                 120                 125

Ile Leu Phe Leu Pro Leu Pro Val Ser Ser Asp
130                 135
```

<210> SEQ ID NO 172
<211> LENGTH: 138
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (65)..(65)
<223> OTHER INFORMATION: Any amino acid

<400> SEQUENCE: 172

```
Lys Pro Pro Gly Asn Tyr Lys Lys Pro Lys Leu Leu Tyr Cys Ser Asn
  1               5                  10                  15

Gly Gly His Phe Leu Arg Ile Leu Pro Asp Gly Thr Val Asp Gly Thr
```

```
                  20                  25                  30

Arg Asp Arg Ser Asp Gln His Ile Gln Leu Gln Leu Ser Ala Glu Ser
            35                  40                  45

Val Gly Glu Val Tyr Ile Lys Ser Thr Glu Thr Gly Gln Tyr Leu Ala
 50                  55                  60

Xaa Asp Thr Asp Gly Leu Leu Tyr Gly Ser Gln Thr Pro Asn Glu Glu
 65                  70                  75                  80

Cys Leu Phe Leu Glu Arg Leu Glu Glu Asn His Tyr Asn Thr Tyr Ile
                85                  90                  95

Ser Lys Lys His Ala Glu Lys Asn Trp Phe Val Gly Leu Lys Lys Asn
            100                 105                 110

Gly Ser Cys Lys Arg Gly Pro Arg Thr His Tyr Gly Gln Lys Ala Ile
            115                 120                 125

Leu Phe Leu Pro Leu Pro Val Ser Ser Asp
            130                 135

<210> SEQ ID NO 173
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (64)..(64)
<223> OTHER INFORMATION: Any amino acid

<400> SEQUENCE: 173

Lys Pro Gly Asn Tyr Lys Lys Pro Lys Leu Leu Tyr Cys Ser Asn Gly
1               5                   10                  15

Gly His Phe Leu Arg Ile Leu Pro Asp Gly Thr Val Asp Gly Thr Arg
                20                  25                  30

Asp Arg Ser Asp Gln His Ile Gln Leu Gln Leu Ser Ala Glu Ser Val
            35                  40                  45

Gly Glu Val Tyr Ile Lys Ser Thr Glu Thr Gly Gln Tyr Leu Ala Xaa
 50                  55                  60

Asp Thr Asp Gly Leu Leu Tyr Gly Ser Gln Thr Pro Asn Glu Glu Cys
 65                  70                  75                  80

Leu Phe Leu Glu Arg Leu Glu Glu Asn His Tyr Asn Thr Tyr Ile Ser
                85                  90                  95

Lys Lys His Ala Glu Lys Asn Trp Phe Val Gly Leu Lys Lys Asn Gly
            100                 105                 110

Ser Cys Lys Arg Gly Pro Arg Thr His Tyr Gly Gln Lys Ala Ile Leu
            115                 120                 125

Phe Leu Pro Leu Pro Val Ser Ser Asp
            130                 135

<210> SEQ ID NO 174
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (67)..(67)
<223> OTHER INFORMATION: Any amino acid

<400> SEQUENCE: 174
```

```
Phe Asn Leu Pro Pro Gly Asn Tyr Lys Lys Pro Lys Leu Leu Tyr Ser
 1               5                  10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
50                  55                  60

Leu Cys Xaa Asp Thr Asp Gly Leu Leu Tyr Gly Ser Gln Thr Pro Asn
65                  70                  75                  80

Glu Glu Cys Leu Phe Leu Glu Arg Leu Glu Asn His Tyr Asn Thr
                85                  90                  95

Tyr Ile Ser Lys Lys His Ala Glu Lys Asn Trp Phe Val Gly Leu Lys
                100                 105                 110

Lys Asn Gly Ser Val Lys Arg Gly Pro Arg Thr His Tyr Gly Gln Lys
            115                 120                 125

Ala Ile Leu Phe Leu Pro Leu Pro Val Ser Ser Asp
130                 135                 140
```

<210> SEQ ID NO 175
<211> LENGTH: 145
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (72)..(72)
<223> OTHER INFORMATION: Any amino acid

<400> SEQUENCE: 175

```
Ala Leu Thr Glu Lys Phe Asn Leu Pro Pro Gly Asn Tyr Lys Lys Pro
 1               5                  10                  15

Lys Leu Leu Tyr Ser Ser Asn Gly Gly His Phe Leu Arg Ile Leu Pro
            20                  25                  30

Asp Gly Thr Val Asp Gly Thr Arg Asp Arg Ser Asp Gln His Ile Gln
        35                  40                  45

Leu Gln Leu Ser Ala Glu Ser Val Gly Glu Val Tyr Ile Lys Ser Thr
50                  55                  60

Glu Thr Gly Gln Tyr Leu Cys Xaa Asp Thr Asp Gly Leu Leu Tyr Gly
65                  70                  75                  80

Ser Gln Thr Pro Asn Glu Glu Cys Leu Phe Leu Glu Arg Leu Glu Glu
                85                  90                  95

Asn His Tyr Asn Thr Tyr Ile Ser Lys Lys His Ala Glu Lys Asn Trp
                100                 105                 110

Phe Val Gly Leu Lys Lys Asn Gly Ser Val Lys Arg Gly Pro Arg Thr
            115                 120                 125

His Tyr Gly Gln Lys Ala Ile Leu Phe Leu Pro Leu Pro Val Ser Ser
130                 135                 140

Asp
145
```

<210> SEQ ID NO 176
<211> LENGTH: 144
<212> TYPE: PRT
<213> ORGANISM: Artificial Sequence
<220> FEATURE:

<223> OTHER INFORMATION: Description of Artificial Sequence: Synthetic
      polypeptide
<220> FEATURE:
<221> NAME/KEY: MOD_RES
<222> LOCATION: (71)..(71)
<223> OTHER INFORMATION: Any amino acid

<400> SEQUENCE: 176

Leu Thr Glu Lys Phe Asn Leu Pro Pro Gly Asn Tyr Lys Lys Pro Lys
1               5                   10                  15

Leu Leu Tyr Ser Ser Asn Gly Gly His Phe Leu Arg Ile Leu Pro Asp
            20                  25                  30

Gly Thr Val Asp Gly Thr Arg Asp Arg Ser Asp Gln His Ile Gln Leu
        35                  40                  45

Gln Leu Ser Ala Glu Ser Val Gly Glu Val Tyr Ile Lys Ser Thr Glu
50                  55                  60

Thr Gly Gln Tyr Leu Cys Xaa Asp Thr Asp Gly Leu Leu Tyr Gly Ser
65                  70                  75                  80

Gln Thr Pro Asn Glu Glu Cys Leu Phe Leu Glu Arg Leu Glu Glu Asn
                85                  90                  95

His Tyr Asn Thr Tyr Ile Ser Lys Lys His Ala Glu Lys Asn Trp Phe
            100                 105                 110

Val Gly Leu Lys Lys Asn Gly Ser Val Lys Arg Gly Pro Arg Thr His
        115                 120                 125

Tyr Gly Gln Lys Ala Ile Leu Phe Leu Pro Leu Pro Val Ser Ser Asp
    130                 135                 140

<210> SEQ ID NO 177
<211> LENGTH: 143
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (70)..(70)
<223> OTHER INFORMATION: Any amino acid

<400> SEQUENCE: 177

Thr Glu Lys Phe Asn Leu Pro Pro Gly Asn Tyr Lys Lys Pro Lys Leu
1               5                   10                  15

Leu Tyr Ser Ser Asn Gly Gly His Phe Leu Arg Ile Leu Pro Asp Gly
            20                  25                  30

Thr Val Asp Gly Thr Arg Asp Arg Ser Asp Gln His Ile Gln Leu Gln
        35                  40                  45

Leu Ser Ala Glu Ser Val Gly Glu Val Tyr Ile Lys Ser Thr Glu Thr
50                  55                  60

Gly Gln Tyr Leu Cys Xaa Asp Thr Asp Gly Leu Leu Tyr Gly Ser Gln
65                  70                  75                  80

Thr Pro Asn Glu Glu Cys Leu Phe Leu Glu Arg Leu Glu Glu Asn His
                85                  90                  95

Tyr Asn Thr Tyr Ile Ser Lys Lys His Ala Glu Lys Asn Trp Phe Val
            100                 105                 110

Gly Leu Lys Lys Asn Gly Ser Val Lys Arg Gly Pro Arg Thr His Tyr
        115                 120                 125

Gly Gln Lys Ala Ile Leu Phe Leu Pro Leu Pro Val Ser Ser Asp
    130                 135                 140

```
<210> SEQ ID NO 178
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (69)..(69)
<223> OTHER INFORMATION: Any amino acid

<400> SEQUENCE: 178

Glu Lys Phe Asn Leu Pro Pro Gly Asn Tyr Lys Lys Pro Lys Leu Leu
1               5                   10                  15

Tyr Ser Ser Asn Gly Gly His Phe Leu Arg Ile Leu Pro Asp Gly Thr
            20                  25                  30

Val Asp Gly Thr Arg Asp Arg Ser Asp Gln His Ile Gln Leu Gln Leu
        35                  40                  45

Ser Ala Glu Ser Val Gly Glu Val Tyr Ile Lys Ser Thr Glu Thr Gly
    50                  55                  60

Gln Tyr Leu Cys Xaa Asp Thr Asp Gly Leu Leu Tyr Gly Ser Gln Thr
65                  70                  75                  80

Pro Asn Glu Glu Cys Leu Phe Leu Glu Arg Leu Glu Glu Asn His Tyr
                85                  90                  95

Asn Thr Tyr Ile Ser Lys Lys His Ala Glu Lys Asn Trp Phe Val Gly
            100                 105                 110

Leu Lys Lys Asn Gly Ser Val Lys Arg Gly Pro Arg Thr His Tyr Gly
        115                 120                 125

Gln Lys Ala Ile Leu Phe Leu Pro Leu Pro Val Ser Ser Asp
    130                 135                 140

<210> SEQ ID NO 179
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (68)..(68)
<223> OTHER INFORMATION: Any amino acid

<400> SEQUENCE: 179

Lys Phe Asn Leu Pro Pro Gly Asn Tyr Lys Lys Pro Lys Leu Leu Tyr
1               5                   10                  15

Ser Ser Asn Gly Gly His Phe Leu Arg Ile Leu Pro Asp Gly Thr Val
            20                  25                  30

Asp Gly Thr Arg Asp Arg Ser Asp Gln His Ile Gln Leu Gln Leu Ser
        35                  40                  45

Ala Glu Ser Val Gly Glu Val Tyr Ile Lys Ser Thr Glu Thr Gly Gln
    50                  55                  60

Tyr Leu Cys Xaa Asp Thr Asp Gly Leu Leu Tyr Gly Ser Gln Thr Pro
65                  70                  75                  80

Asn Glu Glu Cys Leu Phe Leu Glu Arg Leu Glu Glu Asn His Tyr Asn
                85                  90                  95

Thr Tyr Ile Ser Lys Lys His Ala Glu Lys Asn Trp Phe Val Gly Leu
            100                 105                 110

Lys Lys Asn Gly Ser Val Lys Arg Gly Pro Arg Thr His Tyr Gly Gln
        115                 120                 125
```

```
Lys Ala Ile Leu Phe Leu Pro Leu Pro Val Ser Ser Asp
    130                 135                 140
```

<210> SEQ ID NO 180
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (68)..(68)
<223> OTHER INFORMATION: Any amino acid

<400> SEQUENCE: 180

```
Lys Phe Asn Leu Pro Pro Gly Asn Tyr Lys Lys Pro Lys Leu Leu Tyr
1               5                   10                  15

Ser Ser Asn Gly Gly His Phe Leu Arg Ile Leu Pro Asp Gly Thr Val
            20                  25                  30

Asp Gly Thr Arg Asp Arg Ser Asp Gln His Ile Gln Leu Gln Leu Ser
        35                  40                  45

Ala Glu Ser Val Gly Glu Val Tyr Ile Lys Ser Thr Glu Thr Gly Gln
    50                  55                  60

Tyr Leu Cys Xaa Asp Thr Asp Gly Leu Leu Tyr Gly Ser Gln Thr Pro
65                  70                  75                  80

Asn Glu Glu Cys Leu Phe Leu Glu Arg Leu Glu Glu Asn His Tyr Asn
                85                  90                  95

Thr Tyr Ile Ser Lys Lys His Ala Glu Lys Asn Trp Phe Val Gly Leu
            100                 105                 110

Lys Lys Asn Gly Ser Val Lys Arg Gly Pro Arg Thr His Tyr Gly Gln
        115                 120                 125

Lys Ala Ile Leu Phe Leu Pro Leu Pro Val Ser Ser Asp
    130                 135                 140
```

<210> SEQ ID NO 181
<211> LENGTH: 144
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (71)..(71)
<223> OTHER INFORMATION: Any amino acid

<400> SEQUENCE: 181

```
Ala Leu Thr Glu Lys Asn Leu Pro Pro Gly Asn Tyr Lys Lys Pro Lys
1               5                   10                  15

Leu Leu Tyr Ser Ser Asn Gly Gly His Phe Leu Arg Ile Leu Pro Asp
            20                  25                  30

Gly Thr Val Asp Gly Thr Arg Asp Arg Ser Asp Gln His Ile Gln Leu
        35                  40                  45

Gln Leu Ser Ala Glu Ser Val Gly Glu Val Tyr Ile Lys Ser Thr Glu
    50                  55                  60

Thr Gly Gln Tyr Leu Cys Xaa Asp Thr Asp Gly Leu Leu Tyr Gly Ser
65                  70                  75                  80

Gln Thr Pro Asn Glu Glu Cys Leu Phe Leu Glu Arg Leu Glu Glu Asn
                85                  90                  95
```

His Tyr Asn Thr Tyr Ile Ser Lys Lys His Ala Glu Lys Asn Trp Phe
            100                 105                 110

Val Gly Leu Lys Lys Asn Gly Ser Val Lys Arg Gly Pro Arg Thr His
        115                 120                 125

Tyr Gly Gln Lys Ala Ile Leu Phe Leu Pro Leu Pro Val Ser Ser Asp
    130                 135                 140

<210> SEQ ID NO 182
<211> LENGTH: 143
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (70)..(70)
<223> OTHER INFORMATION: Any amino acid

<400> SEQUENCE: 182

Ala Leu Thr Glu Lys Leu Pro Pro Gly Asn Tyr Lys Lys Pro Lys Leu
1               5                   10                  15

Leu Tyr Ser Ser Asn Gly Gly His Phe Leu Arg Ile Leu Pro Asp Gly
            20                  25                  30

Thr Val Asp Gly Thr Arg Asp Arg Ser Asp Gln His Ile Gln Leu Gln
        35                  40                  45

Leu Ser Ala Glu Ser Val Gly Glu Val Tyr Ile Lys Ser Thr Glu Thr
    50                  55                  60

Gly Gln Tyr Leu Cys Xaa Asp Thr Asp Gly Leu Leu Tyr Gly Ser Gln
65                  70                  75                  80

Thr Pro Asn Glu Glu Cys Leu Phe Leu Glu Arg Leu Glu Glu Asn His
                85                  90                  95

Tyr Asn Thr Tyr Ile Ser Lys Lys His Ala Glu Lys Asn Trp Phe Val
            100                 105                 110

Gly Leu Lys Lys Asn Gly Ser Val Lys Arg Gly Pro Arg Thr His Tyr
        115                 120                 125

Gly Gln Lys Ala Ile Leu Phe Leu Pro Leu Pro Val Ser Ser Asp
    130                 135                 140

<210> SEQ ID NO 183
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (69)..(69)
<223> OTHER INFORMATION: Any amino acid

<400> SEQUENCE: 183

Ala Leu Thr Glu Lys Pro Pro Gly Asn Tyr Lys Lys Pro Lys Leu Leu
1               5                   10                  15

Tyr Ser Ser Asn Gly Gly His Phe Leu Arg Ile Leu Pro Asp Gly Thr
            20                  25                  30

Val Asp Gly Thr Arg Asp Arg Ser Asp Gln His Ile Gln Leu Gln Leu
        35                  40                  45

Ser Ala Glu Ser Val Gly Glu Val Tyr Ile Lys Ser Thr Glu Thr Gly
    50                  55                  60

Gln Tyr Leu Cys Xaa Asp Thr Asp Gly Leu Leu Tyr Gly Ser Gln Thr

```
                65                  70                  75                  80
Pro Asn Glu Glu Cys Leu Phe Leu Glu Arg Leu Glu Glu Asn His Tyr
                    85                  90                  95

Asn Thr Tyr Ile Ser Lys Lys His Ala Glu Lys Asn Trp Phe Val Gly
                100                 105                 110

Leu Lys Lys Asn Gly Ser Val Lys Arg Gly Pro Arg Thr His Tyr Gly
            115                 120                 125

Gln Lys Ala Ile Leu Phe Leu Pro Leu Pro Val Ser Ser Asp
        130                 135                 140

<210> SEQ ID NO 184
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (68)..(68)
<223> OTHER INFORMATION: Any amino acid

<400> SEQUENCE: 184

Ala Leu Thr Glu Lys Pro Gly Asn Tyr Lys Lys Pro Lys Leu Leu Tyr
1               5                   10                  15

Ser Ser Asn Gly Gly His Phe Leu Arg Ile Leu Pro Asp Gly Thr Val
            20                  25                  30

Asp Gly Thr Arg Asp Arg Ser Asp Gln His Ile Gln Leu Gln Leu Ser
        35                  40                  45

Ala Glu Ser Val Gly Glu Val Tyr Ile Lys Ser Thr Glu Thr Gly Gln
    50                  55                  60

Tyr Leu Cys Xaa Asp Thr Asp Gly Leu Leu Tyr Gly Ser Gln Thr Pro
65                  70                  75                  80

Asn Glu Glu Cys Leu Phe Leu Glu Arg Leu Glu Glu Asn His Tyr Asn
                85                  90                  95

Thr Tyr Ile Ser Lys Lys His Ala Glu Lys Asn Trp Phe Val Gly Leu
                100                 105                 110

Lys Lys Asn Gly Ser Val Lys Arg Gly Pro Arg Thr His Tyr Gly Gln
            115                 120                 125

Lys Ala Ile Leu Phe Leu Pro Leu Pro Val Ser Ser Asp
        130                 135                 140

<210> SEQ ID NO 185
<211> LENGTH: 144
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (71)..(71)
<223> OTHER INFORMATION: Any amino acid

<400> SEQUENCE: 185

Leu Thr Glu Lys Phe Asn Leu Pro Pro Gly Asn Tyr Lys Lys Pro Lys
1               5                   10                  15

Leu Leu Tyr Ser Ser Asn Gly Gly His Phe Leu Arg Ile Leu Pro Asp
            20                  25                  30

Gly Thr Val Asp Gly Thr Arg Asp Arg Ser Asp Gln His Ile Gln Leu
        35                  40                  45
```

```
Gln Leu Ser Ala Glu Ser Val Gly Glu Val Tyr Ile Lys Ser Thr Glu
             50                  55                  60

Thr Gly Gln Tyr Leu Cys Xaa Asp Thr Asp Gly Leu Leu Tyr Gly Ser
 65                  70                  75                  80

Gln Thr Pro Asn Glu Glu Cys Leu Phe Leu Glu Arg Leu Glu Glu Asn
                 85                  90                  95

His Tyr Asn Thr Tyr Ile Ser Lys Lys His Ala Glu Lys Asn Trp Phe
            100                 105                 110

Val Gly Leu Lys Lys Asn Gly Ser Val Lys Arg Gly Pro Arg Thr His
        115                 120                 125

Tyr Gly Gln Lys Ala Ile Leu Phe Leu Pro Leu Pro Val Ser Ser Asp
    130                 135                 140

<210> SEQ ID NO 186
<211> LENGTH: 143
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (70)..(70)
<223> OTHER INFORMATION: Any amino acid

<400> SEQUENCE: 186

Leu Thr Glu Lys Asn Leu Pro Pro Gly Asn Tyr Lys Pro Lys Leu
 1               5                  10                  15

Leu Tyr Ser Ser Asn Gly Gly His Phe Leu Arg Ile Leu Pro Asp Gly
             20                  25                  30

Thr Val Asp Gly Thr Arg Asp Arg Ser Asp Gln His Ile Gln Leu Gln
         35                  40                  45

Leu Ser Ala Glu Ser Val Gly Glu Val Tyr Ile Lys Ser Thr Glu Thr
     50                  55                  60

Gly Gln Tyr Leu Cys Xaa Asp Thr Asp Gly Leu Leu Tyr Gly Ser Gln
 65                  70                  75                  80

Thr Pro Asn Glu Glu Cys Leu Phe Leu Glu Arg Leu Glu Glu Asn His
                 85                  90                  95

Tyr Asn Thr Tyr Ile Ser Lys Lys His Ala Glu Lys Asn Trp Phe Val
            100                 105                 110

Gly Leu Lys Lys Asn Gly Ser Val Lys Arg Gly Pro Arg Thr His Tyr
        115                 120                 125

Gly Gln Lys Ala Ile Leu Phe Leu Pro Leu Pro Val Ser Ser Asp
    130                 135                 140

<210> SEQ ID NO 187
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (69)..(69)
<223> OTHER INFORMATION: Any amino acid

<400> SEQUENCE: 187

Leu Thr Glu Lys Leu Pro Pro Gly Asn Tyr Lys Pro Lys Leu Leu
 1               5                  10                  15
```

Tyr Ser Ser Asn Gly Gly His Phe Leu Arg Ile Leu Pro Asp Gly Thr
            20                  25                  30

Val Asp Gly Thr Arg Asp Arg Ser Asp Gln His Ile Gln Leu Gln Leu
        35                  40                  45

Ser Ala Glu Ser Val Gly Glu Val Tyr Ile Lys Ser Thr Glu Thr Gly
50                  55                  60

Gln Tyr Leu Cys Xaa Asp Thr Asp Gly Leu Leu Tyr Gly Ser Gln Thr
65                  70                  75                  80

Pro Asn Glu Glu Cys Leu Phe Leu Glu Arg Leu Glu Glu Asn His Tyr
                85                  90                  95

Asn Thr Tyr Ile Ser Lys Lys His Ala Glu Lys Asn Trp Phe Val Gly
            100                 105                 110

Leu Lys Lys Asn Gly Ser Val Lys Arg Gly Pro Arg Thr His Tyr Gly
        115                 120                 125

Gln Lys Ala Ile Leu Phe Leu Pro Leu Pro Val Ser Ser Asp
130                 135                 140

<210> SEQ ID NO 188
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (68)..(68)
<223> OTHER INFORMATION: Any amino acid

<400> SEQUENCE: 188

Leu Thr Glu Lys Pro Pro Gly Asn Tyr Lys Lys Pro Lys Leu Leu Tyr
1               5                   10                  15

Ser Ser Asn Gly Gly His Phe Leu Arg Ile Leu Pro Asp Gly Thr Val
            20                  25                  30

Asp Gly Thr Arg Asp Arg Ser Asp Gln His Ile Gln Leu Gln Leu Ser
        35                  40                  45

Ala Glu Ser Val Gly Glu Val Tyr Ile Lys Ser Thr Glu Thr Gly Gln
50                  55                  60

Tyr Leu Cys Xaa Asp Thr Asp Gly Leu Leu Tyr Gly Ser Gln Thr Pro
65                  70                  75                  80

Asn Glu Glu Cys Leu Phe Leu Glu Arg Leu Glu Glu Asn His Tyr Asn
                85                  90                  95

Thr Tyr Ile Ser Lys Lys His Ala Glu Lys Asn Trp Phe Val Gly Leu
            100                 105                 110

Lys Lys Asn Gly Ser Val Lys Arg Gly Pro Arg Thr His Tyr Gly Gln
        115                 120                 125

Lys Ala Ile Leu Phe Leu Pro Leu Pro Val Ser Ser Asp
130                 135                 140

<210> SEQ ID NO 189
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (67)..(67)
<223> OTHER INFORMATION: Any amino acid

<400> SEQUENCE: 189

Leu Thr Glu Lys Pro Gly Asn Tyr Lys Pro Lys Leu Leu Tyr Ser
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
    50                  55                  60

Leu Cys Xaa Asp Thr Asp Gly Leu Leu Tyr Gly Ser Gln Thr Pro Asn
65              70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
            100                 105                 110

Lys Asn Gly Ser Val Lys Arg Gly Pro Arg Thr His Tyr Gly Gln Lys
        115                 120                 125

Ala Ile Leu Phe Leu Pro Leu Pro Val Ser Ser Asp
    130                 135                 140

<210> SEQ ID NO 190
<211> LENGTH: 143
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (70)..(70)
<223> OTHER INFORMATION: Any amino acid

<400> SEQUENCE: 190

Thr Glu Lys Phe Asn Leu Pro Pro Gly Asn Tyr Lys Pro Lys Leu
1               5                   10                  15

Leu Tyr Ser Ser Asn Gly Gly His Phe Leu Arg Ile Leu Pro Asp Gly
            20                  25                  30

Thr Val Asp Gly Thr Arg Asp Arg Ser Asp Gln His Ile Gln Leu Gln
        35                  40                  45

Leu Ser Ala Glu Ser Val Gly Glu Val Tyr Ile Lys Ser Thr Glu Thr
    50                  55                  60

Gly Gln Tyr Leu Cys Xaa Asp Thr Asp Gly Leu Leu Tyr Gly Ser Gln
65              70                  75                  80

Thr Pro Asn Glu Glu Cys Leu Phe Leu Glu Arg Leu Glu Glu Asn His
                85                  90                  95

Tyr Asn Thr Tyr Ile Ser Lys Lys His Ala Glu Lys Asn Trp Phe Val
            100                 105                 110

Gly Leu Lys Lys Asn Gly Ser Val Lys Arg Gly Pro Arg Thr His Tyr
        115                 120                 125

Gly Gln Lys Ala Ile Leu Phe Leu Pro Leu Pro Val Ser Ser Asp
    130                 135                 140

<210> SEQ ID NO 191
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide

```
<220> FEATURE:
<221> NAME/KEY: MOD_RES
<222> LOCATION: (69)..(69)
<223> OTHER INFORMATION: Any amino acid

<400> SEQUENCE: 191

Thr Glu Lys Asn Leu Pro Pro Gly Asn Tyr Lys Pro Lys Leu Leu
1               5                   10                  15

Tyr Ser Ser Asn Gly Gly His Phe Leu Arg Ile Leu Pro Asp Gly Thr
            20                  25                  30

Val Asp Gly Thr Arg Asp Arg Ser Asp Gln His Ile Gln Leu Gln Leu
        35                  40                  45

Ser Ala Glu Ser Val Gly Glu Val Tyr Ile Lys Ser Thr Glu Thr Gly
50                  55                  60

Gln Tyr Leu Cys Xaa Asp Thr Asp Gly Leu Leu Tyr Gly Ser Gln Thr
65                  70                  75                  80

Pro Asn Glu Glu Cys Leu Phe Leu Glu Arg Leu Glu Glu Asn His Tyr
                85                  90                  95

Asn Thr Tyr Ile Ser Lys Lys His Ala Glu Lys Asn Trp Phe Val Gly
                100                 105                 110

Leu Lys Lys Asn Gly Ser Val Lys Arg Gly Pro Arg Thr His Tyr Gly
            115                 120                 125

Gln Lys Ala Ile Leu Phe Leu Pro Leu Pro Val Ser Ser Asp
        130                 135                 140

<210> SEQ ID NO 192
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (68)..(68)
<223> OTHER INFORMATION: Any amino acid

<400> SEQUENCE: 192

Thr Glu Lys Leu Pro Pro Gly Asn Tyr Lys Pro Lys Leu Leu Tyr
1               5                   10                  15

Ser Ser Asn Gly Gly His Phe Leu Arg Ile Leu Pro Asp Gly Thr Val
            20                  25                  30

Asp Gly Thr Arg Asp Arg Ser Asp Gln His Ile Gln Leu Gln Leu Ser
        35                  40                  45

Ala Glu Ser Val Gly Glu Val Tyr Ile Lys Ser Thr Glu Thr Gly Gln
50                  55                  60

Tyr Leu Cys Xaa Asp Thr Asp Gly Leu Leu Tyr Gly Ser Gln Thr Pro
65                  70                  75                  80

Asn Glu Glu Cys Leu Phe Leu Glu Arg Leu Glu Glu Asn His Tyr Asn
                85                  90                  95

Thr Tyr Ile Ser Lys Lys His Ala Glu Lys Asn Trp Phe Val Gly Leu
                100                 105                 110

Lys Lys Asn Gly Ser Val Lys Arg Gly Pro Arg Thr His Tyr Gly Gln
            115                 120                 125

Lys Ala Ile Leu Phe Leu Pro Leu Pro Val Ser Ser Asp
        130                 135                 140

<210> SEQ ID NO 193
<211> LENGTH: 140
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (67)..(67)
<223> OTHER INFORMATION: Any amino acid

<400> SEQUENCE: 193

Thr Glu Lys Pro Pro Gly Asn Tyr Lys Lys Pro Lys Leu Leu Tyr Ser
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
50                  55                  60

Leu Cys Xaa Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
            100                 105                 110

Lys Asn Gly Ser Val Lys Arg Gly Pro Arg Thr His Tyr Gly Gln Lys
        115                 120                 125

Ala Ile Leu Phe Leu Pro Leu Pro Val Ser Ser Asp
    130                 135                 140

<210> SEQ ID NO 194
<211> LENGTH: 139
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (66)..(66)
<223> OTHER INFORMATION: Any amino acid

<400> SEQUENCE: 194

Thr Glu Lys Pro Gly Asn Tyr Lys Lys Pro Lys Leu Leu Tyr Ser Ser
1               5                   10                  15

Asn Gly Gly His Phe Leu Arg Ile Leu Pro Asp Gly Thr Val Asp Gly
            20                  25                  30

Thr Arg Asp Arg Ser Asp Gln His Ile Gln Leu Gln Leu Ser Ala Glu
        35                  40                  45

Ser Val Gly Glu Val Tyr Ile Lys Ser Thr Glu Thr Gly Gln Tyr Leu
50                  55                  60

Cys Xaa Asp Thr Asp Gly Leu Leu Tyr Gly Ser Gln Thr Pro Asn Glu
65                  70                  75                  80

Glu Cys Leu Phe Leu Glu Arg Leu Glu Glu Asn His Tyr Asn Thr Tyr
                85                  90                  95

Ile Ser Lys Lys His Ala Glu Lys Asn Trp Phe Val Gly Leu Lys Lys
            100                 105                 110

Asn Gly Ser Val Lys Arg Gly Pro Arg Thr His Tyr Gly Gln Lys Ala
        115                 120                 125

Ile Leu Phe Leu Pro Leu Pro Val Ser Ser Asp
```

```
            130                 135

<210> SEQ ID NO 195
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (69)..(69)
<223> OTHER INFORMATION: Any amino acid

<400> SEQUENCE: 195

Glu Lys Phe Asn Leu Pro Pro Gly Asn Tyr Lys Lys Pro Lys Leu Leu
1               5                   10                  15

Tyr Ser Ser Asn Gly Gly His Phe Leu Arg Ile Leu Pro Asp Gly Thr
            20                  25                  30

Val Asp Gly Thr Arg Asp Arg Ser Asp Gln His Ile Gln Leu Gln Leu
        35                  40                  45

Ser Ala Glu Ser Val Gly Glu Val Tyr Ile Lys Ser Thr Glu Thr Gly
50                  55                  60

Gln Tyr Leu Cys Xaa Asp Thr Asp Gly Leu Leu Tyr Gly Ser Gln Thr
65                  70                  75                  80

Pro Asn Glu Glu Cys Leu Phe Leu Glu Arg Leu Glu Glu Asn His Tyr
                85                  90                  95

Asn Thr Tyr Ile Ser Lys Lys His Ala Glu Lys Asn Trp Phe Val Gly
            100                 105                 110

Leu Lys Lys Asn Gly Ser Val Lys Arg Gly Pro Arg Thr His Tyr Gly
            115                 120                 125

Gln Lys Ala Ile Leu Phe Leu Pro Leu Pro Val Ser Ser Asp
            130                 135                 140

<210> SEQ ID NO 196
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (68)..(68)
<223> OTHER INFORMATION: Any amino acid

<400> SEQUENCE: 196

Glu Lys Asn Leu Pro Pro Gly Asn Tyr Lys Lys Pro Lys Leu Leu Tyr
1               5                   10                  15

Ser Ser Asn Gly Gly His Phe Leu Arg Ile Leu Pro Asp Gly Thr Val
            20                  25                  30

Asp Gly Thr Arg Asp Arg Ser Asp Gln His Ile Gln Leu Gln Leu Ser
        35                  40                  45

Ala Glu Ser Val Gly Glu Val Tyr Ile Lys Ser Thr Glu Thr Gly Gln
50                  55                  60

Tyr Leu Cys Xaa Asp Thr Asp Gly Leu Leu Tyr Gly Ser Gln Thr Pro
65                  70                  75                  80

Asn Glu Glu Cys Leu Phe Leu Glu Arg Leu Glu Glu Asn His Tyr Asn
                85                  90                  95

Thr Tyr Ile Ser Lys Lys His Ala Glu Lys Asn Trp Phe Val Gly Leu
            100                 105                 110
```

```
Lys Lys Asn Gly Ser Val Lys Arg Gly Pro Arg Thr His Tyr Gly Gln
        115                 120                 125

Lys Ala Ile Leu Phe Leu Pro Leu Pro Val Ser Ser Asp
    130                 135                 140

<210> SEQ ID NO 197
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (67)..(67)
<223> OTHER INFORMATION: Any amino acid

<400> SEQUENCE: 197

Glu Lys Leu Pro Pro Gly Asn Tyr Lys Lys Pro Lys Leu Leu Tyr Ser
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
50                  55                  60

Leu Cys Xaa Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
            100                 105                 110

Lys Asn Gly Ser Val Lys Arg Gly Pro Arg Thr His Tyr Gly Gln Lys
        115                 120                 125

Ala Ile Leu Phe Leu Pro Leu Pro Val Ser Ser Asp
    130                 135                 140

<210> SEQ ID NO 198
<211> LENGTH: 139
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (66)..(66)
<223> OTHER INFORMATION: Any amino acid

<400> SEQUENCE: 198

Glu Lys Pro Pro Gly Asn Tyr Lys Lys Pro Lys Leu Leu Tyr Ser Ser
1               5                   10                  15

Asn Gly Gly His Phe Leu Arg Ile Leu Pro Asp Gly Thr Val Asp Gly
            20                  25                  30

Thr Arg Asp Arg Ser Asp Gln His Ile Gln Leu Gln Leu Ser Ala Glu
        35                  40                  45

Ser Val Gly Glu Val Tyr Ile Lys Ser Thr Glu Thr Gly Gln Tyr Leu
    50                  55                  60

Cys Xaa Asp Thr Asp Gly Leu Leu Tyr Gly Ser Gln Thr Pro Asn Glu
65                  70                  75                  80
```

```
Glu Cys Leu Phe Leu Glu Arg Leu Glu Glu Asn His Tyr Asn Thr Tyr
                85                  90                  95

Ile Ser Lys Lys His Ala Glu Lys Asn Trp Phe Val Gly Leu Lys Lys
            100                 105                 110

Asn Gly Ser Val Lys Arg Gly Pro Arg Thr His Tyr Gly Gln Lys Ala
        115                 120                 125

Ile Leu Phe Leu Pro Leu Pro Val Ser Ser Asp
        130                 135

<210> SEQ ID NO 199
<211> LENGTH: 138
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (65)..(65)
<223> OTHER INFORMATION: Any amino acid

<400> SEQUENCE: 199

Glu Lys Pro Gly Asn Tyr Lys Lys Pro Lys Leu Leu Tyr Ser Ser Asn
1               5                   10                  15

Gly Gly His Phe Leu Arg Ile Leu Pro Asp Gly Thr Val Asp Gly Thr
            20                  25                  30

Arg Asp Arg Ser Asp Gln His Ile Gln Leu Gln Leu Ser Ala Glu Ser
        35                  40                  45

Val Gly Glu Val Tyr Ile Lys Ser Thr Glu Thr Gly Gln Tyr Leu Cys
    50                  55                  60

Xaa Asp Thr Asp Gly Leu Leu Tyr Gly Ser Gln Thr Pro Asn Glu Glu
65                  70                  75                  80

Cys Leu Phe Leu Glu Arg Leu Glu Glu Asn His Tyr Asn Thr Tyr Ile
                85                  90                  95

Ser Lys Lys His Ala Glu Lys Asn Trp Phe Val Gly Leu Lys Lys Asn
            100                 105                 110

Gly Ser Val Lys Arg Gly Pro Arg Thr His Tyr Gly Gln Lys Ala Ile
        115                 120                 125

Leu Phe Leu Pro Leu Pro Val Ser Ser Asp
        130                 135

<210> SEQ ID NO 200
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (68)..(68)
<223> OTHER INFORMATION: Any amino acid

<400> SEQUENCE: 200

Lys Phe Asn Leu Pro Pro Gly Asn Tyr Lys Lys Pro Lys Leu Leu Tyr
1               5                   10                  15

Ser Ser Asn Gly Gly His Phe Leu Arg Ile Leu Pro Asp Gly Thr Val
            20                  25                  30

Asp Gly Thr Arg Asp Arg Ser Asp Gln His Ile Gln Leu Gln Leu Ser
        35                  40                  45

Ala Glu Ser Val Gly Glu Val Tyr Ile Lys Ser Thr Glu Thr Gly Gln
```

```
                50                  55                  60
Tyr Leu Cys Xaa Asp Thr Asp Gly Leu Leu Tyr Gly Ser Gln Thr Pro
 65                  70                  75                  80

Asn Glu Glu Cys Leu Phe Leu Glu Arg Leu Glu Glu Asn His Tyr Asn
                 85                  90                  95

Thr Tyr Ile Ser Lys Lys His Ala Glu Lys Asn Trp Phe Val Gly Leu
            100                 105                 110

Lys Lys Asn Gly Ser Val Lys Arg Gly Pro Arg Thr His Tyr Gly Gln
        115                 120                 125

Lys Ala Ile Leu Phe Leu Pro Leu Pro Val Ser Ser Asp
    130                 135                 140

<210> SEQ ID NO 201
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (67)..(67)
<223> OTHER INFORMATION: Any amino acid

<400> SEQUENCE: 201

Lys Asn Leu Pro Pro Gly Asn Tyr Lys Lys Pro Lys Leu Leu Tyr Ser
 1               5                  10                  15

Ser Asn Gly Gly His Phe Leu Arg Ile Leu Pro Asp Gly Thr Val Asp
             20                  25                  30

Gly Thr Arg Asp Arg Ser Asp Gln His Ile Gln Leu Gln Leu Ser Ala
         35                  40                  45

Glu Ser Val Gly Glu Val Tyr Ile Lys Ser Thr Glu Thr Gly Gln Tyr
     50                  55                  60

Leu Cys Xaa Asp Thr Asp Gly Leu Leu Tyr Gly Ser Gln Thr Pro Asn
 65                  70                  75                  80

Glu Glu Cys Leu Phe Leu Glu Arg Leu Glu Glu Asn His Tyr Asn Thr
                 85                  90                  95

Tyr Ile Ser Lys Lys His Ala Glu Lys Asn Trp Phe Val Gly Leu Lys
            100                 105                 110

Lys Asn Gly Ser Val Lys Arg Gly Pro Arg Thr His Tyr Gly Gln Lys
        115                 120                 125

Ala Ile Leu Phe Leu Pro Leu Pro Val Ser Ser Asp
    130                 135                 140

<210> SEQ ID NO 202
<211> LENGTH: 139
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (66)..(66)
<223> OTHER INFORMATION: Any amino acid

<400> SEQUENCE: 202

Lys Leu Pro Pro Gly Asn Tyr Lys Lys Pro Lys Leu Leu Tyr Ser Ser
 1               5                  10                  15

Asn Gly Gly His Phe Leu Arg Ile Leu Pro Asp Gly Thr Val Asp Gly
             20                  25                  30
```

```
Thr Arg Asp Arg Ser Asp Gln His Ile Gln Leu Gln Leu Ser Ala Glu
        35                  40                  45

Ser Val Gly Glu Val Tyr Ile Lys Ser Thr Glu Thr Gly Gln Tyr Leu
 50                  55                  60

Cys Xaa Asp Thr Asp Gly Leu Leu Tyr Gly Ser Gln Thr Pro Asn Glu
 65                  70                  75                  80

Glu Cys Leu Phe Leu Glu Arg Leu Glu Glu Asn His Tyr Asn Thr Tyr
                 85                  90                  95

Ile Ser Lys Lys His Ala Glu Lys Asn Trp Phe Val Gly Leu Lys Lys
                100                 105                 110

Asn Gly Ser Val Lys Arg Gly Pro Arg Thr His Tyr Gly Gln Lys Ala
            115                 120                 125

Ile Leu Phe Leu Pro Leu Pro Val Ser Ser Asp
        130                 135

<210> SEQ ID NO 203
<211> LENGTH: 138
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (65)..(65)
<223> OTHER INFORMATION: Any amino acid

<400> SEQUENCE: 203

Lys Pro Pro Gly Asn Tyr Lys Lys Pro Lys Leu Leu Tyr Ser Ser Asn
 1               5                  10                  15

Gly Gly His Phe Leu Arg Ile Leu Pro Asp Gly Thr Val Asp Gly Thr
                 20                  25                  30

Arg Asp Arg Ser Asp Gln His Ile Gln Leu Gln Leu Ser Ala Glu Ser
            35                  40                  45

Val Gly Glu Val Tyr Ile Lys Ser Thr Glu Thr Gly Gln Tyr Leu Cys
 50                  55                  60

Xaa Asp Thr Asp Gly Leu Leu Tyr Gly Ser Gln Thr Pro Asn Glu Glu
 65                  70                  75                  80

Cys Leu Phe Leu Glu Arg Leu Glu Glu Asn His Tyr Asn Thr Tyr Ile
                 85                  90                  95

Ser Lys Lys His Ala Glu Lys Asn Trp Phe Val Gly Leu Lys Lys Asn
                100                 105                 110

Gly Ser Val Lys Arg Gly Pro Arg Thr His Tyr Gly Gln Lys Ala Ile
            115                 120                 125

Leu Phe Leu Pro Leu Pro Val Ser Ser Asp
        130                 135

<210> SEQ ID NO 204
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (64)..(64)
<223> OTHER INFORMATION: Any amino acid

<400> SEQUENCE: 204
```

```
Lys Pro Gly Asn Tyr Lys Lys Pro Lys Leu Leu Tyr Ser Ser Asn Gly
 1               5                  10                  15

Gly His Phe Leu Arg Ile Leu Pro Asp Gly Thr Val Asp Gly Thr Arg
            20                  25                  30

Asp Arg Ser Asp Gln His Ile Gln Leu Gln Leu Ser Ala Glu Ser Val
        35                  40                  45

Gly Glu Val Tyr Ile Lys Ser Thr Glu Thr Gly Gln Tyr Leu Cys Xaa
50                  55                  60

Asp Thr Asp Gly Leu Leu Tyr Gly Ser Gln Thr Pro Asn Glu Glu Cys
65                  70                  75                  80

Leu Phe Leu Glu Arg Leu Glu Glu Asn His Tyr Asn Thr Tyr Ile Ser
                85                  90                  95

Lys Lys His Ala Glu Lys Asn Trp Phe Val Gly Leu Lys Lys Asn Gly
            100                 105                 110

Ser Val Lys Arg Gly Pro Arg Thr His Tyr Gly Gln Lys Ala Ile Leu
        115                 120                 125

Phe Leu Pro Leu Pro Val Ser Ser Asp
    130                 135
```

<210> SEQ ID NO 205
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 205

```
Phe Asn Leu Pro Pro Gly Asn Tyr Lys Lys Pro Val Leu Leu Tyr Cys
 1               5                  10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
            100                 105                 110

Lys Asn Gly Ser Val Lys Arg Gly Pro Arg Thr His Tyr Gly Gln Lys
        115                 120                 125

Ala Ile Leu Phe Leu Val Leu Pro Val Ser Ser Asp
        130                 135                 140
```

<210> SEQ ID NO 206
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 206

```
Phe Asn Leu Pro Pro Gly Asn Tyr Lys Lys Pro Lys Leu Leu Tyr Ser
 1               5                  10                  15
```

```
Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
            35                  40                  45

Glu Ser Val Gly Glu Val Tyr Ile Lys Ser Thr Glu Thr Gly Gln Tyr
 50                  55                  60

Leu Cys Met Asp Thr Asp Gly Leu Leu Tyr Gly Ser Gln Thr Pro Asn
 65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
            100                 105                 110

Lys Asn Gly Ser Val Lys Arg Gly Pro Arg Thr His Tyr Gly Gln Lys
            115                 120                 125

Ala Ile Leu Phe Leu Pro Leu Pro Val Ser Ser Asp
            130                 135                 140

<210> SEQ ID NO 207
<211> LENGTH: 145
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 207

Met Ala Leu Thr Glu Lys Asn Leu Pro Pro Gly Asn Tyr Lys Lys Pro
 1               5                  10                  15

Lys Leu Leu Tyr Ser Ser Asn Gly Gly His Phe Leu Arg Ile Leu Pro
            20                  25                  30

Asp Gly Thr Val Asp Gly Thr Arg Asp Arg Ser Asp Gln His Ile Gln
            35                  40                  45

Leu Gln Leu Ser Ala Glu Ser Val Gly Glu Val Tyr Ile Lys Ser Thr
 50                  55                  60

Glu Thr Gly Gln Tyr Leu Cys Met Asp Thr Asp Gly Leu Leu Tyr Gly
 65                  70                  75                  80

Ser Gln Thr Pro Asn Glu Glu Cys Leu Phe Leu Glu Arg Leu Glu Glu
                85                  90                  95

Asn His Tyr Asn Thr Tyr Ile Ser Lys Lys His Ala Glu Lys Asn Trp
            100                 105                 110

Phe Val Gly Leu Lys Lys Asn Gly Ser Val Lys Arg Gly Pro Arg Thr
            115                 120                 125

His Tyr Gly Gln Lys Ala Ile Leu Phe Leu Pro Leu Pro Val Ser Ser
            130                 135                 140

Asp
145
```